United States Patent [19]

Hillemann

[11] Patent Number: 4,877,442
[45] Date of Patent: Oct. 31, 1989

[54] HERBICIDAL SULFONAMIDES

[75] Inventor: Craig L. Hillemann, Wilmington, Del.

[73] Assignee: E. I. Du Pont de Nemours and Company, Wilmington, Del.

[21] Appl. No.: 257,143

[22] Filed: Oct. 7, 1988

Related U.S. Application Data

[63] Continuation of Ser. No. 916,266, Oct. 7, 1986, abandoned, which is a continuation-in-part of Ser. No. 801,120, Nov. 22, 1985, abandoned, which is a continuation-in-part of Ser. No. 715,511, Mar. 27, 1985, abandoned, which is a continuation-in-part of Ser. No. 613,412, May 24, 1984, abandoned.

[51] Int. Cl.$^4$ .................. C07D 239/69; A01N 43/54
[52] U.S. Cl. ........................................ 71/92; 544/321
[58] Field of Search ............................ 71/92; 544/321

[56] References Cited

U.S. PATENT DOCUMENTS

| 4,394,506 | 7/1983 | Levitt | 544/321 |
| 4,478,635 | 10/1984 | Meyer et al. | 71/92 |
| 4,563,211 | 1/1986 | Wexler et al. | 71/92 |

FOREIGN PATENT DOCUMENTS

| 814874 | 7/1981 | South Africa . |
| 825042 | 7/1982 | South Africa . |
| 825671 | 8/1982 | South Africa . |
| 830127 | 1/1983 | South Africa . |
| 842245 | 3/1984 | South Africa . |
| 842722 | 4/1984 | South Africa . |

*Primary Examiner*—John M. Ford

[57] ABSTRACT

The invention relates to certain herbicidal sulfonamides, agriculturally suitable compositions thereof and a method for their use as a general or selective preemergent or postemergent herbicide or as a plant growth regulant.

51 Claims, No Drawings

HERBICIDAL SULFONAMIDES

RELATED APPLICATION

This application is a continuation of application Ser. No. 06/916,266, abandoned, filed Oct. 7, 1986, which is a continuation-in-part of copending application U.S. Ser. No. 801,120 filed Nov. 22, 1985, now abandoned which is a continuation-in-part of copending application U.S. Ser. No. 715,511 filed Mar. 27,1985 now abandoned which is a continuation-in-part of copending application U.S. Ser. No. 613,412 filed May 24, 1984, now abandoned.

BACKGROUND OF THE INVENTION

This invention relates to certain herbicidal sulfonamides, agriculturally suitable compositions thereof and a method for their use as a general or selective preemergent or postemergent herbicide or as a plant growth regulant.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

The "sulfonylurea" herbicides are an extremely potent class of herbicides discovered within the last few years which generally consist of a sulfonylurea bridge, —SO$_2$NHCONH—, linking two aromatic or heteroaromatic rings.

U.S. Pat. No. 4,394,506 discloses herbicidal ortho-alkoxycarbonylbenzenesulfonamides such as

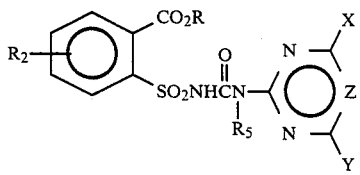

wherein $R_2$ is H, F, Cl, Br, C$_1$–C$_3$ alkyl, NO$_2$, SO$_2$CH$_3$, OCH$_3$, SCH$_3$, CF$_3$, N(CH$_3$)$_2$, NH$_2$ or CN;

X is H, Cl, CH$_3$, OCH$_3$, OCH$_2$CH$_3$ or OCH$_2$CH$_2$OCH$_3$; and

Y is H, halogen, C$_1$–C$_4$ alkyl, C$_1$–C$_4$ substituted alkyl, C$_1$–C$_4$ alkoxy, etc.

South African patent application No. 81/4874 discloses herbicidal sulfonamides of formula

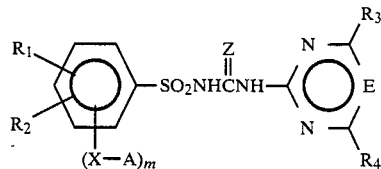

wherein

A is a C$_1$–C$_6$ alkyl radical which is substituted by halogen or various other organic substituents or a C$_2$–C$_6$ alkenyl radical which is substituted or unsubstituted;

X is O, S, SO or SO$_2$;

R$_1$ is H, halogen, C$_1$–C$_5$ alkyl, C$_2$–C$_5$ alkenyl or YR$_5$;

R$_2$ is H, halogen, C$_1$–C$_5$ alkyl, C$_2$–C$_5$ alkenyl, C$_1$–C$_4$ haloalkyl, CO$_2$R$_6$, YR$_5$, NO$_2$ or CONR$_7$R$_8$; and R$_3$ and R$_4$, each independently of the other, are hydrogen, C$_1$–C$_4$ alkyl, C$_1$–C$_4$ alkoxy, C$_1$–C$_4$ alkylthio, C$_1$–C$_4$ haloalkyl, halogen or alkoxyalkyl of at most 4 carbon atoms.

South African patent application No. 82/5042 discloses herbicidal sulfonamides of formula

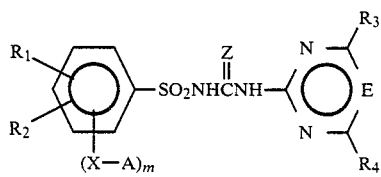

wherein

A is C$_3$–C$_6$ alkynyl;

X is O, S, SO or SO$_2$;

R$_1$ is H, halogen, C$_1$–C$_5$ alkyl, C$_2$–C$_5$ alkenyl or YR$_5$;

R$_2$ is H, halogen, C$_1$–C$_5$ alkyl, C$_2$–C$_5$ alkenyl, C$_1$–C$_4$ haloalkyl, CO$_2$R$_6$, YR$_5$, NO$_2$ or CONR$_7$R$_8$; and R$_3$ and R$_4$, independently of one another, are hydrogen, C$_1$–C$_4$ alkyl, C$_1$–C$_4$ alkoxy, C$_1$–C$_4$ alkylthio, C$_1$–C$_4$ haloalkyl, C$_1$–C$_4$ haloalkoxy, halogen or alkoxyalkyl of at most 4 carbon atoms.

South African patent application No. 82/5671 discloses herbicidal sulfonamides of formulas

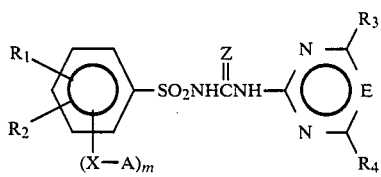

wherein

A is a C$_1$–C$_6$ alkyl radical or a C$_2$–C$_6$ alkenyl radical which is substituted by halogen or various other organic substituents;

X is O, S, SO or SO$_2$;

R$_1$ is H, halogen, C$_1$–C$_5$ alkyl, C$_2$–C$_5$ alkenyl or YR$_5$;

R$_2$ is H, halogen, C$_1$–C$_5$ alkyl, C$_2$–C$_5$ alkenyl, C$_1$–C$_4$ haloalkyl, CO$_2$R$_6$, YR$_5$, NO$_2$ or CONR$_7$R$_8$;

R$_3$ is hydrogen, C$_1$–C$_4$ alkyl, C$_1$–C$_4$ alkoxy, C$_1$–C$_4$ alkylthio, C$_1$–C$_4$ haloalkyl, C$_1$–C$_4$ haloalkoxy, halogen or alkoxyalkyl of at most 4 carbon atoms; and R$_4$ is C$_1$–C$_4$ haloalkoxy or C$_1$–C$_4$ haloalkylthio.

South African patent application No. 83/0127 discloses herbicidal sulfonamides of formula

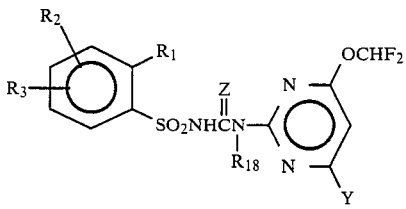

wherein
- $R_1$ is hydrogen, halogen, cyano, nitro, $C_1$-$C_4$ haloalkyl, $C_1$-$C_4$ alkyl, $C_1$-$C_4$ alkoxy, $COR_6$, $NR_7R_8$, $S(O)_m$—$C_1$-$C_4$ alkyl or $SO_2R_9$;
- $R_2$ is H, F, Cl, Br, $NO_2$, $CF_3$, $NR_{20}R_{21}$, $C_1$-$C_2$ alkyl, $C_1$-$C_2$ alkoxy or $S(O)_m$—$C_1$-$C_4$ alkyl;
- $R_3$ is H, F, Cl, Br, $NH_2$, $NO_2$ or $OCH_3$;
- $R_6$ is hydrogen, $C_1$-$C_4$ alkyl, $C_3$-$C_5$ alkenyloxy, $C_3$-$C_5$ alkynyloxy, $C_1$-$C_4$ haloalkyl, $C_1$-$C_5$ alkylthio, phenoxy, benzyloxy, $NR_{10}R_{11}$ or $C_1$-$C_5$ alkoxy which is unsubstituted or substituted by 1–3 halogen atoms or $C_1$-$C_3$ alkoxy;
- $R_{18}$ is hydrogen, $C_1$-$C_3$ alkyl or $C_1$-$C_3$ alkoxy;
- m is 0, 1 or 2; and
- Y is $C_1$-$C_3$ alkyl, $C_1$-$C_3$ haloalkyl, $C_1$-$C_3$ alkoxy, $C_1$-$C_3$ haloalkoxy, $C_2$-$C_3$ alkoxyalkyl, $C_1$-$C_3$ alkylthio, halogen or $NR_{16}R_{17}$.

South African patent application No. 84/2245 discloses herbicidal sulfonamides of formula

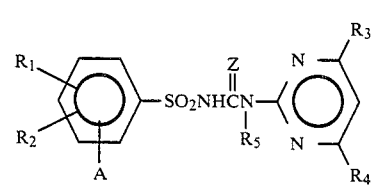

wherein
- A is $C_1$-$C_6$ haloalkyl;
- $R_1$ is hydrogen, halogen, nitro, cyano, $C_1$-$C_4$ alkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, $COR_6$, $NR_7R_8$, $CONR_9R_{10}$ or $SO_2NR_{11}R_{12}$;
- $R_2$ is hydrogen, halogen, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl; and
- $R_3$ and $R_4$, independently of one another, are each hydrogen, halogen, $C_1$-$C_4$ alkyl, $C_1$-$C_4$ haloalkyl, $C_2$-$C_4$ haloalkoxy, $C_1$-$C_4$ alkylthio, $C_1$-$C_4$ haloalkylthio, $C_2$-$C_4$ alkoxyalkyl, $C_1$-$C_4$ alkoxy or $NR_{12}R_{13}$.

South African patent application No. 84/2722 discloses herbicidal benzenesulfonamides of formula

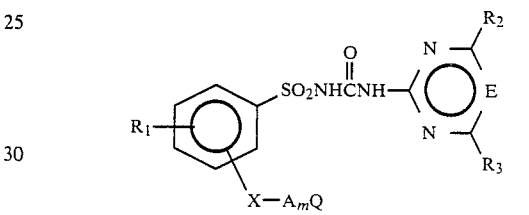

wherein
A is a radical of the formula $CR_6R_7XR_8$, $CR_9R_{10}R_{11}$ or $CHR_7SCQR_{21}$;

- $R_1$ is hydrogen, halogen, nitro, cyano, $C_1$-$C_4$ alkyl, $C_1$-$C_4$ haloalkyl, $YR_{14}$, $CONR_{12}R_{13}$, $NR_{12}R_{13}$, $SONR_{15}R_{16}$, $OSO_2R_{17}$ or $COR_{18}$;
- $R_2$ is hydrogen, halogen, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl;
- $R_3$ and $R_4$, independently of one another, are each hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl or $NR_{19}R_{20}$;
- $R_9$ is hydrogen, halogen, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl;
- $R_{10}$ is hydrogen, halogen or methyl;
- $R_{11}$ is a radical $COR_{24}$ or a $C_1$-$C_4$ alkyl group that is mono- or polysubstituted by substituents selected from the group: cyano, nitro, hydroxyl, $C_1$-$C_4$ alkoxy, $C_1$-$C_4$ alkylthio, etc.
- $R_{18}$ is H, $C_1$-$C_4$ alkoxy and various other organic radicals.

South African patent application No. 83/0041 discloses herbicidal benzenesulfonamides of formula

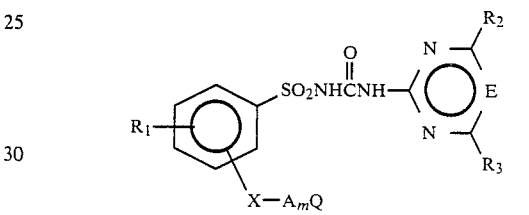

wherein
- $R_1$ is H, halogen, $NO_2$, $C_1$-$C_4$ haloalkyl, $C_1$-$C_4$ alkyl, $C_1$-$C_4$ alkoxy, $C_2$-$C_5$ alkenyl or $C_1$-$C_4$ alkoxycarbonyl;
- $R_2$ is $C_1$-$C_3$ alkyl or $C_1$-$C_3$ alkoxy, each unsubstituted or substituted by 1 to 3 halogen atoms;
- $R_3$ is halogen, H, $NR_4R_5$, $C_1$-$C_3$ alkyl, unsubstituted or substituted by 1 to 3 halogen atoms ro $C_1$-$C_4$ alkoxy, or is $C_1$-$C_3$ alkoxy, unsubstituted or substituted by methoxy, ethoxy, or 1 or 3 halogen atoms;
- A is $C_1$-$C_4$ alkylene or $C_2$-$C_4$ alkenylene, each unsubstituted or substituted by $C_1$-$C_4$ alkyl;
- m is 0 or 1;
- E is N or CH;
- X is oxygen, sulfur, SO or $SO_2$; and
- Q is, in part, OH, CN, $NR_6R_7$, $SO_2R_8$, cycloalkyl or $COCH_1$-$C_6$ alkyl.

South African patent application No. 83/3779 discloses herbicidal benzenesulfonamides of formula

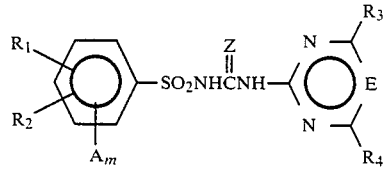

wherein
- A is C≡CR;
- m is 1 or 2;
- E is CH or N;
- Z is oxygen or sulfur,
- R is, in part, H, $C_1$-$C_9$ alkyl or $C_1$-$C_9$ haloalkyl;
- $R_1$ is H, halogen, $C_1$-$C_5$ alkyl, $C_2$-$C_5$ alkenyl or $YR_5$;

$R_2$ is H, halogen, $C_1$-$C_5$ alkyl, $C_2$-$C_5$ alkenyl, $C_1$-$C_4$ haloalkyl, $YR_5$, $CO_2R_6$, $NO_2$ or $CONR_7R_8$;

$R_3$ and $R_4$, each independently of the other, are H, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio, halogen, $C_2$-$C_5$ alkoxyalkyl, $NR_9R_{10}$ or $OCH_2CH_2NR_9R_{10}$.

There is however a continuing need to find herbicides that are more effective and more selective toward agricultural products.

SUMMARY OF THE INVENTION

This invention relates to novel compounds of Formula I, agriculturally suitable compositions containing them and their method-of-use as general or selective preemergent or postemergent herbicides or as plant growth regulants.

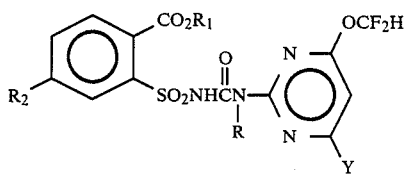

wherein
R is H or $CH_3$;
$R_1$ is $C_1$-$C_3$ alkyl, $C_3$-$C_4$ alkoxylalkyl, $C_2$-$C_4$ haloalkyl, $C_3$-$C_4$ alkenyl or $C_3$-$C_4$ alkynyl;
$R_2$ is $C_1$-$C_3$ alkyl, cyclopropyl, $C_1$-$C_3$ alkoxy, $C_1$-$C_3$ alkylthio, $C_1$-$C_3$ alkylsulfinyl, $C_1$-$C_3$ alkylsulfonyl, allyloxy, allylthio, allysulfinyl, allylsulfonyl, propargyloxy, propargylthio, propargylsulfinyl, propargylsulfonyl, $C_1$-$C_3$ haloalkoxy, $C_1$-$C_3$ alkyl substituted with 1-3 atoms of F or Cl, $C_1$-$C_2$ alkyl substituted with $C_1$-$C_2$ alkoxy, $C_1$-$C_2$ haloalkoxy, $C_1 \propto C_2$ alkylthio, $C_1$-$C_2$ haloalkylthio, $C_1$-$C_2$ alkylsulfinyl, $C_1$-$C_2$ haloalkylsufinyl, $C_1$-$C_2$ alkylsulfonyl, $C_1$-$C_2$ haloalkylsulfonyl, OH or $OC(O)C_1$-$C_2$ alkyl, $C_1$-$C_2$ alkoxy substituted with $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfinyl, $C_1$-$C_2$ haloalkylsulfinyl, $C_1$-$C_2$ alkylsulfonyl, $C_1$-$C_2$ haloalkylsulfonyl or CN, $OCH_2CH_2NH_2$, $OCH_2CH_2NHCH_3$, $OCH_2CH_2N(CH_3)_2$, $C_1$-$C_2$ alkylthio substituted by $C_1$-$C_2$ alkoxy, $C_1$-$C_2$ haloalkoxy, $C_1$-$C_2$ alkylthio, $C_1$-$C_2$ haloalkylthio or CN, $C_1$-$C_3$ haloalkylthio, $C_1$-$C_3$ haloalkylsulfinyl, $C_1$-$C_3$ haloalkylsulfonyl, $C_2$-$C_3$ alkenyl, C≡CH, $NR_bR_c$ or $OC(O)C_1$-$C_2$ alkyl;
$R_b$ is H or $C_1$-$C_2$ alkyl;
$R_c$ is $C_1$-$C_2$ alkyl or $C_1$-$C_2$ haloalkyl;
Y is $CH_3$, $OCH_3$ or $OCF_2H$; and
their agriculturally suitable salts.

In the above definitions, the term "alkyl", used either alone or in compound words such as "alkylthio" or "haloalkyl", denotes straight chain or branched alkyl, e.g., methyl, ethyl, n-propyl or isopropyl.

Alkoxy denotes methoxy, ethoxy, n-propoxy or isopropoxy.

Alkenyl denotes vinyl, 1-propenyl, 2-propenyl or 3-propenyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 3. For example, $C_1$-$C_3$ alkylsulfonyl would designate methylsulfonyl through propylsulfonyl.

Preferred for their higher herbicidal activity, greater plant growth regulant activity and/or more favorable ease of synthesis are:

1. Compounds of Formula I wherein $R_2$ is $C_1$-$C_3$ alkyl, cyclopropyl, $C_1$-$C_3$ alkoxy, $C_1$-$C_3$ alkylthio, $C_1$-$C_3$ alkylsulfinyl, $C_1$-$C_3$ alkylsulfonyl, allyloxy, allylthio, allylsulfinyl, allylsulfonyl, propargyloxy, propargylthio, propargylsulfinyl, propargylsulfonyl, $OCF_2H$, $OCH_2CH_2F$, $OCH_2CHF_2$, $OCH_2CF_3$, $OCH_2CH_2Cl$ or $C_1$-$C_3$ alkyl substituted with 1-3 atoms of F or Cl, $C_1$-$C_2$ alkyl substituted with $OCH_3$ or $SCH_3$.

2. Compounds of Preferred (1) wherein $R_2$ is $C_1$-$C_2$ alkyl, $C_1$-$C_2$ alkoxy, $C_1$-$C_3$ alkylthio, $C_1$-$C_3$ alkylsulfinyl, $C_1$-$C_3$ alkylsulfonyl, $CF_3$, propargyloxy, propargylthio, propargylsulfinyl, propargylsulfonyl, $OCF_2H$, $OCH_2CH_2F$, $OCH_2CHF_2$, $OCH_2CF_3$, $OCH_2CH_2Cl$, $CH_2CH_2OCH_3$ or $CH_2CH_2SCH_3$.

3. Compounds of Preferred (2) wherein
R is H;
$R_1$ is $C_1$-$C_2$ alkyl;
$R_2$ is $C_1$-$C_2$ alkyl, $C_1$-$C_2$ alkoxy, $C_1$-$C_2$ alkylthio, $CF_3$ or $OCF_2H$; and
Y is $CH_3$ or $OCH_3$.

4. Compounds of Preferred (3) wherein $R_2$ is $CH_3$, $OCH_3$, $OCH_2CH_3$ or $CF_3$.

5. Compounds of Formula I wherein $R_2$ is n-propyl, isopropyl, cyclopropyl, n-propoxy, isopropoxy, allyloxy, allylthio, allylsulfinyl, allylsulfonyl, $C_2$-$C_3$ alkenyl, $OC(O)CH_3$, $OC(O)CH_2CH_3$, $CH_2F$, $CHF_2$, $C_2$-$C_3$ alkyl substituted with 1-3 atoms of F, $C_1$-$C_3$ alkyl substituted with 1-3 atoms of Cl, $CH_2OH$, $CH(CH_3)OH$, $CH_2OCH_3$, $CH_2OCH_2CH_3$, $CH_2(CH_3)OCH_3$, $CH_2(CH_3)OCH_2CH_3$, $CH_2SCH_3$, $CH_2SCH_2CH_3$, $CH_2(CH_3)SCH_3$, $CH_2(CH_3)SCH_2CH_3$, $CH_2OC(O)C_1$-$C_2$ alkyl, $CH(CH_3)OC(O)C_1$-$C_2$ alkyl, $CH_2OC_1$-$C_2$ haloalkyl of at least 3 halogens, $CH_2SC_1$-$C_2$ haloalkyl of at least 3 halogens, $CH_2S(O)C_1$-$C_2$ haloalkyl of at least 3 halogens, $CH_2SO_2C_1$-$C_2$ haloalkyl of at least 3 halogens, $CH_{(CH3)}OC_1$-$C_2$ haloalkyl of at least 3 halogens, $CH(CH_3)SC_1$-$C_2$ haloalkyl of at least 3 halogens, $CH(CH_3)S(O)C_1$-$C_2$ haloalkyl of at least 3 halogens, $CH(CH_3)SO_2C_1$-$C_2$ haloalkyl of at least 3 halogens, $CH_2CH_2S(O)C_1$-$C_2$ haloalkyl or $CH_2CH_2SO_2C_1$-$C_2$ haloalkyl.

6. Compounds of Preferred (5) wherein $R_2$ is propyl, isopropyl, cyclopropyl, propoxy, isopropoxy, allyloxy, allylthio, allylsulfinyl, allylsulfonyl, $CH_2OCH_3$, $CH(CH_3)OCH_3$, $CH_2SCH_3$, $CH(CH_3)SCH_3$, $CH_2F$, $CHF_2$, $C_2$-$C_3$ alkyl substituted with 1-3 atoms of F or $C_1$-$C_3$ alkyl substituted with 1-3 atoms of Cl.

7. Compounds of Formula I wherein $R_2$ is $C_1$-$C_3$ alkyl, $OCH_3$, $SCH_3$, $SO_2CH_3$, $CF_3$ or $NR_bR_c$.

8. Compounds of Formula I wherein $R_2$ is $C_1$-$C_2$ alkoxy substituted with CN, $OCH_2CH_2NH_2$, $OCH_2CH_2N(CH_3)$ or $C_1$-$C_2$ alkylthio substituted by CN.

9. Compounds of Preferred (8) wherein $R_2$ is $OCH_2CH_2CN$, $OCH_2CH_2NH_2$, $OCH_2CH_2N(CH_3)$ or $SCH_2CH_2CN$.

10. Compounds of Formula I wherein $R_2$ is $CH_2CH_2OC_1$-$C_2$ alkyl, $CH_2CH_2SC_1$-$C_2$ alkyl, $CH_2CH_2S(O)C_1$-$C_2$ alkyl, $CH_2CH_2SO_2C_1$-$C_2$ alkyl, $CH_2CH_2OC_1$-$C_2$ haloalkyl, $CH_2CH_2SC_1$-$C_2$ haloalkyl, $CH_2OC_1$-$C_2$ haloalkyl of 1 or 2 halogens, $CH_2SC_1$-$C_2$ haloalkyl of 1 or 2 halogens, $CH_2S(O)C_1$-$C_2$ haloalkyl of 1 or 2 halogens, $CH_2SO_2C_1$-$C_2$ haloalkyl of 1 or 2 halogens, $CH(CH_3)OC_1$-$C_2$ haloalkyl of 1 or 2 halogens, $CH(CH_3)SC_1$-$C_2$ haloalkyl of 1 or 2 halogens, $CH(CH_3)S(O)C_1$-$C_2$ haloalkyl of 1 or 2 halogens, or $CH(CH_3)SO_2C_1$-$C_2$ haloalkyl of 1 or 2 halogens.

11. Compounds of Formula I wherein $R_2$ is propargyloxy, propargylthio, propargylsulfinyl or propargylsulfonyl.

12. Compounds of Formula I wherein $R_2$ is allyloxy, allylthio, allylsulfinyl, allylsulfonyl, $C_1$-$C_3$ haloalkoxy, $C_1$-$C_2$ alkoxy substituted with $C_1$-$C_2$ alkoxy, $C_1$-$C_2$ haloalkyl, $C_1$-$C_2$ alkylthio, $C_1$-$C_2$ haloalkylthio, $C_1$-$C_2$ alkylsulfinyl, $C_1$-$C_2$ haloalkylsulfinyl, $C_1$-$C_2$ alkylsulfonyl or $C_1$-$C_2$ haloalkylsulfonyl, $C_1$-$C_3$ haloalkylthio, $C_1$-$C_3$ haloalkylsulfinyl or $C_1$-$C_3$ haloalkylsulfonyl.

13. Compounds of Preferred (12) wherein $R_2$ is allyloxy, allylthio, allylsulfinyl, allylsulfonyl, $OCF_2H$, $OCH_2CF_3$, $OCH_2CH_2OCH_3$, $OCH_2CH_2OCH_2CF_3$, $OCH_2CH_2OCH_2CF_3$, $OCH_2CH_2OCF_2H$, $OCH_2CH_2SCH_3$, $OCH_2CH_2SCH_2CF_3$, $OCH_2CH_2S(O)CH_3$, $OCH_2CH_2S(O)CH_2CF_3$, $OCH_2CH_2SO_2CH_3$, $OCH_2CH_2SO_2CH_2CF_3$, $SCF_2H$, $SCH_2CF_3$, $S(O)CH_2CF_3$ or $SO_2CH_2CF_3$.

14. Compounds of Formula I wherein $R_2$ is $C_1$-$C_3$ haloalkoxy, $C_1$-$C_2$ alkoxy substituted with $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfinyl, $C_1$-$C_2$ haloalkylsulfinyl, $C_1$-$C_2$ alkylsulfonyl or $C_1$-$C_2$ haloalkylsulfonyl, $C_1$-$C_2$ alkylthio substituted by $C_1$-$C_2$ alkoxy, $C_1$-$C_2$ haloalkoxy, $C_1$-$C_2$ alkylthio or $C_1$-$C_2$ haloalkylthio, $C_1$-$C_3$ haloalkylthio, $C_1$-$C_3$ haloalkylsulfinyl or $C_1$-$C_3$ haloalkylsulfonyl.

15. Compounds of Preferred (14) wherein $R_2$ is $OCF_2H$, $OCH_2CF_3$, $OCH_2CH_2OCH_3$, $OCH_2CH_2OCH_2CH_3$, $OCH_2CH_2OCH_2CF_3$, $OCH_2CH_2OCF_2H$, $OCH_2CH_2SCH_3$, $OCH_2CH_2SCH_2CF_3$, $OCH_2CH_2S(O)CH_3$, $OCH_2CH_2S(O)CH_2CF_3$, $OCH_2CH_2SO_2CH_3$, $OCH_2CH_2SO_2CH_2CF_3$, $SCH_2CH_2OCH_3$, $SCH_2CH_2OCH_2CH_3$, $SCH_2CH_2OCH_2CF_3$, $SCH_2CH_2SCH_3$, $SCH_2CH_2SCH_2CF_3$, $SCF_2H$, $SCH_2CF_3$, $S(O)CH_2CF_3$ or $SO_2CH_2CF_3$.

16. Compounds of Formula I wherein $R_2$ is $C_1$-$C_3$ alkyl substituted with 1-3 atoms of F of Cl.

17. Compounds of Preferred (16) wherein $R_2$ is $CF_3$, $CF_2H$, $CFH_2$, $CCl_2H$ or $CH_2Cl$.

18. Compounds of Formula I wherein $R_2$ is $C_1$-$C_2$ alkyl, $C_1$-$C_2$ alkoxy, $C_1$-$C_3$ alkylthio, $C_1$-$C_3$ alkylsulfinyl, $C_1$-$C_3$ alkylsulfonyl, $CF_3$ or $NR_bR_c$.

19. Compounds of Preferred (18) wherein $R_2$ is $CH_3$, $CH_2CH_3$, $OCH_3$, $OCH_2CH_3$, $SCH_3$, $SCH_2CH_3$, $SCH(CH_3)_2$, $S(O)CH_3$, $S(O)CH_2CH_3$, $S(O)CH(CH_3)_2$, $SO_2CH_3$, $SO_2CH_2CH_3$, $SO_2CH(CH_3)_2$, $CF_3$, $NHCH_3$ or $N(CH_3)_2$.

20. Compounds of Formula I wherein $R_2$ is $C\equiv CH$.

Specifically preferred for its highest herbicidal activity, greatest plant growth regulant activity and/or most favorable ease of synthesis is: 2-[[[4-(difluoromethoxy)-6-methoxypyrimidin-2-yl]aminocarbonyl]aminosulfonyl]-4-ethoxybenzoic acid, methyl ester, m.p. 195°-196° C.

The invention also relates to agriculturally suitable compositions for controlling the growth of undesired vegetation comprising an effective amount of a compound recited above and at least one of the following: surfactant, solid or liquid diluent.

The invention also relates to a method for controlling the growth of undesired vegetation which comprises applying to the locus of the crop to be protected an effective amount of a compound of the invention.

DETAILED DESCRIPTION OF THE INVENTION

Synthesis

The compounds of Formula I can be prepared by one or more of the following methods described in Equations 1 to 3 and 14.

As shown in Equation 1, compounds of Formula I can be prepared by reacting an appropriately substituted sulfonyl isocyanate of Formula (1) with an appropriate amino or methylamino heterocycle of Formula (2). Y, R, $R_1$, and $R_2$ are as previously defined.

Equation 1

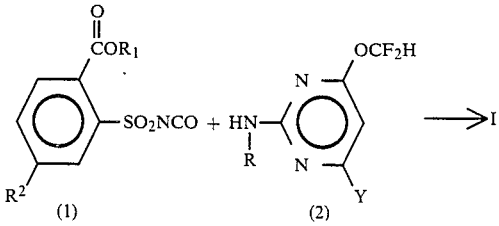

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane, and heptane, or by chromatography on silica gel.

Many of the compounds of Formula I can be prepared by the procedure shown in Equation 2, where Y, R, $R_1$, and $R_2$ are as previously defined.

Equation 2

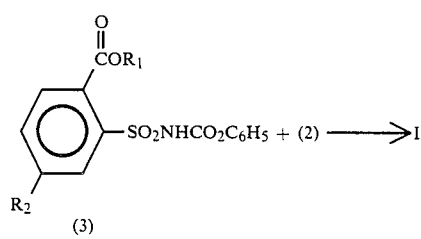

The reaction shown in Equation 2 is carried out by contacting phenyl carbamates of Formula (3) with aminoheterocycles of Formula (2) in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenyl carbamates of Formula (3) can be prepared by the methods described, or modifications thereof known to those skilled in the art, in European patent application 44,808, published Jan. 27, 1982; or South African patent application 82/5042.

Alternatively, many of the compounds of Formula I can be prepared by the method described in Equation 3, where Y, $R_1$, and $R_2$ are as previously defined and R is H.

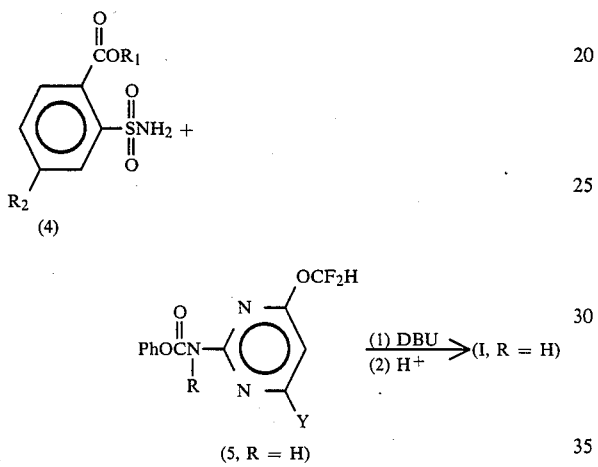

The reaction of Equation 3 can be carried out by contacting equimolar amounts of a sulfonamide of Formula (4) with a heterocyclic phenyl carbamate of Formula (5) in the presence of an equimolar amount of 1,8-diazabicyclo[5.4.0]undec-7-ene (DBU), by methods analogous to those described in South African patent application 83/0441. The phenyl carbamate of Formula (5) can be prepared by methods, or modifications thereof known to those skilled in the art, described in South African patent application 82/5671 and South African patent application 82/5045.

The unsubstituted and substituted alkoxy, allyloxy and propargyloxy benzenesulfonamide intermediates of Formula (4a) can be prepared by one or more of the following general methods.

As shown in Equation 4, one highly useful general route starts from the phenol (6).

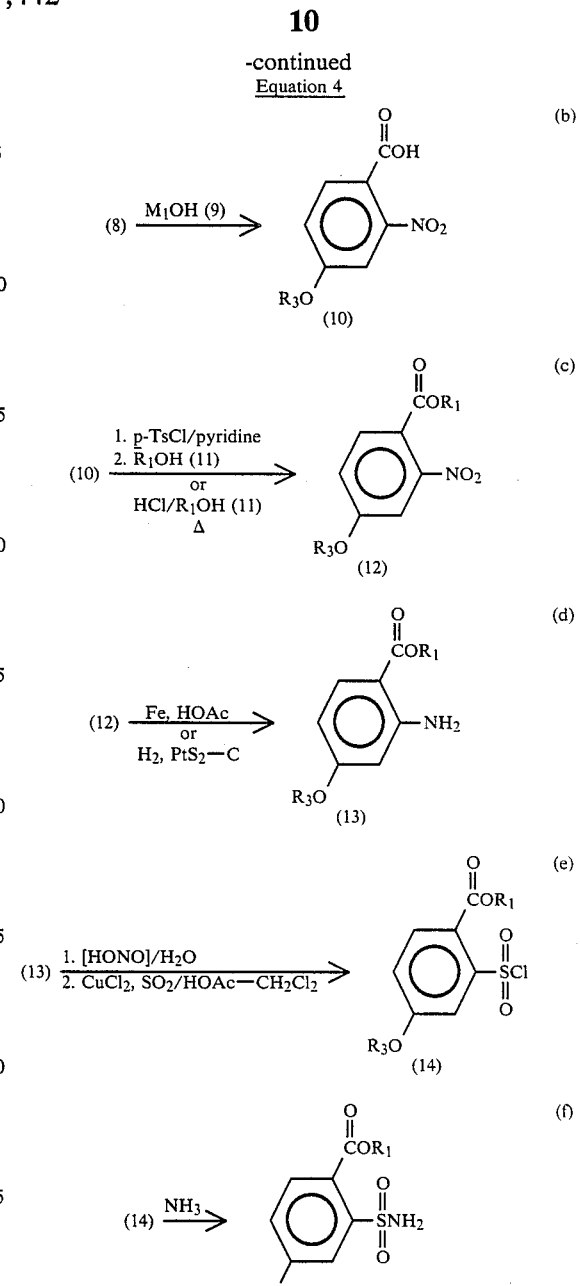

where $R_1$ is as previously defined, and $R_3$ is alkyl, haloalkyl, alkenyl, alkynyl, alkoxyalkyl, haloalkoxyalkyl, alkylthioalkyl, haloalkylthioalkyl, alkylsulfinylalkyl, haloalkylsulfinylalkyl, alkylsulfonylalkyl, haloalkylsulfonylalkyl, or cyanoalkyl. $M_1$ is Na or K. $X_1$ is Cl, Br, I,

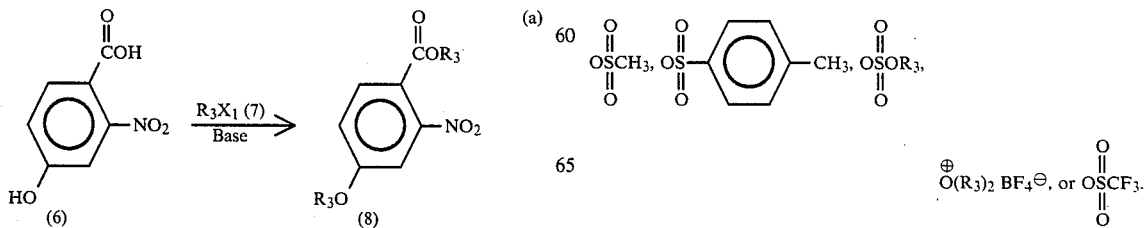

A solution or suspension of 4-hydroxy-2-nitrobenzoic acid (6) in a suitable polar aprotic solvent, such as dichloromethane or N,N-dimethylformamide (DMF), is treated with at least two equivalents of $R_2X_1$ (7) in the presence of at least two equivalents of a suitable base such as N,N-diisopropylethylamine or potassium carbonate and at a temperature between 20° and 155° C. for four to sixteen hours (Equation 4a). If the solvent is miscible with water, it is then evaporated, and the residue is taken up in dichloromethane. The product solution is washed with aqueous sodium or potassium carbonate solution and aqueous hydrochloric acid, and then is dried over a suitable desiccant such as magnesium sulfate. Filtration and evaporation of the solvent leaves (8) in semipurified form. It may be further purified through recrystallization or chromatography on a column of silica gel. The requisite alkylating, alkenylating, and alkynylating agents $R_3X_1$ (7) are either known or may be made by a wide variety of methods known in the art.

In cases where $R_3$ is not the same as $R_1$, the ester (8) is treated with at least one equivalent of sodium or potassium hydroxide in a mixture of water and a suitable organic cosolvent such as ethanol or p-dioxane at a temperature between 20° and 100° C. for four to sixteen hours (Equation 4b). The reaction mixture is then acidified with concentrated hydrochloric acid. If the product separates out in crystalline form, it is collected. Otherwise the aqueous solution is extracted with ether. The ether solution is dried over sodium sulfate and filtered, and the solvent is evaporated to afford the carboxylic acid (10).

To convert carboxylic acid (10) to ester (12), a solution of it in pyridine is treated sequentially with p-toluenesulfonyl chloride and $R_1OH$ (11) according to the general procedure of J. H. Brewster and C. J. Ciotti, Jr., *J. Am. Chem. Soc.* 1955, 77, 6214.

Alternatively, the carboxylic acid (10) may be converted to ester (12) through the use of excess $R_1OH$ (11) and a strong acid catalyst such as hydrogen chloride as reviewed by C. A. Buehler and D. E. Pearson, *Survey of Organic Syntheses*, Wiley-Interscience, New York, 1970, pp 802–807 (Equation 4c).

The nitrobenzene (12) is reduced to the aniline (13) either by use of iron in acetic acid as reviewed by C. A. Buehler and D. E. Pearson (ibid, pp 413–414) or by hydrogenation using platinum sulfide as catalyst and the conditions of F. S. Dovel and H. Greenfield, *J. Am. Chem. Soc.*, 87, 2767 (1965) (Equation 4d). When the other substituents present are not potentially susceptible to hydrogenation of hydrogenolysis, palladium may replace platinum sulfide as catalyst.

The aniline (13) is converted to the sulfonyl chloride (14) using the general procedures of H. Meerwein, G. Dittmar, R. Gollner, K. Hafner, F. Mensch, O. Steinfort, *Chem. Ber.*, 90, 841 (1957) (Equation 4e). To limit the hydrolysis of the product during the coupling step, the use of dichloromethane as a cosolvent is advantageous.

Finally, the sulfonyl chloride (14) is aminated to give (4a) using two equivalents of ammonia in dichloromethane solution at a temperature between −30° and −10° C. (Equation 4f).

Alternatively, many of the sulfonamides (4a) can be prepared via a route shown in Equation 5 starting from 2,4-dihydroxybenzoic acid (15).

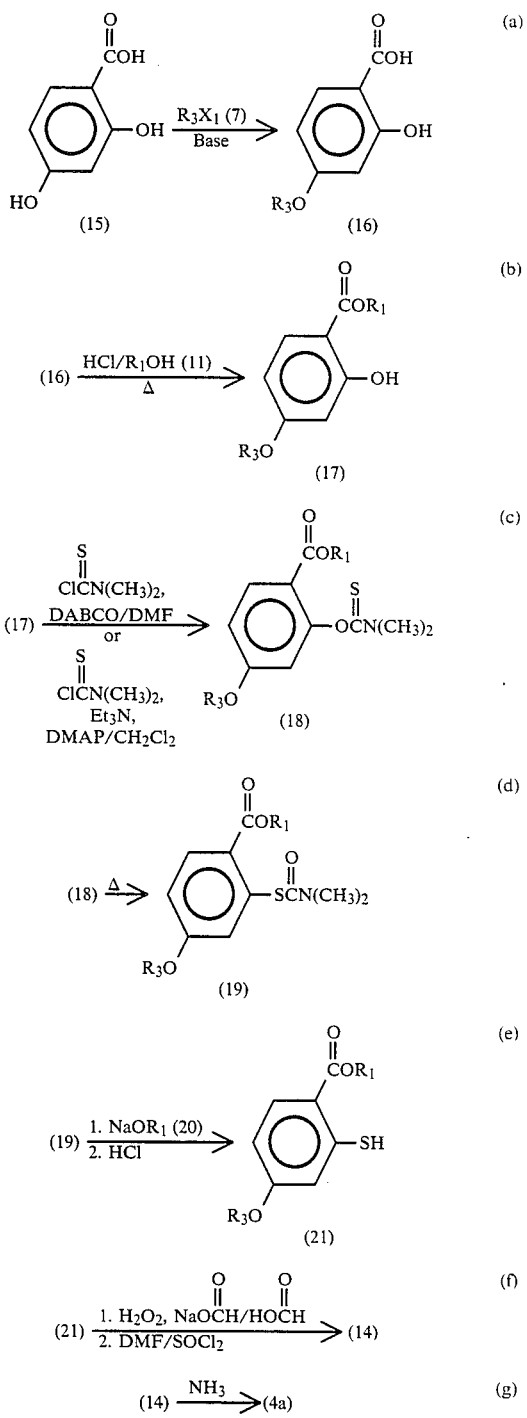

where $M_1$, $R_1$, and $X_1$ are as previously defined and $R_3$ is alkyl, haloalkyl, alkoxyalkyl, haloalkoxyalkyl, alkylsulfonylalkyl, haloalkylsulfonylalkyl, or benzyl.

Phenol (15) is added to a solution of two equivalents of sodium in anhydrous methanol, ethanol, or amyl alcohol. A little more than one equivalent of $R_3X_1$ (7) is added and the mixture is heated at reflux for 4 to 24 hours. The solvent is removed in vacuo and the residue is partitioned between 1N hydrochloric acid and ether. The ether phase is dried over sodium sulfate, and filtered. Evaporation of the ether leaves the phenol (16) (Equation 5a).

The carboxylic acid (16) is converted to ester (17) through the use of excess R₁OH and a strong acid catalyst such as hydrogen chloride as reviewed by C. A. Buehler and D. E. Pearson (op.cit., pp 802-807) (Equation 5b).

The phenol (17) is converted to the thiocarbamate (18) through the use of dimethylthiocarbamoyl chloride and 1,4-diazabicyclo[2.2.2]octane (DABCO) in N,N-dimethylformamide according to the general procedure of M. S. Newman and H. A. Karnes, *J. Org. Chem.* 1966, 31, 3980 (Equation 5c). Alternatively a mixture of the phenol (17), at least one equivalent of dimethylthiocarbamoyl chloride, at least one equivalent of triethylamine (Et₃N), and a catalytic amount of 4-dimethylaminopyridine (DMAP) in dichloromethane is heated at reflux for one to seven days. The reaction mixture is washed with 1N hydrochloric acid and 10% aqueous sodium hydroxide solution, then dried over magnesium sulfate and filtered. Evaporation of the solvent leaves crude (18) which may be purified by chromatography on silica gel or by recrystallization if it is crystalline.

The thiocarbamate (18) is converted to its isomer (19) by heating according to the general procedure of M. S. Newman and H. A. Karnes (op.cit.) (Equation 5d).

To a solution of (19) in anhydrous R₁OH (11) is added little more than one equivalent of NaOR₁ (20). The mixture is heated at 60°-70° C. for 0.5-1 hour. The solvent is removed in vacuo, and the residue is partitioned between dichloromethane and water. The aqueous phase is washed with dichloromethane, acidified with 12N hydrochloric acid, and extracted with dichloromethane. The dichloromethane extracts are dried over sodium sulfate and filtered. Evaporation of the solvent leaves thiol (21) (Equation 5e).

To a mixture of the thiol (21) and at least one equivalent of sodium formate in formic acid is added at least three equivalents of hydrogen peroxide at such a rate as to keep the temperature between 40° and 50° C. The reaction mixture is then heated at 45°-55° C. for 1 to 5 hours. The excess peroxide is destroyed with sodium sulfite, and the solvent is evaporated. The residue is added to excess thionyl chloride, and a catalytic amount of N,N-dimethylformamide (DMF) is added. The mixture is heated at reflux for 8 to 24 hours, and then the solvent is evaporated. The residue is partitioned between water and ether. The ether solution is washed with aqueous sodium bicarbonate solution, dried over magnesium sulfate and filtered. Evaporation of the solvent leaves the sulfonyl chloride (14) (Equation 5f).

Finally the sulfonyl chloride (14) is aminated giving the sulfonamide (4a) as already described for Equation 4f (Equation 5g).

Most of the sulfonamides (4a) can be prepared via the route shown in Equation 6 starting from 6-hydroxysaccharin (22).

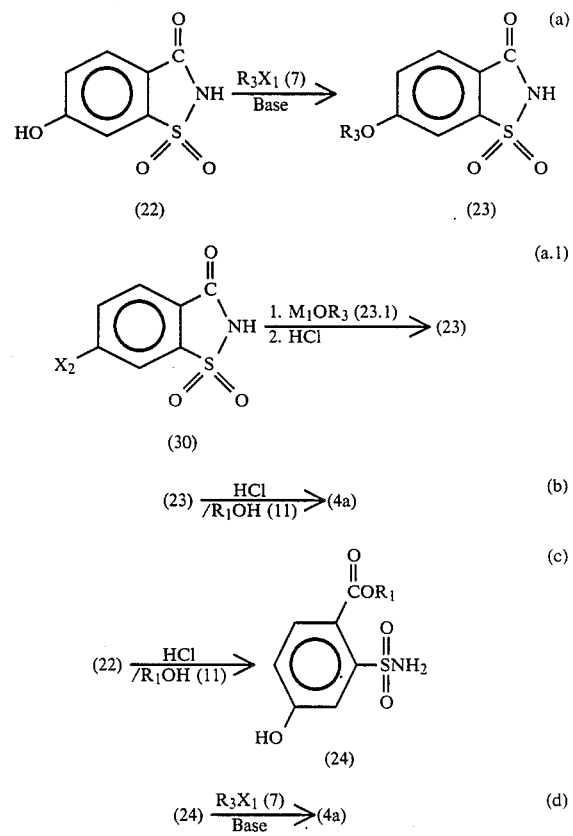

Equation 6 where M₁, R₁, and X₁ are as previously defined, X₂ is F, Cl, Br or I, and R₃ is alkyl, haloalkyl, alkenyl, alkynyl, alkoxyalkyl, haloalkoxyalkyl, alkylthioalkyl, haloalkylthioalkyl, alkylsulfinylalkyl, haloalkylsulfinylalkyl, alkylsulfonylalkyl, haloalkylsulfonylalkyl, or aminoalkyl.

6-Hydroxysaccharin (22) can be prepared as described by C. Finzi and M. Colonna, *Atti. accad. Lincei, Classe, sci, fis., mat. mat.*, 1937, 26, 19 (*Chem. Abst.* 1938, 32, 3762). Alternatively, (4a), where R₁=CH₃, R₃=C₆H₅CH₂ may be prepared via the route described by Equation 5. A solution of this sulfonamide in dichloromethane is treated with one equivalent of 1,8-diazabicyclo[5.4.0]undec-7-ene (DBU). The solvent is evaporated, and the residue is dissolved in minimal water and acidified with concentrated hydrochloric acid to precipitate 6-benzyloxysaccharin. This is dissolved in ethanol containing palladium catalyst. The mixture is hydrogenated at 20°-40° C. and 1-10 psi until hydrogen uptake ceases. Filtration and evaporation of the solvent affords 6-hydroxysaccharin (22).

In the method described by Equation 6a, 6-hydroxysaccharin (22) is added to a solution of two equivalents sodium in anhydrous methanol, ethanol, or amyl alcohol. A little more than one equivalent of R₃X₁ (7) is added and the mixture is heated at reflux for 4 to 24 hours. The solvent is removed in vacuo and the residue is dissolved in minimal water. It is acidified with concentrated hydrochloric acid. If the product crystallizes, it is collected, washed with dilute hydrochloric acid, and dried. If it does not crystallize, the aqueous mixture is extracted with dichloromethane. The dichloromethane phase is dried over sodium sulfate and filtered.

Evaporation of the solvent leaves the saccharin (23) (Equation 6a).

Alternatively, in many cases the saccharin (23) may be prepared by treating a halosaccharin (30) in a polar aprotic solvent such as N,N-dimethylformamide at 20° to 150° C. (90° C. is typical) with at least two equivalents of the corresponding alkoxide of Formula (23.1) until the reaction is done (typically 18 hours). The reaction is worked up by evaporation of the solvent. The residue is dissolved in minimal water and acidified with concentrated hydrochloric acid. If the saccharin (23) crystallizes, it is filtered. Otherwise the aqueous solution is extracted with dichloromethane, and evaporation of the solvent leaves the saccharin (23) (Equation 6a.1).

A solution or suspension of the saccharin (23) in $R_1OH$ (11) is saturated with hydrogen chloride. The mixture is heated at 65°–80° C. for 1–6 hours. The solvent and hydrogen chloride are evaporated. The residue is dissolved in dichloromethane, washed with aqueous sodium bicarbonate solution, dried over sodium sulfate, and filtered. Evaporation of the solvent affords the sulfonamide (4a) (Equation 6b).

Alternatively, saccharin (22) may be opened to the sulfonamide (24) using the conditions already described for the conversion of (23) to (4a) in Equation 6b (Equation 6c). To a solution of the sulfonamide (24) in anhydrous methanol, ethanol, amyl alcohol, or a suitable aprotic solvent such as N,N-dimethylformamide is added one equivalent of sodium or potassium methoxide, ethoxide, or tert-butoxide followed by the alkylating agent $R_3X_1$ (7). The mixture is held at 20°–80° C. for 1–8 hours. The solvent is removed in vacuo, and the residue is dissolved in dichloromethane, washed with aqueous sodium bicarbonate solution, dried over $Na_2SO_4$, and filtered. Evaporation of the solvent affords the sulfonamide (4a) (Equation 6d).

Sulfonamides of Formula (4b) can be prepared by the method shown in Equation 7.

Equation 7

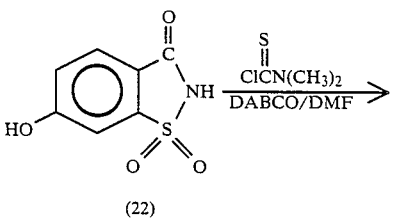

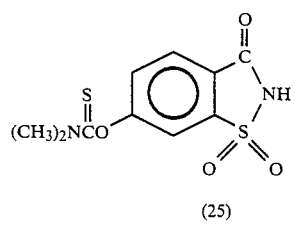

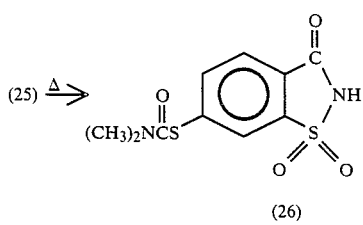

-continued
Equation 7

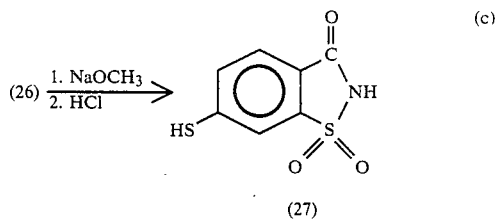

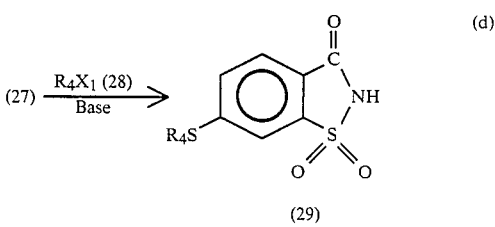

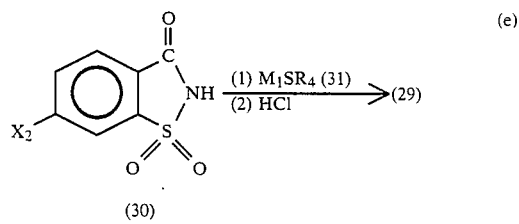

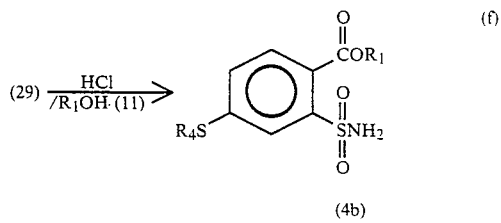

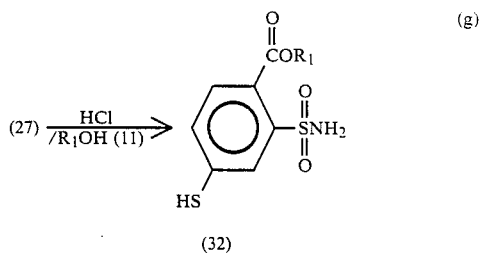

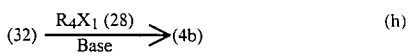

where $M_1$, $R_1$ and $X_1$ are as previously defined, $X_2$ is F, Cl, Br or I, and $R_4$ is alkyl, alkenyl, alkynyl, alkoxyalkyl, haloalkoxyalkyl, alkylthioalkyl, or haloalkylthioalkyl.

The hydroxysaccharin (22) is converted to the thiocarbamate (25) through the use of dimethylthiocarbamoyl chloride and 1,4-diazabicyclo[2.2.2]octane (DABCO) in N,N-dimethylformamide according to the general procedure, or modifications thereof known to those skilled in the art, of M. S. Newman and H. A. Karnes (op.cit.) (Equation 7a).

The thiocarbamate (25) is converted to its isomer (26) by heating according to the general procedure, or modifications thereof known to those skilled in the art, of M. S. Newman and H. A. Karnes (ibid.) (Equation 7b).

To a solution of (26) in anhydrous methanol is added a little more than two equivalents of sodium methoxide. The mixture is heated at 60°-70° C. for 0.5-1 hour. The solvent is removed in vacuo, and the residue is partitioned between dichloromethane and water. The aqueous phase is washed with dichloromethane and acidified with concentrated hydrochloric acid. If the saccharin (27) crystallizes, it is collected, rinsed with dilute cold hydrochloric acid, and dried. If it does not crystallize, the aqueous phase is extracted with dichloromethane. The dichloromethane extracts are dried over sodium sulfate and filtered. Evaporation of the solvent leaves saccharin (27) (Equation 7c).

The mercaptan (27) is added to a solution of two equivalents sodium in anhydrous methanol, ethanol, or amyl alcohol. A little more than one equivalent of $R_4X_1$ (28) is added, and the mixture is heated at reflux for 1 to 8 hours. The requisite alkylating, alkenylating, and alkynylating agents $R_4X_1$ (28) are either known in the art or may be made by a wide variety of methods known in the art.

The solvent is removed in vacuo, and the residue is dissolved in minimal water. It is acidified with concentrated hydrochloric acid. If the saccharin (29) crystallizes, it is collected, washed with cold dilute hydrochloric acid, and dried. If it does not crystallize, the aqueous mixture is extracted with dichloromethane. The dichloromethane phase is dried over sodium sulfate and filtered. Evaporation of the solvent leaves the saccharin (29) (Equation 7d).

Alternatively, in many cases, the saccharin (29) may be prepared by treating a halosaccharin (30) in a polar aprotic solvent such as N,N-dimethylformamide at 20°-100° C. with at least two equivalents of the corresponding thiolate of Formula (31) for 1-24 hours. The reaction is worked up by evaporation of the solvent. The residue is dissolved in minimal water and acidified with concentrated hydrochloric acid. If the saccharin (29) crystallizes, it is filtered. Otherwise the aqueous solution is extracted with dichloromethane, and evaporation of the solvent leaves the saccharin (29) (Equation 7e).

The requisite precursor halosaccharins of Formula (30) may be prepared by conversion of the corresponding 4-halo-2-nitrobenzoic acids to esters of 2-(amino-sulfonyl)-4-halobenzoic acids by use of methods analogous to those described for Equation 4. These esters are closed to the corresponding saccharins of Formula (30) by treatment with DBU according to the general method already described for the preparation of 6-benzyloxysaccharin.

The saccharin (29) is then opened to the sulfonamide (4b) using the conditions already described for the conversion of (23) to (4a) in Equation 6b (Equation 7f).

Alternatively, saccharin (27) may be opened to the sulfonamide (32) using the conditions already described for the conversion of (23) to (4a) in Equation 6b (Equation 7g). The thiol (32) is then converted to (4b) using the method already described for the conversion of (24) to (4a) in Equation 6d (Equation 7h).

Sulfonamides of Formula (4c) can be prepared by the method shown in Equation 8.

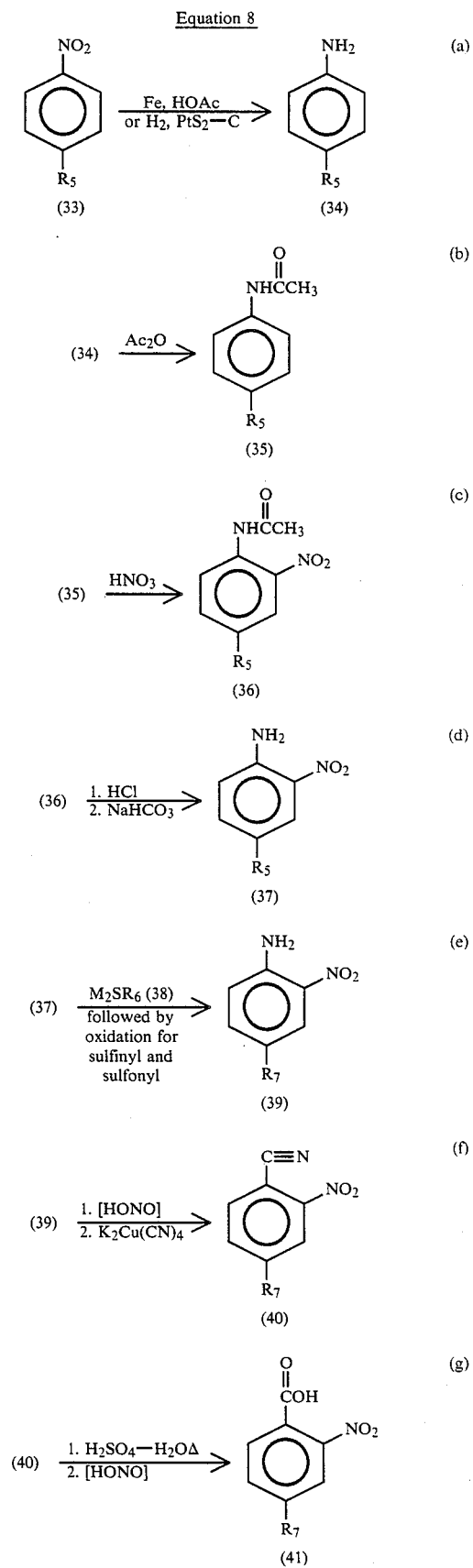

-continued
Equation 8

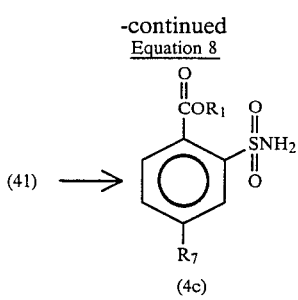

(4c)

where $R_1$ is as previously defined; $R_5$ is alkyl, cyclopropyl, haloalkyl, alkoxyalkyl, haloalkoxyalkyl, alkylsulfonylalkyl, haloalkylsulfonylalkyl, haloalkoxy, alkenyl or alkynyl; $R_6$ is alkyl or haloalkyl; and $R_7$ is alkyl, cyclopropyl, haloalkyl, alkoxyalkyl, haloalkoxyalkyl, alkylthioalkyl, haloalkylthioalkyl, alkylsulfinylalkyl, haloalkylsulfinylalkyl, alkylsulfonylalkyl, haloalkylsulfonylalkyl, haloalkoxy, alkenyl or alkynyl. $M_2$ is Na or K.

The starting nitrobenzenes (33) are either known in the art or may be made by a wide variety of methods known in the art. Some of these methods include the nitration (for a review, see G. Lehmann. H. Eichmann "Formation of Carbon-Nitrogen Bonds" in *Preparative Organic Chemistry*, G. Hilgetag, A. Martini ed., Wiley-Interscience, New York, 1972) of the coupling product obtained from reaction of the appropriate halide with diphenylcuprate (for a review, see G. H. Posner "Substitution Reactions Using Organo-copper Reagents" in *Organic Reactions*, Vol. 22, W. G. Dauben ed., Wiley, New York, 1975).

Another method is the Friedel-Crafts acylation of benzene with the appropriate acid halide or anhydride (for a review, see G. A. Olah, *Friedel-Crafts and Related Reactions*, Volumes I-IV, Wiley-Interscience, New York, 1963-1965), followed by reductive removal of the carbonyl oxidation (for a review, see C. Bischoff, P.-G. Dietrich, E. Höft, D. Murowski, "Formation of Carbon-Hydrogen Bonds" in *Preparative Organic Chemistry*, G. Hilgetag, A. Martini ed., Wiley-Interscience, New York, 1972) and then nitration.

Still another method involves conversion of the appropriate 4-nitrobenzyl alcohols, aldehydes, or ketones to their mono or difluoro alkyl homologues using the conditions reviewed by G. A. Boswell, Jr., W. C. Ripka, R. M. Scribner, C. W. Tullock, "Fluorination by Sulfur Tetrafluoride" and C. M. Sharts, W. A. Sheppard "Modern Methods to Prepare Monofluoroaliphatic Compounds" in *Organic Reactions*, Vol. 21, W. G. Dauben ed., Wiley, New York, 1974).

The nitrobenzene (33) is reduced to the aniline (34) using the conditions already described for the conversion of (12) to (13) in Equation 4d (Equation 8a).

The aniline (34) in a suitable solvent such as benzene is treated with at least one equivalent of acetic anhydride and heated at reflux for 8-24 hours. The reaction mixture is cooled, and if the acetanilide (35) crystallizes, it is collected and dried. If it does not crystallize, the benzene solution is washed with 1N hydrochloric acid and aqueous sodium bicarbonate solution, dried over magnesium sulfate, and filtered. Evaporation of the solvent leaves the acetanilide (35) (Equation 8b).

The acetanilide (35) is then nitrated using the general conditions reviewed by G. Lehmann and H. Teichmann (op.cit.) to give nitroacetanilide (36) (Equation 8c).

A slurry of acetanilie (36) in 1N hydrochloric acid is heated at reflux until all of the solid dissolves. The solution is then made slightly basic with sodium bicarbonate and is extracted with dichloromethane. The dichloromethane extracts are dried over sodium sulfate and filtered. Evaporation of the solvent leaves the aniline (37) (Equation 8d).

As the nitric acid used in the reaction depicted by Equation 8c can act as an oxidizing agent, substituent $R_5$ of aniline (37) cannot contain an alkylthio, haloalkylthio, alkylsulfinyl, or haloalkylsulfinyl group. But $R_5$ can be all of the other substituents allowed for $R_7$ that do not contain an alkylthio, haloalkylthio, alkylsulfinyl, or haloalkylsulfinyl group. In these cases the reaction depicted by Equation 8e is skipped, and aniline (39) used in Equation 8f is prepared as aniline (37).

On the other hand in those cases where $R_7$ does contain an alkylthio, haloalkylthio, alkylsulfinyl, or haloalkylsulfinyl group, the alkylthio-, haloalkylthio-, alkylsulfinyl-, or haloalkylsulfinyl-containing aniline (39) is prepared from a homologous aniline (37) having a $R_5$ substituent containing a displaceable halogen atom at the position where the lower valent sulfur-containing group is to be placed. To effect the displacement of the halogen by an alkylthio or haloalkylthi group, a solution of halide (35) in a suitable solvent such as N,N-dimethylformamide is treated with a little more than one equivalent of the appropriate sodium or potassium alkylthiolate or haloalkylthiolate (38). The mixture is held at 20°-100° C. for 1-8 hours. The solvent is then evaporated, and the residue is partitioned between water and dichloromethane. The dichloromethane solution is dried over sodium sulfate and filtered. Evaporation leaves the alkylthio or haloalkylthio compound (39) respectively.

When the appropriate haloalkylthiolate reagent (38) is unstable to self-condensation, the corresponding hydroxy-, carbonyl-, and/or carboxy-containing alkylthiolate reagent can be used. After formation of the thioether bridge, these oxygen-containing groups can be converted to the desired halogen substitution pattern by use of a wide variety of methods known in the art.

Anilines of Formula (39) where $R_7$ contains an alkylsulfinyl, haloalkylsulfinyl, alkylsulfonyl, or haloalkylsulfonyl group can be prepared by oxidation of the corresponding alkylthio- or haloalkylthio-containing anilines using methods analogous to those described for the conversion of (4b) to (4d) in Equation 9 (Equation 8e).

The aniline (39) is then diazotized and subjected to the Sandmeyer reaction according to the general experimental procedure of G. T. Morgan and E. A. Coulson, *J. Chem. Soc.* 1929, 2551 to give nitrile (40) (Equation 8f).

A suspension of the nitrile (40) in 75-80% aqueous sulfuric acid is heated at 95°-100° C. for 2-5 hours. Then over 1-2 hours and at a temperature of 80°-100° C. 1.5-2.5 equivalents of sodium nitrite is added in small portions. The heating is continued 0.5-1 hour longer, then the mixture is cooled and poured onto excess ice. If the carboxylic acid (41) crystallizes, it is collected, rinsed with ice water and dried. If it does not crystallize, the aqueous mixture is extracted with dichloromethane. The dichloromethane solution is extracted with aqueous 10% sodium carbonate solution. The aqueous extract is made acidic with concentrated hydrochloric acid. If the carboxylic acid (41) then crystallizes, it is collected, rinsed with ice water and dried. If it does not crystallize, the aqueous solution is extracted with ether. The ether extracts are dried over magnesium sulfate and filtered. Evaporation of the solvent leaves carboxylic acid (41) (Equation 8g).

By use of the methods previously described, carboxylic acid (41) can be converted to sulfonamide (4c) (Equation 8h).

Sulfonamides of Formula (4c) where $R_7$ is alkyl substituted with an alkylsulfinyl, haloalkylsulfinyl, alkylsulfonyl, or haloalkylsulfonyl group can be prepared by peracid oxidation of the corresponding sulfonamides of Formula (4c) where $R_7$ is alkyl substituted with an alkylthio or haloalkylthio group using methods analogous to those described for the preparation of sulfinyl sulfonamides of Formula (4d, n=1) and sulfonyl sulfonamides of Formula (4d, n=2) in Equation 9 (vide infra).

The sulfinyl sulfonamides of Formula (4d, n=1) and sulfonyl sulfonamides of Formula (4d, n=2) can be be prepared from the corresponding thio sulfonamides of Formula (4b) as shown in Equation 9.

Equation 9

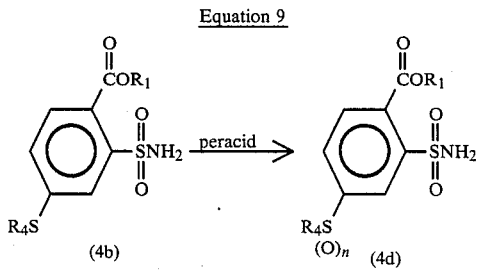

where $R_1$ and $R_4$ are as previously defined and n is 1 or 2.

To prepare the sulfinyl sulfonamides of Formula (4d, n=1) a solution of one equivalent of a peracid, such as 3-chloroperoxybenzoic acid, in an inert solvent, such as dichloromethane, is added to a stirred solution of the appropriate thio sulfonamide (4b) in an inert solvent, such as a mixture of dichloromethane and tetrahydrofuran, at 0°-5° C. The mixture is then warmed to 20°-40° C. When thin layer chromatography has revealed the sulfonamide (4b) to have been oxidized, the mixture is washed in turn with 5% aqueous sodium sulfite solution, saturated aqueous sodium bicarbonate solution, water, and brine, and then dried ($MgSO_4$). Evaporation of the solvent then leaves the sulfinyl sulfonamide of Formula (4d, n=1).

To prepare sulfonyl sulfonamide of Formula (4d, n=2) a solution of more than two equivalents (only two equivalents when $R_4$ is alkenyl or alkynyl) of a peracid, such as 3-chloroperoxybenzoic acid, in an inert solvent, such as 1,2-dichloroethane, is added to a stirred mixture of the appropriate thio sulfonamide (4b) in an inert solvent, such as 1,2-dichloroethane, containing 1-5 mol % of a free radical inhibitor, such as 4,4-thiobis(6-tert-butyl-m-cresol). The mixture is heated to 50°-80° C. When thin layer chromatography shows the thio sulfonamide (4b) and intermediate sulfinyl sulfonamide (4d, n=1) to have been consumed, the mixture is cooled and diluted with tetrahydrofuran to maintain sulfonamide solubility. Using the same work up method as already described for the preparation of sulfinyl sulfonamides (4d, n=1), one obtains the sulfonyl sulfonamides of Formula (4d, n=2).

The amino sulfonamides of Formula (4e) are prepared as shown in Equation 9.1 and discussed below.

Equation 9.1

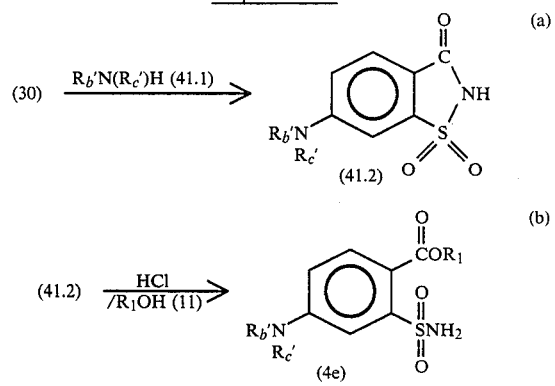

where $R_1$ and $X_2$ are as previously defined, $R_b'$ is H or alkyl, and $R_c'$ is H, alkyl, or haloalkyl.

In most cases the amino saccharins of Formula (41.2) are prepared by treating halo saccharins of Formula (30) with one or more equivalents of the corresponding amine derivatives of Formula (41.1) using one or more of a wide variety of experimental conditions known in the art. In some cases the reaction can be run using an excess of the amine derivative (41.1) as the only solvent and heating the mixture to 30°-200° C. at atmospheric pressure or, if the boiling point of the amine derivative makes necessary, at above atmospheric pressure. In other cases the use of a polar inert solvent such as N,N-dimethylformamide is advantageous. When the amine derivative is itself difficult or expensive to prepare, the amount of it used can be reduced to little more than one equivalent if at least one equivalent of another base such as triethylamine, N,N-diisopropyl-N-ethylamine, diazabicyclo[5.4.0]undec-7-ene, sodium hydride, or n-butyllithium is added to the reaction mixture. Besides reducing the amount of amine derivative needed, the use of at least two equivalents of very strong bases, such as n-butyllithium or sodium hydride, capable of deprotonating the amine derivative can accelerate the rate of the displacement reaction and allow it to proceed at lower temperatures as is well known in the art. The requisite amine derivatives (41.1) are either known or can be made by methods known in the art.

After the displacement reaction is complete the solvent and excess of any volatile amine derivative (41.1) is evaporated and the residue is dissolved in 5% aqueous sodium hydroxide solution. Concentrated hydrochloric acid is added until the pH is 7. If the saccharin (41.2) crystallizes, it is filtered. Otherwise the aqueous solution is saturated with salt and then extracted with dichloromethane, and in most cases evaporation of the dichloromethane leaves the saccharin (41.2). If it does not, the aqueous solution is evaporated to dryness and the residue is continuously extracted with tetrahydrofuran. Evaporation of the solvent then leaves the saccharin (41.2) (Equation 9.1a).

In some cases saccharins of Formula (41.2) may be prepared from saccharins of Formula (41.2) having fewer substituents on the amino group. A variety of methods are well-known in the art for the alkylation of aniline amino groups and their derivatives.

To prepare the sulfonamide of Formula (4e) a solution or suspension of the saccharin (41.2) in the appropriate alcohol $R_1OH$ (11) is saturated with hydrogen chloride. The mixture is heated at 65°-80° C. for 1-12 hours. The solvent and hydrogen chloride are evaporated. The residue is dissolved in a mixture of brine and 5:1 (vol.) dichloromethane-tetrahydrofuran. Sodium carbonate is added to the vigorously stirred mixture until it is made basic. The dichloromethane-tetrahydrofuran phase is then separated, and evaporation of the solvent leaves the sulfonamide of Formula (4e) (Equation 9.1b).

Sulfonyl isocyanates (1) are prepared from the corresponding sulfonamides (4) with compatible $R_2$ substituents by one of the following two general methods.

Equation 10

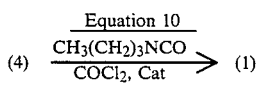

where $R_1$ and $R_2$ are as previously defined.

The sulfonamide (4) and an alkyl isocyanate (e.g. n-butyl isocyanate) in xylene or other solvent boiling above 135° C. are mixed in the presence or absence of a catalytic amount of 1,4-diaza[2.2.2]bicyclooctane (DABCO) and heated to 135°–140° C. After 5–60 minutes phosgene is slowly added to the heated mixture at such a rate that the temperature remains between 133°–135° C. When the consumption of phosgene has ceased, the mixture is cooled and filtered to remove insoluble material. Finally, the solvent, alkyl isocyanate, and excess phosgene are evaporated, leaving the sulfonyl isocyanate (1).

If desired, the alkyl isocyanate-sulfonamide adduct can be made and isolated before reaction with the phosgene. In this case, the sulfonamide (4), alkyl isocyanate, and anhydrous base (e.g., $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (4) is high melting and has low solubility in the phosgenation solvent.

Sulfonyl isocyanates (1) can also be prepared by the following method.

Equation 11

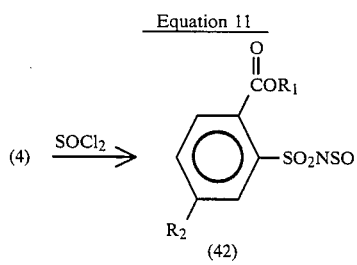

where $R_1$ and $R_2$ are as previously defined and (4) is (4a), (4b), (4c) or (4d).

The sulfonamide (4) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (42) (Equation 11a).

The thionyl chloride is evaporated and the residue is treated with an inert solvent (e.g. toluene) containing at least one equivalent (typically 2–3 equivalents) of phosgene. A catalytic amount of pyridine (typically 0.1 equivalent) is added, and the mixture is heated to about 60°–140° C. with 80°–100° preferred. Conversion to the isocyanate (1) is usually substantially complete within 15 minutes to 3 hours (Equation 11b). The mixture is then cooled and filtered, and the solvent is evaporated, leaving the sulfonyl isocyanate (1).

The heterocyclic amines of Formula (2a) to (2c) below are taught in U.S. Pat. No. 4,478,635.

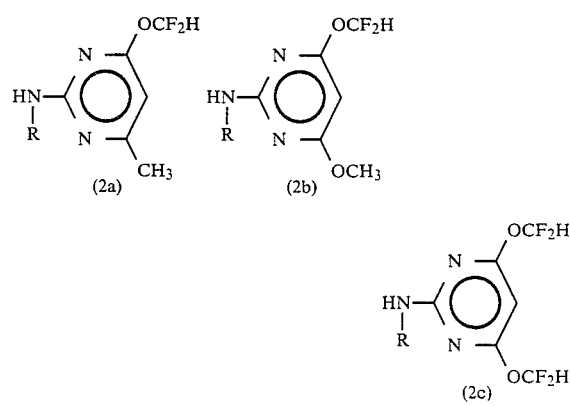

In some cases, heterocycles of Formula (2) may be more easily prepared with R being H than with R being $CH_3$. Many heterocycles (2, R=$CH_3$) can be prepared from the corresponding heterocycles (2, R=H) by one or more of the following two methods.

Equation 12

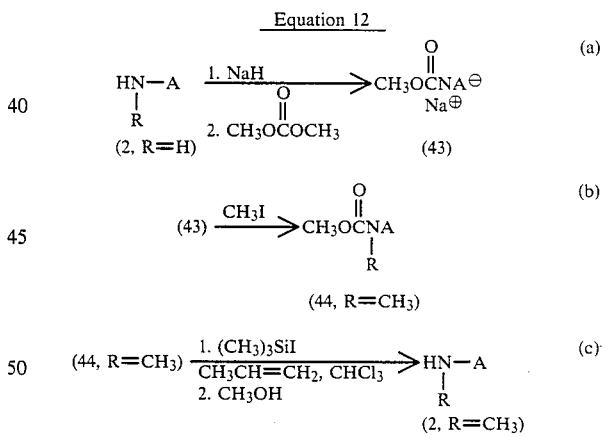

where A is

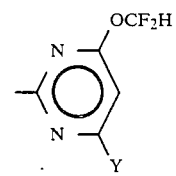

and Y is as previously defined.

In this method, a solution or slurry of the appropriate heterocycle (2, R=H) in a suitable aprotic solvent (e.g., tetrahydrofuan, dioxane, glyme) at 0°–30° C. is treated with two equivalents of sodium hydride. After gas evolution ceases, the reaction mixture is treated with one equivalent of dimethyl carbonate and stirred at 20°-30° C. for 8 to 24 hours to provide a suspension of the sodium salt (43) (Equation 12a).

The reaction mixture containing (43) is treated with at least two equivalents of iodomethane and then heated at 60°-80° C. for 8 to 24 hours. The mixture is cooled and filtered, and the solvent is evaporated. The residue is taken up in dichloromethane, washed with water, and the solvent is evaporated, leaving the N-methyl carbamate (44, R=CH$_3$) (Equation 12b).

The carbamate (44, R=CH$_3$) is dissolved in anhydrous, alcohol-free chloroform saturated with propylene gas. Slightly more than one equivalent (typically 1.1-1.2 equivalents) of iodotrimethylsilane) is added and the stirred solution is heated at 50°-60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice water. If a precipitate forms, it is filtered out, rinsed with ice water and dried to provide (2, R=CH$_3$). If no precipitate forms, the solution is saturated with sodium chloride and extracted with ethyl acetate. Evaporation of the solvent leaves heterocycle (2, R=CH$_3$) (Equation 12c).

Alternatively, the following two-step procedure is useful in many cases.

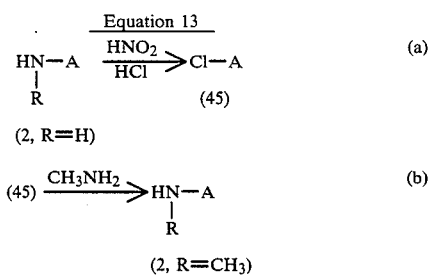

where A is as previously defined.

A solution of the amine (2, R=H) in concentrated hydrochloric acid is treated with sodium nitrite solution and the chloro compound (45) is isolated in the usual manner by filtration of the acidic solution (Equation 13a). A representative procedure is described by Bee and Rose in *J. Chem. Soc. C.* 1966, 2031.

The heterocycle (45) is then treated with at least two equivalents of methylamine in a suitable inert solvent (e.g. tetrahydrofuran, glyme, or diglyme) at a temperature between 20° and 80° C. for 1-18 hours (Equation 13b). The reaction mixture is then cooled and filtered. Evaporation of the solvent leaves (2, R=CH$_3$) contaminated with a little CH$_3$NH$_3$+Cl$^-$ salt. The product may be purified by trituration with ice water or by dissolution in dichloromethane, followed by washing with a small amount of water, drying, and evaporation of solvent. Further purification may be accomplished by recrystallization or column chromatography on silica gel.

As an alternative to the methods already described in which the sulfonamides of Formulae (4a), (4b), (4d), and (4e) are fully elaborated prior to construction of the urea bridge of compounds of Formula I, many compounds of Formula Ia may be prepared by the method described in Equation 14.

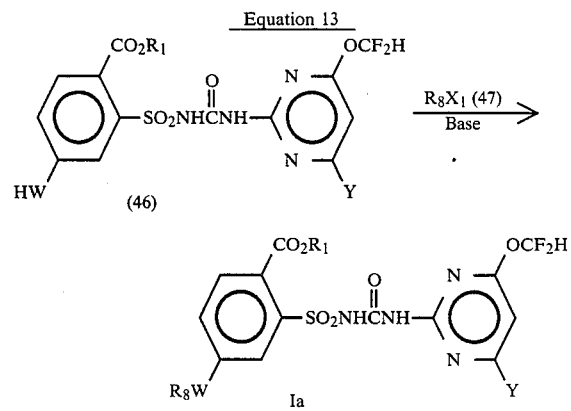

where R$_1$, X$_1$ and Y are as previously defined, W is O, NR$_b$' or S, and R$_8$ is alkyl, haloalkyl, alkenyl, alkynyl, alkoxyalkyl, haloalkoxyalkyl, alkylthioalkyl, haloalkylthioalkyl, alkylsulfinylalkyl, haloalkylsulfinylalkyl, alkylsulfonylalkyl, haloalkylsulfonylalkyl, or cyanoalkyl when W is O; R$_8$ is alkyl, haloalkyl, alkenyl, alkynyl, alkoxyalkyl, haloalkoxyalkyl, alkylthioalkyl, haloalkylthioalkyl, or cyanoalkyl when W is S; and R$_8$ is alkyl or haloalkyl when W is NR$_b$' (R$_b$' is as previously defined).

In this method a solution of the appropriate compound of Formula (46) in a polar solvent such as a mixture of acetonitrile and N,N-dimethylformamide is treated with two equivalents of a strong base such as sodium methoxide or sodium hydride with catalytic methanol followed by a little more than one equivalent of the appropriate alkylating, alkenylating, or alkynylating agent (47). The mixture is held at 20°-60° C. for 2-24 hours. Then the mixture is poured into excess hydrochloric acid. If the compound of Formula Ia crystallizes, it is filtered. Otherwise the aqueous mixture is extracted with dichloromethane, and evaporation of the solvent leaves the compound of Formula Ia. The compounds of Formula (46) are in turn prepared by coupling the appropriate sulfonamides of Formulae (24) (W=O), (32) (W=S), or (4e) (R$_c$'=H) (W=NR$_b$') with the appropriate heterocyclic phenyl carbamates of Formula (5,R=H) according to the general method described for Equation 3.

Many of the compounds of Formula Ia where R$_8$ is alkyl, haloalkyl, alkenyl, alkynyl, alkoxyalkyl, haloalkoxyalkyl, or cyanoalkyl and W is S(O) or S(O)$_2$ can be made by oxidation of the corresponding compounds of Formula Ia where W is S using methods similar to those already described for the conversion of (4b) to (4d) in Equation 9.

The following examples further illustrate the synthesis of this invention.

EXAMPLE 1

Methyl 4-ethoxy-2-hydroxybenzoate

Hydrogen chloride was bubbled into a stirred solution of 4-ethoxy-2-hydroxybenzoic acid (101.0 g, 0.554 mol) in methanol (2000 mL) until the solution was saturated. The solution was heated under reflux for 3 days and then cooled to 15° C. This caused the product to crystallize out. The crystals were collected, rinsed with methanol and hexanes, and dried. Methyl 4-ethoxy-2-hydroxybenzoate was obtained as a pale amber solid (49.3 g) melting at 77°-78° C.

PMR (CDCl$_3$, 90 MHz): δ11.90 (slightly broadened s, 1H, OH); 7.76 (d, 1H, H ortho to CO$_2$CH$_3$): 6.35-6.55 (m, 2H, other aryl H's): 4.06 (q, 2H, OC$\underline{H}_2$CH$_3$); 3.89 (s, 3H, OCH$_3$): 1.41 (t, 3H, OCH$_2$C$\underline{H}_3$). IR (Nujol); 3130 (broad, w, OH): 1668 (s, C=O) cm$^{-1}$. More product was obtained by reworking the mother liquor.

EXAMPLE 2

Methyl 2-[(dimethylamino)thioxomethoxy]-4-ethoxybenzoate

Triethylamine (76.6 mL, 0.550 mol) was added via syringe to a stirred solution of methyl 4-ethoxy-2-hydroxybenzoate (49.3 g, 0.251 mol), 4-dimethylaminopyridine (3.06 g, 0.025 mol), and dimethylthiocarbamoyl chloride (54.4 g, 0.440 mol) in dry dichloromethane (411 mL). The reaction solution was heated at reflux three days and then allowed to stand at room temperature overnight. It was washed with hydrochloric acid (1N, 3×300 mL) and then dried (MgSO$_4$) and filtered. Rotary evaporation of the solvent left crude product (95.2 g) as a brown oil. This was applied to a column of silica gel and eluted with 2:1 followed by 1:1 hexanes-ether. Fractions containing product (R$_f$=0.43, 1:1 hexanes-ether, UV) were rotary evaporated to give partially purified product (60.2 g) as a yellowish solid. Further purification was achieved by additional column chromatography employing a greater silica gel to sample ratio. Finally, the doubly chromatographed product (48.7 g including 7.4 g from another similar run) was recrystallized from boiling methanol (3 mL/g). After cooling in an ice bath, the crystals were collected, rinsed with ice-cold methanol and dried. Methyl 2-[(dimethylamino)thioxomethoxy]-4-ethoxybenzoate was obtained as large white prisms (46.1 g) melting at 77°-79° C.

PMR (CDCl$_3$, 200 MHz); δ7.96 (d, 1h, H ortho to CO$_2$CH$_3$); 7.81 (dd, 1H, H para to OC(S)N); 6.62 (d, 1H, H ortho to OC(S)N; 4.08 (q, 2H, OC$\underline{H}_2$CH$_3$); 3.81 (s, 3H, CO$_2$CH$_3$); 3.47 (s, 3H, NCH$_3$); 3.40 (s, 3H, NCH$_3$); 1.42 (t, 3H, OCH$_2$C$\underline{H}_3$). IR (Nujol): 1715 cm$^{-1}$ (vs. C=O).

EXAMPLE 3

Methyl 2-[(dimethylamino)carbonylthio]-4-ethoxybenzoate

Methyl 2-[(dimethylamino)thioxomethoxy]-4-ethoxybenzoate (28.3 g, 0.100 mol) was heated under nitrogen at 220° C. for 1.5 hours. Thin layer chromatography (6:3:1 CH$_3$Cl$_2$-hexanes-ether, UV) showed a very faint spot at a R$_f$ of 0.63 (starting material) and a very intense spot at a R$_f$ of 0.35 (product). In this case the crude product was used in the next reaction step without further characterization or purification.

Crude product from a similar but smaller scale run was chromatographed on a column of silica gel using 4:1 ether-hexanes as eluant. Fractions containing product (R$_f$=0.40, same solvent, UV) were rotary evaporated to give an oil that slowly crystallized. This was dissolved in a little dichloromethane, diluted with 1-chlorobutane, seeded, and rotary evaporated. The residue was collected, rinsed with hexanes, and dried. Methyl 2-[(dimethylamino)carbonylthio]-4-ethoxybenzoate was obtained as white prisms melting at 65°-67° C. PMR (CDCl$_3$, 200 MHz): δ7.93 (d, 1H, H ortho to CO$_2$CH$_3$); 7.16 (d, 1H, H ortho to SC(O)N); 6.89 (dd, 1H, H para to SC(O)N); 4.08 (q, 2H, OC$\underline{H}_2$CH$_3$); 3.84 (s, 3H, CO$_2$CH$_3$); 3.09 (broad s, 6H, N(C$\underline{H}_3$)$_2$); 1.42 (t, 3H, OCH$_2$C$\underline{H}_3$). IR (Nujol): 1730 (s, ester C=O); 1680 (s, carbonyl C=O) cm$^{-1}$.

EXAMPLE 4

Methyl 4-ethoxy-2-mercaptobenzoate

Methanolic sodium methoxide (4.9M, 22.4 mL, 0.11 mol) was added via syringe to a solution of methyl 2-[(dimethylamino)carbonylthio]-4-ethoxybenzoate (crude, ca. 28.3 g, 0.10 mol) in methanol (100 mL) under nitrogen. The reaction mixture was heated at reflux for 30 minutes, then cooled with the aid of a water bath. Rotary evaporation yielded a solid. This was partitioned between dichloromethane (100 mL) and water (100 mL). The aqueous layer was washed with dichloromethane (3×40 mL), acidified to pH<1 with concentrated hydrochloric acid, and then extracted with dichloromethane (3×40 mL). These dichloromethane extracts were combined, dried (Na$_2$SO$_4$), and filtered. Rotary evaporation yielded methyl 4-ethoxy-2-mercaptobenzoate as an oil (18.4 g) that on standing formed a crystalline solid melting at 42°-44° C. PMR (CDCl$_3$, 200 MHz), δ7.97 (d, 1H, H ortho to CO$_2$CH$_3$); 6.78 (d, 1H, H ortho to SH); 6.64 (dd, 1H, H para to SH); 5.06 (s, 1H, SH); 4.05 (q, 2H, OC$\underline{H}_2$CH$_3$); 3.88 (s, 3H, CO$_2$CH$_3$); 1.42 (t, 3H, OCH$_2$C$\underline{H}_3$). IR (Nujol): 1686 (vs, C=O) cm$^{-1}$.

EXAMPLE 5

Methyl 2-(chlorosulfonyl)-4-ethoxybenzoate

Hydrogen peroxide (30%, 9.79M, 30.7 mL, 300 mmol) was added dropwise to a stirred solution of methyl 4-ethoxy-2-mercaptobenzoate (18.2 g, 85.7 mmol) and sodium formate (11.7 g, 172 mmol) in formic acid (171.4 mL). Through the use of an ice bath, the internal temperature was held to 40°-50° C. during the first half of the hydrogen peroxide addition and 45°-50° C. during the second half of the addition. After completion of the addition and cessation of the exothermic reaction, the mixture was heated at 45°-55° C. for two hours. The excess hydrogen peroxide was destroyed with sodium sulfite, the solution was filtered, and the solvent was rotary evaporated. The residue was slurried in toluene and rotary evaporated. The process was repeated to give the sodium sulfonate salt as a moist white crystalline solid (21.7 g).

Without further purification or characterization, the sodium sulfonate salt was added portionwise to stirred thionyl chloride (150 mL, 2.1 mol). Anhydrous N,N-dimethylformamide (1.0 mL, 13 mmol) was added slowly, and the reaction mixture was heated at reflux overnight. The reaction mixture was then rotary evaporated. Dichloromethane (150 mL) was added, and the solvent was again evaporated. The residue was partitioned between ether (100 mL) and ice water (100 mL). The aqueous layer was extracted with ether (2×50 mL). The combined ether solutions were washed with water (50 mL), saturated aqueous sodium bicarbonate solution (2×50 mL), dried MgSO$_4$), and filtered. Rotary evaporation of the solvent left methyl 2-(chlorosulfonyl)-4-ethoxybenzoate as pale orange oil (22.5 g) that crystallized on scratching. The crystalline solid melted at 45°-48° C. PMR (CDCl$_3$, 200 MHz): δ7.76 (d, 1H, H ortho to CO$_2$CH$_3$); 7.65 (d, 1H, H ortho to SO$_2$Cl); 7.21 (dd, 1H, H para to SO$_2$Cl); 4.16 (q, 2H, OC$\underline{H}_2$CH$_3$); 3.96 (s, 3H, CO$_2$CH$_3$); 1.48 (t, 3H, OCH$_2$C$\underline{H}_3$). IR (Nujol): 1722 (vs, C=O) cm$^{-1}$.

EXAMPLE 6

Methyl 2-(aminosulfonyl)-4-ethoxybenzoate

Liquified ammonia (4.4 mL, 180 mmol) was added to a stirred solution of methyl 2-(chlorosulfonyl)-4-ethoxybenzoate (22.1 g, 79.3 mmol) in dichloromethane (221 mL) at −70° C. The reaction mixture was allowed to warm to −10° C. and was held at this temperature for 30 minutes. The mixture was then poured into water (221 mL). More water and dichloromethane were used for rinsing, and tetrahydrofuran (ca. 40 mL) was also added. The layers were shaken and separated, and the aqueous layer was extracted with dichloromethane (2×221 mL). The combined dichloromethane solutions were washed with water (221 mL), and the aqueous wash was back-extracted with dichloromethane (ca. 120 mL). The combined dichloromethane solutions were dried ($NaSO_4$), and filtered. Rotary evaporation of the solvent left crude product as an off-white crystalline solid (18.1 g). This was dissolved in hot methanol (ca. 200 mL) and hot filtered. The solution was boiled down to a volume corresponding to 3 mL/g methanol. After seeding and cooling with the aid of an ice bath, the crystals were collected, rinsed with ice-cold methanol and hexanes, and dried. Methyl 2-(aminosulfonyl)-4-ethoxybenzoate (15.3g) was obtained as white crystalline needles melting at 146°–148° C. PMR ($CDCl_3$, 200 MHz): δ 7.91 (d, 1H, H ortho to $CO_2CH_3$); 7.68 (d, 1H, H ortho to $SO_2NH_2$); 7.04 (dd, 1H, H para to $SO_2NH_2$); 5.91 (broad s, 2H, $NH_2$); 4.14 (q, 2H, O$\underline{CH_2}$$CH_3$); 3.95 (s, 3H, $CO_2\underline{CH_3}$); 1.45 (t, 3H, $OCH_2\underline{CH_3}$). IR (Nujol): 3348 (m, NH); 3241 (m, NH); 1692 (s, C═O) cm$^{-1}$.

EXAMPLE 7

Methyl 2-[[[4-(difluoromethoxy)-6-methoxypyrimidin-2-yl]aminocarbonyl]aminosulfonyl]-4-ethoxybenzoate To a slurry of 4-difluoromethoxy-6-methoxypyrimidin-2-amine (0.56 g, 2.92 mmol) in dry dichloromethane (5 mL) was added a solution of methyl 4-ethoxy-2-(isocyanatosulfonyl)benzoate (crude, ca. 5.6 mL) in dichloromethane (5 mL). The reaction mixture was heated at reflux for 3 hours, during which time the solid dissolved. On stirring at room temperature for 12 hours a new solid formed. The crude reaction mixture was chromatographed directly on a column of silica gel using as eluant 40:1, 20:1, and finally 10:1 dichloromethane-ether, all containing 2 mL/L acetic acid. The appropriate fractions were diluted with toluene and rotary evaporated to give a solid. The solid was slurried in hexanes, collected, washed with butyl chloride, 1:1 butyl chloride-hexanes, hexanes and air dried. The product was a white crystalline solid melting at 195°–196° C. PMR ($CDCl_3$, 200 MHz): δ 12.02 (bs, 1H); 7.91 (d, 1H); 7.78 (d, 1H); 7.52 (t, 1H); 7.34 (bs, 1H); 7.09 (dd, 1H); 5.97 (s, 1H); 4.17 (q, 2H); 4.12 (s, 3H); 3.87 (s, 3H); 1.46 (t, 3H). IR (Nujol): 1722 (vs, C═O) cm$^{-1}$.

Using the procedures and examples shown above, the compounds in Tables I–IV can be prepared.

STRUCTURES FOR TABLES

TABLE I and TABLE Ia
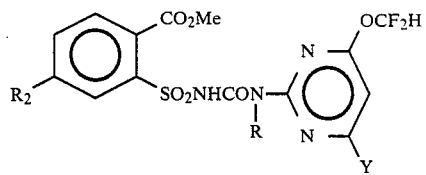

TABLE II and TABLE IIa
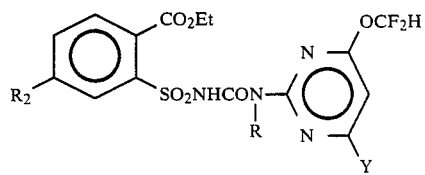

TABLE III and TABLE IIIa
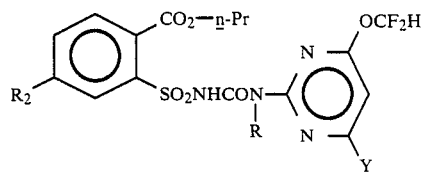

TABLE IV and TABLE IVa
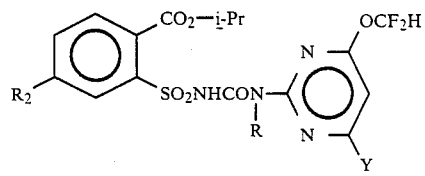

TABLE Va
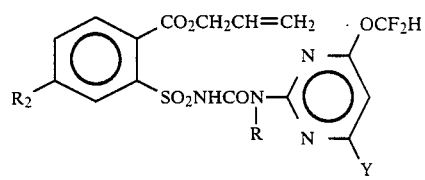

TABLE VIa
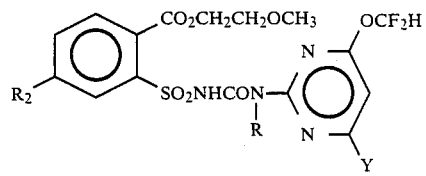

TABLE VIIa
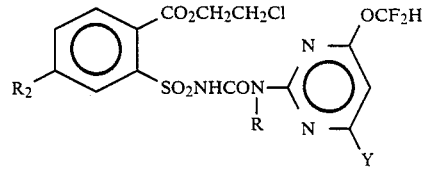

TABLE VIIIa
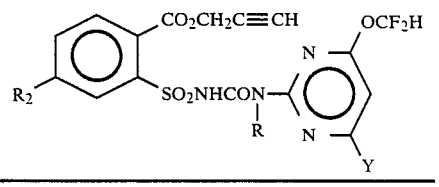

TABLE I $R_1 = CH_3$

| R₂ | R | Y | m.p. (°C.) |
|---|---|---|---|
| Me | H | Me | 187–190 |
| Me | Me | Me | |
| Me | H | OMe | 191–194 |
| Me | Me | OMe | |
| Me | H | OCF₂H | |
| Me | Me | OCF₂H | |
| Et | H | Me | |
| Et | Me | Me | |
| Et | H | OMe | |
| Et | Me | OMe | |
| Et | H | OCF₂H | |
| Et | Me | OCF₂H | |
| Pr | H | Me | |
| Pr | Me | Me | |
| Pr | H | OMe | |
| Pr | Me | OMe | |
| Pr | H | OCF₂H | |
| Pr | Me | OCF₂H | |
| i-Pr | H | Me | |
| i-Pr | Me | Me | |
| i-Pr | H | OMe | |
| i-Pr | Me | OMe | |
| i-Pr | H | OCF₂H | |
| i-Pr | Me | OCF₂H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF₂H | |
| cyclo-Pr | Me | OCF₂H | |
| OMe | H | Me | 167–168 d |
| OMe | Me | Me | |
| OMe | H | OMe | 172–173 |
| OMe | Me | OMe | |
| OMe | H | OCF₂H | 175–177 d |
| OMe | Me | OCF₂H | |
| OEt | H | Me | 183–184 d |
| OEt | Me | Me | |
| OEt | H | OMe | 195–196 |
| OEt | Me | OMe | |
| OEt | H | OCF₂H | 184–185 d |
| OEt | Me | OCF₂H | |
| O—n-Pr | H | Me | |
| O—n-Pr | Me | Me | |
| O—n-Pr | H | OMe | |
| O—n-Pr | Me | OMe | |
| O—n-Pr | H | OCF₂H | |
| O—n-Pr | Me | OCF₂H | |
| O—i-Pr | H | Me | 153–157 |
| O—i-Pr | Me | Me | |
| O—i-Pr | H | OMe | 177–183 |
| O—i-Pr | Me | OMe | |
| O—i-Pr | H | OCF₂H | |
| O—i-Pr | Me | OCF₂H | |
| SMe | H | Me | 153–156 d |
| SMe | Me | Me | |
| SMe | H | OMe | 143–146 |
| SMe | Me | OMe | |
| SMe | H | OCF₂H | 188–190 d |
| SMe | Me | OCF₂H | |
| SEt | H | Me | |
| SEt | Me | Me | |
| SEt | H | OMe | |
| SEt | Me | OMe | |
| SEt | H | OCF₂H | |
| SEt | Me | OCF₂H | |
| S—n-Pr | H | Me | 119–121 |
| S—n-Pr | Me | Me | |
| S—n-Pr | H | OMe | 140–145 |
| S—n-Pr | Me | OMe | |
| S—n-Pr | H | OCF₂H | |
| S—n-Pr | Me | OCF₂H | |
| S—i-Pr | H | Me | |
| S—i-Pr | Me | Me | |
| S—i-Pr | H | OMe | |
| S—i-Pr | Me | OMe | |
| S—i-Pr | H | OCF₂H | |
| S—i-Pr | Me | OCF₂H | |
| O—allyl | H | Me | |
| O—allyl | Me | Me | |
| O—allyl | H | OMe | |
| O—allyl | Me | OMe | |
| O—allyl | H | OCF₂H | |
| O—allyl | Me | OCF₂H | |
| O—propargyl | H | Me | |
| O—propargyl | Me | Me | |
| O—propargyl | H | OMe | |
| O—propargyl | Me | OMe | |
| O—propargyl | H | OCF₂H | |
| O—propargyl | Me | OCF₂H | |
| CH₂F | H | Me | |
| CH₂F | Me | Me | |
| CH₂F | H | OMe | |
| CH₂F | Me | OMe | |
| CH₂F | H | OCF₂H | |
| CH₂F | Me | OCF₂H | |
| CHF₂ | H | Me | |
| CHF₂ | Me | Me | |
| CHF₂ | H | OMe | |
| CHF₂ | Me | OMe | |
| CHF₂ | H | OCF₂H | |
| CHF₂ | Me | OCF₂H | |
| CF₃ | H | Me | 181–184 d |
| CF₃ | Me | Me | |
| CF₃ | H | OMe | 165–167 |
| CF₃ | Me | OMe | |
| CF₃ | H | OCF₂H | 168–170 |
| CF₃ | Me | OCF₂H | |
| CH₂Cl | H | Me | |
| CH₂Cl | Me | Me | |
| CH₂Cl | H | OMe | |
| CH₂Cl | Me | OMe | |
| CH₂Cl | H | OCF₂H | |
| CH₂Cl | Me | OCF₂H | |
| CHCl₂ | H | Me | |
| CHCl₂ | Me | Me | |
| CHCl₂ | H | OMe | |
| CHCl₂ | Me | OMe | |
| CHCl₂ | H | OCF₂H | |
| CHCl₂ | Me | OCF₂H | |
| CCl₃ | H | Me | |
| CCl₃ | Me | Me | |
| CCl₃ | H | OMe | |
| CCl₃ | Me | OMe | |
| CCl₃ | H | OCF₂H | |
| CCl₃ | Me | OCF₂H | |
| CHFCH₃ | H | Me | |
| CHFCH₃ | Me | Me | |
| CHFCH₃ | H | OMe | |
| CHFCH₃ | Me | OMe | |
| CHFCH₃ | H | OCF₂H | |
| CHFCH₃ | Me | OCF₂H | |
| CF₂CH₃ | H | Me | |
| CF₂CH₃ | Me | Me | |
| CF₂CH₃ | H | OMe | |
| CF₂CH₃ | Me | OMe | |
| CF₂CH₃ | H | OCF₂H | |
| CF₂CH₃ | Me | OCF₂H | |
| CH₂CH₂F | H | Me | |
| CH₂CH₂F | Me | Me | |
| CH₂CH₂F | H | OMe | |
| CH₂CH₂F | Me | OMe | |
| CH₂CH₂F | H | OCF₂H | |
| CH₂CH₂F | Me | OCF₂H | |
| CH₂CHF₂ | H | Me | |
| CH₂CHF₂ | Me | Me | |
| CH₂CHF₂ | H | OMe | |
| CH₂CHF₂ | Me | OMe | |
| CH₂CHF₂ | H | OCF₂H | |
| CH₂CHF₂ | Me | OCF₂H | |
| CH₂CF₃ | H | Me | |
| CH₂CF₃ | Me | Me | |
| CH₂CF₃ | H | OMe | |
| CH₂CF₃ | Me | OMe | |
| CH₂CF₃ | H | OCF₂H | |
| CH₂CF₃ | Me | OCF₂H | |
| CHClCH₃ | H | Me | |
| CHClCH₃ | Me | Me | |

TABLE I-continued

| | $R_1 = CH_3$ | | |
|---|---|---|---|
| $R_2$ | R | Y | m.p. (°C.) |
| CHClCH$_3$ | H | OMe | |
| CHClCH$_3$ | Me | OMe | |
| CHClCH$_3$ | H | OCF$_2$H | |
| CHClCH$_3$ | Me | OCF$_2$H | |
| CH$_2$OCH$_3$ | H | Me | |
| CH$_2$OCH$_3$ | Me | Me | |
| CH$_2$OCH$_3$ | H | OMe | |
| CH$_2$OCH$_3$ | Me | OMe | |
| CH$_2$OCH$_3$ | H | OCF$_2$H | |
| CH$_2$OCH$_3$ | Me | OCF$_2$H | |
| (CH$_2$)$_2$OCH$_3$ | H | Me | |
| (CH$_2$)$_2$OCH$_3$ | Me | Me | |
| (CH$_2$)$_2$OCH$_3$ | H | OMe | |
| (CH$_2$)$_2$OCH$_3$ | Me | OMe | |
| (CH$_2$)$_2$OCH$_3$ | H | OCF$_2$H | |
| (CH$_2$)$_2$OCH$_3$ | Me | OCF$_2$H | |
| CH(OCH$_3$)CH$_3$ | H | Me | |
| CH(OCH$_3$)CH$_3$ | Me | Me | |
| CH(OCH$_3$)CH$_3$ | H | OMe | |
| CH(OCH$_3$)CH$_3$ | Me | OMe | |
| CH(OCH$_3$)CH$_3$ | H | OCF$_2$H | |
| CH(OCH$_3$)CH$_3$ | Me | OCF$_2$H | |
| CH$_2$SCH$_3$ | H | Me | |
| CH$_2$SCH$_3$ | Me | Me | |
| CH$_2$SCH$_3$ | H | OMe | |
| CH$_2$SCH$_3$ | Me | OMe | |
| CH$_2$SCH$_3$ | H | OCF$_2$H | |
| CH$_2$SCH$_3$ | Me | OCF$_2$H | |
| (CH$_2$)$_2$SCH$_3$ | H | Me | |
| (CH$_2$)$_2$SCH$_3$ | Me | Me | |
| (CH$_2$)$_2$SCH$_3$ | H | OMe | |
| (CH$_2$)$_2$SCH$_3$ | Me | OMe | |
| (CH$_2$)$_2$SCH$_3$ | H | OCF$_2$H | |
| (CH$_2$)$_2$SCH$_3$ | Me | OCF$_2$H | |
| CH(SCH$_3$)CH$_3$ | H | Me | |
| CH(SCH$_3$)CH$_3$ | Me | Me | |
| CH(SCH$_3$)CH$_3$ | H | OMe | |
| CH(SCH$_3$)CH$_3$ | Me | OMe | |
| CH(SCH$_3$)CH$_3$ | H | OCF$_2$H | |
| CH(SCH$_3$)CH$_3$ | Me | OCF$_2$H | |
| OCF$_2$H | H | Me | |
| OCF$_2$H | Me | Me | |
| OCF$_2$H | H | OMe | |
| OCF$_2$H | Me | OMe | |
| OCF$_2$H | H | OCF$_2$H | |
| OCF$_2$H | Me | OCF$_2$H | |
| OCH$_2$CH$_2$F | H | Me | |
| OCH$_2$CH$_2$F | Me | Me | |
| OCH$_2$CH$_2$F | H | OMe | |
| OCH$_2$CH$_2$F | Me | OMe | |
| OCH$_2$CH$_2$F | H | OCF$_2$H | |
| OCH$_2$CH$_2$F | Me | OCF$_2$H | |
| OCH$_2$CHF$_2$ | H | Me | |
| OCH$_2$CHF$_2$ | Me | Me | |
| OCH$_2$CHF$_2$ | H | OMe | |
| OCH$_2$CHF$_2$ | Me | OMe | |
| OCH$_2$CHF$_2$ | H | OCF$_2$H | |
| OCH$_2$CHF$_2$ | Me | OCF$_2$H | |
| OCH$_2$CF$_3$ | H | Me | |
| OCH$_2$CF$_3$ | Me | Me | |
| OCH$_2$CF$_3$ | H | OMe | |
| OCH$_2$CF$_3$ | Me | OMe | |
| OCH$_2$CF$_3$ | H | OCF$_2$H | |
| OCH$_2$CF$_3$ | Me | OCF$_2$H | |
| O(CH$_2$)$_2$Cl | H | Me | |
| O(CH$_2$)$_2$Cl | Me | Me | |
| O(CH$_2$)$_2$Cl | H | OMe | |
| O(CH$_2$)$_2$Cl | Me | OMe | |
| O(CH$_2$)$_2$Cl | H | OCF$_2$H | |
| O(CH$_2$)$_2$Cl | Me | OCF$_2$H | |
| S(O)Me | H | Me | |
| S(O)Me | Me | Me | |
| S(O)Me | H | OMe | |
| S(O)Me | Me | OMe | |
| S(O)Me | H | OCF$_2$H | |
| S(O)Me | Me | OCF$_2$H | |
| S(O)Et | H | Me | |
| S(O)Et | Me | Me | |
| S(O)Et | H | OMe | |
| S(O)Et | Me | OMe | |
| S(O)Et | H | OCF$_2$H | |
| S(O)Et | Me | OCF$_2$H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF$_2$H | |
| S(O)—n-Pr | Me | OCF$_2$H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF$_2$H | |
| S(O)—i-Pr | Me | OCF$_2$H | |
| SO$_2$Me | H | Me | |
| SO$_2$Me | Me | Me | |
| SO$_2$Me | H | OMe | |
| SO$_2$Me | Me | OMe | |
| SO$_2$Me | H | OCF$_2$H | |
| SO$_2$Me | Me | OCF$_2$H | |
| SO$_2$Et | H | Me | |
| SO$_2$Et | Me | Me | |
| SO$_2$Et | H | OMe | |
| SO$_2$Et | Me | OMe | |
| SO$_2$Et | H | OCF$_2$H | |
| SO$_2$Et | Me | OCF$_2$H | |
| SO$_2$—n-Pr | H | Me | |
| SO$_2$—n-Pr | Me | Me | |
| SO$_2$—n-Pr | H | OMe | |
| SO$_2$—n-Pr | Me | OMe | |
| SO$_2$—n-Pr | H | OCF$_2$H | |
| SO$_2$—n-Pr | Me | OCF$_2$H | |
| SO$_2$—i-Pr | H | Me | |
| SO$_2$—i-Pr | Me | Me | |
| SO$_2$—i-Pr | H | OMe | |
| SO$_2$—i-Pr | Me | OMe | |
| SO$_2$—i-Pr | H | OCF$_2$H | |
| SO$_2$—i-Pr | Me | OCF$_2$H | |
| S—allyl | H | Me | |
| S—allyl | Me | Me | |
| S—allyl | H | OMe | |
| S—allyl | Me | OMe | |
| S—allyl | H | OCF$_2$H | |
| S—allyl | Me | OCF$_2$H | |
| S(O)allyl | H | Me | |
| S(O)allyl | Me | Me | |
| S(O)allyl | H | OMe | |
| S(O)allyl | Me | OMe | |
| S(O)allyl | H | OCF$_2$H | |
| S(O)allyl | Me | OCF$_2$H | |
| SO$_2$allyl | H | Me | |
| SO$_2$allyl | Me | Me | |
| SO$_2$allyl | H | OMe | |
| SO$_2$allyl | Me | OMe | |
| SO$_2$allyl | H | OCF$_2$H | |
| SO$_2$allyl | Me | OCF$_2$H | |
| S—propargyl | H | Me | |
| S—propargyl | Me | Me | |
| S—propargyl | H | OMe | |
| S—propargyl | Me | OMe | |
| S—propargyl | H | OCF$_2$H | |
| S—propargyl | Me | OCF$_2$H | |
| S(O)propargyl | H | Me | |
| S(O)propargyl | Me | Me | |
| S(O)propargyl | H | OMe | |
| S(O)propargyl | Me | OMe | |
| S(O)propargyl | H | OCF$_2$H | |
| S(O)propargyl | Me | OCF$_2$H | |
| SO$_2$propargyl | H | Me | |
| SO$_2$propargyl | Me | Me | |
| SO$_2$propargyl | H | OMe | |
| SO$_2$propargyl | Me | OMe | |
| SO$_2$propargyl | H | OCF$_2$H | |
| SO$_2$propargyl | Me | OCF$_2$H | |

TABLE Ia

| | $R_1 = CH_3$ | | |
|---|---|---|---|
| R₂ | R | Y | m.p. (°C.) |
| CH₂OCH₂CH₃ | H | Me | |
| CH₂OCH₂CH₃ | H | OMe | |
| CH₂OCH₂CH₃ | H | OCF₂H | |
| (CH₂)₂OCH₂CH₃ | H | Me | |
| (CH₂)₂OCH₂CH₃ | H | OMe | |
| (CH₂)₂OCH₂CH₃ | H | OCF₂H | |
| (CH₂)₂OCH₂CH₃ | CH₃ | Me | |
| CH(CH₃)OCH₂CH₃ | H | Me | |
| CH(CH₃)OCH₂CH₃ | H | OMe | |
| CH(CH₃)OCH₂CH₃ | H | OCF₂H | |
| CH₂OCH₂CF₃ | H | Me | |
| CH₂OCH₂CF₃ | H | OMe | |
| CH₂OCH₂CF₃ | H | OCF₂H | |
| (CH₂)₂OCH₂CF₂H | H | Me | |
| (CH₂)₂OCH₂CF₃ | H | OMe | |
| CH₂OCF₂H | H | OCF₂H | |
| CH₂OCH₂CH₂F | CH₃ | OMe | |
| CH₂OCH₂CHF₂ | H | Me | |
| CH₂OCH₂CH₂Br | H | OMe | |
| CH₂OCH₂CH₂Cl | H | OCF₂H | |
| CH₂OCH₂CH₂I | H | Me | |
| CH₂OCF₃ | H | OMe | |
| CH₂SCH₂CH₃ | H | OCF₂H | |
| CH₂SCH₂CH₃ | H | Me | |
| CH₂SCH₂CH₃ | H | OMe | |
| (CH₂)₂SCH₂CH₃ | H | OCF₂H | |
| (CH₂)₂SCH₂CH₃ | CH₃ | OCF₂H | |
| (CH₂)₂SCH₂CH₃ | H | Me | |
| (CH₂)₂SCH₂CH₃ | H | OMe | |
| CH(CH₃)SCH₂CH₃ | H | OCF₂H | |
| CH(CH₃)SCH₂CH₃ | H | Me | |
| CH(CH₃)SCH₂CH₃ | H | OMe | |
| CH₂SCH₂CF₃ | H | OCF₂H | |
| CH₂SCH₂CF₃ | H | Me | |
| CH₂SCH₂CF₃ | H | OMe | |
| (CH₂)₂SCH₂CF₂H | H | OCF₂H | |
| (CH₂)₂S(O)₂CH₃ | H | Me | |
| CH₂S(O)₂CH₂CH₃ | H | OMe | |
| CH₂S(O)₂CH₂CH₃ | H | OCF₂H | |
| CH₂S(O)₂CH₂CH₃ | H | Me | |
| (CH₂)₂S(O)₂CH₂CH₃ | H | OMe | |
| CH(CH₃)S(O)₂CH₃ | H | OCF₂H | |
| CH₂S(O)₂CH₂CF₃ | CH₃ | Me | |
| CH₂S(O)₂CH₂CF₃ | H | Me | |
| CH₂S(O)₂CH₂CF₃ | H | OMe | |
| CH₂S(O)₂CH₂CF₃ | H | OCF₂H | |
| (CH₂)₂S(O)₂CH₂CF₂H | H | Me | |
| (CH₂)₂S(O)₂CH₂CF₃ | H | OMe | |
| CH₂S(O)₂CF₂H | H | OCF₂H | |
| CH₂S(O)₂CH₂CH₂F | H | Me | |
| CH₂S(O)₂CH₂CHF₂ | H | OMe | |
| CH₂S(O)₂CH₂CH₂Br | H | OCF₂H | |
| CH₂S(O)₂CH₂CH₂I | CH₃ | OMe | |
| CH₂S(O)₂CF₃ | H | Me | |
| CH₂S(O)₂CH₂Cl | H | OMe | |
| OCH₂OCH₃ | H | OCF₂H | |
| OCH₂OCH₃ | H | Me | |
| OCH₂OCH₃ | H | OMe | |
| O(CH₂)₂OCH₃ | H | OCF₂H | |
| O(CH₂)₂OCH₃ | H | Me | |
| O(CH₂)₂OCH₃ | H | OMe | |
| O(CH₂)₂OCH₂CH₃ | H | OCF₂H | |
| O(CH₂)₂OCH₂CH₃ | CH₃ | OCF₂H | |
| O(CH₂)₂OCH₂CH₃ | H | Me | |
| O(CH₂)₂OCH₂CH₃ | H | OMe | |
| OCH₂OCH₂CH₃ | H | OCF₂H | |
| (CH₂)₂SCH₂CF₃ | H | Me | |
| CH₂SCF₂H | H | OMe | |
| CH₂SCH₂CH₂F | H | OCF₂H | |
| CH₂SCH₂CHF₂ | H | Me | |
| CH₂SCH₂CH₂Br | H | OMe | |
| CH₂SCH₂CH₂Cl | H | OCF₂H | |
| CH₂SCH₂CH₂I | CH₃ | Me | |
| CH₂SCF₃ | H | Me | |
| CH₂S(O)CH₃ | H | OMe | |
| CH₂S(O)CH₃ | H | OCF₂H | |
| CH₂S(O)CH₃ | H | Me | |
| (CH₂)₂S(O)CH₃ | H | OMe | |
| (CH₂)₂S(O)CH₃ | H | OCF₂H | |
| (CH₂)₂S(O)CH₃ | H | Me | |
| CH₂S(O)CH₂CH₃ | H | OMe | |
| CH₂S(O)CH₂CH₃ | H | OCF₂H | |
| CH₂S(O)CH₂CH₃ | CH₃ | OMe | |
| CH₂S(O)CH₂CH₃ | H | Me | |
| (CH₂)₂S(O)CH₂CH₃ | H | OMe | |
| CH(CH₃)S(O)CH₃ | H | OCF₂H | |
| CH₂S(O)CH₂CF₃ | H | Me | |
| CH₂S(O)CH₂CF₃ | H | OMe | |
| CH₂S(O)CH₂CF₃ | H | OCF₂H | |
| (CH₂)₂S(O)CH₂CF₂H | H | Me | |
| (CH₂)₂S(O)CH₂CF₃ | H | OMe | |
| CH₂S(O)CF₂H | H | OCF₂H | |
| CH₂S(O)CH₂CH₂F | CH₃ | OCF₂H | |
| CH₂S(O)CH₂CHF₂ | H | Me | |
| CH₂S(O)CH₂CH₂Br | H | OMe | |
| CH₂S(O)CH₂CH₂I | H | OCF₂H | |
| CH₂S(O)CF₃ | H | Me | |
| CH₂S(O)₂CH₃ | H | OMe | |
| CH₂S(O)₂CH₃ | H | OCF₂H | |
| CH₂S(O)₂CH₃ | H | Me | |
| (CH₂)₂S(O)₂CH₃ | H | OMe | |
| (CH₂)₂S(O)₂CH₃ | H | OCF₂H | |
| OCH₂OCH₂CF₃ | H | Me | |
| O(CH₂)₂OCH₂CF₃ | H | OMe | |
| O(CH₂)₂OCH₂CF₂H | H | OCF₂H | |
| O(CH₂)₂O(CH₂)₂Cl | H | Me | |
| O(CH₂)₂O(CH₂)₂Br | H | OMe | |
| O(CH₂)₂O(CH₂)₂I | H | OCF₂H | |
| O(CH₂)₂OCF₃ | H | Me | |
| OCH₂SCH₃ | H | OMe | |
| OCH₂SCH₃ | H | OCF₂H | |
| OCH₂SCH₃ | H | Me | |
| O(CH₂)₂SCH₃ | H | OMe | |
| O(CH₂)₂SCH₃ | H | OCF₂H | |
| O(CH₂)₂SCH₃ | CH₃ | Me | |
| O(CH₂)₂SCH₃ | H | Me | |
| O(CH₂)₂SCH₂CH₃ | H | OMe | |
| O(CH₂)₂SCH₂CH₃ | H | OCF₂H | |
| O(CH₂)₂SCH₂CH₃ | H | Me | |
| OCH₂SCH₂CH₃ | H | OMe | |
| OCH₂SCH₂CF₃ | H | OCF₂H | |
| O(CH₂)₂SCH₂CF₃ | H | Me | |
| O(CH₂)₂SCH₂CF₂H | H | OMe | |
| O(CH₂)₂S(CH₂)₂Cl | H | OCF₂H | |
| O(CH₂)₂S(CH₂)₂Br | CH₃ | OMe | |
| O(CH₂)₂S(CH₂)₂I | H | Me | |
| O(CH₂)₂SCF₃ | H | OMe | |
| OCH₂S(O)CH₃ | H | OCF₂H | |
| OCH₂S(O)CH₃ | H | Me | |
| OCH₂S(O)CH₃ | H | OMe | |
| O(CH₂)₂S(O)CH₃ | H | OCF₂H | |
| O(CH₂)₂S(O)CH₃ | H | Me | |
| O(CH₂)₂S(O)CH₃ | H | OMe | |
| O(CH₂)₂S(O)CH₂CH₃ | H | OCF₂H | |
| O(CH₂)₂S(O)CH₂CH₃ | CH₃ | OCF₂H | |
| O(CH₂)₂S(O)CH₂CH₃ | H | Me | |
| O(CH₂)₂S(O)CH₂CH₃ | H | OMe | |
| OCH₂S(O)CH₂CH₃ | H | OCF₂H | |
| OCH₂S(O)CH₂CF₃ | H | Me | |
| O(CH₂)₂S(O)CH₂CF₂H | H | OMe | |
| O(CH₂)₂S(O)(CH₂)₂Cl | H | OCF₂H | |
| O(CH₂)₂S(O)(CH₂)₂Br | H | Me | |
| O(CH₂)₂S(O)(CH₂)₂I | H | OMe | |
| O(CH₂)₂S(O)CF₃ | H | OCF₂H | |
| OCH₂S(O)₂CH₃ | H | Me | |
| OCH₂S(O)₂CH₃ | H | OMe | |
| OCH₂S(O)₂CH₃ | H | OCF₂H | |
| O(CH₂)₂S(O)₂CH₃ | H | Me | |
| O(CH₂)₂S(O)₂CH₃ | H | OMe | |
| O(CH₂)₂S(O)₂CH₃ | H | OCF₂H | |
| O(CH₂)₂S(O)₂CH₂CH₃ | CH₃ | Me | |
| O(CH₂)₂S(O)₂CH₂CH₃ | H | Me | |
| O(CH₂)₂S(O)₂CH₂CH₃ | H | OMe | |
| O(CH₂)₂S(O)₂CH₂CH₃ | H | OCF₂H | |
| OCH₂S(O)₂CH₂CH₃ | H | Me | |
| O(CH₂)₂S(O)₂CH₂CF₃ | H | OMe | |
| O(CH₂)₂S(O)₂CH₂CF₃ | H | OCF₂H | |
| O(CH₂)₂S(O)₂CH₂CF₂H | H | Me | |

TABLE Ia-continued

$R_1 = CH_3$

| R2 | R | Y | m.p. (°C.) |
|---|---|---|---|
| O(CH2)2S(O)2(CH2)2Cl | H | OMe | |
| O(CH2)2S(O)2(CH2)2Br | H | OCF2H | |
| O(CH2)2S(O)2(CH2)2I | CH3 | OMe | |
| O(CH2)2S(O)2CF3 | H | Me | |
| OCH2S(O)2CH2Cl | H | OMe | |
| OCH2S(O)2CF3 | H | OCF2H | |
| O(CH2)2CN | H | Me | |
| O(CH2)2CN | H | OMe | |
| O(CH2)2CN | H | OCF2H | |
| OCH2CN | H | Me | |
| OCH2CN | H | OMe | |
| OCH2CN | H | OCF2H | |
| OCH2CN | CH3 | OCF2H | |
| OCH(CH3)CN | H | Me | |
| O(CH2)2NH2 | H | OMe | |
| O(CH2)2NH2 | H | OCF2H | |
| O(CH2)2NH2 | H | Me | |
| O(CH2)2NHCH3 | H | OMe | |
| O(CH2)2NHCH3 | H | OCF2H | |
| O(CH2)2NHCH3 | H | Me | |
| O(CH2)2N(CH3)2 | H | OMe | |
| O(CH2)2N(CH3)2 | H | OCF2H | |
| O(CH2)2N(CH3)2 | H | Me | |
| SCH2OCH3 | H | OMe | |
| SCH2OCH3 | H | OCF2H | |
| SCH2OCH3 | H | Me | |
| SCH2OCH2CH3 | H | OMe | |
| S(CH2)2OCH3 | H | OCF2H | |
| S(CH2)2OCH3 | CH3 | Me | |
| S(CH2)2OCH3 | H | Me | |
| S(CH2)2OCH3 | H | OMe | |
| S(CH2)2OCH2CH3 | H | OCF2H | |
| S(CH2)2OCH2CF3 | H | Me | |
| SCH2OCH2CF3 | H | OMe | |
| S(CH2)2OCH2CF2H | H | OCF2H | |
| S(CH2)2O(CH2)2Cl | H | Me | |
| S(CH2)2O(CH2)2Br | H | OMe | |
| S(CH2)2O(CH2)2I | H | OCF2H | |
| S(CH2)2OCF3 | CH3 | OMe | |
| SCH2SCH3 | H | Me | |
| SCH2SCH3 | H | OMe | |
| SCH2SCH3 | H | OCF2H | |
| SCH2SCH2CH3 | H | Me | |
| S(CH2)2SCH3 | H | OMe | |
| S(CH2)2SCH3 | H | OCF2H | |
| S(CH2)2SCH3 | H | Me | |
| S(CH2)2SCH2CH3 | H | OMe | |
| SCH(CH3)SCH3 | H | OCF2H | |
| S(CH2)2SCH2CF3 | CH3 | OCF2H | |
| SCH2SCH2CF3 | H | Me | |
| S(CH2)2SCH2CF2H | H | OMe | |
| S(CH2)2S(CH2)2Cl | H | OCF2H | |
| S(CH2)2S(CH2)2Br | H | Me | |
| S(CH2)2S(CH2)2I | H | OMe | |
| S(CH2)2SCF3 | H | OCF2H | |
| SCH2CN | H | Me | |
| SCH2CN | H | OMe | |
| SCH2CN | H | OCF2H | |
| S(CH2)2CN | H | Me | |
| S(CH2)2CN | H | OMe | |
| S(CH2)2CN | H | OCF2H | |
| SCH(CH3)CN | H | Me | |
| SCHF2 | H | OMe | |
| SCHF2 | H | OCF2H | |
| SCHF2 | CH3 | Me | |
| SCHF2 | H | Me | |
| SCF3 | H | OMe | |
| SCH2CFH2 | H | OCF2H | |
| SCH2CF2H | H | Me | |
| SCH2CF3 | H | OMe | |
| SCH2CF3 | H | OCF2H | |
| SCH2CF3 | H | Me | |
| SCH2CF2H | H | OMe | |
| S(CH2)2CFH2 | H | OCF2H | |
| S(CH2)2CClH2 | CH3 | OMe | |
| S(CH2)2ClH2 | H | Me | |
| SCF2CF3 | H | OMe | |
| SCH(CH3)CF3 | H | OCF2H | |
| S(CH2)2CCl3 | H | Me | |
| S(O)CHF2 | H | OMe | |
| S(O)CHF2 | H | OCF2H | |
| S(O)CHF2 | H | Me | |
| S(O)CF3 | H | OMe | |
| S(O)CH2CFH2 | H | OCF2H | |
| S(O)CH2CF2H | CH3 | OCF2H | |
| S(O)CH2CF3 | H | Me | |
| S(O)CH2CF3 | H | OMe | |
| S(O)CH2CF3 | H | OCF2H | |
| S(O)CH2CF2H | H | Me | |
| S(O)(CH2)2CFH2 | H | OMe | |
| S(O)(CH2)2CClH2 | H | OCF2H | |
| S(O)(CH2)2ClH2 | H | Me | |
| S(O)CF2CF3 | H | OMe | |
| S(O)CH(CH3)CF3 | H | OCF2H | |
| S(O)(CH2)2CCl3 | H | Me | |
| S(O)2CHF2 | H | OMe | |
| S(O)2CHF2 | H | OCF2H | |
| S(O)2CHF2 | H | Me | |
| S(O)2CF3 | H | OMe | |
| S(O)2CH2CFH2 | H | OCF2H | |
| S(O)2CH2CF2H | CH3 | Me | |
| S(O)2CH2CF3 | H | Me | |
| S(O)2CH2CF3 | H | OMe | |
| S(O)2CH2CF3 | H | OCF2H | |
| S(O)2CH2CF2H | H | Me | |
| S(O)2(CH2)2CFH2 | H | OMe | |
| S(O)2(CH2)2CClH2 | H | OCF2H | |
| S(O)2(CH2)2ClH2 | H | Me | |
| S(O)2CF2CF3 | H | OMe | |
| S(O)2CH(CH3)CF3 | H | OCF2H | |
| S(O)2(CH2)2CCl3 | CH3 | OMe | |
| S(O)2CH2Cl | H | Me | |
| CH=CH2 | H | OMe | |
| CH=CH2 | H | OCF2H | |
| CH=CH2 | H | Me | |
| CH2CH=CH2 | H | OMe | |
| CH2CH=CH2 | H | OCF2H | |
| CH2CH=CH2 | H | Me | |
| CH=CHCH3 | H | OMe | |
| C(CH3)=CH2 | H | OCF2H | |
| CH=CH2 | CH3 | OCF2H | |
| C≡CH | H | Me | |
| C≡CH | H | OMe | |
| C≡CH | H | OCF2H | |
| CH2C≡CH | H | Me | |
| CH2C≡CH | H | OMe | |
| CH2C≡CH | H | OCF2H | |
| C≡CCH3 | H | Me | |
| C≡CCH3 | H | OMe | |
| C≡CCH3 | H | OCF2H | |
| NH2 | H | Me | |
| NH2 | H | OMe | |
| NH2 | H | OCF2H | |
| NHCH3 | H | Me | |
| NHCH3 | H | OMe | |
| NHCH3 | H | OCF2H | |
| NHCH3 | CH3 | Me | |
| N(CH3)2 | H | Me | |
| N(CH3)2 | H | OMe | |
| N(CH3)2 | H | OCF2H | |
| NHCH2CH3 | H | Me | |
| NHCH2CH3 | H | OMe | |
| NHCH2CH3 | H | OCF2H | |
| N(CH3)CH2CH3 | H | Me | |
| N(CH2CH3)2 | H | OMe | |
| NHCH2CF3 | H | OCF2H | |
| NHCH2CF3 | CH3 | OMe | |
| NHCH2CF3 | H | Me | |
| NHCH2CF3 | H | OMe | |
| N(CH3)CH2CF3 | H | OCF2H | |
| N(CH3)CH2CHF2 | H | Me | |
| N(CH3)(CH2)2F | H | OMe | |
| N(CH3)(CH2)2Cl | H | OCF2H | |
| N(CH3)(CH2)2I | H | Me | |
| N(CH3)(CH2)2Br | H | OMe | |
| NHCF3 | CH3 | OCF2H | |
| NHCF3 | H | Me | |
| NH(CH2)2F | H | OMe | |

TABLE Ia-continued

| | $R_1 = CH_3$ | | |
|---|---|---|---|
| $R_2$ | R | Y | m.p. (°C.) |
| $N(CH_3)CF_2H$ | H | $OCF_2H$ | |
| $NHCF_2H$ | H | Me | |

TABLE II

| | $R_1 = Et$ | | |
|---|---|---|---|
| $R_2$ | R | Y | m.p. (°C.) |
| Me | H | Me | — |
| Me | Me | Me | |
| Me | H | OMe | 121–133 d |
| Me | Me | OMe | |
| Me | H | $OCF_2H$ | 163–165 d |
| Me | Me | $OCF_2H$ | |
| Et | H | Me | |
| Et | Me | Me | |
| Et | H | OMe | |
| Et | Me | OMe | |
| Et | H | $OCF_2H$ | |
| Et | Me | $OCF_2H$ | |
| n-Pr | H | Me | |
| n-Pr | Me | Me | |
| n-Pr | H | OMe | |
| n-Pr | Me | OMe | |
| n-Pr | H | $OCF_2H$ | |
| n-Pr | Me | $OCF_2H$ | |
| i-Pr | H | Me | |
| i-Pr | Me | Me | |
| i-Pr | H | OMe | |
| i-Pr | Me | OMe | |
| i-Pr | H | $OCF_2H$ | |
| i-Pr | Me | $OCF_2H$ | |
| cyclo-Pr | H | Me | |
| cyclo-Pr | Me | Me | |
| cyclo-Pr | H | OMe | |
| cyclo-Pr | Me | OMe | |
| cyclo-Pr | H | $OCF_2H$ | |
| cyclo-Pr | Me | $OCF_2H$ | |
| OMe | H | Me | 172–178 d |
| OMe | Me | Me | |
| OMe | H | OMe | 180–184 d |
| OMe | Me | OMe | |
| OMe | H | $OCF_2H$ | 162–166 |
| OMe | Me | $OCF_2H$ | |
| OEt | H | Me | |
| OEt | Me | Me | |
| OEt | H | OMe | |
| OEt | Me | OMe | |
| OEt | H | $OCF_2H$ | |
| OEt | Me | $OCF_2H$ | |
| O—n-Pr | H | Me | |
| O—n-Pr | Me | Me | |
| O—n-Pr | H | OMe | |
| O—n-Pr | Me | OMe | |
| O—n-Pr | H | $OCF_2H$ | |
| O—n-Pr | Me | $OCF_2H$ | |
| O—i-Pr | H | Me | 164–168 |
| O—i-Pr | Me | Me | |
| O—i-Pr | H | OMe | 147–150 |
| O—i-Pr | Me | OMe | |
| O—i-Pr | H | $OCF_2H$ | |
| O—i-Pr | Me | $OCF_2H$ | |
| SMe | H | Me | 151–155 |
| SMe | Me | Me | |
| SMe | H | OMe | 149–154 |
| SMe | Me | OMe | |
| SMe | H | $OCF_2H$ | |
| SMe | Me | $OCF_2H$ | |
| SEt | H | Me | 134–139 |
| SEt | Me | Me | |
| SEt | H | OMe | 121–126 |
| SEt | Me | OMe | |
| SEt | H | $OCF_2H$ | |
| SEt | Me | $OCF_2H$ | |
| S—n-Pr | H | Me | |
| S—n-Pr | Me | Me | |
| S—n-Pr | H | OMe | 130–134 |
| S—n-Pr | Me | OMe | |
| S—n-Pr | H | $OCF_2H$ | |

TABLE II-continued

| | $R_1 = Et$ | | |
|---|---|---|---|
| $R_2$ | R | Y | m.p. (°C.) |
| S—n-Pr | Me | $OCF_2H$ | |
| S—i-Pr | H | Me | 135–140 |
| S—i-Pr | Me | Me | |
| S—i-Pr | H | OMe | 145–150 |
| S—i-Pr | Me | OMe | |
| S—i-Pr | H | $OCF_2H$ | |
| S—i-Pr | Me | $OCF_2H$ | |
| O—allyl | H | Me | |
| O—allyl | Me | Me | |
| O—allyl | H | OMe | |
| O—allyl | Me | OMe | |
| O—allyl | H | $OCF_2H$ | |
| O—allyl | Me | $OCF_2H$ | |
| O—propargyl | H | Me | |
| O—propargyl | Me | Me | |
| O—propargyl | H | OMe | |
| O—propargyl | Me | OMe | |
| O—propargyl | H | $OCF_2H$ | |
| O—propargyl | Me | $OCF_2H$ | |
| $CH_2F$ | H | Me | |
| $CH_2F$ | Me | Me | |
| $CH_2F$ | H | OMe | |
| $CH_2F$ | Me | OMe | |
| $CH_2F$ | H | $OCF_2H$ | |
| $CH_2F$ | Me | $OCF_2H$ | |
| $CHF_2$ | H | Me | |
| $CHF_2$ | Me | Me | |
| $CHF_2$ | H | OMe | |
| $CHF_2$ | Me | OMe | |
| $CHF_2$ | H | $OCF_2H$ | |
| $CHF_2$ | Me | $OCF_2H$ | |
| $CF_3$ | H | Me | 173–175 |
| $CF_3$ | Me | Me | |
| $CF_3$ | H | OMe | 115–120 |
| $CF_3$ | Me | OMe | |
| $CF_3$ | H | $OCF_2H$ | |
| $CF_3$ | Me | $OCF_2H$ | |
| $CH_2Cl$ | H | Me | |
| $CH_2Cl$ | Me | Me | |
| $CH_2Cl$ | H | OMe | |
| $CH_2Cl$ | Me | OMe | |
| $CH_2Cl$ | H | $OCF_2H$ | |
| $CH_2Cl$ | Me | $OCF_2H$ | |
| $CHCl_2$ | H | Me | |
| $CHCl_2$ | Me | Me | |
| $CHCl_2$ | H | OMe | |
| $CHCl_2$ | Me | OMe | |
| $CHCl_2$ | H | $OCF_2H$ | |
| $CHCl_2$ | Me | $OCF_2H$ | |
| $CCl_3$ | H | Me | |
| $CCl_3$ | Me | Me | |
| $CCl_3$ | H | OMe | |
| $CCl_3$ | Me | OMe | |
| $CCl_3$ | H | $OCF_2H$ | |
| $CCl_3$ | Me | $OCF_2H$ | |
| $CHFCH_3$ | H | Me | |
| $CHFCH_3$ | Me | Me | |
| $CHFCH_3$ | H | OMe | |
| $CHFCH_3$ | Me | OMe | |
| $CHFCH_3$ | H | $OCF_2H$ | |
| $CHFCH_3$ | Me | $OCF_2H$ | |
| $CF_2CH_3$ | H | Me | |
| $CF_2CH_3$ | Me | Me | |
| $CF_2CH_3$ | H | OMe | |
| $CF_2CH_3$ | Me | OMe | |
| $CF_2CH_3$ | H | $OCF_2H$ | |
| $CF_2CH_3$ | Me | $OCF_2H$ | |
| $CH_2CH_2F$ | H | Me | |
| $CH_2CH_2F$ | Me | Me | |
| $CH_2CH_2F$ | H | OMe | |
| $CH_2CH_2F$ | Me | OMe | |
| $CH_2CH_2F$ | H | $OCF_2H$ | |
| $CH_2CH_2F$ | Me | $OCF_2H$ | |
| $CH_2CHF_2$ | H | Me | |
| $CH_2CHF_2$ | Me | Me | |
| $CH_2CHF_2$ | H | OMe | |
| $CH_2CHF_2$ | Me | OMe | |
| $CH_2CHF_2$ | H | $OCF_2H$ | |
| $CH_2CHF_2$ | Me | $OCF_2H$ | |

TABLE II-continued

$R_1 = Et$

| R₂ | R | Y | m.p. (°C.) |
|---|---|---|---|
| CH₂CF₃ | H | Me | |
| CH₂CF₃ | Me | Me | |
| CH₂CF₃ | H | OMe | |
| CH₂CF₃ | Me | OMe | |
| CH₂CF₃ | H | OCF₂H | |
| CH₂CF₃ | Me | OCF₂H | |
| CHClCH₃ | H | Me | |
| CHClCH₃ | Me | Me | |
| CHClCH₃ | H | OMe | |
| CHClCH₃ | Me | OMe | |
| CHClCH₃ | H | OCF₂H | |
| CHClCH₃ | Me | OCF₂H | |
| CH₂OCH₃ | H | Me | |
| CH₂OCH₃ | Me | Me | |
| CH₂OCH₃ | H | OMe | |
| CH₂OCH₃ | Me | OMe | |
| CH₂OCH₃ | H | OCF₂H | |
| CH₂OCH₃ | Me | OCF₂H | |
| (CH₂)₂OCH₃ | H | Me | |
| (CH₂)₂OCH₃ | Me | Me | |
| (CH₂)₂OCH₃ | H | OMe | |
| (CH₂)₂OCH₃ | Me | OMe | |
| (CH₂)₂OCH₃ | H | OCF₂H | |
| (CH₂)₂OCH₃ | Me | OCF₂H | |
| CH(OCH₃)CH₃ | H | Me | |
| CH(OCH₃)CH₃ | Me | Me | |
| CH(OCH₃)CH₃ | H | OMe | |
| CH(OCH₃)CH₃ | Me | OMe | |
| CH(OCH₃)CH₃ | H | OCF₂H | |
| CH(OCH₃)CH₃ | Me | OCF₂H | |
| CH₂SCH₃ | H | Me | |
| CH₂SCH₃ | Me | Me | |
| CH₂SCH₃ | H | OMe | |
| CH₂SCH₃ | Me | OMe | |
| CH₂SCH₃ | H | OCF₂H | |
| CH₂SCH₃ | Me | OCF₂H | |
| (CH₂)₂SCH₃ | H | Me | |
| (CH₂)₂SCH₃ | Me | Me | |
| (CH₂)₂SCH₃ | H | OMe | |
| (CH₂)₂SCH₃ | Me | OMe | |
| (CH₂)₂SCH₃ | H | OCF₂H | |
| (CH₂)₂SCH₃ | Me | OCF₂H | |
| CH(SCH₃)CH₃ | H | Me | |
| CH(SCH₃)CH₃ | Me | Me | |
| CH(SCH₃)CH₃ | H | OMe | |
| CH(SCH₃)CH₃ | Me | OMe | |
| CH(SCH₃)CH₃ | H | OCF₂H | |
| CH(SCH₃)CH₃ | Me | OCF₂H | |
| OCF₂H | H | Me | |
| OCF₂H | Me | Me | |
| OCF₂H | H | OMe | |
| OCF₂H | Me | OMe | |
| OCF₂H | H | OCF₂H | |
| OCF₂H | Me | OCF₂H | |
| OCH₂CH₂F | H | Me | |
| OCH₂CH₂F | Me | Me | |
| OCH₂CH₂F | H | OMe | |
| OCH₂CH₂F | Me | OMe | |
| OCH₂CH₂F | H | OCF₂H | |
| OCH₂CH₂F | Me | OCF₂H | |
| OCH₂CHF₂ | H | Me | |
| OCH₂CHF₂ | Me | Me | |
| OCH₂CHF₂ | H | OMe | |
| OCH₂CHF₂ | Me | OMe | |
| OCH₂CHF₂ | H | OCF₂H | |
| OCH₂CHF₂ | Me | OCF₂H | |
| OCH₂CF₃ | H | Me | |
| OCH₂CF₃ | Me | Me | |
| OCH₂CF₃ | H | OMe | |
| OCH₂CF₃ | Me | OMe | |
| OCH₂CF₃ | H | OCF₂H | |
| OCH₂CF₃ | Me | OCF₂H | |
| O(CH₂)₂Cl | H | Me | |
| O(CH₂)₂Cl | Me | Me | |
| O(CH₂)₂Cl | H | OMe | |
| O(CH₂)₂Cl | Me | OMe | |
| O(CH₂)₂Cl | H | OCF₂H | |
| O(CH₂)₂Cl | Me | OCF₂H | |
| S(O)Me | H | Me | |
| S(O)Me | Me | Me | |
| S(O)Me | H | OMe | |
| S(O)Me | Me | OMe | |
| S(O)Me | H | OCF₂H | |
| S(O)Me | Me | OCF₂H | |
| S(O)Et | H | Me | |
| S(O)Et | Me | Me | |
| S(O)Et | H | OMe | |
| S(O)Et | Me | OMe | |
| S(O)Et | H | OCF₂H | |
| S(O)Et | Me | OCF₂H | |
| S(O)—n-Pr | H | Me | 105–110 |
| S(O)—n-Pr | Me | Me | |
| S(O)—n-Pr | H | OMe | 85–91 |
| S(O)—n-Pr | Me | OMe | |
| S(O)—n-Pr | H | OCF₂H | |
| S(O)—n-Pr | Me | OCF₂H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF₂H | |
| S(O)—i-Pr | Me | OCF₂H | |
| SO₂Me | H | Me | |
| SO₂Me | Me | Me | |
| SO₂Me | H | OMe | |
| SO₂Me | Me | OMe | |
| SO₂Me | H | OCF₂H | |
| SO₂Me | Me | OCF₂H | |
| SO₂Et | H | Me | |
| SO₂Et | Me | Me | |
| SO₂Et | H | OMe | |
| SO₂Et | Me | OMe | |
| SO₂Et | H | OCF₂H | |
| SO₂Et | Me | OCF₂H | |
| SO₂—n-Pr | H | Me | |
| SO₂—n-Pr | Me | Me | |
| SO₂—n-Pr | H | OMe | |
| SO₂—n-Pr | Me | OMe | |
| SO₂—n-Pr | H | OCF₂H | |
| SO₂—n-Pr | Me | OCF₂H | |
| SO₂—i-Pr | H | Me | |
| SO₂—i-Pr | Me | Me | |
| SO₂—i-Pr | H | OMe | |
| SO₂—i-Pr | Me | OMe | |
| SO₂—i-Pr | H | OCF₂H | |
| SO₂—i-Pr | Me | OCF₂H | |
| S—allyl | H | Me | |
| S—allyl | Me | Me | |
| S—allyl | H | OMe | |
| S—allyl | Me | OMe | |
| S—allyl | H | OCF₂H | |
| S—allyl | Me | OCF₂H | |
| S(O)allyl | H | Me | |
| S(O)allyl | Me | Me | |
| S(O)allyl | H | OMe | |
| S(O)allyl | Me | OMe | |
| S(O)allyl | H | OCF₂H | |
| S(O)allyl | Me | OCF₂H | |
| SO₂allyl | H | Me | |
| SO₂allyl | Me | Me | |
| SO₂allyl | H | OMe | |
| SO₂allyl | Me | OMe | |
| SO₂allyl | H | OCF₂H | |
| SO₂allyl | Me | OCF₂H | |
| S—propargyl | H | Me | |
| S—propargyl | Me | Me | |
| S—propargyl | H | OMe | |
| S—propargyl | Me | OMe | |
| S—propargyl | H | OCF₂H | |
| S—propargyl | Me | OCF₂H | |
| S(O)propargyl | H | Me | |
| S(O)propargyl | Me | Me | |
| S(O)propargyl | H | OMe | |
| S(O)propargyl | Me | OMe | |
| S(O)propargyl | H | OCF₂H | |
| S(O)propargyl | Me | OCF₂H | |
| SO₂propargyl | H | Me | |
| SO₂propargyl | Me | Me | |

TABLE II-continued

| | $R_1$ = Et | | | |
|---|---|---|---|---|
| $R_2$ | R | Y | m.p. (°C.) | |
| $SO_2$propargyl | H | OMe | | |
| $SO_2$propargyl | Me | OMe | | |
| $SO_2$propargyl | H | $OCF_2H$ | | |
| $SO_2$propargyl | Me | $OCF_2H$ | | |

TABLE IIa

| | $R_1$ = Et | | |
|---|---|---|---|
| $R_2$ | R | Y | m.p. (°C.) |
| $CH_2OCH_2CH_3$ | H | Me | |
| $CH_2OCH_2CH_3$ | H | OMe | |
| $CH_2OCH_2CH_3$ | H | $OCF_2H$ | |
| $(CH_2)_2OCH_2CH_3$ | H | Me | |
| $(CH_2)_2OCH_2CH_3$ | H | OMe | |
| $(CH_2)_2OCH_2CH_3$ | H | $OCF_2H$ | |
| $(CH_2)_2OCH_2CH_3$ | $CH_3$ | Me | |
| $CH(CH_3)OCH_2CH_3$ | H | Me | |
| $CH(CH_3)OCH_2CH_3$ | H | OMe | |
| $CH(CH_3)OCH_2CH_3$ | H | $OCF_2H$ | |
| $CH_2OCH_2CF_3$ | H | Me | |
| $CH_2OCH_2CF_3$ | H | OMe | |
| $CH_2OCH_2CF_3$ | H | $OCF_2H$ | |
| $(CH_2)_2OCH_2CF_2H$ | H | Me | |
| $(CH_2)_2OCH_2CF_3$ | H | OMe | |
| $CH_2OCF_2H$ | H | $OCF_2H$ | |
| $CH_2OCH_2CH_2F$ | $CH_3$ | OMe | |
| $CH_2OCH_2CHF_2$ | H | Me | |
| $CH_2OCH_2CH_2Br$ | H | OMe | |
| $CH_2OCH_2CH_2Cl$ | H | $OCF_2H$ | |
| $CH_2OCH_2CH_2I$ | H | Me | |
| $CH_2OCF_3$ | H | OMe | |
| $CH_2SCH_2CH_3$ | H | $OCF_2H$ | |
| $CH_2SCH_2CH_3$ | H | Me | |
| $CH_2SCH_2CH_3$ | H | OMe | |
| $(CH_2)_2SCH_2CH_3$ | H | $OCF_2H$ | |
| $(CH_2)_2SCH_2CH_3$ | $CH_3$ | $OCF_2H$ | |
| $(CH_2)_2SCH_2CH_3$ | H | Me | |
| $(CH_2)_2SCH_2CH_3$ | H | OMe | |
| $CH(CH_3)SCH_2CH_3$ | H | $OCF_2H$ | |
| $CH(CH_3)SCH_2CH_3$ | H | Me | |
| $CH(CH_3)SCH_2CH_3$ | H | OMe | |
| $CH_2SCH_2CF_3$ | H | $OCF_2H$ | |
| $CH_2SCH_2CF_3$ | H | Me | |
| $CH_2SCH_2CF_3$ | H | OMe | |
| $(CH_2)_2SCH_2CF_2H$ | H | $OCF_2H$ | |
| $(CH_2)_2S(O)_2CH_3$ | H | Me | |
| $CH_2S(O)_2CH_2CH_3$ | H | OMe | |
| $CH_2S(O)_2CH_2CH_3$ | H | $OCF_2H$ | |
| $CH_2S(O)_2CH_2CH_3$ | H | Me | |
| $(CH_2)_2S(O)_2CH_2CH_3$ | H | OMe | |
| $CH(CH_3)S(O)_2CH_3$ | H | $OCF_2H$ | |
| $CH_2S(O)_2CH_2CF_3$ | $CH_3$ | Me | |
| $CH_2S(O)_2CH_2CF_3$ | H | Me | |
| $CH_2S(O)_2CH_2CF_3$ | H | OMe | |
| $CH_2S(O)_2CH_2CF_3$ | H | $OCF_2H$ | |
| $(CH_2)_2S(O)_2CH_2CF_2H$ | H | Me | |
| $(CH_2)_2S(O)_2CH_2CF_3$ | H | OMe | |
| $CH_2S(O)_2CF_2H$ | H | $OCF_2H$ | |
| $CH_2S(O)_2CH_2CH_2F$ | H | Me | |
| $CH_2S(O)_2CH_2CHF_2$ | H | OMe | |
| $CH_2S(O)_2CH_2CH_2Br$ | H | $OCF_2H$ | |
| $CH_2S(O)_2CH_2CH_2I$ | $CH_3$ | OMe | |
| $CH_2S(O)_2CF_3$ | H | Me | |
| $CH_2S(O)_2CH_2Cl$ | H | OMe | |
| $OCH_2OCH_3$ | H | $OCF_2H$ | |
| $OCH_2OCH_3$ | H | Me | |
| $OCH_2OCH_3$ | H | OMe | |
| $O(CH_2)_2OCH_3$ | H | $OCF_2H$ | |
| $O(CH_2)_2OCH_3$ | H | Me | |
| $O(CH_2)_2OCH_3$ | H | OMe | |
| $O(CH_2)_2OCH_2CH_3$ | H | $OCF_2H$ | |
| $O(CH_2)_2OCH_2CH_3$ | $CH_3$ | $OCF_2H$ | |
| $O(CH_2)_2OCH_2CH_3$ | H | Me | |
| $O(CH_2)_2OCH_2CH_3$ | H | OMe | |
| $OCH_2OCH_2CH_3$ | H | $OCF_2H$ | |
| $(CH_2)_2SCH_2CF_3$ | H | Me | |
| $CH_2SCF_2H$ | H | OMe | |
| $CH_2SCH_2CH_2F$ | H | $OCF_2H$ | |

TABLE IIa-continued

| | $R_1$ = Et | | |
|---|---|---|---|
| $R_2$ | R | Y | m.p. (°C.) |
| $CH_2SCH_2CHF_2$ | H | Me | |
| $CH_2SCH_2CH_2Br$ | H | OMe | |
| $CH_2SCH_2CH_2Cl$ | H | $OCF_2H$ | |
| $CH_2SCH_2CH_2I$ | $CH_3$ | Me | |
| $CH_2SCF_3$ | H | Me | |
| $CH_2S(O)CH_3$ | H | OMe | |
| $CH_2S(O)CH_3$ | H | $OCF_2H$ | |
| $CH_2S(O)CH_3$ | H | Me | |
| $(CH_2)_2S(O)CH_3$ | H | OMe | |
| $(CH_2)_2S(O)CH_3$ | H | $OCF_2H$ | |
| $(CH_2)_2S(O)CH_3$ | H | Me | |
| $CH_2S(O)CH_2CH_3$ | H | OMe | |
| $CH_2S(O)CH_2CH_3$ | H | $OCF_2H$ | |
| $CH_2S(O)CH_2CH_3$ | $CH_3$ | OMe | |
| $CH_2S(O)CH_2CH_3$ | H | Me | |
| $(CH_2)_2S(O)CH_2CH_3$ | H | OMe | |
| $CH(CH_3)S(O)CH_3$ | H | $OCF_2H$ | |
| $CH_2S(O)CH_2CF_3$ | H | Me | |
| $CH_2S(O)CH_2CF_3$ | H | OMe | |
| $CH_2S(O)CH_2CF_3$ | H | $OCF_2H$ | |
| $(CH_2)_2S(O)CH_2CF_2H$ | H | Me | |
| $(CH_2)_2S(O)CH_2CF_3$ | H | OMe | |
| $CH_2S(O)CF_2H$ | H | $OCF_2H$ | |
| $CH_2S(O)CH_2CH_2F$ | $CH_3$ | $OCF_2H$ | |
| $CH_2S(O)CH_2CHF_2$ | H | Me | |
| $CH_2S(O)CH_2CH_2Br$ | H | OMe | |
| $CH_2S(O)CH_2CH_2I$ | H | $OCF_2H$ | |
| $CH_2S(O)CF_3$ | H | Me | |
| $CH_2S(O)_2CH_3$ | H | OMe | |
| $CH_2S(O)_2CH_3$ | H | $OCF_2H$ | |
| $CH_2S(O)_2CH_3$ | H | Me | |
| $(CH_2)_2S(O)_2CH_3$ | H | OMe | |
| $(CH_2)_2S(O)_2CH_3$ | H | $OCF_2H$ | |
| $OCH_2OCH_2CF_3$ | H | Me | |
| $O(CH_2)_2OCH_2CF_3$ | H | OMe | |
| $O(CH_2)_2OCH_2CF_2H$ | H | $OCF_2H$ | |
| $O(CH_2)_2O(CH_2)_2Cl$ | H | Me | |
| $O(CH_2)_2O(CH_2)_2Br$ | H | OMe | |
| $O(CH_2)_2O(CH_2)_2I$ | H | $OCF_2H$ | |
| $O(CH_2)_2OCF_3$ | H | Me | |
| $OCH_2SCH_3$ | H | OMe | |
| $OCH_2SCH_3$ | H | $OCF_2H$ | |
| $OCH_2SCH_3$ | H | Me | |
| $O(CH_2)_2SCH_3$ | H | OMe | |
| $O(CH_2)_2SCH_3$ | H | $OCF_2H$ | |
| $O(CH_2)_2SCH_3$ | $CH_3$ | Me | |
| $O(CH_2)_2SCH_3$ | H | Me | |
| $O(CH_2)_2SCH_2CH_3$ | H | OMe | |
| $O(CH_2)_2SCH_2CH_3$ | H | $OCF_2H$ | |
| $O(CH_2)_2SCH_2CH_3$ | H | Me | |
| $OCH_2SCH_2CH_3$ | H | OMe | |
| $OCH_2SCH_2CF_3$ | H | $OCF_2H$ | |
| $O(CH_2)_2SCH_2CF_3$ | H | Me | |
| $O(CH_2)_2SCH_2CF_2H$ | H | OMe | |
| $O(CH_2)_2S(CH_2)_2Cl$ | H | $OCF_2H$ | |
| $O(CH_2)_2S(CH_2)_2Br$ | $CH_3$ | OMe | |
| $O(CH_2)_2S(CH_2)_2I$ | H | Me | |
| $O(CH_2)_2SCF_3$ | H | OMe | |
| $OCH_2S(O)CH_3$ | H | $OCF_2H$ | |
| $OCH_2S(O)CH_3$ | H | Me | |
| $OCH_2S(O)CH_3$ | H | OMe | |
| $O(CH_2)_2S(O)CH_3$ | H | $OCF_2H$ | |
| $O(CH_2)_2S(O)CH_3$ | H | Me | |
| $O(CH_2)_2S(O)CH_3$ | H | OMe | |
| $O(CH_2)_2S(O)CH_2CH_3$ | H | $OCF_2H$ | |
| $O(CH_2)_2S(O)CH_2CH_3$ | $CH_3$ | $OCF_2H$ | |
| $O(CH_2)_2S(O)CH_2CH_3$ | H | Me | |
| $OCH_2S(O)CH_2CH_3$ | H | OMe | |
| $O(CH_2)_2S(O)CH_2CF_3$ | H | $OCF_2H$ | |
| $OCH_2S(O)CH_2CF_3$ | H | Me | |
| $O(CH_2)_2S(O)CH_2CF_2H$ | H | OMe | |
| $O(CH_2)_2S(O)(CH_2)_2Cl$ | H | $OCF_2H$ | |
| $O(CH_2)_2S(O)(CH_2)_2Br$ | H | Me | |
| $O(CH_2)_2S(O)(CH_2)_2I$ | H | OMe | |
| $O(CH_2)_2S(O)CF_3$ | H | $OCF_2H$ | |
| $OCH_2S(O)_2CH_3$ | H | Me | |
| $OCH_2S(O)_2CH_3$ | H | OMe | |
| $OCH_2S(O)_2CH_3$ | H | $OCF_2H$ | |
| $O(CH_2)_2S(O)_2CH_3$ | H | Me | |

TABLE IIa-continued

R₁ = Et

| R2 | R | Y | m.p. (°C.) |
|---|---|---|---|
| O(CH₂)₂S(O)₂CH₃ | H | OMe | |
| O(CH₂)₂S(O)₂CH₃ | H | OCF₂H | |
| O(CH₂)₂S(O)₂CH₂CH₃ | CH₃ | Me | |
| O(CH₂)₂S(O)₂CH₂CH₃ | H | Me | |
| O(CH₂)₂S(O)₂CH₂CH₃ | H | OMe | |
| O(CH₂)₂S(O)₂CH₂CH₃ | H | OCF₂H | |
| OCH₂S(O)₂CH₂CH₃ | H | Me | |
| OCH₂S(O)₂CH₂CF₃ | H | OMe | |
| O(CH₂)₂S(O)₂CH₂CF₃ | H | OCF₂H | |
| O(CH₂)₂S(O)₂CH₂CF₂H | H | Me | |
| O(CH₂)₂S(O)₂(CH₂)₂Cl | H | OMe | |
| O(CH₂)₂S(O)₂(CH₂)₂Br | H | OCF₂H | |
| O(CH₂)₂S(O)₂(CH₂)₂I | CH₃ | OMe | |
| O(CH₂)₂S(O)₂CF₃ | H | Me | |
| OCH₂S(O)₂CH₂Cl | H | OMe | |
| OCH₂S(O)₂CF₃ | H | OCF₂H | |
| O(CH₂)₂CN | H | Me | |
| O(CH₂)₂CN | H | OMe | |
| O(CH₂)₂CN | H | OCF₂H | |
| OCH₂CN | H | Me | |
| OCH₂CN | H | OMe | |
| OCH₂CN | H | OCF₂H | |
| OCH₂CN | CH₃ | OCF₂H | |
| OCH(CH₃)CN | H | Me | |
| O(CH₂)₂NH₂ | H | OMe | |
| O(CH₂)₂NH₂ | H | OCF₂H | |
| O(CH₂)₂NH₂ | H | Me | |
| O(CH₂)₂NHCH₃ | H | OMe | |
| O(CH₂)₂NHCH₃ | H | OCF₂H | |
| O(CH₂)₂NHCH₃ | H | Me | |
| O(CH₂)₂N(CH₃)₂ | H | OMe | |
| O(CH₂)₂N(CH₃)₂ | H | OCF₂H | |
| O(CH₂)₂N(CH₃)₂ | H | Me | |
| SCH₂OCH₃ | H | OMe | |
| SCH₂OCH₃ | H | OCF₂H | |
| SCH₂OCH₃ | H | Me | |
| SCH₂OCH₂CH₃ | H | OMe | |
| S(CH₂)₂OCH₃ | H | OCF₂H | |
| S(CH₂)₂OCH₃ | CH₃ | Me | |
| S(CH₂)₂OCH₃ | H | Me | |
| S(CH₂)₂OCH₃ | H | OMe | |
| S(CH₂)₂OCH₂CH₃ | H | OCF₂H | |
| S(CH₂)₂OCH₂CF₃ | H | Me | |
| SCH₂OCH₂CF₃ | H | OMe | |
| S(CH₂)₂OCH₂CF₂H | H | OCF₂H | |
| S(CH₂)₂O(CH₂)₂Cl | H | Me | |
| S(CH₂)₂O(CH₂)₂Br | H | OMe | |
| S(CH₂)₂O(CH₂)₂I | H | OCF₂H | |
| S(CH₂)₂OCF₃ | CH₃ | OMe | |
| SCH₂SCH₃ | H | Me | |
| SCH₂SCH₃ | H | OMe | |
| SCH₂SCH₃ | H | OCF₂H | |
| SCH₂SCH₂CH₃ | H | Me | |
| S(CH₂)₂SCH₃ | H | OMe | |
| S(CH₂)₂SCH₃ | H | OCF₂H | |
| S(CH₂)₂SCH₃ | H | Me | |
| S(CH₂)₂SCH₂CH₃ | H | OMe | |
| SCH(CH₃)SCH₃ | H | OCF₂H | |
| S(CH₂)₂SCH₂CF₂ | CH₃ | OCF₂H | |
| SCH₂SCH₂CF₃ | H | Me | |
| S(CH₂)₂SCH₂CF₂H | H | OMe | |
| S(CH₂)₂S(CH₂)₂Cl | H | OCF₂H | |
| S(CH₂)₂S(CH₂)₂Br | H | Me | |
| S(CH₂)₂S(CH₂)₂I | H | OMe | |
| S(CH₂)₂SCF₃ | H | OCF₂H | |
| SCH₂CN | H | Me | |
| SCH₂CN | H | OMe | |
| SCH₂CN | H | OCF₂H | |
| S(CH₂)₂CN | H | Me | |
| S(CH₂)₂CN | H | OMe | |
| S(CH₂)₂CN | H | OCF₂H | |
| SCH(CH₃)CN | H | Me | |
| SCHF₂ | H | OMe | |
| SCHF₂ | H | OCF₂H | |
| SCHF₂ | CH₃ | Me | |
| SCHF₂ | H | Me | |
| SCF₃ | H | OMe | |
| SCH₂CFH₂ | H | OCF₂H | |
| SCH₂CF₂H | H | Me | |
| SCH₂CF₃ | H | OMe | |
| SCH₂CF₃ | H | OCF₂H | |
| SCH₂CF₃ | H | Me | |
| SCH₂CF₂H | H | OMe | |
| S(CH₂)₂CFH₂ | H | OCF₂H | |
| S(CH₂)₂CClH₂ | CH₃ | OMe | |
| S(CH₂)₂CIH₂ | H | Me | |
| SCF₂CF₃ | H | OMe | |
| SCH(CH₃)CF₃ | H | OCF₂H | |
| S(CH₂)₂CCl₃ | H | Me | |
| S(O)CHF₂ | H | OMe | |
| S(O)CHF₂ | H | OCF₂H | |
| S(O)CHF₂ | H | Me | |
| S(O)CF₃ | H | OMe | |
| S(O)CH₂CFH₂ | H | OCF₂H | |
| S(O)CH₂CF₂H | CH₃ | OCF₂H | |
| S(O)CH₂CF₃ | H | Me | |
| S(O)CH₂CF₃ | H | OMe | |
| S(O)CH₂CF₃ | H | OCF₂H | |
| S(O)CH₂CF₂H | H | Me | |
| S(O)(CH₂)₂CFH₂ | H | OMe | |
| S(O)(CH₂)₂CClH₂ | H | OCF₂H | |
| S(O)(CH₂)₂CIH₂ | H | Me | |
| S(O)CF₂CF₃ | H | OMe | |
| S(O)CH(CH₃)CF₃ | H | OCF₂H | |
| S(O)(CH₂)₂CCl₃ | H | Me | |
| S(O)₂CHF₂ | H | OMe | |
| S(O)₂CHF₂ | H | OCF₂H | |
| S(O)₂CHR₂ | H | Me | |
| S(O)₂CF₃ | H | OMe | |
| S(O)₂CH₂CFH₂ | H | OCF₂H | |
| S(O)₂CH₂CF₂H | CH₃ | Me | |
| S(O)₂CH₂CF₃ | H | Me | |
| S(O)₂CH₂CF₃ | H | OMe | |
| S(O)₂CH₂CF₃ | H | OCF₂H | |
| S(O)₂CH₂CF₂H | H | Me | |
| S(O)₂(CH₂)₂CFH₂ | H | OMe | |
| S(O)₂(CH₂)₂CClH₂ | H | OCF₂H | |
| S(O)₂(CH₂)₂CIH₂ | H | Me | |
| S(O)₂CF₂CF₃ | H | OMe | |
| S(O)₂CH(CH₃)CF₃ | H | OCF₂H | |
| S(O)₂(CH₂)₂CCl₃ | CH₃ | OMe | |
| S(O)₂CH₂Cl | H | Me | |
| CH=CH₂ | H | OMe | |
| CH=CH₂ | H | OCF₂H | |
| CH=CH₂ | H | Me | |
| CH₂CH=CH₂ | H | OMe | |
| CH₂CH=CH₂ | H | OCF₂H | |
| CH₂CH=CH₂ | H | Me | |
| CH=CHCH₃ | H | OMe | |
| C(CH₃)=CH₂ | H | OCF₂H | |
| CH=CH₂ | CH₃ | OCF₂H | |
| C≡CH | H | Me | |
| C≡CH | H | OMe | |
| C≡CH | H | OCF₂H | |
| CH₂C≡CH | H | Me | |
| CH₂C≡CH | H | OMe | |
| CH₂C≡CH | H | OCF₂H | |
| C≡CCH₃ | H | Me | |
| C≡CCH₃ | H | OMe | |
| C≡CCH₃ | H | OCF₂H | |
| NH₂ | H | Me | |
| NH₂ | H | OMe | |
| NH₂ | H | OCF₂H | |
| NHCH₃ | H | Me | |
| NHCH₃ | H | OMe | |
| NHCH₃ | H | OCF₂H | |
| NHCH₃ | CH₃ | Me | |
| N(CH₃)₂ | H | Me | |
| N(CH₃)₂ | H | OMe | |
| N(CH₃)₂ | H | OCF₂H | |
| NHCH₂CH₃ | H | Me | |
| NHCH₂CH₃ | H | OMe | |
| NHCH₂CH₃ | H | OCF₂H | |
| N(CH₃)CH₂CH₃ | H | Me | |
| N(CH₂CH₃)₂ | H | OMe | |
| NHCH₂CF₃ | H | OCF₂H | |
| NHCH₂CF₃ | CH₃ | OMe | |
| NHCH₂CF₃ | H | Me | |

TABLE IIa-continued $R_1 = Et$

| R₂ | R | Y | m.p. (°C.) |
|---|---|---|---|
| NHCH₂CF₃ | H | OMe | |
| N(CH₃)CH₂CF₃ | H | OCF₂H | |
| N(CH₃)CH₂CHF₂ | H | Me | |
| N(CH₃)(CH₂)₂F | H | OMe | |
| N(CH₃)(CH₂)₂Cl | H | OCF₂H | |
| N(CH₃)(CH₂)₂I | H | Me | |
| N(CH₃)(CH₂)₂Br | H | OMe | |
| NHCF₃ | CH₃ | OCF₂H | |
| NHCF₃ | H | Me | |
| NH(CH₂)₂F | H | OMe | |
| N(CH₃)CF₂H | H | OCF₂H | |
| NHCF₂H | H | Me | |

TABLE III $R_1 = n\text{-Pr}$

| R₂ | R | Y | m.p. (°C.) |
|---|---|---|---|
| Me | H | Me | |
| Me | Me | Me | |
| Me | H | OMe | |
| Me | Me | OMe | |
| Me | H | OCF₂H | |
| Me | Me | OCF₂H | |
| Et | H | Me | |
| Et | Me | Me | |
| Et | H | OMe | |
| Et | Me | OMe | |
| Et | H | OCF₂H | |
| Et | Me | OCF₂H | |
| n-Pr | H | Me | |
| n-Pr | Me | Me | |
| n-Pr | H | OMe | |
| n-Pr | Me | OMe | |
| n-Pr | H | OCF₂H | |
| n-Pr | Me | OCF₂H | |
| i-Pr | H | Me | |
| i-Pr | Me | Me | |
| i-Pr | H | OMe | |
| i-Pr | Me | OMe | |
| i-Pr | H | OCF₂H | |
| i-Pr | Me | OCF₂H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF₂H | |
| cyclo-Pr | Me | OCF₂H | |
| OMe | H | Me | |
| OMe | Me | Me | |
| OMe | H | OMe | |
| OMe | Me | OMe | |
| OMe | H | OCF₂H | |
| OMe | Me | OCF₂H | |
| OEt | H | Me | |
| OEt | Me | Me | |
| OEt | H | OMe | |
| OEt | Me | OMe | |
| OEt | H | OCF₂H | |
| OEt | Me | OCF₂H | |
| O—n-Pr | H | Me | |
| O—n-Pr | Me | Me | |
| O—n-Pr | H | OMe | |
| O—n-Pr | Me | OMe | |
| O—n-Pr | H | OCF₂H | |
| O—n-Pr | Me | OCF₂H | |
| O—i-Pr | H | Me | |
| O—i-Pr | Me | Me | |
| O—i-Pr | H | OMe | |
| O—i-Pr | Me | OMe | |
| O—i-Pr | H | OCF₂H | |
| O—i-Pr | Me | OCF₂H | |
| SMe | H | Me | |
| SMe | Me | Me | |
| SMe | H | OMe | 117-121 |
| SMe | Me | OMe | |
| SMe | H | OCF₂H | |
| SMe | Me | OCF₂H | |
| SEt | H | Me | |
| SEt | Me | Me | |
| SEt | H | OMe | |
| SEt | Me | OMe | |
| SEt | H | OCF₂H | |
| SEt | Me | OCF₂H | |
| S—n-Pr | -n-Pr | H | Me |
| S—n-Pr | -n-Pr | Me | Me |
| S—n-Pr | -n-Pr | H | OMe |
| S—n-Pr | -n-Pr | Me | OMe |
| S—n-Pr | -n-Pr | H | OCF₂H |
| S—n-Pr | -n-Pr | Me | OCF₂H |
| S—i-Pr | -i-Pr | H | Me |
| S—i-Pr | -i-Pr | Me | Me |
| S—i-Pr | -i-Pr | H | OMe |
| S—i-Pr | -i-Pr | Me | OMe |
| S—i-Pr | -i-Pr | H | OCF₂H |
| S—i-Pr | -i-Pr | Me | OCF₂H |
| O—allyl | H | Me | |
| O—allyl | Me | Me | |
| O—allyl | H | OMe | |
| O—allyl | Me | OMe | |
| O—allyl | H | OCF₂H | |
| O—allyl | Me | OCF₂H | |
| O—propargyl | H | Me | |
| O—propargyl | Me | Me | |
| O—propargyl | H | OMe | |
| O—propargyl | Me | OMe | |
| O—propargyl | H | OCF₂H | |
| O—propargyl | Me | OCF₂H | |
| CH₂F | H | Me | |
| CH₂F | Me | Me | |
| CH₂F | H | OMe | |
| CH₂F | Me | OMe | |
| CH₂F | H | OCF₂H | |
| CH₂F | Me | OCF₂H | |
| CHF₂ | H | Me | |
| CHF₂ | Me | Me | |
| CHF₂ | H | OMe | |
| CHF₂ | Me | OMe | |
| CHF₂ | H | OCF₂H | |
| CHF₂ | Me | OCF₂H | |
| CF₃ | H | Me | |
| CF₃ | Me | Me | |
| CF₃ | H | OMe | |
| CF₃ | Me | OMe | |
| CF₃ | H | OCF₂H | |
| CF₃ | Me | OCF₂H | |
| CH₂Cl | H | Me | |
| CH₂Cl | Me | Me | |
| CH₂Cl | H | OMe | |
| CH₂Cl | Me | OMe | |
| CH₂Cl | H | OCF₂H | |
| CH₂Cl | Me | OCF₂H | |
| CHCl₂ | H | Me | |
| CHCl₂ | Me | Me | |
| CHCl₂ | H | OMe | |
| CHCl₂ | Me | OMe | |
| CHCl₂ | H | OCF₂H | |
| CHCl₂ | Me | OCF₂H | |
| CCl₃ | H | Me | |
| CCl₃ | Me | Me | |
| CCl₃ | H | OMe | |
| CCl₃ | Me | OMe | |
| CCl₃ | H | OCF₂H | |
| CCl₃ | Me | OCF₂H | |
| CHFCH₃ | H | Me | |
| CHFCH₃ | Me | Me | |
| CHFCH₃ | H | OMe | |
| CHFCH₃ | Me | OMe | |
| CHFCH₃ | H | OCF₂H | |
| CHFCH₃ | Me | OCF₂H | |
| CF₂CH₃ | H | Me | |
| CF₂CH₃ | Me | Me | |
| CF₂CH₃ | H | OMe | |
| CF₂CH₃ | Me | OMe | |
| CF₂CH₃ | H | OCF₂H | |
| CF₂CH₃ | Me | OCF₂H | |
| CH₂CH₂F | H | Me | |
| CH₂CH₂F | Me | Me | |

TABLE III-continued

| | $R_1$ = n-Pr | | |
|---|---|---|---|
| $R_2$ | R | Y | m.p. (°C.) |
| $CH_2CH_2F$ | H | OMe | |
| $CH_2CH_2F$ | Me | OMe | |
| $CH_2CH_2F$ | H | $OCF_2H$ | |
| $CH_2CH_2F$ | Me | $OCF_2H$ | |
| $CH_2CHF_2$ | H | Me | |
| $CH_2CHF_2$ | Me | Me | |
| $CH_2CHF_2$ | H | OMe | |
| $CH_2CHF_2$ | Me | OMe | |
| $CH_2CHF_2$ | H | $OCF_2H$ | |
| $CH_2CHF_2$ | Me | $OCF_2H$ | |
| $CH_2CF_3$ | H | Me | |
| $CH_2CF_3$ | Me | Me | |
| $CH_2CF_3$ | H | OMe | |
| $CH_2CF_3$ | Me | OMe | |
| $CH_2CF_3$ | H | $OCF_2H$ | |
| $CH_2CF_3$ | Me | $OCF_2H$ | |
| $CHClCH_3$ | H | Me | |
| $CHClCH_3$ | Me | Me | |
| $CHClCH_3$ | H | OMe | |
| $CHClCH_3$ | Me | OMe | |
| $CHClCH_3$ | H | $OCF_2H$ | |
| $CHClCH_3$ | Me | $OCF_2H$ | |
| $CH_2OCH_3$ | H | Me | |
| $CH_2OCH_3$ | Me | Me | |
| $CH_2OCH_3$ | H | OHe | |
| $CH_2OCH_3$ | Me | OMe | |
| $CH_2OCH_3$ | H | $OCF_2H$ | |
| $CH_2OCH_3$ | Me | $OCF_2H$ | |
| $(CH_2)_2OCH_3$ | H | Me | |
| $(CH_2)_2OCH_3$ | Me | Me | |
| $(CH_2)_2OCH_3$ | H | OMe | |
| $(CH_2)_2OCH_3$ | Me | OMe | |
| $(CH_2)_2OCH_3$ | H | $OCF_2H$ | |
| $(CH_2)_2OCH_3$ | Me | $OCF_2H$ | |
| $CH(OCH_3)CH_3$ | H | Me | |
| $CH(OCH_3)CH_3$ | Me | Me | |
| $CH(OCH_3)CH_3$ | H | OMe | |
| $CH(OCH_3)CH_3$ | Me | OMe | |
| $CH(OCH_3)CH_3$ | H | $OCF_2H$ | |
| $CH(OCH_3)CH_3$ | Me | $OCF_2H$ | |
| $CH_2SCH_3$ | H | Me | |
| $CH_2SCH_3$ | Me | Me | |
| $CH_2SCH_3$ | H | OMe | |
| $CH_2SCH_3$ | Me | OMe | |
| $CH_2SCH_3$ | H | $OCF_2H$ | |
| $CH_2SCH_3$ | Me | $OCF_2H$ | |
| $(CH_2)_2SCH_3$ | H | Me | |
| $(CH_2)_2SCH_3$ | Me | Me | |
| $(CH_2)_2SCH_3$ | H | OMe | |
| $(CH_2)_2SCH_3$ | Me | OMe | |
| $(CH_2)_2SCH_3$ | H | $OCF_2H$ | |
| $(CH_2)_2SCH_3$ | Me | $OCF_2H$ | |
| $CH(SCH_3)CH_3$ | H | Me | |
| $CH(SCH_3)CH_3$ | Me | Me | |
| $CH(SCH_3)CH_3$ | H | OMe | |
| $CH(SCH_3)CH_3$ | Me | OMe | |
| $CH(SCH_3)CH_3$ | H | $OCF_2H$ | |
| $CH(SCH_3)CH_3$ | Me | $OCF_2H$ | |
| $OCF_2H$ | H | Me | |
| $OCF_2H$ | Me | Me | |
| $OCF_2H$ | H | OMe | |
| $OCF_2H$ | Me | OMe | |
| $OCF_2H$ | H | $OCF_2H$ | |
| $OCF_2H$ | Me | $OCF_2H$ | |
| $OCH_2CH_2F$ | H | Me | |
| $OCH_2CH_2F$ | Me | Me | |
| $OCH_2CH_2F$ | H | OMe | |
| $OCH_2CH_2F$ | Me | OMe | |
| $OCH_2CH_2F$ | H | $OCF_2H$ | |
| $OCH_2CH_2F$ | Me | $OCF_2H$ | |
| $OCH_2CHF_2$ | H | Me | |
| $OCH_2CHF_2$ | Me | Me | |
| $OCH_2CHF_2$ | H | OMe | |
| $OCH_2CHF_2$ | Me | OMe | |
| $OCH_2CHF_2$ | H | $OCF_2H$ | |
| $OCH_2CHF_2$ | Me | $OCF_2H$ | |
| $OCH_2CF_3$ | H | Me | |
| $OCH_2CF_3$ | Me | Me | |
| $OCH_2CF_3$ | H | OMe | |
| $OCH_2CF_3$ | Me | OMe | |
| $OCH_2CF_3$ | H | $OCF_2H$ | |
| $OCH_2CF_3$ | Me | $OCF_2H$ | |
| $O(CH_2)_2Cl$ | H | Me | |
| $O(CH_2)_2Cl$ | Me | Me | |
| $O(CH_2)_2Cl$ | H | OMe | |
| $O(CH_2)_2Cl$ | Me | OMe | |
| $O(CH_2)_2Cl$ | H | $OCF_2H$ | |
| $O(CH_2)_2Cl$ | Me | $OCF_2H$ | |
| S(O)Me | H | Me | |
| S(O)Me | Me | Me | |
| S(O)Me | H | OMe | |
| S(O)Me | Me | OMe | |
| S(O)Me | H | $OCF_2H$ | |
| S(O)Me | Me | $OCF_2H$ | |
| S(O)Et | H | Me | |
| S(O)Et | Me | Me | |
| S(O)Et | H | OMe | |
| S(O)Et | Me | OMe | |
| S(O)Et | H | $OCF_2H$ | |
| S(O)Et | Me | $OCF_2H$ | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | $OCF_2H$ | |
| S(O)—n-Pr | Me | $OCF_2H$ | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | $OCF_2H$ | |
| S(O)—i-Pr | Me | $OCF_2H$ | |
| $SO_2Me$ | H | Me | |
| $SO_2Me$ | Me | Me | |
| $SO_2Me$ | H | OMe | |
| $SO_2Me$ | Me | OMe | |
| $SO_2Me$ | H | $OCF_2H$ | |
| $SO_2Me$ | Me | $OCF_2H$ | |
| $SO_2Et$ | H | Me | |
| $SO_2Et$ | Me | Me | |
| $SO_2Et$ | H | OMe | |
| $SO_2Et$ | Me | OMe | |
| $SO_2Et$ | H | $OCF_2H$ | |
| $SO_2Et$ | Me | $OCF_2H$ | |
| $SO_2$—n-Pr | H | Me | |
| $SO_2$—n-Pr | Me | Me | |
| $SO_2$—n-Pr | H | OMe | |
| $SO_2$—n-Pr | Me | OMe | |
| $SO_2$—n-Pr | H | $OCF_2H$ | |
| $SO_2$—n-Pr | Me | $OCF_2H$ | |
| $SO_2$—i-Pr | H | Me | |
| $SO_2$—i-Pr | Me | Me | |
| $SO_2$—i-Pr | H | OMe | |
| $SO_2$—i-Pr | Me | OMe | |
| $SO_2$—i-Pr | H | $OCF_2H$ | |
| $SO_2$—i-Pr | Me | $OCF_2H$ | |
| S—allyl | H | Me | |
| S—allyl | Me | Me | |
| S—allyl | H | OMe | |
| S—allyl | Me | OMe | |
| S—allyl | H | $OCF_2H$ | |
| S—allyl | Me | $OCF_2H$ | |
| S(O)allyl | H | Me | |
| S(O)allyl | Me | Me | |
| S(O)allyl | H | OMe | |
| S(O)allyl | Me | OMe | |
| S(O)allyl | H | $OCF_2H$ | |
| S(O)allyl | Me | $OCF_2H$ | |
| $SO_2$allyl | H | Me | |
| $SO_2$allyl | Me | Me | |
| $SO_2$allyl | H | OMe | |
| $SO_2$allyl | Me | OMe | |
| $SO_2$allyl | H | $OCF_2H$ | |
| $SO_2$allyl | Me | $OCF_2H$ | |
| S—propargyl | H | Me | |
| S—propargyl | Me | Me | |
| S—propargyl | H | OMe | |
| S—propargyl | Me | OMe | |

TABLE III-continued

| | $R_1 = $ n-Pr | | |
|---|---|---|---|
| R₂ | R | Y | m.p. (°C.) |
| S—propargyl | H | OCF₂H | |
| S—propargyl | Me | OCF₂H | |
| S(O)propargyl | H | Me | |
| S(O)propargyl | Me | Me | |
| S(O)propargyl | H | OMe | |
| S(O)propargyl | Me | OMe | |
| S(O)propargyl | H | OCF₂H | |
| S(O)propargyl | Me | OCF₂H | |
| SO₂propargyl | H | Me | |
| SO₂propargyl | Me | Me | |
| SO₂propargyl | H | OMe | |
| SO₂propargyl | Me | OMe | |
| SO₂propargyl | H | OCF₂H | |
| SO₂propargyl | Me | OCF₂H | |

TABLE IIIa

| | $R_1 = $ n-Pr | | |
|---|---|---|---|
| R₂ | R | Y | m.p. (°C.) |
| CH₂OCH₂CH₃ | H | Me | |
| CH₂OCH₂CH₃ | H | OMe | |
| CH₂OCH₂CH₃ | H | OCF₂H | |
| (CH₂)₂OCH₂CH₃ | H | Me | |
| (CH₂)₂OCH₂CH₃ | H | OMe | |
| (CH₂)₂OCH₂CH₃ | H | OCF₂H | |
| (CH₂)₂OCH₂CH₃ | CH₃ | Me | |
| CH(CH₃)OCH₂CH₃ | H | Me | |
| CH(CH₃)OCH₂CH₃ | H | OMe | |
| CH(CH₃)OCH₂CH₃ | H | OCF₂H | |
| CH₂OCH₂CH₃ | H | Me | |
| CH₂OCH₂CF₃ | H | OMe | |
| CH₂OCH₂CF₃ | H | OCF₂H | |
| (CH₂)₂OCH₂CF₂H | H | Me | |
| (CH₂)₂OCH₂CF₃ | H | OMe | |
| CH₂OCF₂H | H | OCF₂H | |
| CH₂OCH₂CH₂F | CH₃ | OMe | |
| CH₂OCH₂CHF₂ | H | Me | |
| CH₂OCH₂CH₂Br | H | OMe | |
| CH₂OCH₂CH₂Cl | H | OCF₂H | |
| CH₂OCH₂CH₂I | H | Me | |
| CH₂OCF₃ | H | OMe | |
| CH₂SCH₂CH₃ | H | OCF₂H | |
| CH₂SCH₂CH₃ | H | Me | |
| CH₂SCH₂CH₃ | H | OMe | |
| (CH₂)₂SCH₂CH₃ | H | OCF₂H | |
| (CH₂)₂SCH₂CH₃ | CH₃ | OCF₂H | |
| (CH₂)₂SCH₂CH₃ | H | Me | |
| (CH₂)₂SCH₂CH₃ | H | OMe | |
| CH(CH₃)SCH₂CH₃ | H | OCF₂H | |
| CH(CH₃)SCH₂CH₃ | H | Me | |
| CH(CH₃)SCH₂CH₃ | H | OMe | |
| CH₂SCH₂CF₃ | H | OCF₂H | |
| CH₂SCH₂CF₃ | H | Me | |
| CH₂SCH₂CF₃ | H | OMe | |
| (CH₂)₂SCH₂CF₂H | H | OCF₂H | |
| (CH₂)₂S(O)₂CH₃ | H | Me | |
| CH₂S(O)₂CH₂CH₃ | H | OMe | |
| CH₂S(O)₂CH₂CH₃ | H | OCF₂H | |
| CH₂S(O)₂CH₂CH₃ | H | Me | |
| (CH₂)₂S(O)₂CH₂CH₃ | H | OMe | |
| CH(CH₃)S(O)₂CH₃ | H | OCF₂H | |
| CH₂S(O)₂CH₂CF₃ | CH₃ | Me | |
| CH₂S(O)₂CH₂CF₃ | H | Me | |
| CH₂S(O)₂CH₂CF₃ | H | OMe | |
| CH₂S(O)₂CH₂CF₃ | H | OCF₂H | |
| (CH₂)₂S(O)₂CH₂CF₂H | H | Me | |
| (CH₂)₂S(O)₂CH₂CF₃ | H | OMe | |
| CH₂S(O)₂CF₂H | H | OCF₂H | |
| CH₂S(O)₂CH₂CH₂F | H | Me | |
| CH₂S(O)₂CH₂CHF₂ | H | OMe | |
| CH₂S(O)₂CH₂CH₂Br | H | OCF₂H | |
| CH₂S(O)₂CH₂CH₂I | CH₃ | OMe | |
| CH₂S(O)₂CF₃ | H | Me | |
| CH₂S(O)₂CH₂Cl | H | OMe | |
| OCH₂OCH₃ | H | OCF₂H | |
| OCH₂OCH₃ | H | Me | |
| OCH₂OCH₃ | H | OMe | |
| O(CH₂)₂OCH₃ | H | OCF₂H | |

TABLE IIIa-continued

| | $R_1 = $ n-Pr | | |
|---|---|---|---|
| R₂ | R | Y | m.p. (°C.) |
| O(CH₂)₂OCH₃ | H | Me | |
| O(CH₂)₂OCH₃ | H | OMe | |
| O(CH₂)₂OCH₂CH₃ | H | OCF₂H | |
| O(CH₂)₂OCH₂CH₃ | CH₃ | OCF₂H | |
| O(CH₂)₂OCH₂CH₃ | H | Me | |
| O(CH₂)₂OCH₂CH₃ | H | OMe | |
| OCH₂OCH₂CH₃ | H | OCF₂H | |
| (CH₂)₂SCH₂CF₃ | H | Me | |
| CH₂SCF₂H | H | OMe | |
| CH₂SCH₂CH₂F | H | OCF₂H | |
| CH₂SCH₂CHF₂ | H | Me | |
| CH₂SCH₂CH₂Br | H | OMe | |
| CH₂SCH₂CH₂Cl | H | OCF₂H | |
| CH₂SCH₂CH₂I | CH₃ | Me | |
| CH₂SCF₃ | H | Me | |
| CH₂S(O)CH₃ | H | OMe | |
| CH₂S(O)CH₃ | H | OCF₂H | |
| CH₂S(O)CH₃ | H | Me | |
| (CH₂)₂S(O)CH₃ | H | OMe | |
| (CH₂)₂S(O)CH₃ | H | OCF₂H | |
| (CH₂)₂S(O)CH₃ | H | Me | |
| CH₂S(O)CH₂CH₃ | H | OMe | |
| CH₂S(O)CH₂CH₃ | H | OCF₂H | |
| CH₂S(O)CH₂CH₃ | CH₃ | OMe | |
| CH₂S(O)CH₂CH₃ | H | Me | |
| (CH₂)₂S(O)CH₂CH₃ | H | OMe | |
| CH(CH₃)S(O)CH₃ | H | OCF₂H | |
| CH₂S(O)CH₂CF₃ | H | Me | |
| CH₂S(O)CH₂CF₃ | H | OMe | |
| CH₂S(O)CH₂CF₃ | H | OCF₂H | |
| (CH₂)₂S(O)CH₂CF₂H | H | Me | |
| (CH₂)₂S(O)CH₂CF₃ | H | OMe | |
| CH₂S(O)CF₂H | H | OCF₂H | |
| CH₂S(O)CH₂CH₂F | CH₃ | OCF₂H | |
| CH₂S(O)CH₂CHF₂ | H | Me | |
| CH₂S(O)CH₂CH₂Br | H | OMe | |
| CH₂S(O)CH₂CH₂I | H | OCF₂H | |
| CH₂S(O)CF₃ | H | Me | |
| CH₂S(O)₂CH₃ | H | OMe | |
| CH₂S(O)₂CH₃ | H | OCF₂H | |
| CH₂S(O)₂CH₃ | H | Me | |
| (CH₂)₂S(O)CH₃ | H | OMe | |
| (CH₂)₂S(O)CH₃ | H | OCF₂H | |
| OCH₂OCH₂CF₃ | H | Me | |
| O(CH₂)₂OCH₂CF₃ | H | OMe | |
| O(CH₂)₂OCH₂CF₂H | H | OCF₂H | |
| O(CH₂)₂O(CH₂)₂Cl | H | Me | |
| O(CH₂)₂O(CH₂)₂Br | H | OMe | |
| O(CH₂)₂O(CH₂)₂I | H | OCF₂H | |
| O(CH₂)₂OCF₃ | H | Me | |
| OCH₂SCH₃ | H | OMe | |
| OCH₂SCH₃ | H | OCF₂H | |
| OCH₂SCH₃ | H | Me | |
| O(CH₂)₂SCH₃ | H | OMe | |
| O(CH₂)₂SCH₃ | H | OCF₂H | |
| O(CH₂)₂SCH₃ | CH₃ | Me | |
| O(CH₂)₂SCH₃ | H | Me | |
| O(CH₂)₂SCH₂CH₃ | H | OMe | |
| O(CH₂)₂SCH₂CH₃ | H | OCF₂H | |
| O(CH₂)₂SCH₂CH₃ | H | Me | |
| OCH₂SCH₂CH₃ | H | OMe | |
| OCH₂SCH₂CF₃ | H | OCF₂H | |
| O(CH₂)₂SCH₂CF₃ | H | Me | |
| O(CH₂)₂SCH₂CF₂H | H | OMe | |
| O(CH₂)₂S(CH₂)₂Cl | H | OCF₂H | |
| O(CH₂)₂S(CH₂)₂Br | CH₃ | OMe | |
| O(CH₂)₂S(CH₂)₂I | H | Me | |
| O(CH₂)₂SCF₃ | H | OMe | |
| OCH₂S(O)CH₃ | H | OCF₂H | |
| OCH₂S(O)CH₃ | H | Me | |
| OCH₂S(O)CH₃ | H | OMe | |
| O(CH₂)₂S(O)CH₃ | H | OCF₂H | |
| O(CH₂)₂S(O)CH₃ | H | Me | |
| O(CH₂)₂S(O)CH₃ | H | OMe | |
| O(CH₂)₂S(O)CH₂CH₃ | H | OCF₂H | |
| O(CH₂)₂S(O)CH₂CH₃ | CH₃ | OCF₂H | |
| O(CH₂)₂S(O)CH₂CH₃ | H | Me | |
| OCH₂S(O)CH₂CH₃ | H | OMe | |
| O(CH₂)₂S(O)CH₂CF₃ | H | OCF₂H | |

TABLE IIIa-continued

| | $R_1$ = n-Pr | | |
|---|---|---|---|
| $R_2$ | R | Y | m.p. (°C.) |
| OCH$_2$S(O)CH$_2$CF$_3$ | H | Me | |
| O(CH$_2$)$_2$S(O)CH$_2$CF$_2$H | H | OMe | |
| O(CH$_2$)$_2$S(O)(CH$_2$)$_2$Cl | H | OCF$_2$H | |
| O(CH$_2$)$_2$S(O)(CH$_2$)$_2$Br | H | Me | |
| O(CH$_2$)$_2$S(O)(CH$_2$)$_2$I | H | OMe | |
| O(CH$_2$)$_2$S(O)CF$_3$ | H | OCF$_2$H | |
| OCH$_2$S(O)$_2$CH$_3$ | H | Me | |
| OCH$_2$S(O)$_2$CH$_3$ | H | OMe | |
| OCH$_2$S(O)$_2$CH$_3$ | H | OCF$_2$H | |
| O(CH$_2$)$_2$S(O)$_2$CH$_3$ | H | Me | |
| O(CH$_2$)$_2$S(O)$_2$CH$_3$ | H | OMe | |
| O(CH$_2$)$_2$S(O)$_2$CH$_3$ | H | OCF$_2$H | |
| O(CH$_2$)$_2$S(O)$_2$CH$_2$CH$_3$ | CH$_3$ | Me | |
| O(CH$_2$)$_2$S(O)$_2$CH$_2$CH$_3$ | H | Me | |
| O(CH$_2$)$_2$S(O)$_2$CH$_2$CH$_3$ | H | OMe | |
| O(CH$_2$)$_2$S(O)$_2$CH$_2$CH$_3$ | H | OCF$_2$H | |
| OCH$_2$S(O)$_2$CH$_2$CH$_3$ | H | Me | |
| OCH$_2$S(O)$_2$CH$_2$CF$_3$ | H | OMe | |
| O(CH$_2$)$_2$S(O)$_2$CH$_2$CF$_3$ | H | OCF$_2$H | |
| O(CH$_2$)$_2$S(O)$_2$CH$_2$CF$_2$H | H | Me | |
| O(CH$_2$)$_2$S(O)$_2$(CH$_2$)$_2$Cl | H | OMe | |
| O(CH$_2$)$_2$S(O)$_2$(CH$_2$)$_2$Br | H | OCF$_2$H | |
| O(CH$_2$)$_2$S(O)$_2$(CH$_2$)$_2$I | CH$_3$ | OMe | |
| O(CH$_2$)$_2$S(O)$_2$CF$_3$ | H | Me | |
| OCH$_2$S(O)$_2$CH$_2$Cl | H | OMe | |
| OCH$_2$S(O)$_2$CF$_3$ | H | OCF$_2$H | |
| O(CH$_2$)$_2$CN | H | Me | |
| O(CH$_2$)$_2$CN | H | OMe | |
| O(CH$_2$)$_2$CN | H | OCF$_2$H | |
| OCH$_2$CN | H | Me | |
| OCH$_2$CN | H | OMe | |
| OCH$_2$CN | H | OCF$_2$H | |
| OCH$_2$CN | CH$_3$ | OCF$_2$H | |
| OCH(CH$_3$)CN | H | Me | |
| O(CH$_2$)$_2$NH$_2$ | H | OMe | |
| O(CH$_2$)$_2$NH$_2$ | H | OCF$_2$H | |
| O(CH$_2$)$_2$NH$_2$ | H | Me | |
| O(CH$_2$)$_2$NHCH$_3$ | H | OMe | |
| O(CH$_2$)$_2$NHCH$_3$ | H | OCF$_2$H | |
| O(CH$_2$)$_2$NHCH$_3$ | H | Me | |
| O(CH$_2$)$_2$N(CH$_3$)$_2$ | H | OMe | |
| O(CH$_2$)$_2$N(CH$_3$)$_2$ | H | OCF$_2$H | |
| O(CH$_2$)$_2$N(CH$_3$)$_2$ | H | Me | |
| SCH$_2$OCH$_3$ | H | OMe | |
| SCH$_2$OCH$_3$ | H | OCF$_2$H | |
| SCH$_2$OCH$_3$ | H | Me | |
| SCH$_2$OCH$_2$CH$_3$ | H | OMe | |
| S(CH$_2$)$_2$OCH$_3$ | H | OCF$_2$H | |
| S(CH$_2$)$_2$OCH$_3$ | CH$_3$ | Me | |
| S(CH$_2$)$_2$OCH$_3$ | H | Me | |
| S(CH$_2$)$_2$OCH$_3$ | H | OMe | |
| S(CH$_2$)$_2$OCH$_2$CH$_3$ | H | OCF$_2$H | |
| S(CH$_2$)$_2$OCH$_2$CF$_3$ | H | Me | |
| SCH$_2$OCH$_2$CF$_3$ | H | OMe | |
| S(CH$_2$)$_2$OCH$_2$CF$_2$H | H | OCF$_2$H | |
| S(CH$_2$)$_2$O(CH$_2$)$_2$Cl | H | Me | |
| S(CH$_2$)$_2$O(CH$_2$)$_2$Br | H | OMe | |
| S(CH$_2$)$_2$O(CH$_2$)$_2$I | H | OCF$_2$H | |
| S(CH$_2$)$_2$OCF$_3$ | CH$_3$ | OMe | |
| SCH$_2$SCH$_3$ | H | Me | |
| SCH$_2$SCH$_3$ | H | OMe | |
| SCH$_2$SCH$_3$ | H | OCF$_2$H | |
| SCH$_2$SCH$_2$CH$_3$ | H | Me | |
| S(CH$_2$)$_2$SCH$_3$ | H | OMe | |
| S(CH$_2$)$_2$SCH$_3$ | H | OCF$_2$H | |
| S(CH$_2$)$_2$SCH$_3$ | H | Me | |
| S(CH$_2$)$_2$SCH$_2$CH$_3$ | H | OMe | |
| SCH(CH$_3$)SCH$_3$ | H | OCF$_2$H | |
| S(CH$_2$)$_2$SCH$_2$CF$_3$ | CH$_3$ | OCF$_2$H | |
| SCH$_2$SCH$_2$CF$_3$ | H | Me | |
| S(CH$_2$)$_2$SCH$_2$CF$_2$H | H | OMe | |
| S(CH$_2$)$_2$S(CH$_2$)$_2$Cl | H | OCF$_2$H | |
| S(CH$_2$)$_2$S(CH$_2$)$_2$Br | H | Me | |
| S(CH$_2$)$_2$S(CH$_2$)$_2$I | H | OMe | |
| S(CH$_2$)$_2$SCF$_3$ | H | OCF$_2$H | |
| SCH$_2$CN | H | Me | |
| SCH$_2$CN | H | OMe | |
| SCH$_2$CN | H | OCF$_2$H | |
| S(CH$_2$)$_2$CN | H | Me | |

| | $R_1$ = n-Pr | | |
|---|---|---|---|
| $R_2$ | R | Y | m.p. (°C.) |
| S(CH$_2$)$_2$CN | H | OMe | |
| S(CH$_2$)$_2$CN | H | OCF$_2$H | |
| SCH(CH$_3$)CN | H | Me | |
| SCHF$_2$ | H | OMe | |
| SCHF$_2$ | H | OCF$_2$H | |
| SCHF$_2$ | CH$_3$ | Me | |
| SCHF$_2$ | H | Me | |
| SCF$_3$ | H | OMe | |
| SCH$_2$CFH$_2$ | H | OCF$_2$H | |
| SCH$_2$CF$_2$H | H | Me | |
| SCH$_2$CF$_3$ | H | OMe | |
| SCH$_2$CF$_3$ | H | OCF$_2$H | |
| SCH$_2$CF$_3$ | H | Me | |
| SCH$_2$CF$_2$H | H | OMe | |
| S(CH$_2$)$_2$CFH$_2$ | H | OCF$_2$H | |
| S(CH$_2$)$_2$CClH$_2$ | CH$_3$ | OMe | |
| S(CH$_2$)$_2$ClH$_2$ | H | Me | |
| SCF$_2$CF$_3$ | H | OMe | |
| SCH(CH$_3$)CF$_3$ | H | OCF$_2$H | |
| S(CH$_2$)$_2$CCl$_3$ | H | Me | |
| S(O)CHF$_2$ | H | OMe | |
| S(O)CHF$_2$ | H | OCF$_2$H | |
| S(O)CHF$_2$ | H | Me | |
| S(O)CF$_3$ | H | OMe | |
| S(O)CH$_2$CFH$_2$ | H | OCF$_2$H | |
| S(O)CH$_2$CF$_2$H | CH$_3$ | OCF$_2$H | |
| S(O)CH$_2$CF$_3$ | H | Me | |
| S(O)CH$_2$CF$_3$ | H | OMe | |
| S(O)CH$_2$CF$_3$ | H | OCF$_2$H | |
| S(O)CH$_2$CF$_2$H | H | Me | |
| S(O)(CH$_2$)$_2$CFH$_2$ | H | OMe | |
| S(O)(CH$_2$)$_2$CClH$_2$ | H | OCF$_2$H | |
| S(O)(CH$_2$)$_2$ClH$_2$ | H | Me | |
| S(O)CF$_2$CF$_3$ | H | OMe | |
| S(O)CH(CH$_3$)CF$_3$ | H | OCF$_2$H | |
| S(O)(CH$_2$)$_2$CCl$_3$ | H | Me | |
| S(O)$_2$CHF$_2$ | H | OMe | |
| S(O)$_2$CHF$_2$ | H | OCF$_2$H | |
| S(O)$_2$CHF$_2$ | H | Me | |
| S(O)$_2$CF$_3$ | H | OMe | |
| S(O)$_2$CH$_2$CFH$_2$ | H | OCF$_2$H | |
| S(O)$_2$CH$_2$CF$_2$H | CH$_3$ | Me | |
| S(O)$_2$CH$_2$CF$_3$ | H | Me | |
| S(O)$_2$CH$_2$CF$_3$ | H | OMe | |
| S(O)$_2$CH$_2$CF$_3$ | H | OCF$_2$H | |
| S(O)$_2$CH$_2$CF$_2$H | H | Me | |
| S(O)$_2$(CH$_2$)$_2$CFH$_2$ | H | OMe | |
| S(O)$_2$(CH$_2$)$_2$CClH$_2$ | H | OCF$_2$H | |
| S(O)$_2$(CH$_2$)$_2$ClH$_2$ | H | Me | |
| S(O)$_2$CF$_2$CF$_3$ | H | OMe | |
| S(O)$_2$CH(CH$_3$)CF$_3$ | H | OCF$_2$H | |
| S(O)$_2$(CH$_2$)$_2$CCl$_3$ | CH$_3$ | OMe | |
| S(O)$_2$CH$_2$Cl | H | Me | |
| CH=CH$_2$ | H | OMe | |
| CH=CH$_2$ | H | OCF$_2$H | |
| CH=CH$_2$ | H | Me | |
| CH$_2$CH=CH$_2$ | H | OMe | |
| CH$_2$CH=CH$_2$ | H | OCF$_2$H | |
| CH$_2$CH=CH$_2$ | H | Me | |
| CH=CHCH$_3$ | H | OMe | |
| C(CH$_3$)=CH$_2$ | H | OCF$_2$H | |
| CH=CH$_2$ | CH$_3$ | OCF$_2$H | |
| C≡CH | H | Me | |
| C≡CH | H | OMe | |
| C≡CH | H | OCF$_2$H | |
| CH$_2$C≡CH | H | Me | |
| CH$_2$C≡CH | H | OMe | |
| CH$_2$C≡CH | H | OCF$_2$H | |
| C≡CCH$_3$ | H | Me | |
| C≡CCH$_3$ | H | OMe | |
| C≡CCH$_3$ | H | OCF$_2$H | |
| NH$_2$ | H | Me | |
| NH$_2$ | H | OMe | |
| NH$_2$ | H | OCF$_2$H | |
| NHCH$_3$ | H | Me | |
| NHCH$_3$ | H | OMe | |
| NHCH$_3$ | H | OCF$_2$H | |
| NHCH$_3$ | CH$_3$ | Me | |
| N(CH$_3$)$_2$ | H | Me | |

TABLE IIIa-continued $R_1 = n\text{-Pr}$

| $R_2$ | R | Y | m.p. (°C.) |
|---|---|---|---|
| N(CH₃)₂ | H | OMe | |
| N(CH₃)₂ | H | OCF₂H | |
| NHCH₂CH₃ | H | Me | |
| NHCH₂CH₃ | H | OMe | |
| NHCH₂CH₃ | H | OCF₂H | |
| N(CH₃)CH₂CH₃ | H | Me | |
| N(CH₂CH₃)₂ | H | OMe | |
| NHCH₂CF₃ | H | OCF₂H | |
| NHCH₂CF₃ | CH₃ | OMe | |
| NHCH₂CF₃ | H | Me | |
| NHCH₂CF₃ | H | OMe | |
| N(CH₃)CH₂CF₃ | H | OCF₂H | |
| N(CH₃)CH₂CHF₂ | H | Me | |
| N(CH₃)(CH₂)₂F | H | OMe | |
| N(CH₃)(CH₂)₂Cl | H | OCF₂H | |
| N(CH₃)(CH₂)₂I | H | Me | |
| N(CH₃)(CH₂)₂Br | H | OMe | |
| NHCF₃ | CH₃ | OCF₂H | |
| NHCF₃ | H | Me | |
| NH(CH₂)₂F | H | OMe | |
| N(CH₃)CF₂H | H | OCF₂H | |
| NHCF₂H | H | Me | |

TABLE IV $R_1 = i\text{-Pr}$

| $R_2$ | R | Y | m.p. (°C.) |
|---|---|---|---|
| Me | H | Me | 173–175 |
| Me | Me | Me | |
| Me | H | OMe | 173–175 |
| Me | Me | OMe | |
| Me | H | OCF₂H | |
| Me | Me | OCF₂H | |
| Et | H | Me | |
| Et | Me | Me | |
| Et | H | OMe | |
| Et | Me | OMe | |
| Et | H | OCF₂H | |
| Et | Me | OCF₂H | |
| n-Pr | H | Me | |
| n-Pr | Me | Me | |
| n-Pr | H | OMe | |
| n-Pr | Me | OMe | |
| n-Pr | H | OCF₂H | |
| n-Pr | Me | OCF₂H | |
| i-Pr | H | Me | |
| i-Pr | Me | Me | |
| i-Pr | H | OMe | |
| i-Pr | Me | OMe | |
| i-Pr | H | OCF₂H | |
| i-Pr | Me | OCF₂H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF₂H | |
| cyclo-Pr | Me | OCF₂H | |
| OMe | H | Me | 128–132 |
| OMe | Me | Me | |
| OMe | H | OMe | 178–183 |
| OMe | Me | OMe | |
| OMe | H | OCF₂H | |
| OMe | Me | OCF₂H | |
| OEt | H | Me | |
| OEt | Me | Me | |
| OEt | H | OMe | |
| OEt | Me | OMe | |
| OEt | H | OCF₂H | |
| OEt | Me | OCF₂H | |
| O—n-Pr | H | Me | |
| O—n-Pr | Me | Me | |
| O—n-Pr | H | OMe | |
| O—n-Pr | Me | OMe | |
| O—n-Pr | H | OCF₂H | |
| O—n-Pr | Me | OCF₂H | |
| O—i-Pr | H | Me | |
| O—i-Pr | Me | Me | |
| O—i-Pr | H | OMe | |

TABLE IV-continued $R_1 = i\text{-Pr}$

| $R_2$ | R | Y | m.p. (°C.) |
|---|---|---|---|
| O—i-Pr | Me | OMe | |
| O—i-Pr | H | OCF₂H | |
| O—i-Pr | Me | OCF₂H | |
| SMe | H | Me | 163–165 |
| SMe | Me | Me | |
| SMe | H | OMe | 127–131 |
| SMe | Me | OMe | |
| SMe | H | OCF₂H | |
| SMe | Me | OCF₂H | |
| SEt | H | Me | |
| SEt | Me | Me | |
| SEt | H | OMe | |
| SEt | Me | OMe | |
| SEt | H | OCF₂H | |
| SEt | Me | OCF₂H | |
| S—n-Pr | H | Me | |
| S—n-Pr | Me | Me | |
| S—n-Pr | H | OMe | |
| S—n-Pr | Me | OMe | |
| S—n-Pr | H | OCF₂H | |
| S—n-Pr | Me | OCF₂H | |
| S—i-Pr | H | Me | |
| S—i-Pr | Me | Me | |
| S—i-Pr | H | OMe | |
| S—i-Pr | Me | OMe | |
| S—i-Pr | H | OCF₂H | |
| S—i-Pr | Me | OCF₂H | |
| O—allyl | H | Me | |
| O—allyl | Me | Me | |
| O—allyl | H | OMe | |
| O—allyl | Me | OMe | |
| O—allyl | H | OCF₂H | |
| O—allyl | Me | OCF₂H | |
| O—propargyl | H | Me | |
| O—propargyl | Me | Me | |
| O—propargyl | H | OMe | |
| O—propargyl | Me | OMe | |
| O—propargyl | H | OCF₂H | |
| O—propargyl | Me | OCF₂H | |
| CH₂F | H | Me | |
| CH₂F | Me | Me | |
| CH₂F | H | OMe | |
| CH₂F | Me | OMe | |
| CH₂F | H | OCF₂H | |
| CH₂F | Me | OCF₂H | |
| CHF₂ | H | Me | |
| CHF₂ | Me | Me | |
| CHF₂ | H | OMe | |
| CHF₂ | Me | OMe | |
| CHF₂ | H | OCF₂H | |
| CHF₂ | Me | OCF₂H | |
| CF₃ | H | Me | 143–146 |
| CF₃ | Me | Me | |
| CF₃ | H | OMe | 137–141 |
| CF₃ | Me | OMe | |
| CF₃ | H | OCF₂H | |
| CF₃ | Me | OCF₂H | |
| CH₂Cl | H | Me | |
| CH₂Cl | Me | Me | |
| CH₂Cl | H | OMe | |
| CH₂Cl | Me | OMe | |
| CH₂Cl | H | OCF₂H | |
| CH₂Cl | Me | OCF₂H | |
| CHCl₂ | H | Me | |
| CHCl₂ | Me | Me | |
| CHCl₂ | H | OMe | |
| CHCl₂ | Me | OMe | |
| CHCl₂ | H | OCF₂H | |
| CHCl₂ | Me | OCF₂H | |
| CCl₃ | H | Me | |
| CCl₃ | Me | Me | |
| CCl₃ | H | OMe | |
| CCl₃ | Me | OMe | |
| CCl₃ | H | OCF₂H | |
| CCl₃ | Me | OCF₂H | |
| CHFCH₃ | H | Me | |
| CHFCH₃ | Me | Me | |
| CHFCH₃ | H | OMe | |
| CHFCH₃ | Me | OMe | |

TABLE IV-continued

R₁ = i-Pr

| R₂ | R | Y | m.p. (°C.) |
|---|---|---|---|
| CHFCH₃ | H | OCF₂H | |
| CHFCH₃ | Me | OCF₂H | |
| CF₂CH₃ | H | Me | |
| CF₂CH₃ | Me | Me | |
| CF₂CH₃ | H | OMe | |
| CF₂CH₃ | Me | OMe | |
| CF₂CH₃ | H | OCF₂H | |
| CF₂CH₃ | Me | OCF₂H | |
| CH₂CH₂F | H | Me | |
| CH₂CH₂F | Me | Me | |
| CH₂CH₂F | H | OMe | |
| CH₂CH₂F | Me | OMe | |
| CH₂CH₂F | H | OCF₂H | |
| CH₂CH₂F | Me | OCF₂H | |
| CH₂CHF₂ | H | Me | |
| CH₂CHF₂ | Me | Me | |
| CH₂CHF₂ | H | OMe | |
| CH₂CHF₂ | Me | OMe | |
| CH₂CHF₂ | H | OCF₂H | |
| CH₂CHF₂ | Me | OCF₂H | |
| CH₂CF₃ | H | Me | |
| CH₂CF₃ | Me | Me | |
| CH₂CF₃ | H | OMe | |
| CH₂CF₃ | Me | OMe | |
| CH₂CF₃ | H | OCF₂H | |
| CH₂CF₃ | Me | OCF₂H | |
| CHClCH₃ | H | Me | |
| CHClCH₃ | Me | Me | |
| CHClCH₃ | H | OMe | |
| CHClCH₃ | Me | OMe | |
| CHClCH₃ | H | OCF₂H | |
| CHClCH₃ | Me | OCF₂H | |
| CH₂OCH₃ | H | Me | |
| CH₂OCH₃ | Me | Me | |
| CH₂OCH₃ | H | OMe | |
| CH₂OCH₃ | Me | OMe | |
| CH₂OCH₃ | H | OCF₂H | |
| CH₂OCH₃ | Me | OCF₂H | |
| (CH₂)₂OCH₃ | H | Me | |
| (CH₂)₂OCH₃ | Me | Me | |
| (CH₂)₂OCH₃ | H | OMe | |
| (CH₂)₂OCH₃ | Me | OMe | |
| (CH₂)₂OCH₃ | H | OCF₂H | |
| (CH₂)₂OCH₃ | Me | OCF₂H | |
| CH(OCH₃)CH₃ | H | Me | |
| CH(OCH₃)CH₃ | Me | Me | |
| CH(OCH₃)CH₃ | H | OMe | |
| CH(OCH₃)CH₃ | Me | OMe | |
| CH(OCH₃)CH₃ | H | OCF₂H | |
| CH(OCH₃)CH₃ | Me | OCF₂H | |
| CH₂SCH₃ | H | Me | |
| CH₂SCH₃ | Me | Me | |
| CH₂SCH₃ | H | OMe | |
| CH₂SCH₃ | Me | OMe | |
| CH₂SCH₃ | H | OCF₂H | |
| CH₂SCH₃ | Me | OCF₂H | |
| (CH₂)₂SCH₃ | H | Me | |
| (CH₂)₂SCH₃ | Me | Me | |
| (CH₂)₂SCH₃ | H | OMe | |
| (CH₂)₂SCH₃ | Me | OMe | |
| (CH₂)₂SCH₃ | H | OCF₂H | |
| (CH₂)₂SCH₃ | Me | OCF₂H | |
| CH(SCH₃)CH₃ | H | Me | |
| CH(SCH₃)CH₃ | Me | Me | |
| CH(SCH₃)CH₃ | H | OMe | |
| CH(SCH₃)CH₃ | Me | OMe | |
| CH(SCH₃)CH₃ | H | OCF₂H | |
| CH(SCH₃)CH₃ | Me | OCF₂H | |
| OCF₂H | H | Me | |
| OCF₂H | Me | Me | |
| OCF₂H | H | OMe | |
| OCF₂H | Me | OMe | |
| OCF₂H | H | OCF₂H | |
| OCF₂H | Me | OCF₂H | |
| OCH₂CH₂F | H | Me | |
| OCH₂CH₂F | Me | Me | |
| OCH₂CH₂F | H | OMe | |
| OCH₂CH₂F | Me | OMe | |
| OCH₂CH₂F | H | OCF₂H | |
| OCH₂CH₂F | Me | OCF₂H | |
| OCH₂CHF₂ | H | Me | |
| OCH₂CHF₂ | Me | Me | |
| OCH₂CHF₂ | H | OMe | |
| OCH₂CHF₂ | Me | OMe | |
| OCH₂CHF₂ | H | OCF₂H | |
| OCH₂CHF₂ | Me | OCF₂H | |
| OCH₂CF₃ | H | Me | |
| OCH₂CF₃ | Me | Me | |
| OCH₂CF₃ | H | OMe | |
| OCH₂CF₃ | Me | OMe | |
| OCH₂CF₃ | H | OCF₂H | |
| OCH₂CF₃ | Me | OCF₂H | |
| O(CH₂)₂Cl | H | Me | |
| O(CH₂)₂Cl | Me | Me | |
| O(CH₂)₂Cl | H | OMe | |
| O(CH₂)₂Cl | Me | OMe | |
| O(CH₂)₂Cl | H | OCF₂H | |
| O(CH₂)₂Cl | Me | OCF₂H | |
| S(O)Me | H | Me | |
| S(O)Me | Me | Me | |
| S(O)Me | H | OMe | |
| S(O)Me | Me | OMe | |
| S(O)Me | H | OCF₂H | |
| S(O)Me | Me | OCF₂H | |
| S(O)Et | H | Me | |
| S(O)Et | Me | Me | |
| S(O)Et | H | OMe | |
| S(O)Et | Me | OMe | |
| S(O)Et | H | OCF₂H | |
| S(O)Et | Me | OCF₂H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF₂H | |
| S(O)—n-Pr | Me | OCF₂H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF₂H | |
| S(O)—i-Pr | Me | OCF₂H | |
| SO₂Me | H | Me | |
| SO₂Me | Me | Me | |
| SO₂Me | H | OMe | |
| SO₂Me | Me | OMe | |
| SO₂Me | H | OCF₂H | |
| SO₂Me | Me | OCF₂H | |
| SO₂Et | H | Me | |
| SO₂Et | Me | Me | |
| SO₂Et | H | OMe | |
| SO₂Et | Me | OMe | |
| SO₂Et | H | OCF₂H | |
| SO₂Et | Me | OCF₂H | |
| SO₂—n-Pr | H | Me | |
| SO₂—n-Pr | Me | Me | |
| SO₂—n-Pr | H | OMe | |
| SO₂—n-Pr | Me | OMe | |
| SO₂—n-Pr | H | OCF₂H | |
| SO₂—n-Pr | Me | OCF₂H | |
| SO₂—i-Pr | H | Me | |
| SO₂—i-Pr | Me | Me | |
| SO₂—i-Pr | H | OMe | |
| SO₂—i-Pr | Me | OMe | |
| SO₂—i-Pr | H | OCF₂H | |
| SO₂—i-Pr | Me | OCF₂H | |
| S—allyl | H | Me | |
| S—allyl | Me | Me | |
| S—allyl | H | OMe | |
| S—allyl | Me | OMe | |
| S—allyl | H | OCF₂H | |
| S—allyl | Me | OCF₂H | |
| S(O)allyl | H | Me | |
| S(O)allyl | Me | Me | |
| S(O)allyl | H | OMe | |
| S(O)allyl | Me | OMe | |
| S(O)allyl | H | OCF₂H | |
| S(O)allyl | Me | OCF₂H | |

TABLE IV-continued

| | $R_1$ = i-Pr | | |
|---|---|---|---|
| $R_2$ | R | Y | m.p. (°C.) |
| SO$_2$allyl | H | Me | |
| SO$_2$allyl | Me | Me | |
| SO$_2$allyl | H | OMe | |
| SO$_2$allyl | Me | OMe | |
| SO$_2$allyl | H | OCF$_2$H | |
| SO$_2$allyl | Me | OCF$_2$H | |
| S—propargyl | H | Me | |
| S—propargyl | Me | Me | |
| S—propargyl | H | OMe | |
| S—propargyl | Me | OMe | |
| S—propargyl | H | OCF$_2$H | |
| S—propargyl | Me | OCF$_2$H | |
| S(O)propargyl | H | Me | |
| S(O)propargyl | Me | Me | |
| S(O)propargyl | H | OMe | |
| S(O)propargyl | Me | OMe | |
| S(O)propargyl | H | OCF$_2$H | |
| S(O)propargyl | Me | OCF$_2$H | |
| SO$_2$propargyl | H | Me | |
| SO$_2$propargyl | Me | Me | |
| SO$_2$propargyl | H | OMe | |
| SO$_2$propargyl | Me | OMe | |
| SO$_2$propargyl | H | OCF$_2$H | |
| SO$_2$propargyl | Me | OCF$_2$H | |

TABLE IVa

| | $R_1$ = i-Pr | | |
|---|---|---|---|
| $R_2$ | R | Y | m.p. (°C.) |
| CH$_2$OCH$_2$CH$_3$ | H | Me | |
| CH$_2$OCH$_2$CH$_3$ | H | OMe | |
| CH$_2$OCH$_2$CH$_3$ | H | OCF$_2$H | |
| (CH$_2$)$_2$OCH$_2$CH$_3$ | H | Me | |
| (CH$_2$)$_2$OCH$_2$CH$_3$ | H | OMe | |
| (CH$_2$)$_2$OCH$_2$CH$_3$ | H | OCF$_2$H | |
| (CH$_2$)$_2$OCH$_2$CH$_3$ | CH$_3$ | Me | |
| CH(CH$_3$)OCH$_2$CH$_3$ | H | Me | |
| CH(CH$_3$)OCH$_2$CH$_3$ | H | OMe | |
| CH(CH$_3$)OCH$_2$CH$_3$ | H | OCF$_2$H | |
| CH$_2$OCH$_2$CF$_3$ | H | Me | |
| CH$_2$OCH$_2$CF$_3$ | H | OMe | |
| CH$_2$OCH$_2$CF$_3$ | H | OCF$_2$H | |
| (CH$_2$)$_2$OCH$_2$CF$_2$H | H | Me | |
| (CH$_2$)$_2$OCH$_2$CF$_3$ | H | OMe | |
| CH$_2$OCF$_2$H | H | OCF$_2$H | |
| CH$_2$OCH$_2$CH$_2$F | CH$_3$ | OMe | |
| CH$_2$OCH$_2$CHF$_2$ | H | Me | |
| CH$_2$OCH$_2$CH$_2$Br | H | OMe | |
| CH$_2$OCH$_2$CH$_2$Cl | H | OCF$_2$H | |
| CH$_2$OCH$_2$CH$_2$I | H | Me | |
| CH$_2$OCF$_3$ | H | OMe | |
| CH$_2$SCH$_2$CH$_3$ | H | OCF$_2$H | |
| CH$_2$SCH$_2$CH$_3$ | H | Me | |
| CH$_2$SCH$_2$CH$_3$ | H | OMe | |
| (CH$_2$)$_2$SCH$_2$CH$_3$ | H | OCF$_2$H | |
| (CH$_2$)$_2$SCH$_2$CH$_3$ | CH$_3$ | OCF$_2$H | |
| (CH$_2$)$_2$SCH$_2$CH$_3$ | H | Me | |
| (CH$_2$)$_2$SCH$_2$CH$_3$ | H | OMe | |
| CH(CH$_3$)SCH$_2$CH$_3$ | H | OCF$_2$H | |
| CH(CH$_3$)SCH$_2$CH$_3$ | H | Me | |
| CH(CH$_3$)SCH$_2$CH$_3$ | H | OMe | |
| CH$_2$SCH$_2$CF$_3$ | H | OCF$_2$H | |
| CH$_2$SCH$_2$CF$_3$ | H | Me | |
| CH$_2$SCH$_2$CF$_3$ | H | OMe | |
| (CH$_2$)$_2$SCH$_2$CF$_2$H | H | OCF$_2$H | |
| (CH$_2$)$_2$S(O)$_2$CH$_3$ | H | Me | |
| CH$_2$S(O)$_2$CH$_2$CH$_3$ | H | OMe | |
| CH$_2$S(O)$_2$CH$_2$CH$_3$ | H | OCF$_2$H | |
| CH$_2$S(O)$_2$CH$_2$CH$_3$ | H | Me | |
| (CH$_2$)$_2$S(O)$_2$CH$_2$CH$_3$ | H | OMe | |
| CH(CH$_3$)S(O)$_2$CH$_3$ | H | OCF$_2$H | |
| CH$_2$S(O)$_2$CH$_2$CF$_3$ | CH$_3$ | Me | |
| CH$_2$S(O)$_2$CH$_2$CF$_3$ | H | Me | |
| CH$_2$S(O)$_2$CH$_2$CF$_3$ | H | OMe | |
| CH$_2$S(O)$_2$CH$_2$CF$_3$ | H | OCF$_2$H | |
| (CH$_2$)$_2$S(O)$_2$CH$_2$CF$_2$H | H | Me | |
| (CH$_2$)$_2$S(O)$_2$CH$_2$CF$_3$ | H | OMe | |
| CH$_2$S(O)$_2$CF$_2$H | H | OCF$_2$H | |

TABLE IVa-continued

| | $R_1$ = i-Pr | | |
|---|---|---|---|
| $R_2$ | R | Y | m.p. (°C.) |
| CH$_2$S(O)$_2$CH$_2$CH$_2$F | H | Me | |
| CH$_2$S(O)$_2$CH$_2$CHF$_2$ | H | OMe | |
| CH$_2$S(O)$_2$CH$_2$CH$_2$Br | H | OCF$_2$H | |
| CH$_2$S(O)$_2$CH$_2$CH$_2$I | CH$_3$ | OMe | |
| CH$_2$S(O)$_2$CF$_3$ | H | Me | |
| CH$_2$S(O)$_2$CH$_2$Cl | H | OMe | |
| OCH$_2$OCH$_3$ | H | OCF$_2$H | |
| OCH$_2$OCH$_3$ | H | Me | |
| OCH$_2$OCH$_3$ | H | OMe | |
| O(CH$_2$)$_2$OCH$_3$ | H | OCF$_2$H | |
| O(CH$_2$)$_2$OCH$_3$ | H | Me | |
| O(CH$_2$)$_2$OCH$_3$ | H | OMe | |
| O(CH$_2$)$_2$OCH$_2$CH$_3$ | H | OCF$_2$H | |
| O(CH$_2$)$_2$OCH$_2$CH$_3$ | CH$_3$ | OCF$_2$H | |
| O(CH$_2$)$_2$OCH$_2$CH$_3$ | H | Me | |
| O(CH$_2$)$_2$OCH$_2$CH$_3$ | H | OMe | |
| OCH$_2$OCH$_2$CH$_3$ | H | OCF$_2$H | |
| (CH$_2$)$_2$SCH$_2$CF$_3$ | H | Me | |
| CH$_2$SCF$_2$H | H | OMe | |
| CH$_2$SCH$_2$CH$_2$F | H | OCF$_2$H | |
| CH$_2$SCH$_2$CHF$_2$ | H | Me | |
| CH$_2$SCH$_2$CH$_2$Br | H | OMe | |
| CH$_2$SCH$_2$CH$_2$Cl | H | OCF$_2$H | |
| CH$_2$SCH$_2$CH$_2$I | CH$_3$ | Me | |
| CH$_2$SCF$_3$ | H | Me | |
| CH$_2$S(O)CH$_3$ | H | OMe | |
| CH$_2$S(O)CH$_3$ | H | OCF$_2$H | |
| CH$_2$S(O)CH$_3$ | H | Me | |
| (CH$_2$)$_2$S(O)CH$_3$ | H | OMe | |
| (CH$_2$)$_2$S(O)CH$_3$ | H | OCF$_2$H | |
| (CH$_2$)$_2$S(O)CH$_3$ | H | Me | |
| CH$_2$S(O)CH$_2$CH$_3$ | H | OMe | |
| CH$_2$S(O)CH$_2$CH$_3$ | H | OCF$_2$H | |
| CH$_2$S(O)CH$_2$CH$_3$ | CH$_3$ | OMe | |
| CH$_2$S(O)CH$_2$CH$_3$ | H | Me | |
| (CH$_2$)$_2$S(O)CH$_2$CH$_3$ | H | OMe | |
| CH(CH$_3$)S(O)CH$_3$ | H | OCF$_2$H | |
| CH$_2$S(O)CH$_2$CF$_3$ | H | Me | |
| CH$_2$S(O)CH$_2$CF$_3$ | H | OMe | |
| CH$_2$S(O)CH$_2$CF$_3$ | H | OCF$_2$H | |
| (CH$_2$)$_2$S(O)CH$_2$CF$_2$H | H | Me | |
| (CH$_2$)$_2$S(O)CH$_2$CF$_3$ | H | OMe | |
| CH$_2$S(O)CF$_2$H | H | OCF$_2$H | |
| CH$_2$S(O)CH$_2$CH$_2$F | CH$_3$ | OCF$_2$H | |
| CH$_2$S(O)CH$_2$CHF$_2$ | H | Me | |
| CH$_2$S(O)CH$_2$CH$_2$Br | H | OMe | |
| CH$_2$S(O)CH$_2$I | H | OCF$_2$H | |
| CH$_2$S(O)CF$_3$ | H | Me | |
| CH$_2$S(O)$_2$CH$_3$ | H | OMe | |
| CH$_2$S(O)$_2$CH$_3$ | H | OCF$_2$H | |
| CH$_2$S(O)$_2$CH$_3$ | H | Me | |
| (CH$_2$)$_2$S(O)$_2$CH$_3$ | H | OMe | |
| (CH$_2$)$_2$S(O)$_2$CH$_3$ | H | OCF$_2$H | |
| OCH$_2$OCH$_2$CF$_3$ | H | Me | |
| O(CH$_2$)$_2$OCH$_2$CF$_3$ | H | OMe | |
| O(CH$_2$)$_2$OCH$_2$CF$_2$H | H | OCF$_2$H | |
| O(CH$_2$)$_2$O(CH$_2$)$_2$Cl | H | Me | |
| O(CH$_2$)$_2$O(CH$_2$)$_2$Br | H | OMe | |
| O(CH$_2$)$_2$O(CH$_2$)$_2$I | H | OCF$_2$H | |
| O(CH$_2$)$_2$OCF$_3$ | H | Me | |
| OCH$_2$SCH$_3$ | H | OMe | |
| OCH$_2$SCH$_3$ | H | OCF$_2$H | |
| OCH$_2$SCH$_3$ | H | Me | |
| O(CH$_2$)$_2$SCH$_3$ | H | OMe | |
| O(CH$_2$)$_2$SCH$_3$ | H | OCF$_2$H | |
| O(CH$_2$)$_2$SCH$_3$ | CH$_3$ | Me | |
| O(CH$_2$)$_2$SCH$_3$ | H | Me | |
| O(CH$_2$)$_2$SCH$_2$CH$_3$ | H | OMe | |
| O(CH$_2$)$_2$SCH$_2$CH$_3$ | H | OCF$_2$H | |
| O(CH$_2$)$_2$SCH$_2$CH$_3$ | H | Me | |
| OCH$_2$SCH$_2$CH$_3$ | H | OMe | |
| OCH$_2$SCH$_2$CF$_3$ | H | OCF$_2$H | |
| O(CH$_2$)$_2$SCH$_2$CF$_3$ | H | Me | |
| O(CH$_2$)$_2$SCH$_2$CF$_2$H | H | OMe | |
| O(CH$_2$)$_2$S(CH$_2$)$_2$Cl | H | OCF$_2$H | |
| O(CH$_2$)$_2$S(CH$_2$)$_2$Br | CH$_3$ | OMe | |
| O(CH$_2$)$_2$S(CH$_2$)$_2$I | H | Me | |
| O(CH$_2$)$_2$SCF$_3$ | H | OMe | |
| OCH$_2$S(O)CH$_3$ | H | OCF$_2$H | |

TABLE IVa-continued

| | $R_1 = $ i-Pr | | |
|---|---|---|---|
| $R_2$ | R | Y | m.p. (°C) |
| OCH$_2$S(O)CH$_3$ | H | Me | |
| OCH$_2$S(O)CH$_3$ | H | OMe | |
| O(CH$_2$)$_2$S(O)CH$_3$ | H | OCF$_2$H | |
| O(CH$_2$)$_2$S(O)CH$_3$ | H | Me | |
| O(CH$_2$)$_2$S(O)CH$_3$ | H | OMe | |
| O(CH$_2$)$_2$S(O)CH$_2$CH$_3$ | H | OCF$_2$H | |
| O(CH$_2$)$_2$S(O)CH$_2$CH$_3$ | CH$_3$ | OCF$_2$H | |
| O(CH$_2$)$_2$S(O)CH$_2$CH$_3$ | H | Me | |
| OCH$_2$S(O)CH$_2$CH$_3$ | H | OMe | |
| O(CH$_2$)$_2$S(O)CH$_2$CF$_3$ | H | OCF$_2$H | |
| OCH$_2$S(O)CH$_2$CF$_3$ | H | Me | |
| O(CH$_2$)$_2$S(O)CH$_2$CF$_2$H | H | OME | |
| O(CH$_2$)$_2$S(O)(CH$_2$)$_2$Cl | H | OCF$_2$H | |
| O(CH$_2$)$_2$S(O)(CH$_2$)$_2$Br | H | Me | |
| O(CH$_2$)$_2$S(O)(CH$_2$)$_2$I | H | OMe | |
| O(CH$_2$)$_2$S(O)CF$_3$ | H | OCF$_2$H | |
| OCH$_2$S(O)$_2$CH$_3$ | H | Me | |
| OCH$_2$S(O)$_2$CH$_3$ | H | OMe | |
| OCH$_2$S(O)$_2$CH$_3$ | H | OCF$_2$H | |
| O(CH$_2$)$_2$S(O)$_2$CH$_3$ | H | Me | |
| O(CH$_2$)$_2$S(O)$_2$CH$_3$ | H | OMe | |
| O(CH$_2$)$_2$S(O)$_2$CH$_3$ | H | OCF$_2$H | |
| O(CH$_2$)$_2$S(O)$_2$CH$_2$CH$_3$ | CH$_3$ | Me | |
| O(CH$_2$)$_2$S(O)$_2$CH$_2$CH$_3$ | H | Me | |
| O(CH$_2$)$_2$S(O)$_2$CH$_2$CH$_3$ | H | OCF$_2$H | |
| OCH$_2$S(O)$_2$CH$_2$CH$_3$ | H | Me | |
| OCH$_2$S(O)$_2$CH$_2$CF$_3$ | H | OMe | |
| O(CH$_2$)$_2$S(O)$_2$CH$_2$CF$_3$ | H | OCF$_2$H | |
| O(CH$_2$)$_2$S(O)$_2$CH$_2$CF$_2$H | H | Me | |
| O(CH$_2$)$_2$S(O)$_2$(CH$_2$)$_2$Cl | H | OMe | |
| O(CH$_2$)$_2$S(O)$_2$(CH$_2$)$_2$Br | H | OCF$_2$H | |
| O(CH$_2$)$_2$S(O)$_2$(CH$_2$)$_2$I | CH$_3$ | OMe | |
| O(CH$_2$)$_2$S(O)$_2$CF$_3$ | H | Me | |
| OCH$_2$S(O)$_2$CH$_2$Cl | H | OMe | |
| OCH$_2$S(O)$_2$CF$_3$ | H | OCF$_2$H | |
| O(CH$_2$)$_2$CN | H | Me | |
| O(CH$_2$)$_2$CN | H | OMe | |
| O(CH$_2$)$_2$CN | H | OCF$_2$H | |
| OCH$_2$CN | H | Me | |
| OCH$_2$CN | H | OMe | |
| OCH$_2$CN | H | OCF$_2$H | |
| OCH$_2$CN | CH$_3$ | OCF$_2$H | |
| OCH(CH$_3$)CN | H | Me | |
| O(CH$_2$)$_2$NH$_2$ | H | OMe | |
| O(CH$_2$)$_2$NH$_2$ | H | OCF$_2$H | |
| O(CH$_2$)$_2$NH$_2$ | H | Me | |
| O(CH$_2$)$_2$NHCH$_3$ | H | OMe | |
| O(CH$_2$)$_2$NHCH$_3$ | H | OCF$_2$H | |
| O(CH$_2$)$_2$NHCH$_3$ | H | Me | |
| O(CH$_2$)$_2$N(CH$_3$)$_2$ | H | OMe | |
| O(CH$_2$)$_2$N(CH$_3$)$_2$ | H | OCF$_2$H | |
| O(CH$_2$)$_2$N(CH$_3$)$_2$ | H | Me | |
| SCH$_2$OCH$_3$ | H | OMe | |
| SCH$_2$OCH$_3$ | H | OCF$_2$H | |
| SCH$_2$OCH$_3$ | H | Me | |
| SCH$_2$OCH$_2$CH$_3$ | H | OMe | |
| S(CH$_2$)$_2$OCH$_3$ | H | OCF$_2$H | |
| S(CH$_2$)$_2$OCH$_3$ | CH$_3$ | Me | |
| S(CH$_2$)$_2$OCH$_3$ | H | Me | |
| S(CH$_2$)$_2$OCH$_3$ | H | OMe | |
| S(CH$_2$)$_2$OCH$_2$CH$_3$ | H | OCF$_2$H | |
| S(CH$_2$)$_2$OCH$_2$CF$_3$ | H | Me | |
| SCH$_2$OCH$_2$CF$_3$ | H | OMe | |
| S(CH$_2$)$_2$OCH$_2$CF$_2$H | H | OCF$_2$H | |
| S(CH$_2$)$_2$O(CH$_2$)$_2$Cl | H | Me | |
| S(CH$_2$)$_2$O(CH$_2$)$_2$Br | H | OMe | |
| S(CH$_2$)$_2$O(CH$_2$)$_2$I | H | OCF$_2$H | |
| S(CH$_2$)$_2$OCF$_3$ | CH$_3$ | OMe | |
| SCH$_2$SCH$_3$ | H | Me | |
| SCH$_2$SCH$_3$ | H | OMe | |
| SCH$_2$SCH$_3$ | H | OCF$_2$H | |
| SCH$_2$SCH$_2$CH$_3$ | H | Me | |
| S(CH$_2$)$_2$SCH$_3$ | H | OMe | |
| S(CH$_2$)$_2$SCH$_3$ | H | OCF$_2$H | |
| S(CH$_2$)$_2$SCH$_3$ | H | Me | |
| S(CH$_2$)$_2$SCH$_2$CH$_3$ | H | OMe | |
| SCH(CH$_3$)SCH$_3$ | H | OCF$_2$H | |
| S(CH$_2$)$_2$SCH$_2$CF$_3$ | CH$_3$ | OCF$_2$H | |
| SCH$_2$SCH$_2$CF$_3$ | H | Me | |
| S(CH$_2$)$_2$SCH$_2$CF$_2$H | H | OMe | |
| S(CH$_2$)$_2$S(CH$_2$)$_2$Cl | H | OCF$_2$H | |
| S(CH$_2$)$_2$S(CH$_2$)$_2$Br | H | Me | |
| S(CH$_2$)$_2$S(CH$_2$)$_2$I | H | OMe | |
| S(CH$_2$)$_2$SCF$_3$ | H | OCF$_2$H | |
| SCH$_2$CN | H | Me | |
| SCH$_2$CN | H | OMe | |
| SCH$_2$CN | H | OCF$_2$H | |
| S(CH$_2$)$_2$CN | H | Me | |
| S(CH$_2$)$_2$CN | H | OMe | |
| S(CH$_2$)$_2$CN | H | OCF$_2$H | |
| SCH(CH$_3$)CN | H | Me | |
| SCHF$_2$ | H | OMe | |
| SCHF$_2$ | H | OCF$_2$H | |
| SCHF$_2$ | CH$_3$ | Me | |
| SCHF$_2$ | H | Me | |
| SCF$_3$ | H | OMe | |
| SCH$_2$CFH$_2$ | H | OCF$_2$H | |
| SCH$_2$CF$_2$H | H | Me | |
| SCH$_2$CF$_3$ | H | OMe | |
| SCH$_2$CF$_3$ | H | OCF$_2$H | |
| SCH$_2$CF$_3$ | H | Me | |
| SCH$_2$CF$_2$H | H | OMe | |
| S(CH$_2$)$_2$CFH$_2$ | H | OCF$_2$H | |
| S(CH$_2$)$_2$CClH$_2$ | CH$_3$ | OMe | |
| S(CH$_2$)$_2$ClH$_2$ | H | Me | |
| SCF$_2$CF$_3$ | H | OMe | |
| SCH(CH$_3$)CF$_3$ | H | OCF$_2$H | |
| S(CH$_2$)$_2$CCl$_3$ | H | Me | |
| S(O)CHF$_2$ | H | OMe | |
| S(O)CHF$_2$ | H | OCF$_2$H | |
| S(O)CHF$_2$ | H | Me | |
| S(O)CF$_3$ | H | OMe | |
| S(O)CH$_2$CFH$_2$ | H | OCF$_2$H | |
| S(O)CH$_2$CF$_2$H | CH$_3$ | OCF$_2$H | |
| S(O)CH$_2$CF$_3$ | H | Me | |
| S(O)CH$_2$CF$_3$ | H | OMe | |
| S(O)CH$_2$CF$_3$ | H | OCF$_2$H | |
| S(O)CH$_2$CF$_2$H | H | Me | |
| S(O)(CH$_2$)$_2$CFH$_2$ | H | OMe | |
| S(O)(CH$_2$)$_2$CClH$_2$ | H | OCF$_2$H | |
| S(O)(CH$_2$)$_2$ClH$_2$ | H | Me | |
| S(O)CF$_2$CF$_3$ | H | OMe | |
| S(O)CH(CH$_3$)CF$_3$ | H | OCF$_2$H | |
| S(O)(CH$_2$)$_2$CCl$_3$ | H | Me | |
| S(O)$_2$CHF$_2$ | H | OMe | |
| S(O)$_2$CHF$_2$ | H | OCF$_2$H | |
| S(O)$_2$CHF$_2$ | H | Me | |
| S(O)$_2$CF$_3$ | H | OMe | |
| S(O)$_2$CH$_2$CFH$_2$ | H | OCF$_2$H | |
| S(O)$_2$CH$_2$CF$_2$H | CH$_3$ | Me | |
| S(O)$_2$CH$_2$CF$_3$ | H | Me | |
| S(O)$_2$CH$_2$CF$_3$ | H | OMe | |
| S(O)$_2$CH$_2$CF$_3$ | H | OCF$_2$H | |
| S(O)$_2$CH$_2$CF$_2$H | H | Me | |
| S(O)$_2$(CH$_2$)$_2$CFH$_2$ | H | OMe | |
| S(O)$_2$(CH$_2$)$_2$CClH$_2$ | H | OCF$_2$H | |
| S(O)$_2$(CH$_2$)$_2$ClH$_2$ | H | Me | |
| S(O)$_2$CF$_2$CF$_3$ | H | OMe | |
| S(O)$_2$CH(CH$_3$)CF$_3$ | H | OCF$_2$H | |
| S(O)$_2$(CH$_2$)$_2$CCl$_3$ | CH$_3$ | OMe | |
| S(O)$_2$CH$_2$Cl | H | Me | |
| CH=CH$_2$ | H | OMe | |
| CH=CH$_2$ | H | OCF$_2$H | |
| CH=CH$_2$ | H | Me | |
| CH$_2$CH=CH$_2$ | H | OMe | |
| CH$_2$CH=CH$_2$ | H | OCF$_2$H | |
| CH$_2$CH=CH$_2$ | H | Me | |
| CH=CHCH$_3$ | H | OMe | |
| C(CH$_3$)=CH$_2$ | H | OCF$_2$H | |
| CH=CH$_2$ | CH$_3$ | OCF$_2$H | |
| C≡CH | H | Me | |
| C≡CH | H | OMe | |
| C≡CH | H | OCF$_2$H | |
| CH$_2$C≡CH | H | Me | |
| CH$_2$C≡CH | H | OMe | |
| CH$_2$C≡CH | H | OCF$_2$H | |
| C≡CCH$_3$ | H | Me | |

TABLE IVa-continued

| | $R_1$ = i-Pr | | |
|---|---|---|---|
| $R_2$ | R | Y | m.p. (°C.) |
| C≡CCH$_3$ | H | OMe | |
| C≡CCH$_3$ | H | OCF$_2$H | |
| NH$_2$ | H | Me | |
| NH$_2$ | H | OMe | |
| NH$_2$ | H | OCF$_2$H | |
| NHCH$_3$ | H | Me | |
| NHCH$_3$ | H | OMe | |
| NHCH$_3$ | H | OCF$_2$H | |
| NHCH$_3$ | CH$_3$ | Me | |
| N(CH$_3$)$_2$ | H | Me | |
| N(CH$_3$)$_2$ | H | OMe | |
| N(CH$_3$)$_2$ | H | OCF$_2$H | |
| NHCH$_2$CH$_3$ | H | Me | |
| NHCH$_2$CH$_3$ | H | OMe | |
| NHCH$_2$CH$_3$ | H | OCF$_2$H | |
| N(CH$_3$)CH$_2$CH$_3$ | H | Me | |
| N(CH$_2$CH$_3$)$_2$ | H | OMe | |
| NHCH$_2$CF$_3$ | H | OCF$_2$H | |
| NHCH$_2$CF$_3$ | CH$_3$ | OMe | |
| NHCH$_2$CF$_3$ | H | Me | |
| NHCH$_2$CF$_3$ | H | OMe | |
| N(CH$_3$)CH$_2$CF$_3$ | H | OCF$_2$H | |
| N(CH$_3$)CH$_2$CHF$_2$ | H | Me | |
| N(CH$_3$)(CH$_2$)$_2$F | H | OMe | |
| N(CH$_3$)(CH$_2$)$_2$Cl | H | OCF$_2$H | |
| N(CH$_3$)(CH$_2$)$_2$I | H | Me | |
| N(CH$_3$)(CH$_2$)$_2$Br | H | OMe | |
| NHCF$_3$ | CH$_3$ | OCF$_2$H | |
| NHCF$_3$ | H | Me | |
| NH(CH$_2$)$_2$F | H | OMe | |
| N(CH$_3$)CF$_2$H | H | OCF$_2$H | |
| NHCF$_2$H | H | Me | |

TABLE Va

| | $R_1$ = CH$_2$CH=CH$_2$ | | |
|---|---|---|---|
| $R_2$ | R | Y | m.p. (°C.) |
| Me | H | Me | |
| Me | Me | Me | |
| Me | H | OMe | |
| Me | Me | OMe | |
| Me | H | OCF$_2$H | |
| Me | Me | OCF$_2$H | |
| Et | H | Me | |
| Et | Me | Me | |
| Et | H | OMe | |
| Et | Me | OMe | |
| Et | H | OCF$_2$H | |
| Et | Me | OCF$_2$H | |
| Pr | H | Me | |
| Pr | Me | Me | |
| Pr | H | OMe | |
| Pr | Me | OMe | |
| Pr | H | OCF$_2$H | |
| Pr | Me | OCF$_2$H | |
| i-Pr | H | Me | |
| i-Pr | Me | Me | |
| i-Pr | H | OMe | |
| i-Pr | Me | OMe | |
| i-Pr | H | OCF$_2$H | |
| i-Pr | Me | OCF$_2$H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF$_2$H | |
| cyclo-Pr | Me | OCF$_2$H | |
| OMe | H | Me | |
| OMe | Me | Me | |
| OMe | H | OMe | |
| OMe | Me | OMe | |
| OMe | H | OCF$_2$H | |
| OMe | Me | OCF$_2$H | |
| OEt | H | Me | |
| OEt | Me | Me | |
| OEt | H | OMe | |
| OEt | Me | OMe | |
| OEt | H | OCF$_2$H | |

TABLE Va-continued

| | $R_1$ = CH$_2$CH=CH$_2$ | | |
|---|---|---|---|
| $R_2$ | R | Y | m.p. (°C.) |
| OEt | Me | OCF$_2$H | |
| O—n-Pr | H | Me | |
| O—n-Pr | Me | Me | |
| O—n-Pr | H | OMe | |
| O—n-Pr | Me | OMe | |
| O—n-Pr | H | OCF$_2$H | |
| O—n-Pr | Me | OCF$_2$H | |
| O—i-Pr | H | Me | |
| O—i-Pr | Me | Me | |
| O—i-Pr | H | OMe | |
| O—i-Pr | Me | OMe | |
| O—i-Pr | H | OCF$_2$H | |
| O—i-Pr | Me | OCF$_2$H | |
| SMe | H | Me | 133–137 |
| SMe | Me | Me | |
| SMe | H | OMe | 126–131 |
| SMe | Me | OMe | |
| SMe | H | OCF$_2$H | |
| SMe | Me | OCF$_2$H | |
| SEt | H | Me | |
| SEt | Me | Me | |
| SEt | H | OMe | |
| SEt | Me | OMe | |
| SEt | H | OCF$_2$H | |
| SEt | Me | OCF$_2$H | |
| S—n-Pr | H | Me | |
| S—n-Pr | Me | Me | |
| S—n-Pr | H | OMe | |
| S—n-Pr | Me | OMe | |
| S—n-Pr | H | OCF$_2$H | |
| S—n-Pr | Me | OCF$_2$H | |
| S—i-Pr | H | Me | |
| S—i-Pr | Me | Me | |
| S—i-Pr | H | OMe | |
| S—i-Pr | Me | OMe | |
| S—i-Pr | H | OCF$_2$H | |
| S—i-Pr | Me | OCF$_2$H | |
| O—allyl | H | Me | |
| O—allyl | Me | Me | |
| O—allyl | H | OMe | |
| O—allyl | Me | OMe | |
| O—allyl | H | OCF$_2$H | |
| O—allyl | Me | OCF$_2$H | |
| O—propargyl | H | Me | |
| O—propargyl | Me | Me | |
| O—propargyl | H | OMe | |
| O—propargyl | Me | OMe | |
| O—propargyl | H | OCF$_2$H | |
| O—propargyl | Me | OCF$_2$H | |
| CH$_2$F | H | Me | |
| CH$_2$F | Me | Me | |
| CH$_2$F | H | OMe | |
| CH$_2$F | Me | OMe | |
| CH$_2$F | H | OCF$_2$H | |
| CH$_2$F | Me | OCF$_2$H | |
| CHF$_2$ | H | Me | |
| CHF$_2$ | Me | Me | |
| CHF$_2$ | H | OMe | |
| CHF$_2$ | Me | OMe | |
| CHF$_2$ | H | OCF$_2$H | |
| CHF$_2$ | Me | OCF$_2$H | |
| CF$_3$ | H | Me | |
| CF$_3$ | Me | Me | |
| CF$_3$ | H | OMe | 87–93 |
| CF$_3$ | Me | OMe | |
| CF$_3$ | H | OCF$_2$H | |
| CF$_3$ | Me | OCF$_2$H | |
| CH$_2$Cl | H | Me | |
| CH$_2$Cl | Me | Me | |
| CH$_2$Cl | H | OMe | |
| CH$_2$Cl | Me | OMe | |
| CH$_2$Cl | H | OCF$_2$H | |
| CH$_2$Cl | Me | OCF$_2$H | |
| CHCl$_2$ | H | Me | |
| CHCl$_2$ | Me | Me | |
| CHCl$_2$ | H | OMe | |
| CHCl$_2$ | Me | OMe | |
| CHCl$_2$ | H | OCF$_2$H | |
| CHCl$_2$ | Me | OCF$_2$H | |

TABLE Va-continued $R_1 = CH_2CH=CH_2$

| R2 | R | Y | m.p. (°C.) |
|---|---|---|---|
| CCl3 | H | Me | |
| CCl3 | Me | Me | |
| CCl3 | H | OMe | |
| CCl3 | Me | OMe | |
| CCl3 | H | OCF2H | |
| CCl3 | Me | OCF2H | |
| CHFCH3 | H | Me | |
| CHFCH3 | Me | Me | |
| CHFCH3 | H | OMe | |
| CHFCH3 | Me | OMe | |
| CHFCH3 | H | OCF2H | |
| CHFCH3 | Me | OCF2H | |
| CF2CH3 | H | Me | |
| CF2CH3 | Me | Me | |
| CF2CH3 | H | OMe | |
| CF2CH3 | Me | OMe | |
| CF2CH3 | H | OCF2H | |
| CF2CH3 | Me | OCF2H | |
| CH2CH2F | H | Me | |
| CH2CH2F | Me | Me | |
| CH2CH2F | H | OMe | |
| CH2CH2F | Me | OMe | |
| CH2CH2F | H | OCF2H | |
| CH2CH2F | Me | OCF2H | |
| CH2CHF2 | H | Me | |
| CH2CHF2 | Me | Me | |
| CH2CHF2 | H | OMe | |
| CH2CHF2 | Me | OMe | |
| CH2CHF2 | H | OCF2H | |
| CH2CHF2 | Me | OCF2H | |
| CH2CF3 | H | Me | |
| CH2CF3 | Me | Me | |
| CH2CF3 | H | OMe | |
| CH2CF3 | Me | OMe | |
| CH2CF3 | H | OCF2H | |
| CH2CF3 | Me | OCF2H | |
| CHClCH3 | H | Me | |
| CHClCH3 | Me | Me | |
| CHClCH3 | H | OMe | |
| CHClCH3 | Me | OMe | |
| CHClCH3 | H | OCF2H | |
| CHClCH3 | Me | OCF2H | |
| CH2OCH3 | H | Me | |
| CH2OCH3 | Me | Me | |
| CH2OCH3 | H | OMe | |
| CH2OCH3 | Me | OMe | |
| CH2OCH3 | H | OCF2H | |
| CH2OCH3 | Me | OCF2H | |
| (CH2)2OCH3 | H | Me | |
| (CH2)2OCH3 | Me | Me | |
| (CH2)2OCH3 | H | OMe | |
| (CH2)2OCH3 | Me | OMe | |
| (CH2)2OCH3 | H | OCF2H | |
| (CH2)2OCH3 | Me | OCF2H | |
| CH(OCH3)CH3 | H | Me | |
| CH(OCH3)CH3 | Me | Me | |
| CH(OCH3)CH3 | H | OMe | |
| CH(OCH3)CH3 | Me | OMe | |
| CH(OCH3)CH3 | H | OCF2H | |
| CH(OCH3)CH3 | Me | OCF2H | |
| CH2SCH3 | H | Me | |
| CH2SCH3 | Me | Me | |
| CH2SCH3 | H | OMe | |
| CH2SCH3 | Me | OMe | |
| CH2SCH3 | H | OCF2H | |
| CH2SCH3 | Me | OCF2H | |
| (CH2)2SCH3 | H | Me | |
| (CH2)2SCH3 | Me | Me | |
| (CH2)2SCH3 | H | OMe | |
| (CH2)2SCH3 | Me | OMe | |
| (CH2)2SCH3 | H | OCF2H | |
| (CH2)2SCH3 | Me | OCF2H | |
| CH(SCH3)CH3 | H | Me | |
| CH(SCH3)CH3 | Me | Me | |
| CH(SCH3)CH3 | H | OMe | |
| CH(SCH3)CH3 | Me | OMe | |
| CH(SCH3)CH3 | H | OCF2H | |
| CH(SCH3)CH3 | Me | OCF2H | |
| OCF2H | H | Me | |
| OCF2H | Me | Me | |
| OCF2H | H | OMe | |
| OCF2H | Me | OMe | |
| OCF2H | H | OCF2H | |
| OCF2H | Me | OCF2H | |
| OCH2CH2F | H | Me | |
| OCH2CH2F | Me | Me | |
| OCH2CH2F | H | OMe | |
| OCH2CH2F | Me | OMe | |
| OCH2CH2F | H | OCF2H | |
| OCH2CH2F | Me | OCF2H | |
| OCH2CHF2 | H | Me | |
| OCH2CHF2 | Me | Me | |
| OCH2CHF2 | H | OMe | |
| OCH2CHF2 | Me | OMe | |
| OCH2CHF2 | H | OCF2H | |
| OCH2CHF2 | Me | OCF2H | |
| OCH2CF3 | H | Me | |
| OCH2CF3 | Me | Me | |
| OCH2CF3 | H | OMe | |
| OCH2CF3 | Me | OMe | |
| OCH2CF3 | H | OCF2H | |
| OCH2CF3 | Me | OCF2H | |
| O(CH2)2Cl | H | Me | |
| O(CH2)2Cl | Me | Me | |
| O(CH2)2Cl | H | OMe | |
| O(CH2)2Cl | Me | OMe | |
| O(CH2)2Cl | H | OCF2H | |
| O(CH2)2Cl | Me | OCF2H | |
| S(O)Me | H | Me | |
| S(O)Me | Me | Me | |
| S(O)Me | H | OMe | |
| S(O)Me | Me | OMe | |
| S(O)Me | H | OCF2H | |
| S(O)Me | Me | OCF2H | |
| S(O)Et | H | Me | |
| S(O)Et | Me | Me | |
| S(O)Et | H | OMe | |
| S(O)Et | Me | OMe | |
| S(O)Et | H | OCF2H | |
| S(O)Et | Me | OCF2H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF2H | |
| S(O)—n-Pr | Me | OCF2H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF2H | |
| S(O)—i-Pr | Me | OCF2H | |
| SO2Me | H | Me | |
| SO2Me | Me | Me | |
| SO2Me | H | OMe | |
| SO2Me | Me | OMe | |
| SO2Me | H | OCF2H | |
| SO2Me | Me | OCF2H | |
| SO2Et | H | Me | |
| SO2Et | Me | Me | |
| SO2Et | H | OMe | |
| SO2Et | Me | OMe | |
| SO2Et | H | OCF2H | |
| SO2Et | Me | OCF2H | |
| SO2—n-Pr | H | Me | |
| SO2—n-Pr | Me | Me | |
| SO2—n-Pr | H | OMe | |
| SO2—n-Pr | Me | OMe | |
| SO2—n-Pr | H | OCF2H | |
| SO2—n-Pr | Me | OCF2H | |
| SO2—i-Pr | H | Me | |
| SO2—i-Pr | Me | Me | |
| SO2—i-Pr | H | OMe | |
| SO2—i-Pr | Me | OMe | |
| SO2—i-Pr | H | OCF2H | |
| SO2—i-Pr | Me | OCF2H | |
| S—allyl | H | Me | |
| S—allyl | Me | Me | |

TABLE Va-continued

| R₂ | R | Y | m.p. (°C.) |
|---|---|---|---|
| \multicolumn{4}{c}{R₁ = CH₂CH=CH₂} | | | |
| S—allyl | H | OMe | |
| S—allyl | Me | OMe | |
| S—allyl | H | OCF₂H | |
| S—allyl | Me | OCF₂H | |
| S(O)allyl | H | Me | |
| S(O)allyl | Me | Me | |
| S(O)allyl | H | OMe | |
| S(O)allyl | Me | OMe | |
| S(O)allyl | H | OCF₂H | |
| S(O)allyl | Me | OCF₂H | |
| SO₂allyl | H | Me | |
| SO₂allyl | Me | Me | |
| SO₂allyl | H | OMe | |
| SO₂allyl | Me | OMe | |
| SO₂allyl | H | OCF₂H | |
| SO₂allyl | Me | OCF₂H | |
| S-propargyl | H | Me | |
| S-propargyl | Me | Me | |
| S-propargyl | H | OMe | |
| S-propargyl | Me | OMe | |
| S-propargyl | H | OCF₂H | |
| S-propargyl | Me | OCF₂H | |
| S(O)propargyl | H | Me | |
| S(O)propargyl | Me | Me | |
| S(O)propargyl | H | OMe | |
| S(O)propargyl | Me | OMe | |
| S(O)propargyl | H | OCF₂H | |
| S(O)propargyl | Me | OCF₂H | |
| SO₂propargyl | H | Me | |
| SO₂propargyl | Me | Me | |
| SO₂propargyl | H | OMe | |
| SO₂propargyl | Me | OMe | |
| SO₂propargyl | H | OCF₂H | |
| SO₂propargyl | Me | OCF₂H | |
| CH₂OCH₂CH₃ | H | Me | |
| CH₂OCH₂CH₃ | H | OMe | |
| CH₂OCH₂CH₃ | H | OCF₂H | |
| (CH₂)₂OCH₂CH₃ | H | Me | |
| (CH₂)₂OCH₂CH₃ | H | OMe | |
| (CH₂)₂OCH₂CH₃ | H | OCF₂H | |
| (CH₂)₂OCH₂CH₃ | CH₃ | Me | |
| CH(CH₃)OCH₂CH₃ | H | Me | |
| CH(CH₃)OCH₂CH₃ | H | OMe | |
| CH(CH₃)OCH₂CH₃ | H | OCF₂H | |
| CH₂OCH₂CF₃ | H | Me | |
| CH₂OCH₂CF₃ | H | OMe | |
| CH₂OCH₂CF₃ | H | OCF₂H | |
| (CH₂)₂OCH₂CF₂H | H | Me | |
| (CH₂)₂OCH₂CF₃ | H | OMe | |
| CH₂OCF₂H | H | OCF₂H | |
| CH₂OCH₂CH₂F | CH₃ | OMe | |
| CH₂OCH₂CHF₂ | H | Me | |
| CH₂OCH₂CH₂Br | H | OMe | |
| CH₂OCH₂CH₂Cl | H | OCF₂H | |
| CH₂OCH₂CH₂I | H | Me | |
| CH₂OCF₃ | H | OMe | |
| CH₂SCH₂CH₃ | H | OCF₂H | |
| CH₂SCH₂CH₃ | H | Me | |
| CH₂SCH₂CH₃ | H | OMe | |
| (CH₂)₂SCH₂CH₃ | H | OCF₂H | |
| (CH₂)₂SCH₂CH₃ | CH₃ | OCF₂H | |
| (CH₂)₂SCH₂CH₃ | H | Me | |
| (CH₂)₂SCH₂CH₃ | H | OMe | |
| CH(CH₃)SCH₂CH₃ | H | OCF₂H | |
| CH(CH₃)SCH₂CH₃ | H | Me | |
| CH(CH₃)SCH₂CH₃ | H | OMe | |
| CH₂SCH₂CF₃ | H | OCF₂H | |
| CH₂SCH₂CF₃ | H | Me | |
| CH₂SCH₂CF₃ | H | OMe | |
| (CH₂)₂SCH₂CF₂H | H | OCF₂H | |
| (CH₂)₂S(O)₂CH₂CH₃ | H | Me | |
| CH₂S(O)₂CH₂CH₃ | H | OMe | |
| CH₂S(O)₂CH₂CH₃ | H | OCF₂H | |
| CH₂S(O)₂CH₂CH₃ | H | Me | |
| (CH₂)₂S(O)₂CH₂CH₃ | H | OMe | |
| CH(CH₃)S(O)₂CH₃ | H | OCF₂H | |
| CH₂S(O)₂CH₂CF₃ | CH₃ | Me | |
| CH₂S(O)₂CH₂CF₃ | H | Me | |
| CH₂S(O)₂CH₂CF₃ | H | OMe | |
| CH₂S(O)₂CH₂CF₃ | H | OCF₂H | |
| (CH₂)₂S(O)₂CH₂CF₂H | H | Me | |
| (CH₂)₂S(O)₂CH₂CF₃ | H | OMe | |
| CH₂S(O)₂CF₂H | H | OCF₂H | |
| CH₂S(O)₂CH₂CH₂F | H | Me | |
| CH₂S(O)₂CH₂CHF₂ | H | OMe | |
| CH₂S(O)₂CH₂CH₂Br | H | OCF₂H | |
| CH₂S(O)₂CH₂CH₂I | CH₃ | OMe | |
| CH₂S(O)₂CF₃ | H | Me | |
| CH₂S(O)₂CH₂Cl | H | OMe | |
| OCH₂OCH₃ | H | OCF₂H | |
| OCH₂OCH₃ | H | Me | |
| OCH₂OCH₃ | H | OMe | |
| O(CH₂)₂OCH₃ | H | OCF₂H | |
| O(CH₂)₂OCH₃ | H | Me | |
| O(CH₂)₂OCH₃ | H | OMe | |
| O(CH₂)₂OCH₂CH₃ | H | OCF₂H | |
| O(CH₂)₂OCH₂CH₃ | CH₃ | OCF₂H | |
| O(CH₂)₂OCH₂CH₃ | H | Me | |
| O(CH₂)₂OCH₂CH₃ | H | OMe | |
| OCH₂OCH₂CH₃ | H | OCF₂H | |
| (CH₂)₂SCH₂CF₃ | H | Me | |
| CH₂SCF₂H | H | OMe | |
| CH₂SCH₂CH₂F | H | OCF₂H | |
| CH₂SCH₂CHF₂ | H | Me | |
| CH₂SCH₂CH₂Br | H | OMe | |
| CH₂SCH₂CH₂Cl | H | OCF₂H | |
| CH₂SCH₂CH₂I | CH₃ | Me | |
| CH₂SCF₃ | H | Me | |
| CH₂S(O)CH₃ | H | OMe | |
| CH₂S(O)CH₃ | H | OCF₂H | |
| CH₂S(O)CH₃ | H | Me | |
| (CH₂)₂S(O)CH₃ | H | OMe | |
| (CH₂)₂S(O)CH₃ | H | OCF₂H | |
| (CH₂)₂S(O)CH₃ | H | Me | |
| CH₂S(O)CH₂CH₃ | H | OMe | |
| CH₂S(O)CH₂CH₃ | H | OCF₂H | |
| CH₂S(O)CH₂CH₃ | CH₃ | OMe | |
| CH₂S(O)CH₂CH₃ | H | Me | |
| (CH₂)₂S(O)CH₂CH₃ | H | OMe | |
| CH(CH₃)S(O)CH₃ | H | OCF₂H | |
| CH₂S(O)CH₂CF₃ | H | Me | |
| CH₂S(O)CH₂CF₃ | H | OMe | |
| CH₂S(O)CH₂CF₃ | H | OCF₂H | |
| (CH₂)₂S(O)CH₂CF₂H | H | Me | |
| (CH₂)₂S(O)CH₂CF₃ | H | OMe | |
| CH₂S(O)CF₂H | H | OCF₂H | |
| CH₂S(O)CH₂CH₂F | CH₃ | OCF₂H | |
| CH₂S(O)CH₂CHF₂ | H | Me | |
| CH₂S(O)CH₂CH₂Br | H | OMe | |
| CH₂S(O)CH₂CH₂I | H | OCF₂H | |
| CH₂S(O)CF₃ | H | Me | |
| CH₂S(O)₂CH₃ | H | OMe | |
| CH₂S(O)₂CH₃ | H | OCF₂H | |
| CH₂S(O)₂CH₃ | H | Me | |
| (CH₂)₂S(O)₂CH₃ | H | OMe | |
| (CH₂)₂S(O)₂CH₃ | H | OCF₂H | |
| OCH₂OCH₂CF₃ | H | Me | |
| O(CH₂)₂OCH₂CF₃ | H | OMe | |
| O(CH₂)₂OCH₂CF₂H | H | OCF₂H | |
| O(CH₂)₂O(CH₂)₂Cl | H | Me | |
| O(CH₂)₂O(CH₂)₂Br | H | OMe | |
| O(CH₂)₂O(CH₂)₂I | H | OCF₂H | |
| O(CH₂)₂OCF₃ | H | Me | |
| OCH₂SCH₃ | H | OMe | |
| OCH₂SCH₃ | H | OCF₂H | |
| OCH₂SCH₃ | H | Me | |
| O(CH₂)₂SCH₃ | H | OMe | |
| O(CH₂)₂SCH₃ | H | OCF₂H | |
| O(CH₂)₂SCH₃ | CH₃ | Me | |
| O(CH₂)₂SCH₃ | H | Me | |
| O(CH₂)₂SCH₃ | H | OMe | |
| O(CH₂)₂SCH₂CH₃ | H | OCF₂H | |
| O(CH₂)₂SCH₂CH₃ | H | Me | |
| O(CH₂)₂SCH₂CH₃ | H | OMe | |
| O(CH₂)₂SCH₂CH₃ | H | OCF₂H | |
| OCH₂SCH₂CH₃ | H | OMe | |
| OCH₂SCH₂CF₃ | H | OCF₂H | |
| O(CH₂)₂SCH₂CF₃ | H | Me | |
| O(CH₂)₂SCH₂CF₂H | H | OMe | |
| O(CH₂)₂S(CH₂)₂Cl | H | OCF₂H | |

TABLE Va-continued $R_1 = CH_2CH=CH_2$

| $R_2$ | R | Y | m.p. (°C.) |
|---|---|---|---|
| O(CH$_2$)$_2$S(CH$_2$)$_2$Br | CH$_3$ | OMe | |
| O(CH$_2$)$_2$S(CH$_2$)$_2$I | H | Me | |
| O(CH$_2$)$_2$SCF$_3$ | H | OMe | |
| OCH$_2$S(O)CH$_3$ | H | OCF$_2$H | |
| OCH$_2$S(O)CH$_3$ | H | Me | |
| OCH$_2$S(O)CH$_3$ | H | OMe | |
| O(CH$_2$)$_2$S(O)CH$_3$ | H | OCF$_2$H | |
| O(CH$_2$)$_2$S(O)CH$_3$ | H | Me | |
| O(CH$_2$)$_2$S(O)CH$_3$ | H | OMe | |
| O(CH$_2$)$_2$S(O)CH$_2$CH$_3$ | H | OCF$_2$H | |
| O(CH$_2$)$_2$S(O)CH$_2$CH$_3$ | CH$_3$ | OCF$_2$H | |
| O(CH$_2$)$_2$S(O)CH$_2$CH$_3$ | H | Me | |
| OCH$_2$S(O)CH$_2$CH$_3$ | H | OMe | |
| O(CH$_2$)$_2$S(O)CH$_2$CF$_3$ | H | OCF$_2$H | |
| OCH$_2$S(O)CH$_2$CF$_3$ | H | Me | |
| O(CH$_2$)$_2$S(O)CH$_2$CF$_2$H | H | OMe | |
| O(CH$_2$)$_2$S(O)(CH$_2$)$_2$Cl | H | OCF$_2$H | |
| O(CH$_2$)$_2$S(O)(CH$_2$)$_2$Br | H | Me | |
| O(CH$_2$)$_2$S(O)(CH$_2$)$_2$I | H | OMe | |
| O(CH$_2$)$_2$S(O)CF$_3$ | H | OCF$_2$H | |
| OCH$_2$S(O)$_2$CH$_3$ | H | Me | |
| OCH$_2$S(O)$_2$CH$_3$ | H | OMe | |
| OCH$_2$S(O)$_2$CH$_3$ | H | OCF$_2$H | |
| O(CH$_2$)$_2$S(O)$_2$CH$_3$ | H | Me | |
| O(CH$_2$)$_2$S(O)$_2$CH$_3$ | H | OMe | |
| O(CH$_2$)$_2$S(O)$_2$CH$_3$ | H | OCF$_2$H | |
| O(CH$_2$)$_2$S(O)$_2$CH$_2$CH$_3$ | CH$_3$ | Me | |
| O(CH$_2$)$_2$S(O)$_2$CH$_2$CH$_3$ | H | Me | |
| O(CH$_2$)$_2$S(O)$_2$CH$_2$CH$_3$ | H | OMe | |
| O(CH$_2$)$_2$S(O)$_2$CH$_2$CH$_3$ | H | OCF$_2$H | |
| OCH$_2$S(O)$_2$CH$_2$CH$_3$ | H | Me | |
| OCH$_2$S(O)$_2$CH$_2$CF$_3$ | H | OMe | |
| O(CH$_2$)$_2$S(O)$_2$CH$_2$CF$_3$ | H | OCF$_2$H | |
| O(CH$_2$)$_2$S(O)$_2$CH$_2$CF$_2$H | H | Me | |
| O(CH$_2$)$_2$S(O)$_2$(CH$_2$)$_2$Cl | H | OMe | |
| O(CH$_2$)$_2$S(O)$_2$(CH$_2$)$_2$Br | H | OCF$_2$H | |
| O(CH$_2$)$_2$S(O)$_2$(CH$_2$)$_2$I | CH$_3$ | OMe | |
| O(CH$_2$)$_2$S(O)$_2$CF$_3$ | H | Me | |
| OCH$_2$S(O)$_2$CH$_2$Cl | H | OMe | |
| OCH$_2$S(O)$_2$CF$_3$ | H | OCF$_2$H | |
| O(CH$_2$)$_2$CN | H | Me | |
| O(CH$_2$)$_2$CN | H | OMe | |
| O(CH$_2$)$_2$CN | H | OCF$_2$H | |
| OCH$_2$CN | H | Me | |
| OCH$_2$CN | H | OMe | |
| OCH$_2$CN | H | OCF$_2$H | |
| OCH$_2$CN | CH$_3$ | OCF$_2$H | |
| OCH(CH$_3$)CN | H | Me | |
| O(CH$_2$)$_2$NH$_2$ | H | OMe | |
| O(CH$_2$)$_2$NH$_2$ | H | OCF$_2$H | |
| O(CH$_2$)$_2$NH$_2$ | H | Me | |
| O(CH$_2$)$_2$NHCH$_3$ | H | OMe | |
| O(CH$_2$)$_2$NHCH$_3$ | H | OCF$_2$H | |
| O(CH$_2$)$_2$NHCH$_3$ | H | Me | |
| O(CH$_2$)$_2$N(CH$_3$)$_2$ | H | OMe | |
| O(CH$_2$)$_2$N(CH$_3$)$_2$ | H | OCF$_2$H | |
| O(CH$_2$)$_2$N(CH$_3$)$_2$ | H | Me | |
| SCH$_2$OCH$_3$ | H | OMe | |
| SCH$_2$OCH$_3$ | H | OCF$_2$H | |
| SCH$_2$OCH$_3$ | H | Me | |
| SCH$_2$OCH$_2$CH$_3$ | H | OMe | |
| S(CH$_2$)$_2$OCH$_3$ | H | OCF$_2$H | |
| S(CH$_2$)$_2$OCH$_3$ | CH$_3$ | Me | |
| S(CH$_2$)$_2$OCH$_3$ | H | Me | |
| S(CH$_2$)$_2$OCH$_3$ | H | OMe | |
| S(CH$_2$)$_2$OCH$_2$CH$_3$ | H | OCF$_2$H | |
| S(CH$_2$)$_2$OCH$_2$CF$_3$ | H | Me | |
| SCH$_2$OCH$_2$CF$_3$ | H | OMe | |
| S(CH$_2$)$_2$OCH$_2$CF$_2$H | H | OCF$_2$H | |
| S(CH$_2$)$_2$O(CH$_2$)$_2$Cl | H | Me | |
| S(CH$_2$)$_2$O(CH$_2$)$_2$Br | H | OMe | |
| S(CH$_2$)$_2$O(CH$_2$)$_2$I | H | OCF$_2$H | |
| S(CH$_2$)$_2$OCF$_3$ | CH$_3$ | OMe | |
| SCH$_2$SCH$_3$ | H | Me | |
| SCH$_2$SCH$_3$ | H | OMe | |
| SCH$_2$SCH$_3$ | H | OCF$_2$H | |
| SCH$_2$SCH$_2$CH$_3$ | H | Me | |
| S(CH$_2$)$_2$SCH$_3$ | H | OMe | |
| S(CH$_2$)$_2$SCH$_3$ | H | OCF$_2$H | |
| S(CH$_2$)$_2$SCH$_3$ | H | Me | |
| S(CH$_2$)$_2$SCH$_2$CH$_3$ | H | OMe | |
| SCH(CH$_3$)SCH$_3$ | H | OCF$_2$H | |
| S(CH$_2$)$_2$SCH$_2$CF$_3$ | CH$_3$ | OCF$_2$H | |
| SCH$_2$SCH$_2$CF$_3$ | H | Me | |
| S(CH$_2$)$_2$SCH$_2$CF$_2$H | H | OMe | |
| S(CH$_2$)$_2$S(CH$_2$)$_2$Cl | H | OCF$_2$H | |
| S(CH$_2$)$_2$S(CH$_2$)$_2$Br | H | Me | |
| S(CH$_2$)$_2$S(CH$_2$)$_2$I | H | OMe | |
| S(CH$_2$)$_2$SCF$_3$ | H | OCF$_2$H | |
| SCH$_2$CN | H | Me | |
| SCH$_2$CN | H | OMe | |
| SCH$_2$CN | H | OCF$_2$H | |
| S(CH$_2$)$_2$CN | H | Me | |
| S(CH$_2$)$_2$CN | H | OMe | |
| S(CH$_2$)$_2$CN | H | OCF$_2$H | |
| SCH(CH$_3$)CN | H | Me | |
| SCHF$_2$ | H | OMe | |
| SCHF$_2$ | H | OCF$_2$H | |
| SCHF$_2$ | CH$_3$ | Me | |
| SCHF$_2$ | H | Me | |
| SCF$_3$ | H | OMe | |
| SCH$_2$CFH$_2$ | H | OCF$_2$H | |
| SCH$_2$CF$_2$H | H | Me | |
| SCH$_2$CF$_3$ | H | OMe | |
| SCH$_2$CF$_3$ | H | OCF$_2$H | |
| SCH$_2$CF$_3$ | H | Me | |
| SCH$_2$CF$_2$H | H | OMe | |
| S(CH$_2$)$_2$CFH$_2$ | H | OCF$_2$H | |
| S(CH$_2$)$_2$CClH$_2$ | CH$_3$ | OMe | |
| S(CH$_2$)$_2$CIH$_2$ | H | Me | |
| SCF$_2$CF$_3$ | H | OMe | |
| SCH(CH$_3$)CF$_3$ | H | OCF$_2$H | |
| S(CH$_2$)$_2$CCl$_3$ | H | Me | |
| S(O)CHF$_2$ | H | OMe | |
| S(O)CHF$_2$ | H | OCF$_2$H | |
| S(O)CHF$_2$ | H | Me | |
| S(O)CF$_3$ | H | OMe | |
| S(O)CH$_2$CFH$_2$ | H | OCF$_2$H | |
| S(O)CH$_2$CF$_2$H | CH$_3$ | OCF$_2$H | |
| S(O)CH$_2$CF$_3$ | H | Me | |
| S(O)CH$_2$CF$_3$ | H | OMe | |
| S(O)CH$_2$CF$_3$ | H | OCF$_2$H | |
| S(O)CH$_2$CF$_2$H | H | Me | |
| S(O)(CH$_2$)$_2$CFH$_2$ | H | OMe | |
| S(O)(CH$_2$)$_2$CClH$_2$ | H | OCF$_2$H | |
| S(O)(CH$_2$)$_2$CIH$_2$ | H | Me | |
| S(O)CF$_2$CF$_3$ | H | OMe | |
| S(O)CH(CH$_3$)CF$_3$ | H | OCF$_2$H | |
| S(O)(CH$_2$)$_2$CCl$_3$ | H | Me | |
| S(O)$_2$CHF$_2$ | H | OMe | |
| S(O)$_2$CHF$_2$ | H | OCF$_2$H | |
| S(O)$_2$CHF$_2$ | H | Me | |
| S(O)$_2$CF$_3$ | H | OMe | |
| S(O)$_2$CH$_2$CFH$_2$ | H | OCF$_2$H | |
| S(O)$_2$CH$_2$CF$_2$H | CH$_3$ | Me | |
| S(O)$_2$CH$_2$CF$_3$ | H | Me | |
| S(O)$_2$CH$_2$CF$_3$ | H | OMe | |
| S(O)$_2$CH$_2$CF$_3$ | H | OCF$_2$H | |
| S(O)$_2$CH$_2$CF$_2$H | H | Me | |
| S(O)$_2$(CH$_2$)$_2$CFH$_2$ | H | OMe | |
| S(O)$_2$(CH$_2$)$_2$CClH$_2$ | H | OCF$_2$H | |
| S(O)$_2$(CH$_2$)$_2$CIH$_2$ | H | Me | |
| S(O)$_2$CF$_2$CF$_3$ | H | OMe | |
| S(O)$_2$CH(CH$_3$)CF$_3$ | H | OCF$_2$H | |
| S(O)$_2$(CH$_2$)$_2$CCl$_3$ | CH$_3$ | OMe | |
| S(O)$_2$CH$_2$Cl | H | Me | |
| CH=CH$_2$ | H | OMe | |
| CH=CH$_2$ | H | OCF$_2$H | |
| CH=CH$_2$ | H | Me | |
| CH$_2$CH=CH$_2$ | H | OMe | |
| CH$_2$CH=CH$_2$ | H | OCF$_2$H | |
| CH$_2$CH=CH$_2$ | H | Me | |
| CH=CHCH$_3$ | H | OMe | |
| C(CH$_3$)=CH$_2$ | H | OCF$_2$H | |
| CH=CH$_2$ | CH$_3$ | OCF$_2$H | |
| C≡CH | H | Me | |
| C≡CH | H | OMe | |
| C≡CH | H | OCF$_2$H | |

TABLE Va-continued $R_1 = CH_2CH=CH_2$

| R_2 | R | Y | m.p. (°C.) |
|---|---|---|---|
| CH_2C≡CH | H | Me | |
| CH_2C≡CH | H | OMe | |
| CH_2C≡CH | H | OCF_2H | |
| C≡CCH_3 | H | Me | |
| C≡CCH_3 | H | OMe | |
| C≡CCH_3 | H | OCF_2H | |
| NH_2 | H | Me | |
| NH_2 | H | OMe | |
| NH_2 | H | OCF_2H | |
| NHCH_3 | H | Me | |
| NHCH_3 | H | OMe | |
| NHCH_3 | H | OCF_2H | |
| NHCH_3 | CH_3 | Me | |
| N(CH_3)_2 | H | Me | |
| N(CH_3)_2 | H | OMe | |
| N(CH_3)_2 | H | OCF_2H | |
| NHCH_2CH_3 | H | Me | |
| NHCH_2CH_3 | H | OMe | |
| NHCH_2CH_3 | H | OCF_2H | |
| N(CH_3)CH_2CH_3 | H | Me | |
| N(CH_2CH_3)_2 | H | OMe | |
| NHCH_2CF_3 | H | OCF_2H | |
| NHCH_2CF_3 | CH_3 | OMe | |
| NHCH_2CF_3 | H | Me | |
| NHCH_2CF_3 | H | OMe | |
| N(CH_3)CH_2CF_3 | H | OCF_2H | |
| N(CH_3)CH_2CHF_2 | H | Me | |
| N(CH_3)(CH_2)_2F | H | OMe | |
| N(CH_3)(CH_2)_2Cl | H | OCF_2H | |
| N(CH_3)(CH_2)_2I | H | Me | |
| N(CH_3)(CH_2)_2Br | H | OMe | |
| NHCF_3 | CH_3 | OCF_2H | |
| NHCF_3 | H | Me | |
| NH(CH_2)_2F | H | OMe | |
| N(CH_3)CF_2H | H | OCF_2H | |
| NHCF_2H | H | Me | |

TABLE VIa $R_1 = CH_2CH_2OCH_3$

| R_2 | R | Y | m.p. (°C.) |
|---|---|---|---|
| Me | H | Me | |
| Me | Me | Me | |
| Me | H | OMe | |
| Me | Me | OMe | |
| Me | H | OCF_2H | |
| Me | Me | OCF_2H | |
| Et | H | Me | |
| Et | Me | Me | |
| Et | H | OMe | |
| Et | Me | OMe | |
| Et | H | OCF_2H | |
| Et | Me | OCF_2H | |
| Pr | H | Me | |
| Pr | Me | Me | |
| Pr | H | OMe | |
| Pr | Me | OMe | |
| Pr | H | OCF_2H | |
| Pr | Me | OCF_2H | |
| i-Pr | H | Me | |
| i-Pr | Me | Me | |
| i-Pr | H | OMe | |
| i-Pr | Me | OMe | |
| i-Pr | H | OCF_2H | |
| i-Pr | Me | OCF_2H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF_2H | |
| cyclo-Pr | Me | OCF_2H | |
| OMe | H | Me | |
| OMe | Me | Me | |
| OMe | H | OMe | |
| OMe | Me | OMe | |
| OMe | H | OCF_2H | |
| OMe | Me | OCF_2H | |
| OEt | H | Me | |

TABLE VIa-continued $R_1 = CH_2CH_2OCH_3$

| R_2 | R | Y | m.p. (°C.) |
|---|---|---|---|
| OEt | Me | Me | |
| OEt | H | OMe | |
| OEt | Me | OMe | |
| OEt | H | OCF_2H | |
| OEt | Me | OCF_2H | |
| O—n-Pr | H | Me | |
| O—n-Pr | Me | Me | |
| O—n-Pr | H | OMe | |
| O—n-Pr | Me | OMe | |
| O—n-Pr | H | OCF_2H | |
| O—n-Pr | Me | OCF_2H | |
| O—i-Pr | H | Me | |
| O—i-Pr | Me | Me | |
| O—i-Pr | H | OMe | |
| O—i-Pr | Me | OMe | |
| O—i-Pr | H | OCF_2H | |
| O—i-Pr | Me | OCF_2H | |
| SMe | H | Me | |
| SMe | Me | Me | |
| SMe | H | OMe | |
| SMe | Me | OMe | |
| SMe | H | OCF_2H | |
| SMe | Me | OCF_2H | |
| SEt | H | Me | |
| SEt | Me | Me | |
| SEt | H | OMe | |
| SEt | Me | OMe | |
| SEt | H | OCF_2H | |
| SEt | Me | OCF_2H | |
| S—n-Pr | H | Me | |
| S—n-Pr | Me | Me | |
| S—n-Pr | H | OMe | |
| S—n-Pr | Me | OMe | |
| S—n-Pr | H | OCF_2H | |
| S—n-Pr | Me | OCF_2H | |
| S—i-Pr | H | Me | |
| S—i-Pr | Me | Me | |
| S—i-Pr | H | OMe | |
| S—i-Pr | Me | OMe | |
| S—i-Pr | H | OCF_2H | |
| S—i-Pr | Me | OCF_2H | |
| O—allyl | H | Me | |
| O—allyl | Me | Me | |
| O—allyl | H | OMe | |
| O—allyl | Me | OMe | |
| O—allyl | H | OCF_2H | |
| O—allyl | Me | OCF_2H | |
| O—propargyl | H | Me | |
| O—propargyl | Me | Me | |
| O—propargyl | H | OMe | |
| O—propargyl | Me | OMe | |
| O—propargyl | H | OCF_2H | |
| O—propargyl | Me | OCF_2H | |
| CH_2F | H | Me | |
| CH_2F | Me | Me | |
| CH_2F | H | OMe | |
| CH_2F | Me | OMe | |
| CH_2F | H | OCF_2H | |
| CH_2F | Me | OCF_2H | |
| CHF_2 | H | Me | |
| CHF_2 | Me | Me | |
| CHF_2 | H | OMe | |
| CHF_2 | Me | OMe | |
| CHF_2 | H | OCF_2H | |
| CHF_2 | Me | OCF_2H | |
| CF_3 | H | Me | |
| CF_3 | Me | Me | |
| CF_3 | H | OMe | |
| CF_3 | Me | OMe | |
| DF_3 | H | OCF_2H | |
| CF_3 | Me | OCF_2H | |
| CH_2Cl | H | Me | |
| CH_2Cl | Me | Me | |
| CH_2Cl | H | OMe | |
| CH_2Cl | Me | OMe | |
| CH_2Cl | H | OCF_2H | |
| CH_2Cl | Me | OCF_2H | |
| CHCl_2 | H | Me | |
| CHCl_2 | Me | Me | |

TABLE VIa-continued $R_1 = CH_2CH_2OCH_3$

| R₂ | R | Y | m.p. (°C.) |
|---|---|---|---|
| CHCl₂ | H | OMe | |
| CHCl₂ | Me | OMe | |
| CHCl₂ | H | OCF₂H | |
| CHCl₂ | Me | OCF₂H | |
| CCl₃ | H | Me | |
| CCl₃ | Me | Me | |
| CCl₃ | H | OMe | |
| CCl₃ | Me | OMe | |
| CCl₃ | H | OCF₂H | |
| CCl₃ | Me | OCF₂H | |
| CHFCH₃ | H | Me | |
| CHFCH₃ | Me | Me | |
| CHFCH₃ | H | OMe | |
| CHFCH₃ | Me | OMe | |
| CHFCH₃ | H | OCF₂H | |
| CHFCH₃ | Me | OCF₂H | |
| CF₂CH₃ | H | Me | |
| CF₂CH₃ | Me | Me | |
| CF₂CH₃ | H | OMe | |
| CF₂CH₃ | Me | OMe | |
| CF₂CH₃ | H | OCF₂H | |
| CF₂CH₃ | Me | OCF₂H | |
| CH₂CH₂F | H | Me | |
| CH₂CH₂F | Me | Me | |
| CH₂CH₂F | H | OMe | |
| CH₂CH₂F | Me | OMe | |
| CH₂CH₂F | H | OCF₂H | |
| CH₂CH₂F | Me | OCF₂H | |
| CH₂CHF₂ | H | Me | |
| CH₂CHF₂ | Me | Me | |
| CH₂CHF₂ | H | OMe | |
| CH₂CHF₂ | Me | OMe | |
| CH₂CHF₂ | H | OCF₂H | |
| CH₂CHF₂ | Me | OCF₂H | |
| CH₂CF₃ | H | Me | |
| CH₂CF₃ | Me | Me | |
| CH₂CF₃ | H | OMe | |
| CH₂CF₃ | Me | OMe | |
| CH₂CF₃ | H | OCF₂H | |
| CH₂CF₃ | Me | OCF₂H | |
| CHClCH₃ | H | Me | |
| CHClCH₃ | Me | Me | |
| CHClCH₃ | H | OMe | |
| CHClCH₃ | Me | OMe | |
| CHClCH₃ | H | OCF₂H | |
| CHClCH₃ | Me | OCF₂H | |
| CH₂OCH₃ | H | Me | |
| CH₂OCH₃ | Me | Me | |
| CH₂OCH₃ | H | OMe | |
| CH₂OCH₃ | Me | OMe | |
| CH₂OCH₃ | H | OCF₂H | |
| CH₂OCH₃ | Me | OCF₂H | |
| (CH₂)₂OCH₃ | H | Me | |
| (CH₂)₂OCH₃ | Me | Me | |
| (CH₂)₂OCH₃ | H | OMe | |
| (CH₂)₂OCH₃ | Me | OMe | |
| (CH₂)₂OCH₃ | H | OCF₂H | |
| (CH₂)₂OCH₃ | Me | OCF₂H | |
| CH(OCH₃)CH₃ | H | Me | |
| CH(OCH₃)CH₃ | Me | Me | |
| CH(OCH₃)CH₃ | H | OMe | |
| CH(OCH₃)CH₃ | Me | OMe | |
| CH(OCH₃)CH₃ | H | OCF₂H | |
| CH(OCH₃)CH₃ | Me | OCF₂H | |
| CH₂SCH₃ | H | Me | |
| CH₂SCH₃ | Me | Me | |
| CH₂SCH₃ | H | OMe | |
| CH₂SCH₃ | Me | OMe | |
| CH₂SCH₃ | H | OCF₂H | |
| CH₂SCH₃ | Me | OCF₂H | |
| (CH₂)₂SCH₃ | H | Me | |
| (CH₂)₂SCH₃ | Me | Me | |
| (CH₂)₂SCH₃ | H | OMe | |
| (CH₂)₂SCH₃ | Me | OMe | |
| (CH₂)₂SCH₃ | Me | OCF₂H | |
| (CH₂)₂SCH₃ | Me | OCF₂H | |
| CH(SCH₃)CH₃ | H | Me | |
| CH(SCH₃)CH₃ | Me | Me | |
| CH(SCH₃)CH₃ | H | OMe | |
| CH(SCH₃)CH₃ | Me | OMe | |
| CH(SCH₃)CH₃ | H | OCF₂H | |
| CH(SCH₃)CH₃ | Me | OCF₂H | |
| OCF₂H | H | Me | |
| OCF₂H | Me | Me | |
| OCF₂H | H | OMe | |
| OCF₂H | Me | OMe | |
| OCF₂H | H | OCF₂H | |
| OCF₂H | Me | OCF₂H | |
| OCH₂CH₂F | H | Me | |
| OCH₂CH₂F | Me | Me | |
| OCH₂CH₂F | H | OMe | |
| OCH₂CH₂F | Me | OMe | |
| OCH₂CH₂F | H | OCF₂H | |
| OCH₂CH₂F | Me | OCF₂H | |
| OCH₂CHF₂ | H | Me | |
| OCH₂CHF₂ | Me | Me | |
| OCH₂CHF₂ | H | OMe | |
| OCH₂CHF₂ | Me | OMe | |
| OCH₂CHF₂ | H | OCF₂H | |
| OCH₂CHF₂ | Me | OCF₂H | |
| OCH₂CF₃ | H | Me | |
| OCH₂CF₃ | Me | Me | |
| OCH₂CF₃ | H | OMe | |
| OCH₂CF₃ | Me | OMe | |
| OCH₂CF₃ | H | OCF₂H | |
| OCH₂CF₃ | Me | OCF₂H | |
| O(CH₂)₂Cl | H | Me | |
| O(CH₂)₂Cl | Me | Me | |
| O(CH₂)₂Cl | H | OMe | |
| O(CH₂)₂Cl | Me | OMe | |
| O(CH₂)₂Cl | H | OCF₂H | |
| O(CH₂)₂Cl | Me | OCF₂H | |
| S(O)Me | H | Me | |
| S(O)Me | Me | Me | |
| S(O)Me | H | OMe | |
| S(O)Me | Me | OMe | |
| S(O)Me | H | OCF₂H | |
| S(O)Me | Me | OCF₂H | |
| S(O)Et | H | Me | |
| S(O)Et | Me | Me | |
| S(O)Et | H | OMe | |
| S(O)Et | Me | OMe | |
| S(O)Et | H | OCF₂H | |
| S(O)Et | Me | OCF₂H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF₂H | |
| S(O)—n-Pr | Me | OCF₂H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF₂H | |
| S(O)—i-Pr | Me | OCF₂H | |
| SO₂Me | H | Me | |
| SO₂Me | Me | Me | |
| SO₂Me | H | OMe | |
| SO₂Me | Me | OMe | |
| SO₂Me | H | OCF₂H | |
| SO₂Me | Me | OCF₂H | |
| SO₂Et | H | Me | |
| SO₂Et | Me | Me | |
| SO₂Et | H | OMe | |
| SO₂Et | Me | OMe | |
| SO₂Et | H | OCF₂H | |
| SO₂Et | Me | OCF₂H | |
| SO₂—n-Pr | H | Me | |
| SO₂—n-Pr | Me | Me | |
| SO₂—n-Pr | H | OMe | |
| SO₂—n-Pr | Me | OMe | |
| SO₂—n-Pr | H | OCF₂H | |
| SO₂—n-Pr | Me | OCF₂H | |
| SO₂—i-Pr | H | Me | |
| SO₂—i-Pr | Me | Me | |
| SO₂—i-Pr | H | OMe | |
| SO₂—i-Pr | Me | OMe | |

TABLE VIa-continued $R_1 = CH_2CH_2OCH_3$

| $R_2$ | R | Y | m.p. (°C.) |
|---|---|---|---|
| $SO_2$—i-Pr | H | $OCF_2H$ | |
| $SO_2$—i-Pr | Me | $OCF_2H$ | |
| S—allyl | H | Me | |
| S—allyl | Me | Me | |
| S—allyl | H | OMe | |
| S—allyl | Me | OMe | |
| S—allyl | H | $OCF_2H$ | |
| S—allyl | Me | $OCF_2H$ | |
| S(O)allyl | H | Me | |
| S(O)allyl | Me | Me | |
| S(O)allyl | H | OMe | |
| S(O)allyl | Me | OMe | |
| S(O)allyl | H | $OCF_2H$ | |
| S(O)allyl | Me | $OCF_2H$ | |
| $SO_2$allyl | H | Me | |
| $SO_2$allyl | Me | Me | |
| $SO_2$allyl | H | OMe | |
| $SO_2$allyl | Me | OMe | |
| $SO_2$allyl | H | $OCF_2H$ | |
| $SO_2$allyl | Me | $OCF_2H$ | |
| S—propargyl | H | Me | |
| S—propargyl | Me | Me | |
| S—propargyl | H | OMe | |
| S—propargyl | Me | OMe | |
| S—propargyl | H | $OCF_2H$ | |
| S—propargyl | Me | $OCF_2H$ | |
| S(O)propargyl | H | Me | |
| S(O)propargyl | Me | Me | |
| S(O)propargyl | H | OMe | |
| S(O)propargyl | Me | OMe | |
| S(O)propargyl | H | $OCF_2H$ | |
| S(O)propargyl | Me | $OCF_2H$ | |
| $SO_2$propargyl | H | Me | |
| $SO_2$propargyl | Me | Me | |
| $SO_2$propargyl | H | OMe | |
| $SO_2$propargyl | Me | OMe | |
| $SO_2$propargyl | H | $OCF_2H$ | |
| $SO_2$propargyl | Me | $OCF_2H$ | |
| $CH_2OCH_2CH_3$ | H | Me | |
| $CH_2OCH_2CH_3$ | H | OMe | |
| $CH_2OCH_2CH_3$ | H | $OCF_2H$ | |
| $(CH_2)_2OCH_2CH_3$ | H | Me | |
| $(CH_2)_2OCH_2CH_3$ | H | OMe | |
| $(CH_2)_2OCH_2CH_3$ | H | $OCF_2H$ | |
| $(CH_2)_2OCH_2CH_3$ | $CH_3$ | Me | |
| $CH(CH_3)OCH_2CH_3$ | H | Me | |
| $CH(CH_3)OCH_2CH_3$ | H | OMe | |
| $CH(CH_3)OCH_2CH_3$ | H | $OCF_2H$ | |
| $CH_2OCH_2CF_3$ | H | Me | |
| $CH_2OCH_2CF_3$ | H | OMe | |
| $CH_2OCH_2CF_3$ | H | $OCF_2H$ | |
| $(CH_2)_2OCH_2CF_2H$ | H | Me | |
| $(CH_2)_2OCH_2CF_2H$ | H | OMe | |
| $CH_2OCF_2H$ | H | $OCF_2H$ | |
| $CH_2OCH_2CH_2F$ | $CH_3$ | OMe | |
| $CH_2OCH_2CHF_2$ | H | Me | |
| $CH_2OCH_2CH_2Br$ | H | OMe | |
| $CH_2OCH_2CH_2Cl$ | H | $OCF_2H$ | |
| $CH_2OCH_2CH_2I$ | H | Me | |
| $CH_2OCF_3$ | H | OMe | |
| $CH_2SCH_2CH_3$ | H | $OCF_2H$ | |
| $CH_2SCH_2CH_3$ | H | Me | |
| $CH_2SCH_2CH_3$ | H | OMe | |
| $(CH_2)_2SCH_2CH_3$ | H | $OCF_2H$ | |
| $(CH_2)_2SCH_2CH_3$ | $CH_3$ | $OCF_2H$ | |
| $(CH_2)_2SCH_2CH_3$ | H | Me | |
| $(CH_2)_2SCH_2CH_3$ | H | OMe | |
| $CH(CH_3)SCH_2CH_3$ | H | $OCF_2H$ | |
| $CH(CH_3)SCH_2CH_3$ | H | Me | |
| $CH(CH_3)SCH_2CH_3$ | H | OMe | |
| $CH_2SCH_2CF_3$ | H | $OCF_2H$ | |
| $CH_2SCH_2CF_3$ | H | Me | |
| $CH_2SCH_2CF_3$ | H | OMe | |
| $(CH_2)_2SCH_2CF_2H$ | H | $OCF_2H$ | |
| $(CH_2)_2S(O)_2CH_3$ | H | Me | |
| $CH_2S(O)_2CH_2CH_3$ | H | OMe | |
| $CH_2S(O)_2CH_2CH_3$ | H | $OCF_2H$ | |
| $CH_2S(O)_2CH_2CH_3$ | H | Me | |
| $(CH_2)_2S(O)_2CH_2CH_3$ | H | OMe | |
| $CH(CH_3)S(O)_2CH_3$ | H | $OCF_2H$ | |
| $CH_2S(O)_2CH_2CF_3$ | $CH_3$ | Me | |
| $CH_2S(O)_2CH_2CF_3$ | H | Me | |
| $CH_2S(O)_2CH_2CF_3$ | H | OMe | |
| $CH_2S(O)_2CH_2CF_3$ | H | $OCF_2H$ | |
| $(CH_2)_2S(O)_2CH_2CF_2H$ | H | Me | |
| $(CH_2)_2S(O)_2CH_2CF_3$ | H | OMe | |
| $CH_2S(O)_2CF_2H$ | H | $OCF_2H$ | |
| $CH_2S(O)_2CH_2CH_2F$ | H | Me | |
| $CH_2S(O)_2CH_2CHF_2$ | H | OMe | |
| $CH_2S(O)_2CH_2CH_2Br$ | H | $OCF_2H$ | |
| $CH_2S(O)_2CH_2CH_2I$ | $CH_3$ | OMe | |
| $CH_2S(O)_2CF_3$ | H | Me | |
| $CH_2S(O)_2CH_2Cl$ | H | OMe | |
| $OCH_2OCH_3$ | H | $OCF_2H$ | |
| $OCH_2OCH_3$ | H | Me | |
| $OCH_2OCH_3$ | H | OMe | |
| $O(CH_2)_2OCH_3$ | H | $OCF_2H$ | |
| $O(CH_2)_2OCH_3$ | H | Me | |
| $O(CH_2)_2OCH_3$ | H | OMe | |
| $O(CH_2)_2OCH_2CH_3$ | H | $OCF_2H$ | |
| $O(CH_2)_2OCH_2CH_3$ | $CH_3$ | $OCF_2H$ | |
| $O(CH_2)_2OCH_2CH_3$ | H | Me | |
| $O(CH_2)_2OCH_2CH_3$ | H | OMe | |
| $OCH_2OCH_2CH_3$ | H | $OCF_2H$ | |
| $(CH_2)_2SCH_2CF_3$ | H | Me | |
| $CH_2SCF_2H$ | H | OMe | |
| $CH_2SCH_2CH_2F$ | H | $OCF_2H$ | |
| $CH_2SCH_2CHF_2$ | H | Me | |
| $CH_2SCH_2CH_2Br$ | H | OMe | |
| $CH_2SCH_2CH_2Cl$ | H | $OCF_2H$ | |
| $CH_2SCH_2CH_2I$ | $CH_3$ | Me | |
| $CH_2SCF_3$ | H | Me | |
| $CH_2S(O)CH_3$ | H | OMe | |
| $CH_2S(O)CH_3$ | H | $OCF_2H$ | |
| $CH_2S(O)CH_3$ | H | Me | |
| $(CH_2)_2S(O)CH_3$ | H | OMe | |
| $(CH_2)_2S(O)CH_3$ | H | $OCF_2H$ | |
| $(CH_2)_2S(O)CH_3$ | H | Me | |
| $CH_2S(O)CH_2CH_3$ | H | OMe | |
| $CH_2S(O)CH_2CH_3$ | H | $OCF_2H$ | |
| $CH_2S(O)CH_2CH_3$ | $CH_3$ | OMe | |
| $CH_2S(O)CH_2CH_3$ | H | Me | |
| $(CH_2)_2S(O)CH_2CH_3$ | H | OMe | |
| $CH(CH_3S(O)CH_3$ | H | $OCF_2H$ | |
| $CH_2S(O)CH_2CF_3$ | H | Me | |
| $CH_2S(O)CH_2CF_3$ | H | OMe | |
| $CH_2S(O)CH_2CF_3$ | H | $OCF_2H$ | |
| $(CH_2)_2S(O)CH_2CF_2H$ | H | Me | |
| $(CH_2)_2S(O)CH_2CF_3$ | H | OMe | |
| $CH_2S(O)CF_2H$ | H | $OCF_2H$ | |
| $CH_2S(O)CH_2CH_2F$ | $CH_3$ | $OCF_2H$ | |
| $CH_2S(O)CH_2CHF_2$ | H | Me | |
| $CH_2S(O)CH_2CH_2Br$ | H | OMe | |
| $CH_2S(O)CH_2CH_2I$ | H | $OCF_2H$ | |
| $CH_2S(O)CF_3$ | H | Me | |
| $CH_2S(O)_2CH_3$ | H | OMe | |
| $CH_2S(O)_2CH_3$ | H | $OCF_2H$ | |
| $CH_2S(O)_2CH_3$ | H | Me | |
| $(CH_2)_2S(O)_2CH_3$ | H | OMe | |
| $(CH_2)_2S(O)_2CH_3$ | H | $OCF_2H$ | |
| $OCH_2OCH_2CF_3$ | H | Me | |
| $O(CH_2)_2OCH_2CF_3$ | H | OMe | |
| $O(CH_2)_2OCH_2CF_2H$ | H | $OCF_2H$ | |
| $O(CH_2)_2O(CH_2)_2Cl$ | H | Me | |
| $O(CH_2)_2O(CH_2)_2Br$ | H | OMe | |
| $O(CH_2)_2O(CH_2)_2I$ | H | $OCF_2H$ | |
| $O(CH_2)_2OCF_3$ | H | Me | |
| $OCH_2SCH_3$ | H | OMe | |
| $OCH_2SCH_3$ | H | $OCF_2H$ | |
| $OCH_2SCH_3$ | H | Me | |
| $O(CH_2)_2SCH_3$ | H | OMe | |
| $O(CH_2)_2SCH_3$ | H | $OCF_2H$ | |
| $O(CH_2)_2SCH_3$ | $CH_3$ | Me | |
| $O(CH_2)_2SCH_3$ | H | Me | |
| $O(CH_2)_2SCH_2CH_3$ | H | OMe | |
| $O(CH_2)_2SCH_2CH_3$ | H | $OCF_2H$ | |
| $O(CH_2)_2SCH_2CH_3$ | H | Me | |
| $OCH_2SCH_2CH_3$ | H | OMe | |

TABLE VIa-continued

| R₂ | R₁ = CH₂CH₂OCH₃ | | m.p. (°C.) |
|---|---|---|---|
| | R | Y | |
| OCH₂SCH₂CF₃ | H | OCF₂H | |
| O(CH₂)₂SCH₂CF₂H | H | Me | |
| O(CH₂)₂SCH₂CF₂H | H | OMe | |
| O(CH₂)₂S(CH₂)₂Cl | H | OCF₂H | |
| O(CH₂)₂S(CH₂)₂Br | CH₃ | OMe | |
| O(CH₂)₂S(CH₂)₂I | H | Me | |
| O(CH₂)₂SCF₃ | H | OMe | |
| OCH₂S(O)CH₃ | H | OCF₂H | |
| OCH₂S(O)CH₃ | H | Me | |
| OCH₂S(O)CH₃ | H | OMe | |
| O(CH₂)₂S(O)CH₃ | H | OCF₂H | |
| O(CH₂)₂S(O)CH₃ | H | Me | |
| O(CH₂)₂S(O)CH₃ | H | OMe | |
| O(CH₂)₂S(O)CH₂CH₃ | H | OCF₂H | |
| O(CH₂)₂S(O)CH₂CH₃ | CH₃ | OCF₂H | |
| O(CH₂)₂S(O)CH₂CH₃ | H | Me | |
| OCH₂S(O)CH₂CH₃ | H | OMe | |
| O(CH₂)₂S(O)CH₂CF₃ | H | OCF₂H | |
| OCH₂S(O)CH₂CF₃ | H | Me | |
| O(CH₂)₂S(O)CH₂CF₂H | H | OMe | |
| O(CH₂)₂S(O)(CH₂)₂Cl | H | OCF₂H | |
| O(CH₂)₂S(O)(CH₂)₂Br | H | Me | |
| O(CH₂)₂S(O)(CH₂)₂I | H | OMe | |
| O(CH₂)₂S(O)CF₃ | H | OCF₂H | |
| OCH₂S(O)₂CH₃ | H | Me | |
| OCH₂S(O)₂CH₃ | H | OMe | |
| OCH₂S(O)₂CH₃ | H | OCF₂H | |
| O(CH₂)₂S(O)₂CH₃ | H | Me | |
| O(CH₂)₂S(O)₂CH₃ | H | OMe | |
| O(CH₂)₂S(O)₂CH₃ | H | OCF₂H | |
| O(CH₂)₂S(O)₂CH₂CH₃ | CH₃ | Me | |
| O(CH₂)₂S(O)₂CH₂CH₃ | H | Me | |
| O(CH₂)₂S(O)₂CH₂CH₃ | H | OMe | |
| O(CH₂)₂S(O)₂CH₂CH₃ | H | OCF₂H | |
| OCH₂S(O)₂CH₂CH₃ | H | Me | |
| OCH₂S(O)₂CH₂CF₃ | H | OMe | |
| O(CH₂)₂S(O)₂CH₂CF₃ | H | OCF₂H | |
| O(CH₂)₂S(O)₂CH₂CF₂H | H | Me | |
| O(CH₂)₂S(O)₂(CH₂)₂Cl | H | OMe | |
| O(CH₂)₂S(O)₂(CH₂)₂Br | H | OCF₂H | |
| O(CH₂)₂S(O)₂(CH₂)₂I | CH₃ | OMe | |
| O(CH₂)₂S(O)₂CF₃ | H | Me | |
| OCH₂S(O)₂CH₂Cl | H | OMe | |
| OCH₂S(O)₂CF₃ | H | OCF₂H | |
| O(CH₂)₂CN | H | Me | |
| O(CH₂)₂CN | H | OMe | |
| O(CH₂)₂CN | H | OCF₂H | |
| OCH₂CN | H | Me | |
| OCH₂CN | H | OMe | |
| OCH₂CN | H | OCF₂H | |
| OCH₂CN | CH₃ | OCF₂H | |
| OCH(CH₃)CN | H | Me | |
| O(CH₂)₂NH₂ | H | OMe | |
| O(CH₂)₂NH₂ | H | OCF₂H | |
| O(CH₂)₂NH₂ | H | Me | |
| O(CH₂)₂NHCH₃ | H | OMe | |
| O(CH₂)₂NHCH₃ | H | OCF₂H | |
| O(CH₂)₂NHCH₃ | H | Me | |
| O(CH₂)₂N(CH₃)₂ | H | OMe | |
| O(CH₂)₂N(CH₃)₂ | H | OCF₂H | |
| O(CH₂)₂N(CH₃)₂ | H | Me | |
| SCH₂OCH₃ | H | OMe | |
| SCH₂OCH₃ | H | OCF₂H | |
| SCH₂OCH₃ | H | Me | |
| SCH₂OCH₂CH₃ | H | OMe | |
| S(CH₂)₂OCH₃ | H | OCF₂H | |
| S(CH₂)₂OCH₃ | CH₃ | Me | |
| S(CH₂)₂OCH₃ | H | Me | |
| S(CH₂)₂OCH₃ | H | OMe | |
| S(CH₂)₂OCH₂CH₃ | H | OCF₂H | |
| S(CH₂)₂OCH₂CF₃ | H | Me | |
| SCH₂OCH₂CF₃ | H | OMe | |
| S(CH₂)₂OCH₂CF₂H | H | OCF₂H | |
| S(CH₂)₂O(CH₂)₂Cl | H | Me | |
| S(CH₂)₂O(CH₂)₂Br | H | OMe | |
| S(CH₂)₂O(CH₂)₂I | H | OCF₂H | |
| S(CH₂)₂OCF₃ | CH₃ | OMe | |
| SCH₂SCH₃ | H | Me | |
| SCH₂SCH₃ | H | OMe | |

TABLE VIa-continued

| R₂ | R₁ = CH₂CH₂OCH₃ | | m.p. (°C.) |
|---|---|---|---|
| | R | Y | |
| SCH₂SCH₃ | H | OCF₂H | |
| SCH₂SCH₂CH₃ | H | Me | |
| S(CH₂)₂SCH₃ | H | OMe | |
| S(CH₂)₂SCH₃ | H | OCF₂H | |
| S(CH₂)₂SCH₃ | H | Me | |
| S(CH₂)₂SCH₂CH₃ | H | OMe | |
| SCH(CH₃)SCH₃ | H | OCF₂H | |
| S(CH₂)₂SCH₂CF₃ | CH₃ | OCF₂H | |
| SCH₂SCH₂CF₃ | H | Me | |
| S(CH₂)₂SCH₂CF₂H | H | OMe | |
| S(CH₂)₂S(CH₂)₂Cl | H | OCF₂H | |
| S(CH₂)₂S(CH₂)₂Br | H | Me | |
| S(CH₂)₂S(CH₂)₂I | H | OMe | |
| S(CH₂)₂SCF₃ | H | OCF₂H | |
| SCH₂CN | H | Me | |
| SCH₂CN | H | OMe | |
| SCH₂CN | H | OCF₂H | |
| S(CH₂)₂CN | H | Me | |
| S(CH₂)₂CN | H | OMe | |
| S(CH₂)₂CN | H | OCF₂H | |
| SCH(CH₃)CN | H | Me | |
| SCHF₂ | H | OMe | |
| SCHF₂ | H | OCF₂H | |
| SCHF₂ | CH₃ | Me | |
| SCHF₂ | H | Me | |
| SCF₃ | H | OMe | |
| SCH₂CFH | H | OCF₂H | |
| SCH₂CF₂H | H | Me | |
| SCH₂CF₃ | H | OMe | |
| SCH₂CF₃ | H | OCF₂H | |
| SCH₂CF₃ | H | Me | |
| SCH₂CF₂H | H | OMe | |
| S(CH₂)₂CFH₂ | H | OCF₂H | |
| S(CH₂)₂CClH₂ | CH₃ | OMe | |
| S(CH₂)₂CIH₂ | H | Me | |
| SCF₂CF₃ | H | OMe | |
| SCH(CH₃)CF₃ | H | OCF₂H | |
| S(CH₂)₂CCl₃ | H | Me | |
| S(O)CHF₂ | H | OMe | |
| S(O)CHF₂ | H | OCF₂H | |
| S(O)CHF₂ | H | Me | |
| S(O)CF₃ | H | OMe | |
| S(O)CH₂CFH₂ | H | OCF₂H | |
| S(O)CH₂CF₂H | CH₃ | OCF₂H | |
| S(O)CH₂CF₃ | H | Me | |
| S(O)CH₂CF₃ | H | OMe | |
| S(O)CH₂CF₃ | H | OCF₂H | |
| S(O)CH₂CF₂H | H | Me | |
| S(O)(CH₂)₂CFH₂ | H | OMe | |
| S(O)(CH₂)₂CClH₂ | H | OCF₂H | |
| S(O)(CH₂)₂CIH₂ | H | Me | |
| S(O)CF₂CF₃ | H | OMe | |
| S(O)CH(CH₃)CF₃ | H | OCF₂H | |
| S(O)(CH₂)₂CCl₃ | H | Me | |
| S(O)₂CHF₂ | H | OMe | |
| S(O)₂CHF₂ | H | OCF₂H | |
| S(O)₂CHF₂ | H | Me | |
| S(O)₂CF₃ | H | OMe | |
| S(O)₂CH₂CFH₂ | H | OCF₂H | |
| S(O)₂CH₂CF₂H | H | Me | |
| S(O)₂CH₂CF₂H | CH₃ | Me | |
| S(O)₂CH₂CF₃ | H | Me | |
| S(O)₂CH₂CF₃ | H | OMe | |
| S(O)₂CH₂CF₃ | H | OCF₂H | |
| S(O)₂CH₂CF₂H | H | Me | |
| S(O)₂(CH₂)₂CFH₂ | H | OMe | |
| S(O)₂(CH₂)₂CClH₂ | H | OCF₂H | |
| S(O)₂(CH₂)₂CIH₂ | H | Me | |
| S(O)₂CF₂CF₃ | H | OMe | |
| S(O)₂CH(CH₃)CF₃ | H | OCF₂H | |
| S(O)₂(CH₂)₂CCl₃ | CH₃ | OMe | |
| S(O)₂CH₂Cl | H | Me | |
| CH=CH₂ | H | OMe | |
| CH=CH₂ | H | OCF₂H | |
| CH=CH₂ | H | Me | |
| CH₂CH=CH₂ | H | OMe | |
| CH₂CH=CH₂ | H | OCF₂H | |
| CH₂CH=CH₂ | H | Me | |
| CH=CHCH₃ | H | OMe | |
| C(CH₃)=CH₂ | H | OCF₂H | |

TABLE VIa-continued $R_1 = CH_2CH_2OCH_3$

| R₂ | R | Y | m.p. (°C.) |
|---|---|---|---|
| CH=CH₂ | CH₃ | OCF₂H | |
| CH=CH | H | Me | |
| CH=CH | H | OMe | |
| CH=CH | H | OCF₂H | |
| CH₂C≡CH | H | Me | |
| CH₂C≡CH | H | OMe | |
| CH₂C≡CH | H | OCF₂H | |
| C≡CCH₃ | H | Me | |
| C≡CCH₃ | H | OMe | |
| C≡CCH₃ | H | OCF₂H | |
| NH₂ | H | Me | |
| NH₂ | H | OMe | |
| NH₂ | H | OCF₂H | |
| NHCH₃ | H | Me | |
| NHCH₃ | H | OMe | |
| NHCH₃ | H | OCF₂H | |
| NHCH₃ | CH₃ | Me | |
| N(CH₃)₂ | H | Me | |
| N(CH₃)₂ | H | OMe | |
| N(CH₃)₂ | H | OCF₂H | |
| NHCH₂CH₃ | H | Me | |
| NHCH₂CH₃ | H | OMe | |
| NHCH₂CH₃ | H | OCF₂H | |
| N(CH₃)CH₂CH₃ | H | Me | |
| N(CH₂CH₃)₂ | H | OMe | |
| NHCH₂CF₃ | H | OCF₂H | |
| NHCH₂CF₃ | CH₃ | OMe | |
| NHCH₂CF₃ | H | Me | |
| NHCH₂CF₃ | H | OMe | |
| N(CH₃)CH₂CF₃ | H | OCF₂H | |
| N(CH₃)CH₂CHF₂ | H | Me | |
| N(CH₃)(CH₂)₂F | H | OMe | |
| N(CH₃)(CH₂)₂Cl | H | OCF₂H | |
| N(CH₃)(CH₂)₂I | H | Me | |
| N(CH₃)(CH₂)₂Br | H | OMe | |
| NHCF₃ | CH₃ | OCF₂H | |
| NHCF₃ | H | Me | |
| NH(CH₂)₂F | H | OMe | |
| N(CH₃)CF₂H | H | OCF₂H | |
| NHCF₂H | H | Me | |

TABLE VIIa $R_1 = CH_2CH_2Cl$

| R₂ | R | Y | m.p. (°C.) |
|---|---|---|---|
| Me | H | Me | |
| Me | Me | Me | |
| Me | H | OMe | |
| Me | Me | OMe | |
| Me | H | OCF₂H | |
| Me | Me | OCF₂H | |
| Et | H | Me | |
| Et | Me | Me | |
| Et | H | OMe | |
| Et | Me | OMe | |
| Et | H | OCF₂H | |
| Et | Me | OCF₂H | |
| Pr | H | Me | |
| Pr | Me | Me | |
| Pr | H | OMe | |
| Pr | Me | OMe | |
| Pr | H | OCF₂H | |
| Pr | Me | OCF₂H | |
| i-Pr | H | Me | |
| i-Pr | Me | Me | |
| i-Pr | H | OMe | |
| i-Pr | Me | OMe | |
| i-Pr | H | OCF₂H | |
| i-Pr | Me | OCF₂H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF₂H | |
| cyclo-Pr | Me | OCF₂H | |
| OMe | H | Me | |
| OMe | Me | Me | |
| OMe | H | OMe | |

TABLE VIIa-continued $R_1 = CH_2CH_2Cl$

| R₂ | R | Y | m.p. (°C.) |
|---|---|---|---|
| OMe | Me | OMe | |
| OMe | H | OCF₂H | |
| OMe | Me | OCF₂H | |
| OEt | H | Me | |
| OEt | Me | Me | |
| OEt | H | OMe | |
| OEt | Me | OMe | |
| OEt | H | OCF₂H | |
| OEt | Me | OCF₂H | |
| O—n-Pr | H | Me | |
| O—n-Pr | Me | Me | |
| O—n-Pr | H | OMe | |
| O—n-Pr | Me | OMe | |
| O—n-Pr | H | OCF₂H | |
| O—n-Pr | Me | OCF₂H | |
| O—i-Pr | H | Me | |
| O—i-Pr | Me | Me | |
| O—i-Pr | H | OMe | |
| O—i-Pr | Me | OMe | |
| O—i-Pr | H | OCF₂H | |
| O—i-Pr | Me | OCF₂H | |
| SMe | H | Me | |
| SMe | Me | Me | |
| SMe | H | OMe | |
| SMe | Me | OMe | |
| SMe | H | OCF₂H | |
| SMe | Me | OCF₂H | |
| SEt | H | Me | |
| SEt | Me | Me | |
| SEt | H | OMe | |
| SEt | Me | OMe | |
| SEt | H | OCF₂H | |
| SEt | Me | OCF₂H | |
| S—n-Pr | H | Me | |
| S—n-Pr | Me | Me | |
| S—n-Pr | H | OMe | |
| S—n-Pr | Me | OMe | |
| S—n-Pr | H | OCF₂H | |
| S—n-Pr | Me | OCF₂H | |
| S—i-Pr | H | Me | |
| S—i-Pr | Me | Me | |
| S—i-Pr | H | OMe | |
| S—i-Pr | Me | OMe | |
| S—i-Pr | H | OCF₂H | |
| S—i-Pr | Me | OCF₂H | |
| O—allyl | H | Me | |
| O—allyl | Me | Me | |
| O—allyl | H | OMe | |
| O—allyl | Me | OMe | |
| O—allyl | H | OCF₂H | |
| O—allyl | Me | OCF₂H | |
| O—propargyl | H | Me | |
| O—propargyl | Me | Me | |
| O—propargyl | H | OMe | |
| O—propargyl | Me | OMe | |
| O—propargyl | H | OCF₂H | |
| O—propargyl | Me | OCF₂H | |
| CH₂F | H | Me | |
| CH₂F | Me | Me | |
| CH₂F | H | OMe | |
| CH₂F | Me | OMe | |
| CH₂F | H | OCF₂H | |
| CH₂F | Me | OCF₂H | |
| CHF₂ | H | Me | |
| CHF₂ | Me | Me | |
| CHF₂ | H | OMe | |
| CHF₂ | Me | OMe | |
| CHF₂ | H | OCF₂H | |
| CHF₂ | Me | OCF₂H | |
| CF₃ | H | Me | |
| CF₃ | Me | Me | |
| CF₃ | H | OMe | |
| CF₃ | Me | OMe | |
| CF₃ | H | OCF₂H | |
| CF₃ | Me | OCF₂H | |
| CH₂Cl | H | Me | |
| CH₂Cl | Me | Me | |
| CH₂Cl | H | OMe | |
| CH₂Cl | Me | OMe | |

TABLE VIIa-continued $R_1 = CH_2CH_2Cl$

| R2 | R | Y | m.p. (°C.) |
|---|---|---|---|
| CH2Cl | H | OCF2H | |
| CH2Cl | Me | OCF2H | |
| CHCl2 | H | Me | |
| CHCl2 | Me | Me | |
| CHCl2 | H | OMe | |
| CHCl2 | Me | OMe | |
| CHCl2 | H | OCF2H | |
| CHCl2 | Me | OCF2H | |
| CCl3 | H | Me | |
| CCl3 | Me | Me | |
| CCl3 | H | OMe | |
| CCl3 | Me | OMe | |
| CCl3 | H | OCF2H | |
| CCl3 | Me | OCF2H | |
| CHFCH3 | H | Me | |
| CHFCH3 | Me | Me | |
| CHFCH3 | H | OMe | |
| CHFCH3 | Me | OMe | |
| CHFCH3 | H | OCF2H | |
| CHFCH3 | Me | OCF2H | |
| CF2CH3 | H | Me | |
| CF2CH3 | Me | Me | |
| CF2CH3 | H | OMe | |
| CF2CH3 | Me | OMe | |
| CF2CH3 | H | OCF2H | |
| CF2CH3 | Me | OCF2H | |
| CH2CH2F | H | Me | |
| CH2CH2F | Me | Me | |
| CH2CH2F | H | OMe | |
| CH2CH2F | Me | OMe | |
| CH2CH2F | H | OCF2H | |
| CH2CH2F | Me | OCF2H | |
| CH2CHF2 | H | Me | |
| CH2CHF2 | Me | Me | |
| CH2CHF2 | H | OMe | |
| CH2CHF2 | Me | OMe | |
| CH2CHF2 | H | OCF2H | |
| CH2CHF2 | Me | OCF2H | |
| CH2CF3 | H | Me | |
| CH2CF3 | Me | Me | |
| CH2CF3 | H | OMe | |
| CH2CF3 | Me | OMe | |
| CH2CF3 | H | OCF2H | |
| CH2CF3 | Me | OCF2H | |
| CHClCH3 | H | Me | |
| CHClCH3 | Me | Me | |
| CHClCH3 | H | OMe | |
| CHClCH3 | Me | OMe | |
| CHClCH3 | H | OCF2H | |
| CHClCH3 | Me | OCF2H | |
| CH2OCH3 | H | Me | |
| CH2OCH3 | Me | Me | |
| CH2OCH3 | H | OMe | |
| CH2OCH3 | Me | OMe | |
| CH2OCH3 | H | OCF2H | |
| CH2OCH3 | Me | OCF2H | |
| (CH2)2OCH3 | H | Me | |
| (CH2)2OCH3 | Me | Me | |
| (CH2)2OCH3 | H | OMe | |
| (CH2)2OCH3 | Me | OMe | |
| (CH2)2OCH3 | H | OCF2H | |
| (CH2)2OCH3 | Me | OCF2H | |
| CH(OCH3)CH3 | H | Me | |
| CH(OCH3)CH3 | Me | Me | |
| CH(OCH3)CH3 | H | OMe | |
| CH(OCH3)CH3 | Me | OMe | |
| CH(OCH3)CH3 | H | OCF2H | |
| CH(OCH3)CH3 | Me | OCF2H | |
| CH2SCH3 | H | Me | |
| CH2SCH3 | Me | Me | |
| CH2SCH3 | H | OMe | |
| CH2SCH3 | Me | OMe | |
| CH2SCH3 | H | OCF2H | |
| CH2SCH3 | Me | OCF2H | |
| (CH2)2SCH3 | H | Me | |
| (CH2)2SCH3 | Me | Me | |
| (CH2)2SCH3 | H | OMe | |
| (CH2)2SCH3 | Me | OMe | |
| (CH2)2SCH3 | H | OCF2H | |
| (CH2)2SCH3 | Me | OCF2H | |
| CH(SCH3)CH3 | H | Me | |
| CH(SCH3)CH3 | Me | Me | |
| CH(SCH3)CH3 | H | OMe | |
| CH(SCH3)CH3 | Me | OMe | |
| CH(SCH3)CH3 | H | OCF2H | |
| CH(SCH3)CH3 | Me | OCF2H | |
| OCF2H | H | Me | |
| OCF2H | Me | Me | |
| OCF2H | H | OMe | |
| OCF2H | Me | OMe | |
| OCF2H | H | OCF2H | |
| OCF2H | Me | OCF2H | |
| OCH2CH2F | H | Me | |
| OCH2CH2F | Me | Me | |
| OCH2CH2F | H | OMe | |
| OCH2CH2F | Me | OMe | |
| OCH2CH2F | H | OCF2H | |
| OCH2CH2F | Me | OCF2H | |
| OCH2CHF2 | H | Me | |
| OCH2CHF2 | Me | Me | |
| OCH2CHF2 | H | OMe | |
| OCH2CHF2 | Me | OMe | |
| OCH2CHF2 | H | OCF2H | |
| OCH2CHF2 | Me | OCF2H | |
| OCH2CF3 | H | Me | |
| OCH2CF3 | Me | Me | |
| OCH2CF3 | H | OMe | |
| OCH2CF3 | Me | OMe | |
| OCH2CF3 | H | OCF2H | |
| OCH2CF3 | Me | OCF2H | |
| O(CH2)2Cl | H | Me | |
| O(CH2)2Cl | Me | Me | |
| O(CH2)2Cl | H | OMe | |
| O(CH2)2Cl | Me | OMe | |
| O(CH2)2Cl | H | OCF2H | |
| O(CH2)2Cl | Me | OCF2H | |
| S(O)Me | H | Me | |
| S(O)Me | Me | Me | |
| S(O)Me | H | OMe | |
| S(O)Me | Me | OMe | |
| S(O)Me | H | OCF2H | |
| S(O)Me | Me | OCF2H | |
| S(O)Et | H | Me | |
| S(O)Et | Me | Me | |
| S(O)Et | H | OMe | |
| S(O)Et | Me | OMe | |
| S(O)Et | H | OCF2H | |
| S(O)Et | Me | OCF2H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF2H | |
| S(O)—n-Pr | Me | OCF2H | |
| S(O)—i-Pr | H | Me | |
| S(O)—i-Pr | Me | Me | |
| S(O)—i-Pr | H | OMe | |
| S(O)—i-Pr | Me | Me | |
| S(O)—i-Pr | H | OCF2H | |
| S(O)—i-Pr | Me | OCF2H | |
| SO2Me | H | Me | |
| SO2Me | Me | Me | |
| SO2Me | H | OMe | |
| SO2Me | Me | OMe | |
| SO2Me | H | OCF2H | |
| SO2Me | Me | OCF2H | |
| SO2Et | H | Me | |
| SO2Et | Me | Me | |
| SO2Et | H | OMe | |
| SO2Et | Me | OMe | |
| SO2Et | H | OCF2H | |
| SO2Et | Me | OCF2H | |
| SO2—n-Pr | H | Me | |
| SO2—n-Pr | Me | Me | |
| SO2—n-Pr | H | OMe | |
| SO2—n-Pr | Me | OMe | |
| SO2—n-Pr | H | OCF2H | |
| SO2—n-Pr | Me | OCF2H | |

TABLE VIIa-continued $R_1 = CH_2CH_2Cl$

| $R_2$ | R | Y | m.p. (°C.) |
|---|---|---|---|
| $SO_2$—i-Pr | H | Me | |
| $SO_2$—i-Pr | Me | Me | |
| $SO_2$—i-Pr | H | OMe | |
| $SO_2$—i-Pr | Me | OMe | |
| $SO_2$—i-Pr | H | $OCF_2H$ | |
| $SO_2$—i-Pr | Me | $OCF_2H$ | |
| S—allyl | H | Me | |
| S—allyl | Me | Me | |
| S—allyl | H | OMe | |
| S—allyl | Me | OMe | |
| S—allyl | H | $OCF_2H$ | |
| S—allyl | Me | $OCF_2H$ | |
| S(O)allyl | H | Me | |
| S(O)allyl | Me | Me | |
| S(O)allyl | H | OMe | |
| S(O)allyl | Me | OMe | |
| S(O)allyl | H | $OCF_2H$ | |
| S(O)allyl | Me | $OCF_2H$ | |
| $SO_2$allyl | H | Me | |
| $SO_2$allyl | Me | Me | |
| $SO_2$allyl | H | OMe | |
| $SO_2$allyl | Me | OMe | |
| $SO_2$allyl | H | $OCF_2H$ | |
| $SO_2$allyl | Me | $OCF_2H$ | |
| S—propargyl | H | Me | |
| S—propargyl | Me | Me | |
| S—propargyl | H | OMe | |
| S—propargyl | Me | OMe | |
| S—propargyl | H | $OCF_2H$ | |
| S—propargyl | Me | $OCF_2H$ | |
| S(O)propargyl | H | Me | |
| S(O)propargyl | Me | Me | |
| S(O)propargyl | H | OMe | |
| S(O)propargyl | Me | OMe | |
| S(O)propargyl | H | $OCF_2H$ | |
| S(O)propargyl | Me | $OCF_2H$ | |
| $SO_2$propargyl | H | Me | |
| $SO_2$propargyl | Me | Me | |
| $SO_2$propargyl | H | OMe | |
| $SO_2$propargyl | Me | OMe | |
| $SO_2$propargyl | H | $OCF_2H$ | |
| $SO_2$propargyl | Me | $OCF_2H$ | |
| $CH_2OCH_2CH_3$ | H | Me | |
| $CH_2OCH_2CH_3$ | H | OMe | |
| $CH_2OCH_2CH_3$ | H | $OCF_2H$ | |
| $(CH_2)_2OCH_2CH_3$ | H | Me | |
| $(CH_2)_2OCH_2CH_3$ | H | OMe | |
| $(CH_2)_2OCH_2CH_3$ | H | $OCF_2H$ | |
| $(CH_2)_2OCH_2CH_3$ | $CH_3$ | Me | |
| $CH(CH_3)OCH_2CH_3$ | H | Me | |
| $CH(CH_3)OCH_2CH_3$ | H | OMe | |
| $CH(CH_3)OCH_2CH_3$ | H | $OCF_2H$ | |
| $CH_2OCH_2CF_3$ | H | Me | |
| $CH_2OCH_2CF_3$ | H | OMe | |
| $CH_2OCH_2CF_3$ | H | $OCF_2H$ | |
| $(CH_2)_2OCH_2CF_2H$ | H | Me | |
| $(CH_2)_2OCH_2CF_3$ | H | OMe | |
| $CH_2OCF_2H$ | H | $OCF_2H$ | |
| $CH_2OCH_2CH_2F$ | $CH_3$ | OMe | |
| $CH_2OCH_2CHF_2$ | H | Me | |
| $CH_2OCH_2CH_2Br$ | H | OMe | |
| $CH_2OCH_2CH_2Cl$ | H | $OCF_2H$ | |
| $CH_2OCH_2CH_2I$ | H | Me | |
| $CH_2OCF_3$ | H | OMe | |
| $CH_2SCH_2CH_3$ | H | $OCF_2H$ | |
| $CH_2SCH_2CH_3$ | H | Me | |
| $CH_2SCH_2CH_3$ | H | OMe | |
| $(CH_2)_2SCH_2CH_3$ | H | $OCF_2H$ | |
| $(CH_2)_2SCH_2CH_3$ | $CH_3$ | $OCF_2H$ | |
| $(CH_2)_2SCH_2CH_3$ | H | Me | |
| $(CH_2)_2SCH_2CH_3$ | H | OMe | |
| $CH(CH_3)SCH_2CH_3$ | H | $OCF_2H$ | |
| $CH(CH_3)SCH_2CH_3$ | H | Me | |
| $CH(CH_3)SCH_2CH_3$ | H | OMe | |
| $CH_2SCH_2CF_3$ | H | $OCF_2H$ | |
| $CH_2SCH_2CF_3$ | H | Me | |
| $CH_2SCH_2CF_3$ | H | OMe | |
| $(CH_2)_2SCH_2CF_2H$ | H | $OCF_2H$ | |
| $(CH_2)_2S(O)CH_3$ | H | Me | |
| $CH_2S(O)_2CH_2CH_3$ | H | OMe | |
| $CH_2S(O)_2CH_2CH_3$ | H | $OCF_2H$ | |
| $CH_2S(O)_2CH_2CH_3$ | H | Me | |
| $(CH_2)_2S(O)_2CH_2CH_3$ | H | OMe | |
| $CH(CH_3)S(O)_2CH_3$ | H | $OCF_2H$ | |
| $CH_2S(O)_2CH_2CF_3$ | $CH_3$ | Me | |
| $CH_2S(O)_2CH_2CF_3$ | H | Me | |
| $CH_2S(O)_2CH_2CF_3$ | H | OMe | |
| $CH_2S(O)_2CH_2CF_3$ | H | $OCF_2H$ | |
| $(CH_2)_2S(O)_2CH_2CF_2H$ | H | Me | |
| $(CH_2)_2S(O)_2CH_2CF_3$ | H | OMe | |
| $CH_2S(O)_2CF_2H$ | H | $OCF_2H$ | |
| $CH_2S(O)_2CH_2CH_2F$ | H | Me | |
| $CH_2S(O)_2CH_2CHF_2$ | H | OMe | |
| $CH_2S(O)_2CH_2CH_2Br$ | H | $OCF_2H$ | |
| $CH_2S(O)_2CH_2CH_2I$ | $CH_3$ | OMe | |
| $CH_2S(O)_2CF_3$ | H | Me | |
| $CH_2S(O)_2CH_2Cl$ | H | OMe | |
| $OCH_2OCH_3$ | H | $OCF_2H$ | |
| $OCH_2OCH_3$ | H | Me | |
| $OCH_2OCH_3$ | H | OMe | |
| $O(CH_2)_2OCH_3$ | H | $OCF_2H$ | |
| $O(CH_2)_2OCH_3$ | H | Me | |
| $O(CH_2)_2OCH_3$ | H | OMe | |
| $O(CH_2)_2OCH_2CH_3$ | H | $OCF_2H$ | |
| $O(CH_2)_2OCH_2CH_3$ | $CH_3$ | $OCF_2H$ | |
| $O(CH_2)_2OCH_2CH_3$ | H | Me | |
| $O(CH_2)_2OCH_2CH_3$ | H | OMe | |
| $OCH_2OCH_2CH_3$ | H | $OCF_2H$ | |
| $(CH_2)_2SCH_2CF_3$ | H | Me | |
| $CH_2SCF_2H$ | H | OMe | |
| $CH_2SCH_2CH_2F$ | H | $OCF_2H$ | |
| $CH_2SCH_2CHF_2$ | H | Me | |
| $CH_2SCH_2CH_2Br$ | H | OMe | |
| $CH_2SCH_2CH_2Cl$ | H | $OCF_2H$ | |
| $CH_2SCH_2CH_2I$ | $CH_3$ | Me | |
| $CH_2SCF_3$ | H | Me | |
| $CH_2S(O)CH_3$ | H | OMe | |
| $CH_2S(O)CH_3$ | H | $OCF_2H$ | |
| $CH_2S(O)CH_3$ | H | Me | |
| $(CH_2)_2S(O)CH_3$ | H | OMe | |
| $(CH_2)_2S(O)CH_3$ | H | $OCF_2H$ | |
| $(CH_2)_2S(O)CH_3$ | H | Me | |
| $CH_2S(O)CH_2CH_3$ | H | OMe | |
| $CH_2S(O)CH_2CH_3$ | H | $OCF_2H$ | |
| $CH_2S(O)CH_2CH_3$ | $CH_3$ | OMe | |
| $CH_2S(O)CH_2CH_3$ | H | Me | |
| $(CH_2)_2S(O)CH_2CH_3$ | H | OMe | |
| $CH(CH_3)S(O)CH_3$ | H | $OCF_2H$ | |
| $CH_2S(O)CH_2CF_3$ | H | Me | |
| $CH_2S(O)CH_2CF_3$ | H | OMe | |
| $CH_2S(O)CH_2CF_3$ | H | $OCF_2H$ | |
| $(CH_2)_2S(O)CH_2CF_2H$ | H | Me | |
| $(CH_2)_2S(O)CH_2CF_3$ | H | OMe | |
| $CH_2S(O)CF_2H$ | H | $OCF_2H$ | |
| $CH_2S(O)CH_2CH_2F$ | $CH_3$ | $OCF_2H$ | |
| $CH_2S(O)CH_2CHF_2$ | H | Me | |
| $CH_2S(O)CH_2CH_2Br$ | H | OMe | |
| $CH_2S(O)CH_2CH_2I$ | H | $OCF_2H$ | |
| $CH_2S(O)CF_3$ | H | Me | |
| $CH_2S(O)_2CH_3$ | H | OMe | |
| $CH_2S(O)_2CH_3$ | H | $OCF_2H$ | |
| $CH_2S(O)_2CH_3$ | H | Me | |
| $(CH_2)_2S(O)_2CH_3$ | H | OMe | |
| $(CH_2)_2S(O)_2CH_3$ | H | $OCF_2H$ | |
| $OCH_2OCH_2CF_3$ | H | Me | |
| $O(CH_2)_2OCH_2CF_3$ | H | OMe | |
| $O(CH_2)_2OCH_2CF_2H$ | H | $OCF_2H$ | |
| $O(CH_2)_2O(CH_2)_2Cl$ | H | Me | |
| $O(CH_2)_2O(CH_2)_2Br$ | H | OMe | |
| $O(CH_2)_2O(CH_2)_2I$ | H | $OCF_2H$ | |
| $O(CH_2)_2OCF_3$ | H | Me | |
| $OCH_2SCH_3$ | H | OMe | |
| $OCH_2SCH_3$ | H | $OCF_2H$ | |
| $OCH_2SCH_3$ | H | Me | |
| $O(CH_2)_2SCH_3$ | H | OMe | |
| $O(CH_2)_2SCH_3$ | H | $OCF_2H$ | |
| $O(CH_2)_2SCH_3$ | $CH_3$ | Me | |
| $O(CH_2)_2SCH_3$ | H | Me | |

TABLE VIIa-continued

$R_1 = CH_2CH_2Cl$

| $R_2$ | R | Y | m.p. (°C.) |
|---|---|---|---|
| $O(CH_2)_2SCH_2CH_3$ | H | OMe | |
| $O(CH_2)_2SCH_2CH_3$ | H | $OCF_2H$ | |
| $O(CH_2)_2SCH_2CH_3$ | H | Me | |
| $OCH_2SCH_2CH_3$ | H | OMe | |
| $OCH_2SCH_2CF_3$ | H | $OCF_2H$ | |
| $O(CH_2)_2SCH_2CF_3$ | H | Me | |
| $O(CH_2)_2SCH_2CF_2H$ | H | OMe | |
| $O(CH_2)_2S(CH_2)_2Cl$ | H | $OCF_2H$ | |
| $O(CH_2)_2S(CH_2)_2Br$ | $CH_3$ | OMe | |
| $O(CH_2)_2S(CH_2)_2I$ | H | Me | |
| $O(CH_2)_2SCF_3$ | H | OMe | |
| $OCH_2S(O)CH_3$ | H | $OCF_2H$ | |
| $OCH_2S(O)CH_3$ | H | Me | |
| $OCH_2S(O)CH_3$ | H | OMe | |
| $O(CH_2)_2S(O)CH_3$ | H | $OCF_2H$ | |
| $O(CH_2)_2S(O)CH_3$ | H | Me | |
| $O(CH_2)_2S(O)CH_3$ | H | OMe | |
| $O(CH_2)_2S(O)CH_2CH_3$ | H | $OCF_2H$ | |
| $O(CH_2)_2S(O)CH_2CH_3$ | $CH_3$ | $OCF_2H$ | |
| $O(CH_2)_2S(O)CH_2CH_3$ | H | Me | |
| $OCH_2S(O)CH_2CH_3$ | H | OMe | |
| $O(CH_2)_2S(O)CH_2CF_3$ | H | $OCF_2H$ | |
| $OCH_2S(O)CH_2CF_3$ | H | Me | |
| $O(CH_2)_2S(O)CH_2CF_2H$ | H | OMe | |
| $O(CH_2)_2S(O)(CH_2)_2Cl$ | H | $OCF_2H$ | |
| $O(CH_2)_2S(O)(CH_2)_2Br$ | H | Me | |
| $O(CH_2)_2S(O)(CH_2)_2I$ | H | OMe | |
| $O(CH_2)_2S(O)CF_3$ | H | $OCF_2H$ | |
| $OCH_2S(O)_2CH_3$ | H | Me | |
| $OCH_2S(O)_2CH_3$ | H | OMe | |
| $OCH_2S(O)_2CH_3$ | H | $OCF_2H$ | |
| $O(CH_2)_2S(O)_2CH_3$ | H | Me | |
| $O(CH_2)_2S(O)_2CH_3$ | H | OMe | |
| $O(CH_2)_2S(O)_2CH_3$ | H | $OCF_2H$ | |
| $O(CH_2)_2S(O)_2CH_2CH_3$ | $CH_3$ | Me | |
| $O(CH_2)_2S(O)_2CH_2CH_3$ | H | Me | |
| $O(CH_2)_2S(O)_2CH_2CH_3$ | H | OMe | |
| $O(CH_2)_2S(O)_2CH_2CH_3$ | H | $OCF_2H$ | |
| $OCH_2S(O)_2CH_2CH_3$ | H | Me | |
| $OCH_2S(O)_2CH_2CF_3$ | H | OMe | |
| $O(CH_2)_2S(O)_2CH_2CF_3$ | H | $OCF_2H$ | |
| $O(CH_2)_2S(O)_2CH_2CF_2H$ | H | Me | |
| $O(CH_2)_2S(O)_2(CH_2)_2Cl$ | H | OMe | |
| $O(CH_2)_2S(O)_2(CH_2)_2Br$ | H | $OCF_2H$ | |
| $O(CH_2)_2S(O)_2(CH_2)_2I$ | $CH_3$ | OMe | |
| $O(CH_2)_2S(O)_2CF_3$ | H | Me | |
| $OCH_2S(O)_2CH_2Cl$ | H | OMe | |
| $OCH_2S(O)_2CF_3$ | H | $OCF_2H$ | |
| $O(CH_2)_2CN$ | H | Me | |
| $O(CH_2)_2CN$ | H | OMe | |
| $O(CH_2)_2CN$ | H | $OCF_2H$ | |
| $OCH_2CN$ | H | Me | |
| $OCH_2CN$ | H | OMe | |
| $OCH_2CN$ | H | $OCF_2H$ | |
| $OCH_2CN$ | $CH_3$ | $OCF_2H$ | |
| $OCH(CH_3)CN$ | H | Me | |
| $O(CH_2)_2NH_2$ | H | OMe | |
| $O(CH_2)_2NH_2$ | H | $OCF_2H$ | |
| $O(CH_2)_2NH_2$ | H | Me | |
| $O(CH_2)_2NHCH_3$ | H | OMe | |
| $O(CH_2)_2NHCH_3$ | H | $OCF_2H$ | |
| $O(CH_2)_2NHCH_3$ | H | Me | |
| $O(CH_2)_2N(CH_3)_2$ | H | OMe | |
| $O(CH_2)_2N(CH_3)_2$ | H | $OCF_2H$ | |
| $O(CH_2)_2N(CH_3)_2$ | H | Me | |
| $SCH_2OCH_3$ | H | OMe | |
| $SCH_2OCH_3$ | H | $OCF_2H$ | |
| $SCH_2OCH_3$ | H | Me | |
| $SCH_2OCH_2CH_3$ | H | OMe | |
| $S(CH_2)_2OCH_3$ | H | $OCF_2H$ | |
| $S(CH_2)_2OCH_3$ | $CH_3$ | Me | |
| $S(CH_2)_2OCH_3$ | H | Me | |
| $S(CH_2)_2OCH_3$ | H | OMe | |
| $S(CH_2)_2OCH_2CH_3$ | H | $OCF_2H$ | |
| $SCH_2OCH_2CF_3$ | H | Me | |
| $SCH_2OCH_2CF_3$ | H | OMe | |
| $S(CH_2)_2OCH_2CF_2H$ | H | $OCF_2H$ | |
| $S(CH_2)_2O(CH_2)_2Cl$ | H | Me | |
| $S(CH_2)_2O(CH_2)_2Br$ | H | OMe | |
| $S(CH_2)_2O(CH_2)_2I$ | H | $OCF_2H$ | |
| $S(CH_2)_2OCF_3$ | $CH_3$ | OMe | |
| $SCH_2SCH_3$ | H | Me | |
| $SCH_2SCH_3$ | H | OMe | |
| $SCH_2SCH_3$ | H | $OCF_2H$ | |
| $SCH_2SCH_2CH_3$ | H | Me | |
| $S(CH_2)_2SCH_3$ | H | OMe | |
| $S(CH_2)_2SCH_3$ | H | $OCF_2H$ | |
| $S(CH_2)_2SCH_3$ | H | Me | |
| $S(CH_2)_2SCH_2CH_3$ | H | OMe | |
| $SCH(CH_3)SCH_3$ | H | $OCF_2H$ | |
| $S(CH_2)_2SCH_2CF_3$ | $CH_3$ | $OCF_2H$ | |
| $SCH_2SCH_2CF_3$ | H | Me | |
| $S(CH_2)_2SCH_2CF_2H$ | H | OMe | |
| $S(CH_2)_2S(CH_2)_2Cl$ | H | $OCF_2H$ | |
| $S(CH_2)_2S(CH_2)_2Br$ | H | Me | |
| $S(CH_2)_2S(CH_2)_2I$ | H | OMe | |
| $S(CH_2)_2SCF_3$ | H | $OCF_2H$ | |
| $SCH_2CN$ | H | Me | |
| $SCH_2CN$ | H | OMe | |
| $SCH_2CN$ | H | $OCF_2H$ | |
| $S(CH_2)_2CN$ | H | Me | |
| $S(CH_2)_2CN$ | H | OMe | |
| $S(CH_2)_2CN$ | H | $OCF_2H$ | |
| $SCH(CH_3)CN$ | H | Me | |
| $SCHF_2$ | H | OMe | |
| $SCHF_2$ | H | $OCF_2H$ | |
| $SCHF_2$ | $CH_3$ | Me | |
| $SCHF_2$ | H | Me | |
| $SCF_3$ | H | OMe | |
| $SCH_2CFH_2$ | H | $OCF_2H$ | |
| $SCH_2CF_2H$ | H | Me | |
| $SCH_2CF_3$ | H | OMe | |
| $SCH_2CF_3$ | H | $OCF_2H$ | |
| $SCH_2CF_2H$ | H | Me | |
| $SCH_2CF_2H$ | H | OMe | |
| $S(CH_2)_2CFH_2$ | H | $OCF_2H$ | |
| $S(CH_2)_2CClH_2$ | $CH_3$ | OMe | |
| $S(CH_2)_2CIH_2$ | H | Me | |
| $SCF_2CF_3$ | H | OMe | |
| $SCH(CH_3)CF_3$ | H | $OCF_2H$ | |
| $S(CH_2)_2CCl_3$ | H | Me | |
| $S(O)CHF_2$ | H | OMe | |
| $S(O)CHF_2$ | H | $OCF_2H$ | |
| $S(O)CHF_2$ | H | Me | |
| $S(O)CF_3$ | H | OMe | |
| $S(O)CH_2CFH_2$ | H | $OCF_2H$ | |
| $S(O)CH_2CF_2H$ | $CH_3$ | $OCF_2H$ | |
| $S(O)CH_2CF_3$ | H | Me | |
| $S(O)CH_2CF_3$ | H | OMe | |
| $S(O)CH_2CF_3$ | H | $OCF_2H$ | |
| $S(O)CH_2CF_2H$ | H | Me | |
| $S(O)(CH_2)_2CFH_2$ | H | OMe | |
| $S(O)(CH_2)_2CClH_2$ | H | $OCF_2H$ | |
| $S(O)(CH_2)_2CIH_2$ | H | Me | |
| $S(O)CF_2CF_3$ | H | OMe | |
| $S(O)CH(CH_3)CF_3$ | H | $OCF_2H$ | |
| $S(O)(CH_2)_2CCl_3$ | H | Me | |
| $S(O)_2CHF_2$ | H | OMe | |
| $S(O)_2CHF_2$ | H | $OCF_2H$ | |
| $S(O)_2CHF_2$ | H | Me | |
| $S(O)_2CF_3$ | H | OMe | |
| $S(O)_2CH_2CFH_2$ | H | $OCF_2H$ | |
| $S(O)_2CH_2CF_2H$ | $CH_3$ | Me | |
| $S(O)_2CH_2CF_3$ | H | Me | |
| $S(O)_2CH_2CF_3$ | H | OMe | |
| $S(O)_2CH_2CF_3$ | H | $OCF_2H$ | |
| $S(O)_2CH_2CF_2H$ | H | Me | |
| $S(O)_2(CH_2)_2CFH_2$ | H | OMe | |
| $S(O)_2(CH_2)_2CClH_2$ | H | $OCF_2H$ | |
| $S(O)_2(CH_2)_2CIH_2$ | H | Me | |
| $S(O)_2CF_2CF_3$ | H | OMe | |
| $S(O)_2CH(CH_3)CF_3$ | H | $OCF_2H$ | |
| $S(O)_2(CH_2)_2CCl_3$ | $CH_3$ | OMe | |
| $S(O)_2CH_2Cl$ | H | Me | |
| $CH=CH_2$ | H | OMe | |
| $CH=CH_2$ | H | $OCF_2H$ | |
| $CH=CH_2$ | H | Me | |
| $CH_2CH=CH_2$ | H | OMe | |

TABLE VIIa-continued $R_1 = CH_2CH_2Cl$

| R₂ | R | Y | m.p. (°C.) |
|---|---|---|---|
| CH₂CH=CH₂ | H | OCF₂H | |
| CH₂CH=CH₂ | H | Me | |
| CH=CHCH₃ | H | OMe | |
| C(CH₃)=CH₂ | H | OCF₂H | |
| CH=CH₂ | CH₃ | OCF₂H | |
| C≡CH | H | Me | |
| C≡CH | H | OMe | |
| C≡CH | H | OCF₂H | |
| CH₂C≡CH | H | Me | |
| CH₂C≡CH | H | OMe | |
| CH₂C≡CH | H | OCF₂H | |
| C≡CCH₃ | H | Me | |
| C≡CCH₃ | H | OMe | |
| C≡CCH₃ | H | OCF₂H | |
| NH₂ | H | Me | |
| NH₂ | H | OMe | |
| NH₂ | H | OCF₂H | |
| NHCH₃ | H | Me | |
| NHCH₃ | H | OMe | |
| NHCH₃ | H | OCF₂H | |
| NHCH₃ | CH₃ | Me | |
| N(CH₃)₂ | H | Me | |
| N(CH₃)₂ | H | OMe | |
| N(CH₃)₂ | H | OCF₂H | |
| NHCH₂CH₃ | H | Me | |
| NHCH₂CH₃ | H | OMe | |
| NHCH₂CH₃ | H | OCF₂H | |
| N(CH₃)CH₂CH₃ | H | Me | |
| N(CH₂CH₃)₂ | H | OMe | |
| NHCH₂CF₃ | H | OCF₂H | |
| NHCH₂CF₃ | CH₃ | OMe | |
| NHCH₂CF₃ | H | Me | |
| NHCH₂CF₃ | H | OMe | |
| N(CH₃)CH₂CF₃ | H | OCF₂H | |
| N(CH₃)CH₂CHF₂ | H | Me | |
| N(CH₃)(CH₂)₂F | H | OMe | |
| N(CH₃)(CH₂)₂Cl | H | OCF₂H | |
| N(CH₃)(CH₂)₂I | H | Me | |
| N(CH₃)(CH₂)₂Br | H | OMe | |
| NHCF₃ | CH₃ | OCF₂H | |
| NHCF₃ | H | Me | |
| NH(CH₂)₂F | H | OMe | |
| N(CH₃)CF₂H | H | OCF₂H | |
| NHCF₂H | H | Me | |

TABLE VIIIa $R_1 = CH_2C≡CH$

| R₂ | R | Y | m.p. (°C.) |
|---|---|---|---|
| Me | H | Me | |
| Me | Me | Me | |
| Me | H | OMe | |
| Me | Me | OMe | |
| Me | H | OCF₂H | |
| Me | Me | OCF₂H | |
| Et | H | Me | |
| Et | Me | Me | |
| Et | H | OMe | |
| Et | Me | OMe | |
| Et | H | OCF₂H | |
| Et | Me | OCF₂H | |
| Pr | H | Me | |
| Pr | Me | Me | |
| Pr | H | OMe | |
| Pr | Me | OMe | |
| Pr | H | OCF₂H | |
| Pr | Me | OCF₂H | |
| i-Pr | H | Me | |
| i-Pr | Me | Me | |
| i-Pr | H | OMe | |
| i-Pr | Me | OMe | |
| i-Pr | H | OCF₂H | |
| i-Pr | Me | OCF₂H | |
| cyclo-Pr | H | Me | |
| cyclo-Pr | Me | Me | |
| cyclo-Pr | H | OMe | |
| cyclo-Pr | Me | OMe | |
| cyclo-Pr | H | OCF₂H | |

TABLE VIIIa-continued $R_1 = CH_2C≡CH$

| R₂ | R | Y | m.p. (°C.) |
|---|---|---|---|
| cyclo-Pr | Me | OCF₂H | |
| OMe | H | Me | |
| OMe | Me | Me | |
| OMe | H | OMe | |
| OMe | Me | OMe | |
| OMe | H | OCF₂H | |
| OMe | Me | OCF₂H | |
| OEt | H | Me | |
| OEt | Me | Me | |
| OEt | H | OMe | |
| OEt | Me | OMe | |
| OEt | H | OCF₂H | |
| OEt | Me | OCF₂H | |
| O—n-Pr | H | Me | |
| O—n-Pr | Me | Me | |
| O—n-Pr | H | OMe | |
| O—n-Pr | Me | OMe | |
| O—n-Pr | H | OCF₂H | |
| O—n-Pr | Me | OCF₂H | |
| O—i-Pr | H | Me | |
| O—i-Pr | Me | Me | |
| O—i-Pr | H | OMe | |
| O—i-Pr | Me | OMe | |
| O—i-Pr | H | OCF₂H | |
| O—i-Pr | Me | OCF₂H | |
| SMe | H | Me | |
| SMe | Me | Me | |
| SMe | H | OMe | |
| SMe | Me | OMe | |
| SMe | H | OCF₂H | |
| SMe | Me | OCF₂H | |
| SEt | H | Me | |
| SEt | Me | Me | |
| SEt | H | OMe | |
| SEt | Me | OMe | |
| SEt | H | OCF₂H | |
| SEt | Me | OCF₂H | |
| S—n-Pr | H | Me | |
| S—n-Pr | Me | Me | |
| S—n-Pr | H | OMe | |
| S—n-Pr | Me | OMe | |
| S—n-Pr | H | OCF₂H | |
| S—n-Pr | Me | OCF₂H | |
| S—i-Pr | H | Me | |
| S—i-Pr | Me | Me | |
| S—i-Pr | H | OMe | |
| S—i-Pr | Me | OMe | |
| S—i-Pr | H | OCF₂H | |
| S—i-Pr | Me | OCF₂H | |
| O—allyl | H | Me | |
| O—allyl | Me | Me | |
| O—allyl | H | OMe | |
| O—allyl | Me | OMe | |
| O—allyl | H | OCF₂H | |
| O—allyl | Me | OCF₂H | |
| O—propargyl | H | Me | |
| O—propargyl | Me | Me | |
| O—propargyl | H | OMe | |
| O—propargyl | Me | OMe | |
| O—propargyl | H | OCF₂H | |
| O—propargyl | Me | OCF₂H | |
| CH₂F | H | Me | |
| CH₂F | Me | Me | |
| CH₂F | H | OMe | |
| CH₂F | Me | OMe | |
| CH₂F | H | OCF₂H | |
| CH₂F | Me | OCF₂H | |
| CHF₂ | H | Me | |
| CHF₂ | Me | Me | |
| CHF₂ | H | OMe | |
| CHF₂ | Me | OMe | |
| CHF₂ | H | OCF₂H | |
| CHF₂ | Me | OCF₂H | |
| CF₃ | H | Me | |
| CF₃ | Me | Me | |
| CF₃ | H | OMe | |
| CF₃ | Me | OMe | |
| CF₃ | H | OCF₂H | |
| CF₃ | Me | OCF₂H | |

TABLE VIIIa-continued $R_1 = CH_2C\equiv CH$

| $R_2$ | R | Y | m.p. (°C.) |
|---|---|---|---|
| CH$_2$Cl | H | Me | |
| CH$_2$Cl | Me | Me | |
| CH$_2$Cl | H | OMe | |
| CH$_2$Cl | Me | OMe | |
| CH$_2$Cl | H | OCF$_2$H | |
| CH$_2$Cl | Me | OCF$_2$H | |
| CHCl$_2$ | H | Me | |
| CHCl$_2$ | Me | Me | |
| CHCl$_2$ | H | OMe | |
| CHCl$_2$ | Me | OMe | |
| CHCl$_2$ | H | OCF$_2$H | |
| CHCl$_2$ | Me | OCF$_2$H | |
| CCl$_3$ | H | Me | |
| CCl$_3$ | Me | Me | |
| CCl$_3$ | H | OMe | |
| CCl$_3$ | Me | OMe | |
| CCl$_3$ | H | OCF$_2$H | |
| CCl$_3$ | Me | OCF$_2$H | |
| CHFCH$_3$ | H | Me | |
| CHFCH$_3$ | Me | Me | |
| CHFCH$_3$ | H | OMe | |
| CHFCH$_3$ | Me | OMe | |
| CHFCH$_3$ | H | OCF$_2$H | |
| CHFCH$_3$ | Me | OCF$_2$H | |
| CF$_2$CH$_3$ | H | Me | |
| CF$_2$CH$_3$ | Me | Me | |
| CF$_2$CH$_3$ | H | OMe | |
| CF$_2$CH$_3$ | Me | OMe | |
| CF$_2$CH$_3$ | H | OCF$_2$H | |
| CF$_2$CH$_3$ | Me | OCF$_2$H | |
| CH$_2$CH$_2$F | H | Me | |
| CH$_2$CH$_2$F | Me | Me | |
| CH$_2$CH$_2$F | H | OMe | |
| CH$_2$CH$_2$F | Me | OMe | |
| CH$_2$CH$_2$F | H | OCF$_2$H | |
| CH$_2$CH$_2$F | Me | OCF$_2$H | |
| CH$_2$CHF$_2$ | H | Me | |
| CH$_2$CHF$_2$ | Me | Me | |
| CH$_2$CHF$_2$ | H | OMe | |
| CH$_2$CHF$_2$ | Me | OMe | |
| CH$_2$CHF$_2$ | H | OCF$_2$H | |
| CH$_2$CHF$_2$ | Me | OCF$_2$H | |
| CH$_2$CF$_3$ | H | Me | |
| CH$_2$CF$_3$ | Me | Me | |
| CH$_2$CF$_3$ | H | OMe | |
| CH$_2$CF$_3$ | Me | OMe | |
| CH$_2$CF$_3$ | H | OCF$_2$H | |
| CH$_2$CF$_3$ | Me | OCF$_2$H | |
| CHClCH$_3$ | H | Me | |
| CHClCH$_3$ | Me | Me | |
| CHClCH$_3$ | H | OMe | |
| CHClCH$_3$ | Me | OMe | |
| CHClCH$_3$ | H | OCF$_2$H | |
| CHClCH$_3$ | Me | OCF$_2$H | |
| CH$_2$OCH$_3$ | H | Me | |
| CH$_2$OCH$_3$ | Me | Me | |
| CH$_2$OCH$_3$ | H | OMe | |
| CH$_2$OCH$_3$ | Me | OMe | |
| CH$_2$OCH$_3$ | H | OCF$_2$H | |
| CH$_2$OCH$_3$ | Me | OCF$_2$H | |
| (CH$_2$)$_2$OCH$_3$ | H | Me | |
| (CH$_2$)$_2$OCH$_3$ | Me | Me | |
| (CH$_2$)$_2$OCH$_3$ | H | OMe | |
| (CH$_2$)$_2$OCH$_3$ | Me | OMe | |
| (CH$_2$)$_2$OCH$_3$ | H | OCF$_2$H | |
| (CH$_2$)$_2$OCH$_3$ | Me | OCF$_2$H | |
| CH(OCH$_3$)CH$_3$ | H | Me | |
| CH(OCH$_3$)CH$_3$ | Me | Me | |
| CH(OCH$_3$)CH$_3$ | H | OMe | |
| CH(OCH$_3$)CH$_3$ | Me | OMe | |
| CH(OCH$_3$)CH$_3$ | H | OCF$_2$H | |
| CH(OCH$_3$)CH$_3$ | Me | OCF$_2$H | |
| CH$_2$SCH$_3$ | H | Me | |
| CH$_2$SCH$_3$ | Me | Me | |
| CH$_2$SCH$_3$ | H | OMe | |
| CH$_2$SCH$_3$ | Me | OMe | |
| CH$_2$SCH$_3$ | H | OCF$_2$H | |
| CH$_2$SCH$_3$ | Me | OCF$_2$H | |
| (CH$_2$)$_2$SCH$_3$ | H | Me | |
| (CH$_2$)$_2$SCH$_3$ | Me | Me | |
| (CH$_2$)$_2$SCH$_3$ | H | OMe | |
| (CH$_2$)$_2$SCH$_3$ | Me | OMe | |
| (CH$_2$)$_2$SCH$_3$ | H | OCF$_2$H | |
| (CH$_2$)$_2$SCH$_3$ | Me | OCF$_2$H | |
| CH(SCH$_3$)CH$_3$ | H | Me | |
| CH(SCH$_3$)CH$_3$ | Me | Me | |
| CH(SCH$_3$)CH$_3$ | H | OMe | |
| CH(SCH$_3$)CH$_3$ | Me | OMe | |
| CH(SCH$_3$)CH$_3$ | H | OCF$_2$H | |
| CH(SCH$_3$)CH$_3$ | Me | OCF$_2$H | |
| OCF$_2$H | H | Me | |
| OCF$_2$H | Me | Me | |
| OCF$_2$H | H | OMe | |
| OCF$_2$H | Me | OMe | |
| OCF$_2$H | H | OCF$_2$H | |
| OCF$_2$H | Me | OCF$_2$H | |
| OCH$_2$CH$_2$F | H | Me | |
| OCH$_2$CH$_2$F | Me | Me | |
| OCH$_2$CH$_2$F | H | OMe | |
| OCH$_2$CH$_2$F | Me | OMe | |
| OCH$_2$CH$_2$F | H | OCF$_2$H | |
| OCH$_2$CH$_2$F | Me | OCF$_2$H | |
| OCH$_2$CHF$_2$ | H | Me | |
| OCH$_2$CHF$_2$ | Me | Me | |
| OCH$_2$CHF$_2$ | H | OMe | |
| OCH$_2$CHF$_2$ | Me | OMe | |
| OCH$_2$CHF$_2$ | H | OCF$_2$H | |
| OCH$_2$CHF$_2$ | Me | OCF$_2$H | |
| OCH$_2$CF$_3$ | H | Me | |
| OCH$_2$CF$_3$ | Me | Me | |
| OCH$_2$CF$_3$ | H | OMe | |
| OCH$_2$CF$_3$ | Me | OMe | |
| OCH$_2$CF$_3$ | H | OCF$_2$H | |
| OCH$_2$CF$_3$ | Me | OCF$_2$H | |
| O(CH$_2$)$_2$Cl | H | Me | |
| O(CH$_2$)$_2$Cl | Me | Me | |
| O(CH$_2$)$_2$Cl | H | OMe | |
| O(CH$_2$)$_2$Cl | Me | OMe | |
| O(CH$_2$)$_2$Cl | H | OCF$_2$H | |
| O(CH$_2$)$_2$Cl | Me | OCF$_2$H | |
| S(O)Me | H | Me | |
| S(O)Me | Me | Me | |
| S(O)Me | H | OMe | |
| S(O)Me | Me | OMe | |
| S(O)Me | H | OCF$_2$H | |
| S(O)Me | Me | OCF$_2$H | |
| S(O)Et | H | Me | |
| S(O)Et | Me | Me | |
| S(O)Et | H | OMe | |
| S(O)Et | Me | OMe | |
| S(O)Et | H | OCF$_2$H | |
| S(O)Et | Me | OCF$_2$H | |
| S(O)—n-Pr | H | Me | |
| S(O)—n-Pr | Me | Me | |
| S(O)—n-Pr | H | OMe | |
| S(O)—n-Pr | Me | OMe | |
| S(O)—n-Pr | H | OCF$_2$H | |
| S(O)—n-Pr | Me | OCF$_2$H | |
| S(O)—i-Pr | H | Me | |
| S(O)—i-Pr | Me | Me | |
| S(O)—i-Pr | H | OMe | |
| S(O)—i-Pr | Me | OMe | |
| S(O)—i-Pr | H | OCF$_2$H | |
| S(O)—i-Pr | Me | OCF$_2$H | |
| SO$_2$Me | H | Me | |
| SO$_2$Me | Me | Me | |
| SO$_2$Me | H | OMe | |
| SO$_2$Me | Me | OMe | |
| SO$_2$Me | H | OCF$_2$H | |
| SO$_2$Me | Me | OCF$_2$H | |
| SO$_2$Et | H | Me | |
| SO$_2$Et | Me | Me | |
| SO$_2$Et | H | OMe | |
| SO$_2$Et | Me | OMe | |
| SO$_2$Et | H | OCF$_2$H | |
| SO$_2$Et | Me | OCF$_2$H | |
| SO$_2$—n-Pr | H | Me | |
| SO$_2$—n-Pr | Me | Me | |

TABLE VIIIa-continued

| | $R_1 = CH_2C\equiv CH$ | | | |
|---|---|---|---|---|
| R₂ | R | Y | m.p. (°C.) | |
| SO₂—n-Pr | H | OMe | | |
| SO₂—n-Pr | Me | OMe | | |
| SO₂—n-Pr | H | OCF₂H | | |
| SO₂—n-Pr | Me | OCF₂H | | |
| SO₂—i-Pr | H | Me | | |
| SO₂—i-Pr | Me | Me | | |
| SO₂—i-Pr | H | OMe | | |
| SO₂—i-Pr | Me | OMe | | |
| SO₂—i-Pr | H | OCF₂H | | |
| SO₂—i-Pr | Me | OCF₂H | | |
| S—allyl | H | Me | | |
| S—allyl | Me | Me | | |
| S—allyl | H | OMe | | |
| S—allyl | Me | OMe | | |
| S—allyl | H | OCF₂H | | |
| S—allyl | Me | OCF₂H | | |
| S(O)allyl | H | Me | | |
| S(O)allyl | Me | Me | | |
| S(O)allyl | H | OMe | | |
| S(O)allyl | Me | OMe | | |
| S(O)allyl | H | OCF₂H | | |
| S(O)allyl | Me | OCF₂H | | |
| SO₂allyl | H | Me | | |
| SO₂allyl | Me | Me | | |
| SO₂allyl | H | OMe | | |
| SO₂allyl | Me | OMe | | |
| SO₂allyl | H | OCF₂H | | |
| SO₂allyl | Me | OCF₂H | | |
| S—propargyl | H | Me | | |
| S—propargyl | Me | Me | | |
| S—propargyl | H | OMe | | |
| S—propargyl | Me | OMe | | |
| S—propargyl | H | OCF₂H | | |
| S—propargyl | Me | OCF₂H | | |
| S(O)propargyl | H | Me | | |
| S(O)propargyl | Me | Me | | |
| S(O)propargyl | H | OMe | | |
| S(O)propargyl | Me | OMe | | |
| S(O)propargyl | H | OCF₂H | | |
| S(O)propargyl | Me | OCF₂H | | |
| SO₂propargyl | H | Me | | |
| SO₂propargyl | Me | Me | | |
| SO₂propargyl | H | OMe | | |
| SO₂propargyl | Me | OMe | | |
| SO₂propargyl | H | OCF₂H | | |
| SO₂propargyl | Me | OCF₂H | | |
| CH₂OCH₂CH₃ | H | Me | | |
| CH₂OCH₂CH₃ | H | OMe | | |
| CH₂OCH₂CH₃ | H | OCF₂H | | |
| (CH₂)₂OCH₂CH₃ | H | Me | | |
| (CH₂)₂OCH₂CH₃ | H | OMe | | |
| (CH₂)₂OCH₂CH₃ | H | OCF₂H | | |
| (CH₂)₂OCH₂CH₃ | CH₃ | Me | | |
| CH(CH₃)OCH₂CH₃ | H | Me | | |
| CH(CH₃)OCH₂CH₃ | H | OMe | | |
| CH(CH₃)OCH₂CH₃ | H | OCF₂H | | |
| CH₂OCH₂CF₃ | H | Me | | |
| CH₂OCH₂CF₃ | H | OMe | | |
| CH₂OCH₂CF₃ | H | OCF₂H | | |
| (CH₂)₂OCH₂CF₂H | H | Me | | |
| (CH₂)₂OCH₂CF₃ | H | OMe | | |
| CH₂OCF₂H | H | OCF₂H | | |
| CH₂OCH₂CH₂F | CH₃ | OMe | | |
| CH₂OCH₂CHF₂ | H | Me | | |
| CH₂OCH₂CH₂Br | H | OMe | | |
| CH₂OCH₂CH₂Cl | H | OCF₂H | | |
| CH₂OCH₂CH₂I | H | Me | | |
| CH₂OCF₃ | H | OMe | | |
| CH₂SCH₂CH₃ | H | OCF₂H | | |
| CH₂SCH₂CH₃ | H | Me | | |
| CH₂SCH₂CH₃ | H | OMe | | |
| (CH₂)₂SCH₂CH₃ | H | OCF₂H | | |
| (CH₂)₂SCH₂CH₃ | CH₃ | OCF₂H | | |
| (CH₂)₂SCH₂CH₃ | H | Me | | |
| (CH₂)₂SCH₂CH₃ | H | OMe | | |
| CH(CH₃)SCH₂CH₃ | H | OCF₂H | | |
| CH(CH₃)SCH₂CH₃ | H | Me | | |
| CH(CH₃)SCH₂CH₃ | H | OMe | | |
| CH₂SCH₂CF₃ | H | OCF₂H | | |
| CH₂SCH₂CF₃ | H | Me | | |
| CH₂SCH₂CF₃ | H | OMe | | |
| (CH₂)₂SCH₂CF₂H | H | OCF₂H | | |
| (CH₂)₂S(O)₂CH₃ | H | Me | | |
| CH₂S(O)₂CH₂CH₃ | H | OMe | | |
| CH₂S(O)₂CH₂CH₃ | H | OCF₂H | | |
| CH₂S(O)₂CH₂CH₃ | H | Me | | |
| (CH₂)₂S(O)₂CH₂CH₃ | H | OMe | | |
| CH(CH₃)S(O)₂CH₃ | H | OCF₂H | | |
| CH₂S(O)₂CH₂CF₃ | CH₃ | Me | | |
| CH₂S(O)₂CH₂CF₃ | H | Me | | |
| CH₂S(O)₂CH₂CF₃ | H | OMe | | |
| CH₂S(O)₂CH₂CF₃ | H | OCF₂H | | |
| (CH₂)₂S(O)₂CH₂CF₂H | H | Me | | |
| (CH₂)₂S(O)₂CF₂CF₃ | H | OMe | | |
| CH₂S(O)₂CF₂H | H | OCF₂H | | |
| CH₂S(O)₂CH₂CH₂F | H | Me | | |
| CH₂S(O)₂CH₂CHF₂ | H | OMe | | |
| CH₂S(O)₂CH₂CH₂Br | H | OCF₂H | | |
| CH₂S(O)₂CH₂CH₂I | CH₃ | OMe | | |
| CH₂S(O)₂CF₃ | H | Me | | |
| CH₂S(O)₂CH₂Cl | H | OMe | | |
| OCH₂OCH₃ | H | OCF₂H | | |
| OCH₂OCH₃ | H | Me | | |
| OCH₂OCH₃ | H | OMe | | |
| O(CH₂)₂OCH₃ | H | OCF₂H | | |
| O(CH₂)₂OCH₃ | H | Me | | |
| O(CH₂)₂OCH₃ | H | OMe | | |
| O(CH₂)₂OCH₂CH₃ | H | OCF₂H | | |
| O(CH₂)₂OCH₂CH₃ | CH₃ | OCF₂H | | |
| O(CH₂)₂OCH₂CH₃ | H | Me | | |
| O(CH₂)₂OCH₂CH₃ | H | OMe | | |
| OCH₂OCH₂CH₃ | H | OCF₂H | | |
| (CH₂)₂SCH₂CF₃ | H | Me | | |
| CH₂SCF₂H | H | OMe | | |
| CH₂SCH₂CH₂F | H | OCF₂H | | |
| CH₂SCH₂CHF₂ | H | Me | | |
| CH₂SCH₂CH₂Br | H | OMe | | |
| CH₂SCH₂CH₂Cl | H | OCF₂H | | |
| CH₂SCH₂CH₂I | CH₃ | Me | | |
| CH₂SCF₃ | H | Me | | |
| CH₂S(O)CH₃ | H | OMe | | |
| CH₂S(O)CH₃ | H | OCF₂H | | |
| CH₂S(O)CH₃ | H | Me | | |
| (CH₂)₂S(O)CH₃ | H | OMe | | |
| (CH₂)₂S(O)CH₃ | H | OCF₂H | | |
| (CH₂)₂S(O)CH₃ | H | Me | | |
| CH₂S(O)CH₂CH₃ | H | OMe | | |
| CH₂S(O)CH₂CH₃ | H | OCF₂H | | |
| CH₂S(O)CH₂CH₃ | CH₃ | OMe | | |
| CH₂S(O)CH₂CH₃ | H | Me | | |
| (CH₂)₂S(O)CH₂CH₃ | H | OMe | | |
| CH(CH₃)S(O)CH₃ | H | OCF₂H | | |
| CH₂S(O)CH₂CF₃ | H | Me | | |
| CH₂S(O)CH₂CF₃ | H | OMe | | |
| CH₂S(O)CH₂CF₃ | H | OCF₂H | | |
| (CH₂)₂S(O)CH₂CF₂H | H | Me | | |
| (CH₂)₂S(O)CH₂CF₃ | H | OMe | | |
| CH₂S(O)CF₂H | H | OCF₂H | | |
| CH₂S(O)CH₂CH₂F | CH₃ | OCF₂H | | |
| CH₂S(O)CH₂CHF₂ | H | Me | | |
| CH₂S(O)CH₂CH₂Br | H | OMe | | |
| CH₂S(O)CH₂CH₂I | H | OCF₂H | | |
| CH₂S(O)CF₃ | H | Me | | |
| CH₂S(O)₂CH₃ | H | OMe | | |
| CH₂S(O)₂CH₃ | H | OCF₂H | | |
| CH₂S(O)₂CH₃ | H | Me | | |
| (CH₂)₂S(O)₂CH₃ | H | OMe | | |
| (CH₂)₂S(O)₂CH₃ | H | OCF₂H | | |
| OCH₂OCH₂CF₃ | H | Me | | |
| O(CH₂)₂OCH₂CF₃ | H | OMe | | |
| O(CH₂)₂OCH₂CF₂H | H | OCF₂H | | |
| O(CH₂)₂O(CH₂)₂Cl | H | Me | | |
| O(CH₂)₂O(CH₂)₂Br | H | OMe | | |
| O(CH₂)₂O(CH₂)₂I | H | OCF₂H | | |
| O(CH₂)₂OCF₃ | H | Me | | |
| OCH₂SCH₃ | H | OMe | | |
| OCH₂SCH₃ | H | OCF₂H | | |
| OCH₂SCH₃ | H | Me | | |

TABLE VIIIa-continued

| | R₁ = CH₂C≡CH | | |
|---|---|---|---|
| R₂ | R | Y | m.p. (°C.) |
| O(CH₂)₂SCH₃ | H | OMe | |
| O(CH₂)₂SCH₃ | H | OCF₂H | |
| O(CH₂)₂SCH₃ | CH₃ | Me | |
| O(CH₂)₂SCH₃ | H | Me | |
| O(CH₂)₂SCH₂CH₃ | H | OMe | |
| O(CH₂)₂SCH₂CH₃ | H | OCF₂H | |
| O(CH₂)₂SCH₂CH₃ | H | Me | |
| OCH₂SCH₂CH₃ | H | OMe | |
| OCH₂SCH₂CF₃ | H | OCF₂H | |
| O(CH₂)₂SCH₂CF₃ | H | Me | |
| O(CH₂)₂SCH₂CF₂H | H | OMe | |
| O(CH₂)₂S(CH₂)₂Cl | H | OCF₂H | |
| O(CH₂)₂S(CH₂)₂Br | CH₃ | OMe | |
| O(CH₂)₂S(CH₂)₂I | H | Me | |
| O(CH₂)₂SCF₃ | H | OMe | |
| OCH₂S(O)CH₃ | H | OCF₂H | |
| OCH₂S(O)CH₃ | H | Me | |
| OCH₂S(O)CH₃ | H | OMe | |
| O(CH₂)₂S(O)CH₃ | H | OCF₂H | |
| O(CH₂)₂S(O)CH₃ | H | Me | |
| O(CH₂)₂S(O)CH₃ | H | OMe | |
| O(CH₂)₂S(O)CH₂CH₃ | H | OCF₂H | |
| O(CH₂)₂S(O)CH₂CH₃ | CH₃ | OCF₂H | |
| O(CH₂)₂S(O)CH₂CH₃ | H | Me | |
| OCH₂S(O)CH₂CH₃ | H | OMe | |
| O(CH₂)₂S(O)CH₂CF₃ | H | OCF₂H | |
| OCH₂S(O)CH₂CF₃ | H | Me | |
| O(CH₂)₂S(O)CH₂CF₂H | H | OMe | |
| O(CH₂)₂S(O)(CH₂)₂Cl | H | OCF₂H | |
| O(CH₂)₂S(O)(CH₂)₂Br | H | Me | |
| O(CH₂)₂S(O)(CH₂)₂I | H | OMe | |
| O(CH₂)₂S(O)CF₃ | H | OCF₂H | |
| OCH₂S(O)₂CH₃ | H | Me | |
| OCH₂S(O)₂CH₃ | H | OMe | |
| OCH₂S(O)₂CH₃ | H | OCF₂H | |
| O(CH₂)₂S(O)₂CH₃ | H | Me | |
| O(CH₂)₂S(O)₂CH₃ | H | OCF₂H | |
| O(CH₂)₂S(O)₂CH₂CH₃ | CH₃ | Me | |
| O(CH₂)₂S(O)₂CH₂CH₃ | H | Me | |
| O(CH₂)₂S(O)₂CH₂CH₃ | H | OMe | |
| O(CH₂)₂S(O)₂CH₂CH₃ | H | OCF₂H | |
| OCH₂S(O)₂CH₂CH₃ | H | Me | |
| OCH₂S(O)₂CH₂CF₃ | H | OMe | |
| O(CH₂)₂S(O)₂CH₂CF₃ | H | OCF₂H | |
| O(CH₂)₂S(O)₂CH₂CF₂H | H | Me | |
| O(CH₂)₂S(O)₂(CH₂)₂Cl | H | OMe | |
| O(CH₂)₂S(O)₂(CH₂)₂Br | H | OCF₂H | |
| O(CH₂)₂S(O)₂(CH₂)₂I | CH₃ | OMe | |
| O(CH₂)₂S(O)₂CF₃ | H | Me | |
| OCH₂S(O)₂Cl | H | OMe | |
| OCH₂S(O)₂CF₃ | H | OCF₂H | |
| O(CH₂)₂CN | H | Me | |
| O(CH₂)₂CN | H | OMe | |
| O(CH₂)₂CN | H | OCF₂H | |
| OCH₂CN | H | Me | |
| OCH₂CN | H | OMe | |
| OCH₂CN | H | OCF₂H | |
| OCH₂CN | CH₃ | OCF₂H | |
| OCH(CH₃)CN | H | Me | |
| O(CH₂)₂NH₂ | H | OMe | |
| O(CH₂)₂NH₂ | H | OCF₂H | |
| O(CH₂)₂NH₂ | H | Me | |
| O(CH₂)₂NHCH₃ | H | OMe | |
| O(CH₂)₂NHCH₃ | H | OCF₂H | |
| O(CH₂)₂NHCH₃ | H | Me | |
| O(CH₂)₂N(CH₃)₂ | H | OMe | |
| O(CH₂)₂N(CH₃)₂ | H | OCF₂H | |
| O(CH₂)₂N(CH₃)₂ | H | Me | |
| SCH₂OCH₃ | H | OMe | |
| SCH₂OCH₃ | H | OCF₂H | |
| SCH₂OCH₃ | H | Me | |
| SCH₂OCH₂CH₃ | H | OMe | |
| S(CH₂)₂OCH₃ | H | OCF₂H | |
| S(CH₂)₂OCH₃ | CH₃ | Me | |
| S(CH₂)₂OCH₃ | H | Me | |
| S(CH₂)₂OCH₃ | H | OMe | |
| S(CH₂)₂OCH₂CH₃ | H | OCF₂H | |
| S(CH₂)₂OCH₂CF₃ | H | Me | |
| SCH₂OCH₂CF₃ | H | OMe | |
| S(CH₂)₂OCH₂CF₂H | H | OCF₂H | |
| S(CH₂)₂O(CH₂)₂Cl | H | Me | |
| S(CH₂)₂O(CH₂)₂Br | H | Ome | |
| S(CH₂)₂O(CH₂)₂I | H | OCF₂H | |
| S(CH₂)₂OCF₃ | CH₃ | OMe | |
| SCH₂SCH₃ | H | Me | |
| SCH₂SCH₃ | H | OMe | |
| SCH₂SCH₃ | H | OCF₂H | |
| SCH₂SCH₂CH₃ | H | Me . | |
| S(CH₂)₂SCH₃ | H | OMe | |
| S(CH₂)₂SCH₃ | H | OCF₂H | |
| S(CH₂)₂SCH₃ | H | Me | |
| S(CH₂)₂SCH₂CH₃ | H | OMe | |
| SCH(CH₃)SCH₃ | H | OCF₂H | |
| S(CH₂)₂SCH₂CF₃ | CH₃ | OCF₂H | |
| SCH₂SCH₂CF₃ | H | Me | |
| S(CH₂)₂SCH₂CF₂H | H | OMe | |
| S(CH₂)₂S(CH₂)₂Cl | H | OCF₂H | |
| S(CH₂)₂S(CH₂)₂Br | H | OMe | |
| S(CH₂)₂S(CH₂)₂I | H | OMe | |
| S(CH₂)₂SCF₃ | H | OCF₂H | |
| SCH₂CN | H | Me | |
| SCH₂CN | H | OMe | |
| SCH₂CN | H | OCF₂H | |
| S(CH₂)₂CN | H | Me | |
| S(CH₂)₂CN | H | OMe | |
| S(CH₂)₂CN | H | OCF₂H | |
| SCH(CH₃)CN | H | Me | |
| SCHF₂ | H | OMe | |
| SCHF₂ | H | OCF₂H | |
| SCHF₂ | CH₃ | Me | |
| SCHF₂ | H | Me | |
| SCF₃ | H | OMe | |
| SCH₂CFH₂ | H | OCF₂H | |
| SCH₂CF₂H | H | Me | |
| SCH₂CF₃ | H | OMe | |
| SCH₂CF₃ | H | OCF₂H | |
| SCH₂CF₃ | H | Me | |
| SCH₂CF₂H | H | OMe | |
| S(CH₂)₂CFH₂ | H | OCF₂H | |
| S(CH₂)₂CClH₂ | CH₃ | OMe | |
| S(CH₂)₂CIH₂ | H | Me | |
| SCF₂CF₃ | H | OMe | |
| SCH(CH₃)CF₃ | H | OCF₂H | |
| S(CH₂)₂CCl₃ | H | Me | |
| S(O)CHF₂ | H | OMe | |
| S(O)CHF₂ | H | OCF₂H | |
| S(O)CHF₂ | H | Me | |
| S(O)CF₃ | H | OMe | |
| S(O)CH₂CFH₂ | H | OCF₂H | |
| S(O)CH₂CF₂H | CH₃ | OCF₂H | |
| S(O)CH₂CF₃ | H | Me | |
| S(O)CH₂CF₃ | H | OMe | |
| S(O)CH₂CF₃ | H | OCF₂H | |
| S(O)CH₂CF₂H | H | Me | |
| S(O)(CH₂)₂CFH₂ | H | OMe | |
| S(O)(CH₂)₂CClH₂ | H | OCF₂H | |
| S(O)(CH₂)₂CIH₂ | H | Me | |
| S(O)CF₂CF₃ | H | OMe | |
| S(O)CH(CH₃)CF₃ | H | OCF₂H | |
| S(O)(CH₂)₂CCl₃ | H | Me | |
| S(O)₂CHF₂ | H | OMe | |
| S(O)₂CHF₂ | H | OCF₂H | |
| S(O)₂CHF₂ | H | Me | |
| S(O)₂CF₃ | H | OMe | |
| S(O)₂CH₂CFH₂ | H | OCF₂H | |
| S(O)₂CH₂CF₂H | CH₃ | Me | |
| S(O)₂CH₂CF₃ | H | Me | |
| S(O)₂CH₂CF₃ | H | OMe | |
| S(O)₂CH₂CF₃ | H | OCF₂H | |
| S(O)₂CH₂CF₂H | H | Me | |
| S(O)₂(CH₂)₂CFH₂ | H | OMe | |
| S(O)₂(CH₂)₂CClH₂ | H | OCF₂H | |
| S(O)₂(CH₂)₂CIH₂ | H | Me | |
| S(O)₂CF₂CF₃ | H | OMe | |
| S(O)₂CH(CH₃)CF₃ | H | OCF₂H | |
| S(O)₂(CH₂)₂CCl₃ | CH₃ | OMe | |
| S(O)₂CH₂Cl | H | Me | |

TABLE VIIIa-continued

| | $R_1 = CH_2C\equiv CH$ | | |
|---|---|---|---|
| $R_2$ | R | Y | m.p. (°C.) |
| CH=CH$_2$ | H | OMe | |
| CH=CH$_2$ | H | OCF$_2$H | |
| CH=CH$_2$ | H | Me | |
| CH$_2$CH=CH$_2$ | H | OMe | |
| CH$_2$CH=CH$_2$ | H | OCF$_2$H | |
| CH$_2$CH=CH$_2$ | H | Me | |
| CH=CHCH$_3$ | H | OMe | |
| C(CH$_3$)=CH$_2$ | H | OCF$_2$H | |
| CH=CH$_2$ | CH$_3$ | OCF$_2$H | |
| C≡CH | H | Me | |
| C≡CH | H | OMe | |
| C≡CH | H | OCF$_2$H | |
| CH$_2$C≡CH | H | Me | |
| CH$_2$C≡CH | H | OMe | |
| CH$_2$C≡CH | H | OCF$_2$H | |
| C≡CCH$_3$ | H | Me | |
| C≡CCH$_3$ | H | OMe | |
| C≡CCH$_3$ | H | OCF$_2$H | |
| NH$_2$ | H | Me | |
| NH$_2$ | H | OMe | |
| NH$_2$ | H | OCF$_2$H | |
| NHCH$_3$ | H | Me | |
| NHCH$_3$ | H | OMe | |
| NHCH$_3$ | H | OCF$_2$H | |
| NHCH$_3$ | CH$_3$ | Me | |
| N(CH$_3$)$_2$ | H | Me | |
| N(CH$_3$)$_2$ | H | OMe | |
| N(CH$_3$)$_2$ | H | OCF$_2$H | |
| NHCH$_2$CH$_3$ | H | Me | |
| NHCH$_2$CH$_3$ | H | OMe | |
| NHCH$_2$CH$_3$ | H | OCF$_2$H | |
| N(CH$_3$)CH$_2$CH$_3$ | H | Me | |
| N(CH$_2$CH$_3$)$_2$ | H | OMe | |
| NHCH$_2$CF$_3$ | H | OCF$_2$H | |
| NHCH$_2$CF$_3$ | CH$_3$ | OMe | |
| NHCH$_2$CF$_3$ | H | Me | |
| NHCH$_2$CF$_3$ | H | OMe | |
| N(CH$_3$)CH$_2$CF$_3$ | H | OCF$_2$H | |
| N(CH$_3$)CH$_2$CHF$_2$ | H | Me | |
| N(CH$_3$)(CH$_2$)$_2$F | H | OMe | |
| N(CH$_3$)(CH$_2$)$_2$Cl | H | OCF$_2$H | |
| N(CH$_3$)(CH$_2$)$_2$I | H | Me | |
| N(CH$_3$)(CH$_2$)$_2$Br | H | OMe | |
| NHCF$_3$ | CH$_3$ | OCF$_2$H | |
| NHCF$_3$ | H | Me | |
| NH(CH$_2$)$_2$F | H | OMe | |
| N(CH$_3$)CF$_2$H | H | OCF$_2$H | |
| NHCF$_2$H | H | Me | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE IX

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 8

| Wettable Powder | |
|---|---|
| 2-[[[4-(difluoromethoxy)-6-methoxypyrimidin-2-yl]aminocarbonyl]aminosulfonl]-4-ethoxybenzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

| Wettable Powder | |
|---|---|
| 2-[[[4-(difluoromethoxy)-6-methoxypyrimidin-2-yl]aminocarbonyl]aminosulfonyl]-4-ethoxybenzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 10

| Granule | |
|---|---|
| Wettable Powder of Example 9 | 5% |
| attapulgite granules (U.S.S. 20-40 mesh; 0.84-0.42 mm) | 95% |

A slurry of wettable powder containing 25% solids is sprayed on the surface of attapulgite granules while tumbling in a double-cone blender. The granules are dried and packaged.

EXAMPLE 11

| Extruded Pellet | |
|---|---|
| 2-[[[4-(difluoromethoxy)-6-methoxypyrimidin-2-yl]aminocarbonyl]aminosulfonyl]-4-ethoxybenzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

| Oil Suspension | |
|---|---|
| 2-[[[4-(difluoromethoxy)-6-methoxypyrimidin-2-yl]aminocarbonyl]aminosulfonyl]-4-ethoxybenzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Wettable Powder | |
|---|---|
| 2-[[[4-(difluoromethoxy)-6-methoxypyrimidin-2-yl]aminocarbonyl]aminosulfonyl]-4-ethoxybenzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

| Low Strength Granule | |
|---|---|
| 2-[[[4-(difluoromethoxy)-6-methoxypyrimidin-2-yl]aminocarbonyl]aminosulfonyl]-4-ethoxybenzoic acid, methyl ester | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| 2-[[[4-(difluoromethoxy)-6-methoxypyrimidin-2-yl]aminocarbonyl]aminosulfonyl]-4-ethoxybenzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Solution | |
|---|---|
| 2-[[[4-(difluoromethoxy)-6-methoxypyrimidin-2-yl]aminocarbonyl]aminosulfonyl]-4-ethoxybenzoic | |

-continued

| Solution | |
|---|---|
| acid, methyl ester | 5% |
| water | 95% |

The salt is added directly to the water with stirring to produce the solution, which may then be packaged for use.

EXAMPLE 17

| Low Strength Granule | |
|---|---|
| 2-[[[4-(difluoromethoxy)-6-methoxypyrimidin-2-yl]aminocarbonyl]aminosulfonyl]-4-ethoxybenzoic acid, methyl ester | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
|---|---|
| 2-[[[4-(difluoromethoxy)-6-methoxypyrimidin-2-yl]aminocarbonyl]aminosulfonyl]-4-ethoxybenzoic acid, methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 19

| High Strength Concentrate | |
|---|---|
| 2-[[[4-(difluoromethoxy)-6-methoxypyrimidin-2-yl]aminocarbonyl]aminosulfonyl]-4-ethoxybenzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

| Wettable Powder | |
|---|---|
| 2-[[[4-(difluoromethoxy)-6-methoxypyrimidin-2-yl]aminocarbonyl]aminosulfonyl]-4-ethoxybenzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

| Wettable Powder | |
|---|---|
| 2-[[[4-(difluoromethoxy)-6-methoxypyrimidin-2-yl]aminocarbonyl]aminosulfonyl]-4-ethoxybenzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

| Oil Suspension | |
|---|---|
| 2-[[[4-(difluoromethoxy)-6-methoxypyrimidin-2-yl]aminocarbonyl]aminosulfonyl]-4-ethoxybenzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 23

| Dust | |
|---|---|
| 2-[[[4-(difluoromethoxy)-6-methoxypyrimidin-2-yl]aminocarbonyl]aminosulfonyl]-4-ethoxybenzoic acid, ethyl ester | 10% |
| attapulite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 24

| Emulsifiable Concentrate | |
|---|---|
| 2-[[[4-(difluoromethoxy)-6-methoxypyrimidin-2-yl]aminocarbonyl]aminosulfonyl]-4-ethoxybenzoic acid, methyl ester | 20% |
| chlorobenzene | 74% |
| sorbitan monostearate and polyoxyethylene | |

-continued

| | |
|---|---|
| Emulsifiable Concentrate | |
| condensates thereof | 6% |

The ingredients are combined and stirred to produce a solution which can be emulsified in water for application.

UTILITY

Test results indicate that the compounds of the present invention are highly active preemergent or postemergent herbicides or plant growth regulators. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat, barley, corn and rice. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.004 to 10 kg/ha, the lower rates being suggested for use on lighter soils and/or those having a low organic matter content, for plant growth modification or for situations where only short-term persistence is required.

The compounds of the invention may be used in combination with any other commercial herbicides. They are particularly useful in combination with the following herbicides.

| Common Name | Chemical Name |
|---|---|
| acifluorfen | 5-[2-chloro-4-(trifluoromethyl)phenoxy]-2-nitrobenzoic acid |
| acrolein | acrolein |
| alachlor | 2-chloro-2',6'-diethyl-N—(methoxymethyl)-acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-$\alpha,\alpha,\alpha$-trifluoro-2,6-dinitro-p-toluidine |
| bensulide | O,O—diisopropyl phosphorodithioate S—ester with N—(2-mercaptoethyl)-benzenesulfonamide |
| bentazon | 3-isopropyl-1H—2,1,3-benzothiadiazin-4(3H)—one 2,2-dioxide |
| benzipram | 3,5-dimethyl-N—(1-methylethyl)-N—(phenylmethyl)benzamide |
| benzoylprop | N—benzoyl-N—(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N—(butoxymethyl)-2-chloro-2',6'-diethylacetanilide |
| butam | 2,2-dimethyl-N—(1-methylethyl)-N—(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| butylate | S—ethyl-diisobutylthiocarbamate |
| cacodylic acid | hydroxydimethylarsine oxide |
| carbetamide | D-N—ethyllactamide carbanilate (ester) |
| CDAA | N—N—diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| chlorsulfuron | 2-chloro-N—[(4-methoxy-6-methyl-1,3,5-triazin-2-yl)aminocarbonyl]benzenesulfonamide |
| chlortoluron | N'—(3-chloro-4-methylphenyl-N',N'—dimethylurea |
| cisanilide | cis-2,5-dimethyl-N—phenyl-1-pyrrolidinecarboxamide |
| CMA | calcium methanearsonate |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N—[5-(2-chloro-1,1-dimethylethyl)-1,3,4-thiadiazol-2-yl] cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H—1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S—(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]-propanoic acid |
| diethatyl | N—(chloroacetyl)-N—(2,6-diethylphenyl)-glycine |
| difenzoquat | 1,2-dimethyl-3,5-diphenyl-1H—pyrazolium |
| dinitramine | $N^4,N^4$—diethyl-$\alpha,\alpha,\alpha$-trifluoro-3,5-dinitrotoluene-2,4-diamine |
| dinoseb | 2-sec-butyl-4,6-dinitrophenol |
| diphenamide | N,N—dimethyl-2,2-diphenylacetamide |
| dipropetryn | 2-(ethylthio)-4,6-bis(isopropylamino)-s-triazine |
| diquat | 6,7-dihydrodipyrido[1,2-a:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyl-oxy)phenoxy)propanoate |
| fenuron | 1,1-dimethyl-3-phenylurea |
| fenuron TCA | 1,1-dimethyl-3-phenylurea mono(trichloroacetate) |
| flamprop | N—benzoyl-N—(3-chloro-4-fluorophenyl)-DL-alanine |
| fluchloralin | N—(2-chloroethyl)-2,6-dinitro-N—propyl-4-(trifluoromethyl)aniline |
| fluometuron | 1,1-dimethyl-3-($\alpha,\alpha,\alpha$-trifluoro-m-tolyl)-urea |
| fluorodifen | p-nitrophenyl $\alpha,\alpha,\alpha$-trifluoro-2-nitro- |

| | -continued |
|---|---|
| fluridone | p-tolyl ether<br>1-methyl-3-phenyl-5-[3-(trifluoro-methyl)phenyl]-4(1H)—pyridinone |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| hexaflurate | potassium hexafluoroarsenate |
| hexazinone | 3-cyclohexyl-6-(dimethylamino)-1-methyl-1,3,5-triazine-2,4(1H,3H)—dione |
| imazaquin | 2-(4,5-dihydro-4-methyl-4-(1-methyl-ethyl)-5-oxo-1H—imidazol-2-yl)-3-quinolinecarboxylic acid |
| ioxynil | 4-hydroxy-3,5-diiodobenzonitrile |
| isopropalin | 2,6-dinitro-N,N—dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H—cyclopenta-pyrimidine-2,4(3H,5H)—dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N—[(2,4-dimethyl-5-[[(trifluoromethyl)-sulfonyl]amino]phenyl]acetamide |
| methal-propalin | N—(2-methyl-2-propenyl)-2,6-dinitro-N—propyl-4-(trifluoromethyl)benzenamide |
| methabenz-thiazuron | 1,3-dimethyl-3-(2-benzothiazolyl)urea |
| metham | sodium methyldithiocarbamate |
| methazole | 2-(3,4-dichlorophenyl)-4-methyl-1,2,4-oxadiazolidine-3,5-dione |
| methoxuron | N'—(3-chloro-4-methoxyphenyl)N,N—dimethylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| metsulfuron methyl | 2-[[(4-methoxy-6-methyl-1,3,5-triazine-2-yl)aminocarbonyl]aminosulfonyl]ben-zoic acid, methyl ester |
| molinate | S—ethyl hexahydro-1H—azepine-1-carbo-thioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-(α-naphthoxy)-N,N—diethylpropion-amide |
| naptalam | N—1-naphthylphthalamic acid |
| neburon | 1-butyl-3-(3,4-dichlorophenyl)-1-methyl-urea |
| nitralin | 4-(methylsulfonyl)-2,6-dinitro-N,N—dipropylaniline |
| nitrofen | 2,4-dichlorophenyl p-nitrophenyl ether |
| nitrofluorfen | 2-chloro-1-(4-nitrophenoxy)-4-(tri-fluoromethyl)benzene |
| norea | 3-(hexahydro-4,7-methanoindan-5-yl)-1,1-dimethylurea |
| norflurazon | 4-chloro-5-(methylamino)-2-(α,α,α-tri-fluoro-m-tolyl)-3(2H)—pyridazinone |
| oryzalin | 3,4-dinitro-N,N—dipropylsulfanilamide |
| oxadiazon | 2-tert-butyl-4-(2,4-dichloro-5-isopro-poxyphenyl)Δ²-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N—(1-ethylpropyl)-3,4-dimethyl-2,6-dinitrobenzenamine |
| perfluidone | 1,1,1-trifluoro-N—[2-methyl-4-(phenyl-sulfonyl)phenyl]methanesulfonamide |
| picloram | 4-amino-3,5,6-trichloropicolinic acid |

| | -continued |
|---|---|
| procyazine | 2-[[4-chloro-6-(cyclopropylamino)-1,3,5-triazine-2-yl]amino]-2-methylpropane-nitrile |
| profluralin | N—(cyclopropylmethyl)-α,α,α-trifluoro-2,6-dinitro-N—propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro N—(1,1-dimethyl-2-propyn-yl)benzamide |
| propachlor | 2-chloro-N—isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitro-phenyl]sulfonyl]-S,S—dimethylsulfil-imine |
| prynachlor | 2-chloro-N—(1-methyl-2-propynyl)acet-anilide |
| quinofop ethyl | 2-[4-(6-chloroquinoxalin-2-yloxy)phen-oxypropanoic acid, ethyl ester |
| secbumeton | N—ethyl-6-methoxy-N'(1-methylpropyl)-1,3,5-triazine-2,4-diamine |
| sethoxydim | 2-[1-(ethoxyimino)butyl]-5-[2-(ethyl-thio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)ethylsulfonyl] -pyridine-N—oxide |
| TCA | trichloroacetic acid |
| tebuthiuron | N—[5-(1,1-dimethylethyl)-1,3,4-thiadi-azol-2-yl]-N,N'—dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]-acetamide |
| terbuthyl-azine | 2-(tert-butylamino)-4-chloro-6-(ethyl-amino)-s-triazine |
| terbutol | 2,6-di-tert-butyl-p-tolyl methylcar-bamate |
| terbutryn | 2-(tert-butylamino)-4-(ethylamino)-6-(methylthio)-s-triazine |
| tetrafluron | N,N—dimethyl-N'—[3-(1,1,2,2-tetrafluoro-ethoxy)phenyl]urea |
| thiobencarb | S—[(4-chlorophenyl)methyl] diethylcar-bamothioate |
| triallate | S—(2,3,3-trichloroallyl)diisopropylthio-carbamate |
| trifluralin | α,α,α-trifluoro-2,6-dinitro-N,N—propyl-p-toluidine |
| trimeturon | 1-(p-chlorophenyl)-2,3,3-trimethylpseu-dourea |
| vernolate | S—propyl dipropylthiocarbamate |
| 2,3,6-TBA[b] | ethyl 5-[2-chloro-4-(trifluoromethyl)-phenoxy]-2-nitrobenzoic acid<br>2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |

| Trade Name or Code Number | Chemical Name |
|---|---|
| "Cinch" | exo-1-methyl-4-(1-methylethyl)-2-[(2-methylphenyl)methoxy]-7-oxabicyclo-[2.2.1]heptane |
| AC 263,499 | 2-[4,5-dihydro-4-methyl-4-(1-methyl-ethyl)-5-oxo-1H—imidazol-2-yl]-5-ethyl-3-pyridinecarboxylic acid |
| Harmony ™ | 3-[[(4-methoxy-6-methyl-1,3,5-triazin-2-yl)aminocarbonyl]aminosulfonyl]-2-thiophenecarboxylic acid, methyl ester |
| PPG-1013 | 5-(2-chloro-4-(trifluoromethyl)phenoxy)-2-nitroacetophenone oxime-O—acetic acid, methyl ester |
| DOWCO 453 ME | 2-(4-(3-chloro-5-trifluoromethylpyridin-2-yloxy)phenoxy)propanoic acid, methyl |

| | |
|---|---|
| | ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl-p-toluic acid, methyl ester |
| AC 252,925 | 2-(4-isopropyl-4-methyl-5-oxo-2-imidazolin-2-yl)nicotinic acid with isopropyl amine (1:1) |
| DPX-L5300 | 2-[[N—(4-methoxy-6-methyl-1,3,5-triazine-2-yl)-N—methylaminocarbonyl]-aminosulfonyl]benzoic acid, methyl ester |
| — | 2-Butyl-2,3-dihydro-N—[(4-methoxy-6-methylpyrimidin-2-yl)aminocarbonyl]-1,2-benzisothiazole-7-sulfonamide-1,1-dioxide |
| — | 2-Butyl-2,3-dihydro-N—[(4,6-dimethoxypyrimidin-2-yl)aminocarbonyl]-1,2-benzisothiazole-7-sulfonamide-1,1-dioxide |

The herbicidal properties of the subject compounds were discovered in a number of greenhouse tests. The test procedures and results follow.

TEST A

Seeds of crabgrass (Digitaria sp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effects;
S=albinism;
U=unusual pigmentation;
X=axillary stimulation; and
6Y=abscised buds or flowers.
—=no test

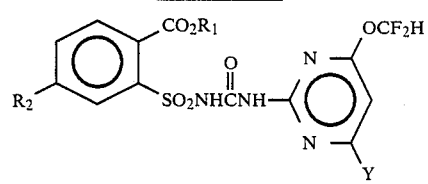

Compounds

| Compound | $R_1$ | $R_2$ | Y |
|---|---|---|---|
| 1 | $CH_3$ | $OCH_3$ | $OCH_3$ |
| 2 | $CH_3CH_2$ | $OCH_3$ | $OCH_3$ |
| 3 | $CH_3CH_2$ | $OCH_3$ | $OCF_2H$ |
| 4 | $CH_3CH_2$ | $OCH_3$ | $CH_3$ |
| 5 | $CH_3$ | $OCH_2CH_3$ | $OCH_3$ |
| 6 | $CH_3$ | $SCH_3$ | $OCH_3$ |

TABLE A

| | Cmpd. 1 | Cmpd. 2 | Cmpd. 3 |
|---|---|---|---|
| Rate kg/ha | 0.05 | 0.05 | 0.05 |
| POSTEMERGENCE | | | |
| Morningglory | 9C | 10C | 9C |
| Cocklebur | 10C | 3C,8H | 5C,9G |
| Nutsedge | 9C | 9G | 9G |
| Crabgrass | 3C,6G | 0 | 4G |
| Barnyardgrass | 5C,9H | 3C,3H | 1C |
| Wild Oats | 2G | 0 | 0 |
| Wheat | 2G | 0 | 0 |
| Corn | 3C,9H | 0 | 1C |
| Soybean | 5C,9G | 3C,8G | 3C,8H |
| Rice | 3C,6G | 0 | 0 |
| Sorghum | 3C,9H | 9H | 3C,9H |
| Sugar beet | 10C | 10C | 9C |
| Cotton | 9C | 9G | 9G |
| SicklePod | 9C | 9C | 4C,5H |
| PREEMERGENCE | | | |
| Morningglory | 9G | 8G | 9G |
| Cocklebur | 8H | 8G | 3C,5H |
| Nutsedge | 10E | 10E | 10E |
| Crabgrass | 0 | 0 | 2G |
| Barnyardgrass | 5C,9H | 6G | 4G |
| Wild Oats | 2C,3H | 2C | 1C |
| Wheat | 6G | 2C,4G | 0 |
| Corn | 2C,8G | 5G | 5G |
| Soybean | 3C,8H | 2C,7H | 1H |
| Rice | 8G | 5G | 2G |
| Sorghum | 6C,9H | 3C,9H | 3C,9H |
| Sugar beet | 5C,9G | 10E | 3C,8G |
| Cotton | 9G | 6G | 7G |
| Sicklepod | 2C,7G | 2C,4G | 2G |
| | Cmpd. 4 | Cmpd. 5 | Cmpd. 6 |
| Rate kg/ha | 0.05 | 0.05 | 0.05 |
| POSTEMERGENCE | | | |
| Morningglory | 2C,2H | 10C | 10C |
| Cocklebur | 3C,8G | 10C | 5C,9G |
| Nutsedge | 5G | 4C,8G | 2C,9G |
| Crabgrass | 3G | 2G | 1H |
| Barnyardgrass | 1C | 3H | 4C,9H |
| Wild Oats | 1C | 0 | 4C,8G |
| Wheat | 2G | 0 | 5C,9G |
| Corn | 0 | 1H | 4C,9H |
| Soybean | 2C,2H | 5C,9G | 5C,9G |
| Rice | 1C | 5G | 4C.8G |
| Sorghum | 2C,6G | 2C,5G | 9C |
| Sugar beet | 3C,5G | 10C | 9C |
| Cotton | 2C,8G | 9C | 9C |
| Sicklepod | 3C,5G | 9C | 9C |
| PREEMERGENCE | | | |
| Morningglory | 9C | 9G | 9G |
| Cocklebur | — | 8H | 9H |
| Nutsedge | 10E | 3C,7G | 10E |
| Crabgrass | 0 | 0 | 2C |
| Barnyardgrass | 5G | 3C | 5C,9H |
| Wild Oats | 5G | 2C | 5C,9G |
| Wheat | 5G | 4C | 10C |

TABLE A-continued

| | | | |
|---|---|---|---|
| Corn | 5G | 2C,7G | 9G |
| Soybean | 0 | 8H | 4C,7H |
| Rice | 2C,7G | 2C,8G | 9H |
| Sorghum | 2C,5G | 7G | 9H |
| Sugar beet | 2G | 9C | 5C,9G |
| Cotton | 7G | 8G | 8G |
| Sicklepod | 9G | 3C | 3C,7G |

TEST B

Postemergence

Two round pans (25 cm diameter by 12.5 cm deep) were filled with Sassafras sandy loam soil. One pan was planted with blackgrass (*Alopecurus myosuroides*), sugar beets, nutsedge (*Cyperus rotundus*) tubers, rape (*Brassica napus*), crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass, sugar beets, nutsedge, rape, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 100 where 0=no effect, and 100=complete control. A dash (—) response means no test.

Response ratings are contained in Table B.

TABLE B

| Compound 1 | | | | |
|---|---|---|---|---|
| POSTEMERGENCE | | | | |
| Rate g/ha | 62 | 16 | 4 | 1 |
| Corn | 100 | 90 | 80 | 40 |
| Wheat | 0 | 0 | 0 | 0 |
| Rice | 100 | 100 | 60 | 50 |
| Soybean | 100 | 100 | 100 | 80 |
| Cotton | 100 | 100 | 90 | 30 |
| Sugar beet | 100 | 100 | 100 | 90 |
| Rape | 100 | 100 | 100 | 80 |
| Crabgrass | 50 | 30 | 0 | 0 |
| Johnsongrass | 40 | 30 | 0 | 0 |
| Blackgrass | 100 | 100 | 90 | 60 |
| Barnyardgrass | 50 | 0 | 0 | 0 |
| Nutsedge | 100 | 100 | 90 | 40 |
| Giant Foxtail | 20 | 0 | 0 | 0 |
| Wild Oats | 30 | 0 | 0 | 0 |
| Cocklebur | 100 | 100 | 90 | 50 |
| Morningglory | 100 | 100 | 90 | 80 |
| Teaweed | 90 | 50 | 0 | 0 |
| Sicklepod | 100 | 100 | 70 | 20 |
| Jimsonweed | 100 | 90 | 40 | 0 |
| Velvetleaf | 100 | 100 | 100 | 80 |
| PREEMERGENCE | | | | |
| Rate g/ha | 250 | 62 | 16 | |
| Corn | 100 | 60 | 20 | |
| Wheat | 0 | 0 | 0 | |
| Rice | 100 | 100 | 80 | |
| Soybean | 90 | 20 | 0 | |
| Cotton | 80 | 30 | 0 | |
| Sugar beet | 100 | 90 | 70 | |
| Rape | 100 | 90 | 70 | |
| Crabgrass | 70 | 50 | 0 | |
| Johnsongrass | 90 | 90 | 30 | |
| Blackgrass | 100 | 100 | 80 | |
| Barnyardgrass | 90 | 60 | 0 | |
| Nutsedge | 100 | 90 | 50 | |
| Giant Foxtail | 60 | 20 | 0 | |
| Wild Oats | 70 | 40 | 0 | |
| Cocklebur | 90 | 80 | 60 | |
| Morningglory | 90 | 90 | 60 | |
| Teaweed | 90 | 80 | 20 | |
| Sicklepod | 90 | 80 | 30 | |
| Jimsonweed | 100 | 90 | 80 | |
| Velvetleaf | 100 | 100 | 90 | |
| Compound 2 | | | | |
| POSTEMERGENCE | | | | |
| Rate g/ha | 250 | 62 | 16 | 4 |
| Corn | 70 | 30 | 0 | 0 |
| Wheat | 40 | 0 | 0 | 0 |
| Rice | 50 | 0 | 0 | 0 |
| Soybean | 100 | 100 | 100 | 80 |
| Cotton | 70 | 40 | 20 | 0 |
| Sugar beet | 100 | 100 | 90 | 80 |
| Rape | 100 | 100 | 100 | 80 |
| Crabgrass | 30 | 0 | 0 | 0 |
| Johnsongrass | 100 | 70 | 30 | 0 |
| Blackgrass | 100 | 100 | 60 | 20 |
| Barnyardgrass | 70 | 50 | 20 | 0 |
| Nutsedge | 100 | 100 | 90 | 40 |
| Giant Foxtail | 60 | 20 | 0 | 0 |
| Wild Oats | 20 | 0 | 0 | 0 |
| Cocklebur | 100 | 100 | 100 | 80 |
| Morningglory | 100 | 100 | 90 | 50 |
| Teaweed | 80 | 40 | 20 | 0 |
| Sicklepod | 100 | 100 | 80 | 20 |
| Jimsonweed | 100 | 70 | 30 | 0 |
| Velvetleaf | 100 | 100 | 100 | 60 |
| PREEMERGENCE | | | | |
| Rate g/ha | 250 | 62 | 16 | 4 |
| Corn | 60 | 30 | 0 | 0 |
| Wheat | 0 | 0 | 0 | 0 |
| Rice | 90 | 80 | 70 | 30 |
| Soybean | 90 | 60 | 20 | 0 |
| Cotton | 20 | 0 | 0 | 0 |
| Sugar beet | 100 | 100 | 70 | 30 |
| Rape | 100 | 100 | 90 | 50 |
| Crabgrass | 50 | 0 | 0 | 0 |
| Johnsongrass | 100 | 70 | 0 | 0 |
| Blackgrass | 100 | 100 | 100 | 80 |
| Barnyardgrass | 60 | 50 | 0 | 0 |
| Nutsedge | 100 | 80 | 30 | 0 |
| Giant Foxtail | 60 | 20 | 0 | 0 |
| Wild Oats | 0 | 0 | 0 | 0 |
| Cocklebur | 80 | 60 | 40 | 30 |
| Morningglory | 80 | 70 | 40 | 0 |
| Teaweed | 80 | 80 | 30 | 0 |
| Sicklepod | 80 | 40 | 0 | 0 |
| Jimsonweed | 100 | 100 | 30 | 0 |
| Velvetleaf | 100 | 100 | 40 | 0 |
| Compound 3 | | | | |
| POSTEMERGENCE | | | | |
| Rate g/ha | 250 | 62 | 16 | |
| Corn | 0 | 0 | 0 | |
| Wheat | 0 | 0 | 0 | |
| Rice | 0 | 0 | 0 | |
| Soybean | 90 | 80 | 20 | |
| Cotton | 60 | 0 | 0 | |
| Sugar beet | 30 | 0 | 0 | |
| Rape | 100 | 90 | 60 | |
| Crabgrass | 0 | 0 | 0 | |

TABLE B-continued

| | | | |
|---|---|---|---|
| Johnsongrass | 90 | 50 | 20 |
| Blackgrass | 100 | 90 | 80 |
| Barnyardgrass | 50 | 20 | 0 |
| Nutsedge | 80 | 50 | 0 |
| Giant Foxtail | 30 | 0 | 0 |
| Wild Oats | 0 | 0 | 0 |
| Cocklebur | 90 | 80 | 50 |
| Morningglory | 0 | 0 | 0 |
| Teaweed | 60 | 20 | 0 |
| Sicklepod | 60 | 0 | 0 |
| Jimsonweed | 90 | 70 | 20 |
| Velvetleaf | 100 | 70 | 30 |

PREEMERGENCE

| Rate g/ha | 250 | 62 | 16 |
|---|---|---|---|
| Corn | 20 | 0 | 0 |
| Wheat | 20 | 0 | 0 |
| Rice | 90 | 90 | 20 |
| Soybean | 20 | 0 | 0 |
| Cotton | 0 | 0 | 0 |
| Sugar beet | 90 | 70 | 20 |
| Rape | 100 | 90 | 50 |
| Crabgrass | 60 | 0 | 0 |
| Johnsongrass | 100 | 90 | 40 |
| Blackgrass | 100 | 90 | 80 |
| Barnyardgrass | 80 | 60 | 20 |
| Nutsedge | 90 | 80 | 60 |
| Giant Foxtail | 70 | 40 | 0 |
| Wild Oats | 0 | 0 | 0 |
| Cocklebur | 90 | 50 | 0 |
| Morningglory | 60 | 0 | 0 |
| Teaweed | 80 | 30 | 0 |
| Sicklepod | 0 | 0 | 0 |
| Jimsonweed | 90 | 70 | 20 |
| Velvetleaf | 90 | 60 | 0 |

Compound 4

POSTEMERGENCE

| Rate g/ha | 250 | 62 | 16 |
|---|---|---|---|
| Corn | 10 | 0 | 0 |
| Wheat | 70 | 20 | 0 |
| Rice | 0 | 0 | 0 |
| Soybean | 10 | 0 | 0 |
| Cotton | 70 | 40 | 0 |
| Sugar beet | 20 | 0 | 0 |
| Rape | 70 | 50 | 0 |
| Crabgrass | 0 | 0 | 0 |
| Johnsongrass | 90 | 70 | 30 |
| Blackgrass | 80 | 70 | 0 |
| Barnyardgrass | 80 | 50 | 0 |
| Nutsedge | 30 | 0 | 0 |
| Giant Foxtail | 30 | 0 | 0 |
| Wild Oats | 0 | 0 | 0 |
| Cocklebur | 90 | 80 | 50 |
| Morningglory | 0 | 0 | 0 |
| Teaweed | 50 | 0 | 0 |
| Sicklepod | 30 | 0 | 0 |
| Jimsonweed | 70 | 60 | 0 |
| Velvetleaf | 80 | 70 | 20 |

PREEMERGENCE

| Rate g/ha | 250 | 62 | 16 |
|---|---|---|---|
| Corn | 0 | 0 | 0 |
| Wheat | 0 | 0 | 0 |
| Rice | 80 | 30 | 0 |
| Soybean | 0 | 0 | 0 |
| Cotton | 20 | 0 | 0 |
| Sugar beet | 0 | 0 | 0 |
| Rape | 90 | 60 | 20 |
| Crabgrass | 70 | 30 | 0 |
| Johnsongrass | 80 | 50 | 0 |
| Blackgrass | 90 | 70 | 40 |
| Barnyardgrass | 70 | 40 | 0 |
| Nutsedge | 90 | 70 | 20 |
| Giant Foxtail | 60 | 40 | 0 |
| Wild Oats | 30 | 0 | 0 |
| Cocklebur | 50 | 0 | 0 |
| Morningglory | 0 | 0 | 0 |
| Teaweed | 80 | 60 | 30 |
| Sicklepod | 30 | 0 | 0 |
| Jimsonweed | 90 | 70 | 20 |
| Velvetleaf | 80 | 30 | 0 |

Compound 5

POSTEMERGENCE

| Rate g/ha | 62 | 16 | 4 | 1 |
|---|---|---|---|---|
| Corn | 0 | 0 | 0 | 0 |
| Wheat | 0 | 0 | 0 | 0 |
| Rice | 0 | 0 | 0 | 0 |
| Soybean | 100 | 100 | 90 | 30 |
| Cotton | 50 | 30 | 20 | 0 |
| Sugar beet | 100 | 100 | 90 | 40 |
| Rape | 100 | 100 | 100 | 60 |
| Crabgrass | 30 | 0 | 0 | 0 |
| Johnsongrass | 40 | 20 | 0 | 0 |
| Blackgrass | 90 | 70 | 20 | 0 |
| Barnyardgrass | 0 | 0 | 0 | 0 |
| Nutsedge | 0 | 0 | 0 | 0 |
| Giant Foxtail | 0 | 0 | 0 | 0 |
| Wild Oats | 0 | 0 | 0 | 0 |
| Cocklebur | 100 | 80 | 30 | 0 |
| Morningglory | 100 | 100 | 30 | 0 |
| Teaweed | 30 | 0 | 0 | 0 |
| Sicklepod | 30 | 0 | 0 | 0 |
| Jimsonweed | 80 | 50 | 20 | 0 |
| Velvetleaf | 100 | 100 | 40 | 0 |

PREEMERGENCE

| Rate g/ha | 250 | 62 | 16 |
|---|---|---|---|
| Corn | 20 | 0 | 0 |
| Wheat | 0 | 0 | 0 |
| Rice | 100 | 80 | 0 |
| Soybean | 40 | 0 | 0 |
| Cotton | 0 | 0 | 0 |
| Sugar beet | 100 | 60 | 0 |
| Rape | 100 | 90 | 30 |
| Crabgrass | 0 | 0 | 0 |
| Johnsongrass | 30 | 0 | 0 |
| Blackgrass | 100 | 90 | 90 |
| Barnyardgrass | 50 | 0 | 0 |
| Nutsedge | 50 | 0 | 0 |
| Giant Foxtail | 20 | 0 | 0 |
| Wild Oats | 0 | 0 | 0 |
| Cocklebur | 90 | 90 | 70 |
| Morningglory | 80 | 30 | 0 |
| Teaweed | 80 | 70 | 30 |
| Sicklepod | 70 | 30 | 0 |
| Jimsonweed | 90 | 80 | 70 |
| Velvetleaf | 90 | 80 | 50 |

Compound 6

POSTEMERGENCE

| Rate g/ha | 62 | 16 | 4 |
|---|---|---|---|
| Corn | 80 | 40 | 20 |
| Wheat | 50 | 0 | 0 |
| Rice | 70 | 0 | 0 |
| Soybean | 100 | 90 | 80 |
| Cotton | 70 | 70 | 0 |
| Sugarbeet | 100 | 90 | 70 |
| Rape | 100 | 90 | 80 |
| Crabgrass | 40 | 0 | 0 |
| Johnsongrass | 100 | 90 | 50 |
| Blackgrass | 100 | 90 | 80 |
| Barnyardgrass | 70 | 30 | 0 |
| Nutsedge | 100 | 70 | 0 |
| Giant Foxtail | 50 | 20 | 0 |
| Wild Oats | 50 | 0 | 0 |
| Cocklebur | 100 | 90 | 70 |
| Morningglory | 100 | 100 | 70 |
| Teaweed | 80 | 20 | 0 |
| Sicklepod | 90 | 20 | 0 |
| Jimsonweed | 90 | 90 | 60 |
| Velvetleaf | 100 | 90 | 20 |

PREEMERGENCE

| Rate g/ha | 250 | 62 | 16 | 4 |
|---|---|---|---|---|
| Corn | 90 | 30 | 0 | 0 |
| Wheat | 90 | 20 | 0 | 0 |
| Rice | 100 | 100 | 80 | 60 |
| Soybean | 90 | 60 | 20 | 0 |
| Cotton | 40 | 0 | 0 | 0 |
| Sugar beet | 100 | 90 | 80 | 40 |
| Rape | 100 | 90 | 80 | 20 |

TABLE B-continued

| | | | | |
|---|---|---|---|---|
| Crabgrass | 50 | 0 | 0 | 0 |
| Johnsongrass | 90 | 90 | 30 | 0 |
| Blackgrass | 100 | 100 | 90 | 70 |
| Barnyardgrass | 100 | 90 | 30 | 0 |
| Nutsedge | 100 | 80 | 0 | 0 |
| Giant Foxtail | 100 | 90 | 40 | 0 |
| Wild Oats | 90 | 80 | 60 | 60 |
| Cocklebur | 90 | 80 | 50 | 0 |
| Morningglory | 90 | 80 | 30 | 0 |
| Teaweed | 80 | 60 | 20 | 0 |
| Sicklepod | 80 | 70 | 0 | 0 |
| Jimsonweed | 90 | 90 | 60 | 20 |
| Velvetleaf | 100 | 80 | 60 | 0 |

TEST C

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), rapeseed (*Brassica napus*) and Italian ryegrass (*Lolium multiflorum*). The other pan was planted with seeds of Russian thistle (*Salsola kali*), kochia (*Kochia scoparia*), speedwell (*Veronica persica*), shepherd's purse (*Capsella bursa-pastoris*), *Matricaria inodora*, black nightshade (*Solanum nigrum*), wild buckwheat (*Polygonum convolvulus*), Galium aparine and sugar beets. The above two pans were treated preemergence. At the same time two pans in which the above plant species were growing were treated postemergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C.

TABLE C

| | Compound 3 Postemergence | | | |
|---|---|---|---|---|
| Rate kg/ha | 0.125 | 0.064 | 0.032 | 0.016 |
| wheat | 0 | 0 | 0 | 0 |
| barley | 0 | 2G | 0 | 0 |
| wild oats | 0 | 0 | 0 | 0 |
| cheatgrass | 0 | 0 | 0 | 0 |
| blackgrass | 9G | 8G | 7G | 6G |
| annual bluegrass | 3G | 0 | 0 | 0 |
| green foxtail | 0 | 0 | 0 | 0 |
| Italian ryegrass | 2G | 0 | 0 | 0 |
| rapeseed | 8G | 7G | 5G | 3G |
| *Matricaria inodora* | 10C | 8G | 5G | 4G |
| galium aparine | 8G | 10C | 3G | 5G |
| Russian thistle | 0 | 0 | 0 | 0 |
| shepherd's purse | 10C | 10C | 10C | 10C |
| kochia | 0 | 0 | 0 | 0 |
| black nightshade | 0 | 0 | 0 | 0 |
| speedwell | 5G | 3G | 0 | 0 |
| wild buckwheat | 0 | 0 | 0 | 0 |
| sugar beet | 4G | 5G | 4G | 2G |

| | Postemergence | | |
|---|---|---|---|
| Rate kg/ha | 0.008 | 0.004 | 0.002 |
| wheat | 0 | 0 | 0 |
| barley | 0 | 0 | 0 |
| wild oats | 0 | 0 | 0 |
| cheatgrass | 0 | 0 | 0 |

TABLE C-continued

| | | | |
|---|---|---|---|
| blackgrass | 6G | 2G | 0 |
| annual bluegrass | 0 | 0 | 0 |
| green foxtail | 0 | 0 | 0 |
| Italian ryegrass | 0 | 0 | 0 |
| rapeseed | 3G | 2G | 0 |
| *Matricaria inodora* | 4G | 4G | 3G |
| galium aparine | 3G | 3G | 0 |
| Russian thistle | 0 | 0 | 0 |
| shepherd's purse | 8G | 6G | 4G |
| kochia | 0 | 0 | 0 |
| black nightshade | 0 | 0 | 0 |
| speedwell | 0 | 0 | 0 |
| wild buckwheat | 0 | 0 | 0 |
| sugar beet | 0 | 0 | 0 |

| | Compound 3 Preemergence | | | |
|---|---|---|---|---|
| Rate kg/ha | 0.125 | 0.064 | 0.032 | 0.016 |
| wheat | 0 | 0 | 0 | 0 |
| barley | 0 | 0 | 0 | 0 |
| wild oats | 0 | 0 | 0 | 0 |
| cheatgrass | 5G | 0 | 0 | 0 |
| blackgrass | 9G | 9G | 6G | 5G |
| annual bluegrass | 0 | 0 | 0 | 0 |
| green foxtail | 0 | 0 | 0 | 0 |
| Italian ryegrass | 0 | 0 | 0 | 0 |
| rapeseed | 9G | 6G | 2G | 0 |
| *Matricaria inodora* | 7G | 7G | 5G | 4G |
| galium aparine | 5G | 5G | 3G | 0 |
| Russian thistle | 0 | 0 | 0 | 0 |
| shepherd's purse | 9G | 8G | 8G | 8G |
| kochia | 10C | 5G | 0 | 0 |
| black nightshade | 6G | 3G | 2G | 0 |
| speedwell | 10C | 8G | 7G | 0 |
| wild buckwheat | 7G | 0 | 0 | 0 |
| sugar beet | 8G | 7G | 2G | 4G |

| | Preemergence | | |
|---|---|---|---|
| Rate kg/ha | 0.008 | 0.004 | 0.002 |
| wheat | 0 | 0 | 0 |
| barley | 0 | 0 | 0 |
| wild oats | 0 | 0 | 0 |
| cheatgrass | 0 | 0 | 0 |
| blackgrass | 5G | 4G | 2G |
| annual bluegrass | 0 | 0 | 0 |
| green foxtail | 0 | 0 | 0 |
| Italian ryegrass | 0 | 0 | 0 |
| rapeseed | 0 | 0 | 0 |
| *Matricaria inodora* | 2G | 0 | 0 |
| galium aparine | 0 | 0 | 0 |
| Russian thistle | 0 | 0 | 0 |
| shepherd's purse | 8G | 7G | 4G |
| kochia | 0 | 0 | 0 |
| black nightshade | 0 | 0 | 0 |
| speedwell | 0 | 0 | 0 |
| wild buckwheat | 0 | 0 | 0 |
| sugar beet | 2G | 0 | 0 |

| | Compound 5 Postemergence | | | |
|---|---|---|---|---|
| Rate kg/ha | 0.125 | 0.064 | 0.032 | 0.016 |
| wheat | 1G | 0 | 0 | 0 |
| barley | 2G | 0 | 0 | 0 |
| wild oats | 0 | 0 | 0 | 0 |
| cheatgrass | 5G | 2G | 2G | 0 |
| blackgrass | 8G | 8G | 7G | 6G |
| annual bluegrass | 4G | 3G | 2G | 0 |
| green foxtail | 0 | 0 | 0 | 0 |
| Italian ryegrass | 2G | 0 | 0 | 0 |
| rapeseed | 10C | 10C | 10C | 10C |
| *Matricaria inodora* | 10C | 10C | 10C | 10C |
| galium aparine | 10C | 10C | 10C | 10C |
| Russian thistle | 10C | 10C | 10C | 10C |
| shepherd's purse | 10C | 10C | 9G,7C | 9G,7C |
| kochia | 10C | 10C | 10C | 8G |
| black nightshade | 10C | 10C | 9G,7C | 9G,7C |
| speedwell | 10C | 10C | 10C | 10C |
| wild buckwheat | 10C | 10C | 0 | 0 |
| sugar beet | 10C | 10C | 10C | 10C |

| | Postemergence | | | |
|---|---|---|---|---|
| Rate kg/ha | 0.008 | 0.004 | 0.002 | 0.001 |

TABLE C-continued

| | | | | |
|---|---|---|---|---|
| wheat | 0 | 0 | 0 | 0 |
| barley | 0 | 0 | 0 | 0 |
| wild oats | 0 | 0 | 0 | 0 |
| cheatgrass | 0 | 0 | 0 | 0 |
| blackgrass | 2G | 0 | 0 | 0 |
| annual bluegrass | 0 | 0 | 0 | 0 |
| green foxtail | 0 | 0 | 0 | 0 |
| Italian ryegrass | 0 | 0 | 0 | 0 |
| rapeseed | 10C | 10C | 10C | 10C |
| *Matricaria inodora* | 10C | 10C | 7G | 6G |
| galium aparine | 10C | 7G | 4G | 4G |
| Russian thistle | 10C | 9G | 9G | 8G |
| shepherd's purse | 10C | 9G,5C | 7G | 7G |
| kochia | 8G | 8G | 6G | 5G |
| black nightshade | 9G,7C | 9G,5C | 7G | 6G |
| speedwell | 10C | 9G | 6G | 6G |
| wild buckwheat | 0 | 0 | 0 | 0 |
| sugar beet | 10C | 10C | 9G | 8G |

Compound 5
Preemergence

| Rate kg/ha | 0.125 | 0.064 | 0.032 | 0.016 |
|---|---|---|---|---|
| wheat | 0 | 0 | 0 | 0 |
| barley | 0 | 0 | 0 | 0 |
| wild oats | 0 | 0 | 0 | 0 |
| cheatgrass | 5G | 4G | 4G | 3G |
| blackgrass | 6G | 6G | 6G | 4G |
| annual bluegrass | 4G | 4G | 3G | 0 |
| green foxtail | 0 | 0 | 0 | 0 |
| Italian ryegrass | 4G | 2G | 2G | 0 |
| rapeseed | 9G | 6G | 3G | 3G |
| *Matricaria inodora* | 9G | 8G | 8G | 8G |
| galium aparine | 7G | 7G | 7G | 7G |
| Russian thistle | 4G | 3G | 0 | 0 |
| shepherd's purse | 9G | 8G | 8G | 7G |
| kochia | 7G | 5G | 0 | 0 |
| black nightshade | 9G,5G | 8G | 4G | 3G |
| speedwell | 8G | 8G | 7G | 5G |
| wild buckwheat | 4G | 3G | 0 | 0 |
| sugar beet | 7G | 6G | 5G | 5G |

Preemergence

| Rate kg/ha | 0.008 | 0.004 | 0.002 | 0.001 |
|---|---|---|---|---|
| wheat | 0 | 0 | 0 | 0 |
| barley | 0 | 0 | 0 | 0 |
| wild oats | 0 | 0 | 0 | 0 |
| cheatgrass | 1G | 0 | 0 | 0 |
| blackgrass | 4G | 2G | 0 | 0 |
| annual bluegrass | 0 | 0 | 0 | 0 |
| green foxtail | 0 | 0 | 0 | 0 |
| Italian ryegrass | 0 | 0 | 0 | 0 |
| rapeseed | 3G | 3G | 3G | 3G |
| *Matricaria inodora* | 7G | 7G | 0 | 0 |
| galium aparine | 6G | 0 | 0 | 0 |
| Russian thistle | 0 | 0 | 0 | 0 |
| shepherd's purse | 3G | 0 | 0 | 0 |
| kochia | 0 | 0 | 0 | 0 |
| black nightshade | 0 | 0 | 0 | 0 |
| speedwell | 0 | 0 | 0 | 0 |
| wild buckwheat | 0 | 0 | 0 | 0 |
| sugar beet | 4G | 2G | 0 | 0 |

What is claimed is:

1. A compound of the structural formula

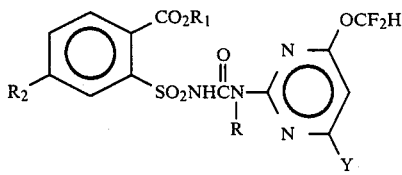

wherein
R is H or $CH_3$;
$R_1$ is $C_1$-$C_3$ alkyl, $C_3$-$C_4$ alkoxyalkyl, $C_2$-$C_4$ haloalkyl, $C_3$-$C_4$ alkenyl or $C_3$-$C_4$ alkynyl;
$R_2$ is $C_1$-$C_3$ alkyl, cyclopropyl, $C_1$-$C_3$ alkylthio, $C_1$-$C_3$ alkylsulfinyl, $C_1$-$C_3$ alkylsulfonyl, allyloxy, allylthio, allylsulfinyl, allylsulfonyl, propargyloxy, propargylthio, propargylsulfinyl, propargylsulfonyl, $OCF_2H$, $C_2$-$C_3$ haloalkoxy, $C_1$-$C_3$ alkyl substituted with 1-3 atoms of F or Cl, $C_1$-$C_2$ alkyl substituted with $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfinyl, $C_1$-$C_2$ haloalkylsulfinyl, $C_1$-$C_2$ alkylsulfonyl, $C_1$-$C_2$ haloalkylsulfonyl, OH or $OC(O)C_1$-$C_2$ alkyl, $C_1$-$C_2$ alkoxy substituted with $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfinyl, $C_1$-$C_2$ haloalkylsulfinyl, $C_1$-$C_2$ alkylsulfonyl, $C_1$-$C_2$ haloalkylsulfonyl or CN, $OCH_2CH_2NH_2$, $OCH_2CH_2NHCH_3$, $OCH_2CH_2N(CH_3)_2$, $C_1$-$C_2$ alkylthio substituted by $C_1$-$C_2$ alkoxy, $C_1$-$C_2$ haloalkoxy, $C_1$-$C_2$ alkylthio, $C_1$-$C_2$ haloalkylthio or CN, $SCF_2H$, $C_2$-$C_3$ haloalkylthio, $C_1$-$C_3$ haloalkylsulfinyl, $C_1$-$C_3$ haloalkylsulfonyl, $C_2$-$C_3$ alkenyl, $NR_bR_c$ or $OC(O)C_1$-$C_2$ alkyl;
$R_b$ is H or $C_1$-$C_2$ alkyl;
$R_c$ is $C_1$-$C_2$ alkyl or $C_1$-$C_2$ haloalkyl;
Y is, $OCH_3$ and
their agriculturally suitable salts.

2. The compounds of claim 1 wherein
$R_2$ is $C_1$-$C_3$ alkyl, cyclopropyl, $C_1$-$C_3$ alkylthio, $C_1$-$C_3$ alkylsulfinyl, $C_1$-$C_3$ alkylsulfonyl, allyloxy, allylthio, allylsulfinyl, allylsulfonyl, propargyloxy, propargylthio, propargylsulfinyl, propargylsulfonyl, $OCF_2H$, $OCH_2CH_2F$, $OCH_2CHF_2$, $OCH_2CF_3$, $OCH_2CH_2Cl$ or $C_1$-$C_3$ alkyl substituted with 1-3 atoms of F or Cl, $C_1$-$C_2$ alkyl substituted with $OCH_3$ or $SCH_3$.

3. The compounds of claim 2 wherein
$R_2$ is $C_1$-$C_2$ alkyl, $C_1$-$C_2$ alkoxy, $C_1$-$C_3$ alkylthio, $C_1$-$C_3$ alkylsulfinyl, $C_1$-$C_3$ alkylsulfonyl, $CF_3$, propargyloxy, propargylthio, propargylsulfinyl, propargylsulfonyl, $OCF_2H$, $OCH_2CH_2F$, $OCH_2CHF_2$, $OCH_2CF_3$, $OCH_2CH_2Cl$, $CH_2CH_2OCH_3$ or $CH_2CH_2SCH_3$.

4. The compounds of claim 3 wherein
R is H;
$R_1$ is $C_1$-$C_2$ alkyl;
$R_2$ is $C_1$-$C_2$ alkyl, $C_1$-$C_2$ alkylthio, $CF_3$ or $OCF_2H$; and
Y is $CH_3$ or $OCH_3$.

5. The compounds of claim 4 wherein
$R_2$ is $CH_3$, $OCH_2CH_3$ or $CF_3$.

6. The compounds of claim 1 wherein
$R_2$ is n-propyl, isopropyl, cyclopropyl, allylthio, allylsulfinyl, allylsulfonyl, $C_2$-$C_3$ alkenyl, $OC(O)CH_3$, $OC(O)CH_2CH_3$, $CH_2F$, $CHF_2$, $C_2$-$C_3$ alkyl substituted with 1-3 atoms of F, $C_1$-$C_3$ alkyl substituted with 1-3 atoms of Cl, $CH_2OH$, $CH(CH_3)OH$, $CH_2OCH_3$, $CH_2OCH_2CH_3$, $CH_2(CH_3)OCH_3$, $CH_2(CH_3)OCH_2CH_3$, $CH_2SCH_3$, $CH_2SCH_2CH_3$, $CH_2(CH_3)SCH_3$, $CH_2(CH_3)SCH_2CH_3$, $CH_2OC(O)C_1$-$C_2$ alkyl, $CH(CH_3)OC(O)C_1$-$C_2$ alkyl, $CH_2OC_1$-$C_2$ haloalkyl of at least 3 halogens, $CH_2SC_1$-$C_2$ haloalkyl of at least 3 halogens, $CH_2S(O)C_1$-$C_2$ haloalkyl of at least 3 halogens, $CH_2SO_2C_1$-$C_2$ haloalkyl of at least 3 halogens, $CH(CH_3)OC_1$-$C_2$ haloalkyl of at least 3 halogens, $CH(CH_3)SC_1$-$C_2$ haloalkyl of at least 3 halogens, $CH(CH_3)S(O)C_1$-$C_2$ haloalkyl of at least 3 halogens, $CH(CH_3)SO_2C_1$-$C_2$ haloalkyl of at least 3 halogens, $CH_2CH_2S(O)C_1$-$C_2$ haloalkyl or $CH_2CH_2SO_2C_1$-$C_2$ haloalkyl.

7. The compounds of claim 6 wherein

115

$R_2$ is propyl, isopropyl, cyclopropyl, allylthio, allylsulfinyl, allylsulfonyl, $CH_2OCH_3$, $CH(CH_3)OCH_3$, $CH_2SCH_3$, $CH(CH_3)SCH_3$, $CH_2F$, $CHF_2$, $C_2-C_3$ alkyl substituted with 1-3 atoms of F or $C_1-C_3$ alkyl substituted with 1-3 atoms of Cl.

8. The compounds of claim 1 wherein
$R_2$ is $C_1-C_3$ alkyl, $SCH_3$, $SO_2CH_3$, $CF_3$ or $NR_bR_c$.

9. The compounds of claim 1 wherein
$R_2$ is $C_1-C_2$ alkoxy substituted with CN, $OCH_2CH_2NH_2$, $OCH_2CH_2N(CH_3)$ or $C_1-C_2$ alkylthio substituted by CN.

10. The compounds of claim 9 wherein
$R_2$ is $OCH_2CH_2CN$, $OCH_2CH_2NH_2$, $OCH_2CH_2N(CH_3)$ or $SCH_2CH_2CN$.

11. The compounds of claim 1 wherein
$R_2$ is $CH_2CH_2OC_1-C_2$ alkyl, $CH_2CH_2SC_1-C_2$ alkyl, $CH_2CH_2S(O)C_1-C_2$ alkyl, $CH_2CH_2SO_2C_1-C_2$ alkyl, $CH_2CH_2OC_1-C_2$ haloalkyl, $CH_2CH_2CH_2SC_1-C_2$ haloalkyl, $CH_2OC_1-C_2$ haloalkyl of 1 or 2 halogens, $CHHd\ 2SC_1-C_2$ haloalkyl of 1 or 2 halogens, $CH_2S(O)C_1-C_2$ haloalkyl of 1 or 2 halogens, $CH_2SO_2C_1-C_2$ haloalkyl of 1 or 2 halogens, $CH(CH_2)OC_1-C_2$ haloalkyl of 1 or 2 halogens, $CH(CH_3)SC_1-C_2$ haloalkyl of 1 or 2 halogens, $CH(CH_3)S(O)C_1-C_2$ haloalkyl of 1 or 2 halogens, or $CH(CH_3)SO_2C_1-C_2$ haloalkyl of 1 or 2 halogens.

12. The compounds of claim 1 wherein
$R_2$ is propargyloxy, propargylsulfinyl or propargylsulfonyl.

13. The compounds of claim 1 wherein
$R_2$ is allyloxy, allylthio, allylsulfinyl, allylsulfonyl, $OCF_2H$, $C_2-C_3$ haloalkoxy, $C_1-C_2$ alkoxy substituted with $C_1-C_2$ alkoxy, $C_1-C_2$ haloalkyl, $C_1-C_2$ alkylthio, $C_1-C_2$ haloalkylthio, $C_1-C_2$ alkylsulfinyl, $C_1-C_2$-haloalkylsulfinyl, $C_1-C_2$ alkylsulfonyl or $C_1-C_2$ haloalkylsulfonyl, $SCF_2H$, $C_2-C_3$ haloalkylthio, $C_1-C_3$ haloalkylsulfinyl or $C_1-C_3$ haloalkylsulfonyl.

14. The compounds of claim 13 wherein
$R_2$ is allyloxy, allylthio, allylsulfinyl, allylsulfonyl, $OCF_2H$, $OCH_2CF_3$, $OCH_2CH_2OCH_3$, $OCH_2CH_2OCH_2CH_3$, $OCH_2CH_2OCH_2CF_3$, $OCH_2CH_2OCF_2H$, $OCH_2CH_2SCH_3$, $OCH_2CH_2SCH_2CF_3$, $OCH_2CH_2S(O)CH_3$, $OCH_2CH_2S(O)CH_2CF_3$, $OCH_2CH_2SO_2CH_3$, $OCH_2CH_2SO_2CH_2CF_3$, $SCF_2H$, $SCH_2CF_3$, $S(O)CH_2CF_3$ or $SO_2CH_2CF_3$.

15. The compounds of claim 1 wherein
$R_2$ is $OCF_2H$, $C_2-C_3$ haloalkoxy, $C_1-C_2$ alkoxy substituted with $C_1-C_2$ alkoxy, $C_1-C_2$ haloalkoxy, $C_1-C_2$ alkylthio, $C_1-C_2$ haloalkylthio, $C_1-C_2$ alkylsulfinyl, $C_1-C_2$ haloalkylsulfinyl, $C_1-C_2$ alkylsulfonyl or $C_1-C_2$ haloalkylsulfonyl, $C_1-C_2$ alkylthio substituted by $C_1-C_2$ alkoxy, $C_1-C_2$ haloalkoxy, $C_1-C_2$ alkylthio or $C_1-C_2$ haloalkylthio, $SCF_2H$, $C_2-C_3$ haloalkylthio, $C_1-C_3$ haloalkylsulfinyl or $C_1-C_3$ haloalkylsulfonyl.

16. The compounds of claim 15 wherein
$R_2$ is $OCF_2H$, $OCH_2CF_3$, $OCH_2CH_2OCH_3$, $OCH_2CH_2OCH_2CH_3$, $OCH_2CH_2OCH_2CF_3$, $OCH_2CH_2OCF_2H$, $OCH_2CH_2SCH_3$, $OCH_2CH_2SCH_2CF_3$, $OCH_2CH_2S(O)CH_3$, $OCH_2CH_2S(O)CH_2CF_3$, $OCH_2CH_2SO_2CH_3$, $OCH_2CH_2SO_2CH_2CF_3$, $SCH_2CH_2OCH_3$, $SCH_2CH_2OCH_2CH_3$, $SCH_2CH_2OCH_2CF_3$, $SCH_2CH_2SCH_3$, $SCH_2CH_2SCH_2CF_3$, $SCF_2H$, $SCH_2CF_3$, $S(O)CH_2CF_3$ or $SO_2CH_2CF_3$.

17. The compounds of claim 1 wherein
$R_2$ is $C_1-C_3$ alkyl substituted with 1-3 atoms of F or Cl.

18. The compounds of claim 17 wherein
$R_2$ is $CF_3$, $CF_2H$, $CFH_2$, $CCL_2H$ or $CH_2Cl$.

116

19. The compounds of claim 1 wherein
$R_2$ is $C_1-C_2$ alkyl, $C_1-C_3$ alkylthio, $C_1-C_3$ alkylsulfinyl, $C_1-C_3$ alkylsulfonyl, $CF_3$ or $NR_bR_c$.

20. The compounds of claim 19 wherein
$R_2$ is $CH_3$, $CH_2CH_3$, $OCH_3$, $OCH_2CH_3$, $SCH_3$, $SCH_2CH_3$, $SCH(CH_3)_2$, $S(O)CH_3$, $S(O)CH_2CH_3$, $S(O)CH(CH_3)_2$, $SO_2CH_3$, $SO_2CH_2CH_3$, $SO_2CH(CH_3)_2$, $CF_3$, $NHCH_3$ or $N(CH_3)_2$.

21. The compound of claim 1 that is 2-[[[4-(difluoromethoxy)-6-methoxypyrimidin-2-yl]aminocarbonyl]aminosulfonyl]-4-ethoxybenzoic acid, methyl ester.

22. An agriculturally suitable composition for controlling the growth of undesired vegetation comprising an effective amount of a compound of claim 1 and at least one of the following: surfactant, solid or liquid diluent.

23. An agriculturally suitable composition for controlling the growth of undesired vegetation comprising an effective amount of a compound of claim 2 and at least one of the following: surfactant, solid or liquid diluent.

24. An agriculturally suitable composition for controlling the growth of undesirable vegetation comprising an effective amount of a compound of claim 3 and at least one of the following: surfactant, solid or liquid diluent.

25. An agriculturally suitable composition for controlling the growth of undesired vegetation comprising an effective amount of a compound of claim 4 and at least one of the following: surfactant, solid or liquid diluent.

26. An agriculturally suitable composition for controlling the growth of undesired vegetation comprising an effective amount of a compound of claim 5 and at least one of the following: surfactant, solid or liquid diluent.

27. An agriculturally suitable composition for controlling the growth of undesired vegetation comprising an effective amount of a compound of claim 6 and at least one of the following: surfactant, solid or liquid diluent.

28. An agriculturally suitable composition for controlling the growth of undesired vegetation comprising an effective amount of a compound of claim 8 and at least one of the following: surfactant, solid or liquid diluent.

29. An agriculturally suitable composition for controlling the growth of undesired vegetation comprising an effective amount of a compound of claim 9 and at least one of the following: surfactant, solid or liquid diluent.

30. An agriculturally suitable composition for controlling the growth of undesired vegetation comprising an effective amount of a compound of claim 11 and at least one of the following: surfactant, solid or liquid diluent.

31. An agriculturally suitable composition for controlling the growth of undesired vegetation comprising an effective amount of a compound of claim 12 and at least one of the following: surfactant, solid or liquid diluent.

32. An agriculturally suitable composition for controlling the growth of undesired vegetation comprising an effective amount of a compound of claim 13 and at least one of the following: surfactant, solid or liquid diluent.

33. An agriculturally suitable composition for controlling the growth of undesired vegetation comprising an effective amount of a compound of claim 15 and at least one of the following: surfactant, solid or liquid diluent.

34. An agriculturally suitable composition for controlling the growth of undesired vegetation comprising an effective amount of a compound of claim 17 and at least one of the following: surfactant, solid or liquid diluent.

35. An agriculturally suitable composition for controlling the growth of undesired vegetation comprising an effective amount of a compound of claim 19 and at least one of the following: surfactant, solid or liquid diluent.

36. An agriculturally suitable composition for controlling the growth of undesired vegetation comprising an effective amount of a compound of claim 21 and at least one of the following: surfactant, solid or liquid diluent.

37. A method for controlling the growth of undesired vegetation which comprises applying to the locus of the crop to be protected an effective amount of a compound of claim 1.

38. A method for controlling the growth of undesired vegetation which comprises applying to the locus of the crop to be protected an effective amount of a compound of claim 2.

39. A method for controlling the growth of undesired vegetation which comprises applying to the locus of the crop to be protected an effective amount of a compound of claim 3.

40. A method for controlling the growth of undesired vegetation which comprises applying to the locus of the crop to be protected an effective amount of a compound of claim 4.

41. A method for controlling the growth of undesired vegetation which comprises applying to the locus of the crop to be protected an effective amount of a compound of claim 5.

42. A method for controlling the growth of undesired vegetation which comprises applying to the locus of the crop to be protected an effective amount of a compound of claim 6.

43. A method for controlling the growth of undesired vegetation which comprises applying to the locus of the crop to be protected an effective amount of a compound of claim 8.

44. A method for controlling the growth of undesired vegetation which comprises applying to the locus of the crop to be protected an effective amount of a compound of claim 9.

45. A method for controlling the growth of undesired vegetation which comprises applying to the locus of the crop to be protected an effective amount of a compound of claim 11.

46. A method for controlling the growth of undesired vegetation which comprises applying to the locus of the crop to be protected an effective amount of a compound of claim 12.

47. A method for controlling the growth of undesired vegetation which comprises applying to the locus of the crop to be protected an effective amount of a compound of claim 13.

48. A method for controlling the growth of undesired vegetation which comprises applying to the locus of the crop to be protected an effective amount of a compound of claim 15.

49. A method for controlling the growth of undesired vegetation which comprises applying to the locus of the crop to be protected an effective amount of a compound of claim 17.

50. A method for controlling the growth of undesired vegetation which comprises applying to the locus of the crop to be protected an effective amount of a compound of claim 19.

51. A method for controlling the growth of undesired vegetation which comprises applying to the locus of the crop to be protected an effective amount of a compound of claim 21.

* * * * *